(12) United States Patent
Labib et al.

(10) Patent No.: US 11,648,341 B2
(45) Date of Patent: May 16, 2023

(54) CARTRIDGES AND SYSTEMS FOR OUTSIDE-IN FLOW IN MEMBRANE-BASED THERAPIES

(71) Applicant: Novaflux Inc., Princeton, NJ (US)

(72) Inventors: Mohamed E. Labib, Princeton, NJ (US); Stanislav S. Dukhin, Goldens Bridge, NY (US); Thomas Kelly, Highland Park, IL (US); Peter Materna, Metuchen, NJ (US)

(73) Assignee: Novaflux Inc., Princeton, NJ (US)

( * ) Notice: Subject to any disclaimer, the term of this patent is extended or adjusted under 35 U.S.C. 154(b) by 155 days.

(21) Appl. No.: 16/583,612

(22) Filed: Sep. 26, 2019

(65) Prior Publication Data

US 2020/0197595 A1    Jun. 25, 2020

Related U.S. Application Data

(63) Continuation of application No. 14/752,414, filed on Jun. 26, 2015, now Pat. No. 10,426,884.

(51) Int. Cl.
*A61M 1/16* (2006.01)
*A61M 1/34* (2006.01)
(Continued)

(52) U.S. Cl.
CPC ............ *A61M 1/3643* (2013.01); *A61M 1/34* (2013.01); *A61M 1/365* (2014.02);
(Continued)

(58) Field of Classification Search
CPC .. A61M 1/3643; A61M 1/365; A61M 1/1625; A61M 1/32; A61M 1/325;
(Continued)

(56) References Cited

U.S. PATENT DOCUMENTS 3,827,563 A    8/1974   Boe et al.
4,038,191 A    7/1977   Davis et al.
(Continued)

FOREIGN PATENT DOCUMENTS

EP    0 001 736 A1    5/1979
EP    0 167 162 A2    1/1986
(Continued)

OTHER PUBLICATIONS

Ayaka Hirano et al., "Experimental evaluation of flow and dialysis performance of hollow-fiber dialyzers with different packing densities," Journal of Artificial Organs, vol. 15, pp. 168-17 (2012).
(Continued)

*Primary Examiner* — Benjamin L Lebron
(74) *Attorney, Agent, or Firm* — Merchant & Gould P.C.

(57) ABSTRACT

Embodiments of the invention pertain to cartridges, systems and methods for performing hemodialysis and related extracorporeal blood treatment modalities and therapies, in which blood flows in the inter fiber space and dialysate flows in the lumens of hollow fibers. Appropriate connectors and fitting orientations may be provided. There may be provided orbital distributors, fanning of fibers, and features to promote uniformity of fiber spacing in the fiber bundle. Orbital distributors may contain contoured surfaces, flow redirectors, non-uniform-conductance flow elements, through-wall distributors, and other features. There may be subdivision of the fiber bundle into two groups of fibers with separate control fluid to each group. Appropriate systems may be provided for various therapies. Flow past the fibers may be parallel, transverse or other configuration. These various features may enable long-term application to all dialysis and ultrafiltration related therapies, and also to other therapies and to applications including implantables, portables and wearables.

17 Claims, 76 Drawing Sheets

(51) Int. Cl.
  *A61M 1/36* (2006.01)
  *B01D 63/02* (2006.01)
  *B01D 69/00* (2006.01)
  B01D 61/14 (2006.01)
  B01D 61/24 (2006.01)

(52) U.S. Cl.
  CPC ........ *A61M 1/3644* (2014.02); *A61M 1/3646* (2014.02); *A61M 1/3647* (2014.02); *A61M 1/3649* (2014.02); *B01D 63/02* (2013.01); *B01D 63/022* (2013.01); *B01D 69/00* (2013.01); A61M 1/1625 (2014.02); A61M 1/342 (2013.01); A61M 1/3413 (2013.01); A61M 2206/10 (2013.01); B01D 61/14 (2013.01); B01D 61/24 (2013.01); B01D 2313/04 (2013.01); B01D 2313/08 (2013.01); B01D 2313/10 (2013.01); B01D 2319/022 (2013.01); B01D 2319/025 (2013.01); B01D 2319/04 (2013.01); B01D 2319/06 (2013.01)

(58) Field of Classification Search
  CPC .. A61M 1/342; A61M 1/3417; A61M 1/3413; A61M 1/3437; A61M 1/3434; A61M 1/1065; A61M 1/1037; A61M 1/1096; A61M 1/106; A61M 1/122; A61M 1/1006; A61M 1/267; A61M 1/1698; A61M 1/1672; A61M 2206/10; A61M 2205/15; A61M 2202/0498; A61M 2209/06; A61M 1/34; A61M 1/3644; A61M 1/3646; A61M 1/3647; A61M 1/3649; B01D 69/00; B01D 61/142; B01D 61/18; B01D 61/243; B01D 61/145; B01D 61/58; B01D 2313/13; B01D 2313/44; B01D 2313/04; B01D 63/02; B01D 63/022; B01D 63/024; B01D 63/16; B01D 63/021; B01D 63/04; B01D 65/02; B01D 65/08; B01D 65/022; B01D 2315/06; B01D 2321/04; B01D 2321/16; B01D 2321/168; B01D 2321/185; B01D 2321/2058; B01D 2321/21; B01D 2321/34; B01D 2313/90; B01D 2313/14; B01D 2313/20; B01D 2313/08; B01D 2313/10; B01D 2313/12; B01D 2313/21; B01D 61/14; B01D 61/24
  See application file for complete search history.

(56) References Cited

U.S. PATENT DOCUMENTS

| | | | |
|---|---|---|---|
| 4,146,480 A | 3/1979 | Holanek et al. |
| 4,164,468 A | 8/1979 | Raible |
| 4,179,380 A | 12/1979 | Amicel et al. |
| 4,201,673 A | 5/1980 | Kanno et al. |
| 4,212,744 A | 7/1980 | Oota |
| 4,220,535 A | 9/1980 | Leonard |
| 4,271,023 A | 6/1981 | Giovannetti et al. |
| 4,346,006 A | 8/1982 | Kopp et al. |
| 4,374,088 A | 2/1983 | Stenberg et al. |
| 4,396,510 A | 8/1983 | Hsei |
| 4,620,965 A | 11/1986 | Fukusawa et al. |
| 4,666,603 A | 5/1987 | Madsen et al. |
| 4,707,268 A | 11/1987 | Shah et al. |
| 4,789,473 A | 12/1988 | Mathieu et al. |
| 4,861,485 A | 8/1989 | Fecondini |
| 4,906,375 A | 3/1990 | Heilmann |
| 4,921,612 A | 5/1990 | Sirkar |
| 4,929,259 A | 5/1990 | Caskey et al. |
| 4,990,251 A | 2/1991 | Spranger et al. |
| 5,037,610 A | 8/1991 | Fukusawa et al. |
| 5,072,498 A | 12/1991 | Raff et al. |
| 5,096,582 A | 3/1992 | Lombardi et al. |
| 5,106,579 A | 4/1992 | Fukazawa et al. |
| 5,139,741 A | 8/1992 | Hagiwara |
| 5,143,612 A | 9/1992 | Hamanaka et al. |
| 5,162,101 A | 11/1992 | Cosentino et al. |
| 5,162,102 A | 11/1992 | Nogawa et al. |
| 5,188,801 A | 2/1993 | Fini |
| 5,198,110 A | 3/1993 | Hanai et al. |
| 5,256,294 A | 10/1993 | van Reis |
| 5,522,998 A | 6/1996 | Polaschegg |
| 5,525,144 A | 6/1996 | Gollan |
| 5,578,267 A | 11/1996 | Cosentino et al. |
| 5,626,759 A | 5/1997 | Krantz et al. |
| 5,700,372 A | 12/1997 | Takesawa et al. |
| 5,730,712 A | 3/1998 | Falkvall et al. |
| 5,779,897 A | 7/1998 | Kalthod et al. |
| 5,833,896 A | 11/1998 | Jacobs et al. |
| 5,871,693 A | 2/1999 | Lindsay |
| 5,882,516 A | 3/1999 | Gross et al. |
| 5,942,112 A | 8/1999 | Ishak |
| 6,074,559 A | 6/2000 | Hahmann et al. |
| 6,149,817 A | 11/2000 | Peterson et al. |
| 6,264,627 B1 | 7/2001 | Liska et al. |
| 6,346,090 B1 | 2/2002 | Liska et al. |
| 6,368,557 B1 | 4/2002 | Piplani et al. |
| 6,432,309 B1 | 8/2002 | Fuke et al. |
| 6,478,969 B2 | 11/2002 | Brantley et al. |
| 6,495,101 B1 | 12/2002 | Yokoyama et al. |
| 6,555,006 B2 | 4/2003 | van Reis |
| 6,596,167 B2 | 7/2003 | Ji et al. |
| 6,613,279 B1 | 9/2003 | Elgas et al. |
| 6,623,441 B1 | 9/2003 | Kihara et al. |
| 6,623,638 B2 | 9/2003 | Watkins et al. |
| 6,638,477 B1 | 10/2003 | Treu et al. |
| 6,719,907 B2 | 4/2004 | Collins et al. |
| 6,764,761 B2 | 7/2004 | Eu et al. |
| 6,811,542 B2 | 11/2004 | Liska et al. |
| 6,890,315 B1 | 5/2005 | Levin et al. |
| 6,994,824 B2 | 2/2006 | Mochizuki et al. |
| 7,128,837 B2 | 10/2006 | Behrendt et al. |
| 7,250,108 B2 | 7/2007 | Boivin et al. |
| 7,267,658 B2 | 9/2007 | Treu et al. |
| 7,285,106 B2 | 10/2007 | Collins et al. |
| 7,316,780 B1 | 1/2008 | Fendya et al. |
| 7,335,334 B2 | 2/2008 | Olsen et al. |
| 7,410,582 B2 | 8/2008 | Bernard et al. |
| 7,537,701 B2 | 5/2009 | Mahendran et al. |
| 7,585,412 B2 | 9/2009 | Gorsuch |
| 7,713,412 B2 | 5/2010 | Heilmann et al. |
| 7,776,219 B2 | 8/2010 | Brugger et al. |
| 7,790,029 B2 | 9/2010 | Dannenmaier et al. |
| 8,136,675 B2 | 3/2012 | Buck |
| 8,182,686 B2 | 5/2012 | Witthaus et al. |
| 8,187,410 B2 | 5/2012 | Noh et al. |
| 8,202,428 B2 | 6/2012 | Heilmann et al. |
| 8,229,546 B2 | 7/2012 | Falken et al. |
| 8,246,826 B2 | 8/2012 | Wilt et al. |
| 8,343,347 B2 | 1/2013 | Collins et al. |
| 8,387,804 B2 | 3/2013 | Buck et al. |
| 8,394,049 B2 | 3/2013 | Reggiani et al. |
| 8,430,832 B2 | 4/2013 | Humes et al. |
| 8,444,587 B2 | 5/2013 | Kelly et al. |
| 8,496,826 B2 | 7/2013 | Uchi et al. |
| 8,596,467 B2 | 12/2013 | Krause |
| 8,603,021 B2 | 12/2013 | Levin et al. |
| 8,747,980 B2 | 6/2014 | Bikson et al. |
| 8,795,220 B2 | 8/2014 | Reggiani et al. |
| 8,834,780 B2 | 9/2014 | Ying |
| 8,877,062 B2 | 11/2014 | Mullick et al. |
| 8,883,008 B2 | 11/2014 | Mishkin |
| 8,992,463 B2 | 3/2015 | Hogard et al. |
| 9,005,152 B2 | 4/2015 | Kelly et al. |
| 9,216,246 B2 | 12/2015 | Kelly et al. |
| 9,248,409 B2 | 2/2016 | Noh et al. |
| 9,254,464 B2 | 2/2016 | Keller et al. |
| 9,352,283 B2 | 5/2016 | Ying et al. |
| 10,369,263 B2 | 8/2019 | Labib et al. |
| 10,399,040 B2 | 9/2019 | Labib et al. |

(56) References Cited

U.S. PATENT DOCUMENTS

| | | | |
|---|---|---|---|
| 10,426,884 | B2 | 10/2019 | Labib et al. |
| 2001/0037964 | A1 | 11/2001 | Won et al. |
| 2002/0091350 | A1 | 7/2002 | Belson |
| 2002/0103453 | A1 | 8/2002 | Burbank et al. |
| 2002/0190000 | A1 | 12/2002 | Baurmeister |
| 2002/0195390 | A1 | 12/2002 | Zha et al. |
| 2003/0075498 | A1 | 4/2003 | Watkins et al. |
| 2006/0041216 | A1 | 2/2006 | McLaughlin et al. |
| 2006/0243653 | A1* | 11/2006 | Heinrich ............ B01D 63/027 210/321.74 |
| 2007/0007193 | A1 | 1/2007 | Uchi et al. |
| 2007/0107884 | A1 | 5/2007 | Sirkar et al. |
| 2007/0119781 | A1 | 5/2007 | Huang et al. |
| 2009/0004053 | A1 | 1/2009 | Kenley |
| 2009/0008341 | A1* | 1/2009 | Townson ............ B01D 63/065 210/336 |
| 2009/0124963 | A1 | 5/2009 | Hogard et al. |
| 2009/0218274 | A1 | 9/2009 | Sakashita et al. |
| 2009/0234266 | A1 | 9/2009 | Solomon et al. |
| 2009/0321344 | A1 | 12/2009 | Lee et al. |
| 2010/0000936 | A1 | 1/2010 | Osabe et al. |
| 2010/0089817 | A1 | 4/2010 | Heilmann et al. |
| 2010/0125235 | A1 | 5/2010 | Cauley, III et al. |
| 2011/0011786 | A1 | 1/2011 | Feichtner et al. |
| 2012/0043271 | A1 | 2/2012 | Maurer |
| 2012/0234746 | A1 | 9/2012 | Howard et al. |
| 2012/0318727 | A1 | 12/2012 | Kawatani et al. |
| 2013/0094997 | A1 | 4/2013 | Wang et al. |
| 2014/0158605 | A1 | 6/2014 | Mishkin |
| 2014/0208948 | A1 | 7/2014 | Cao |
| 2015/0314057 | A1 | 11/2015 | Labib et al. |
| 2016/0051936 | A1 | 2/2016 | Kim et al. |
| 2016/0129172 | A1 | 5/2016 | Hornung et al. |
| 2016/0375188 | A1 | 12/2016 | Labib et al. |
| 2017/0106341 | A1 | 4/2017 | Labib et al. |
| 2020/0061274 | A1 | 2/2020 | Labib et al. |
| 2020/0129929 | A1 | 4/2020 | Labib et al. |

FOREIGN PATENT DOCUMENTS

| | | |
|---|---|---|
| EP | 0 217 759 A1 | 4/1987 |
| EP | 1 634 639 A1 | 3/2006 |
| EP | 1 790 364 A1 | 5/2007 |
| EP | 1 964 603 A1 | 9/2008 |
| EP | 2 083 939 B1 | 11/2010 |
| EP | 2 659 914 A1 | 11/2013 |
| EP | 2 796 185 A1 | 10/2014 |
| JP | 53-30990 | 3/1978 |
| JP | 56-100605 | 8/1981 |
| JP | 2006088148 A | 4/2006 |
| WO | WO 2004056460 | 7/2004 |
| WO | WO 2008/088293 A1 | 7/2008 |
| WO | WO 2010/128044 A1 | 11/2010 |
| WO | WO 2011/032154 A1 | 3/2011 |
| WO | WO 2011/105495 A1 | 9/2011 |
| WO | WO 2013/094533 A1 | 6/2013 |
| WO | WO 2015/118046 A1 | 8/2015 |
| WO | WO 2015/153370 A2 | 10/2015 |
| WO | WO 2017/048224 A1 | 3/2017 |
| WO | WO 2017/053805 A1 | 3/2017 |

OTHER PUBLICATIONS

C. Ronco et al., "Dialysate flow distribution in hollow fiber hemodialyzers with different dialysate pathway configurations," The International Journal of Artificial Organs, vol. 23, No. 9, pp. 601-609 (2000).

Churn K. Poh et al., "Effect of Flow Baffles on the Dialysate Flow Distribution of Hollow-Fiber Hemodialyzers: A Nonintrusive Experimental Sstudy Using MRI," Journal of Biomechanical Engineering, Transactions of the ASME, vol. 125, pp. 481-489 (Aug. 2003).

Churn K. Poh et al., "Effect of Spacer Yarns on the Dialysate Flow Distribution of Hemodialysers: A Magnetic Resonance Imaging Study," ASAIO Journal, vol. 49, pp. 440-448 (2003).

Claudio Ronco et al., "Flow distribution analysis by helical scanning in polysulfone hemodialyzers: Effects of fiber structure and design on flow patterns and solute clearances," Hemodialysis International, vol. 10, pp. 380-388 (2006).

Claudio Ronco, "Fluid Mechanics and Crossfiltration in Hollow-Fiber Hemodialyzers," Contributions to Nephrology, vol. 158, pp. 34-49 (2007).

Dukhin et al., "Outside-in hemofiltration for prolonged operation without clogging," Journal of Membrane Science, vol. 464, pp. 173-178 (2014).

Fealy et al., "The Effect of Circuit "Down-Time" on Uraemic Control During Continuous Veno-Venous Haemofiltration," Critical Care and Resuscitation, vol. 4, pp. 266-270 (2002).

Feng Ding et al., "A Biomimetic Membrane Device That Modulates the Excessive Inflammatory Response to Sepsis," PLoS ONE, vol. 6, Issue 4, e18584, pp. 1-14 (Apr. 2011).

Feng Shen et al., "Threshold Response of Initiation of Blood Coagulation by Tissue Factor in Patterned Microfluidic Capillaries is Controlled by Shear Rate," Arteriosclerosis, Thrombosis, and Vascular Biology, vol. 28, pp. 2035-2041 (2008) and Supp.

Frank Lipnizki et al., "Mass transfer performance for hollow fibre modules with shell-side axial feed flow: using an engineering approach to develop a framework," Journal of Membrane Science, vol. 193, pp. 195-208 (2001).

Grudtner et al., "Histological analysis of cobalt-chromium stents with and without Camouflage polymer coating: experimental porcine carotid artery model," Vascular, vol. 19, No. 2, pp. 89-96 (2011).

Hashimoto et al., "Effect of Shear Rate on Clot Growth at Foreign Surfaces," Artificial Organs, Abstract (Nov. 1985).

Horng-Ruey Chua et al., "Circuit lifespan during continuous renal replacement therapy for combined liver and kidney failure," Journal of Critical Care, vol. 27, pp. 744.e7-744.e15 (2012).

International Search Report and Written Opinion for Application No. PCT/US2016/050004 dated Apr. 28, 2016.

Jasmin Wu et al., "Shell-side mass transfer performance of randomly packed hollow fiber modules," Journal of Membrane Science, vol. 172, pp. 59-74 (2000).

John K. Leypoldt et al., "Hollow Fiber Shape Alters Solute Clearances in High Flux Hemodialyzers," ASAIO Journal, vol. 49, pp. 81-87 (2003).

Ken-ichiro Yamamoto et al., "Computational Evaluation of Dialysis Fluid Flow in Dialyzers With Variously Designed Jackets," Artificial Organs, vol. 33, No. 6, pp. 481-486 (2009).

Linneweber et al., "The effect of surface roughness on activation of the coagulation system and platelet adhesion in rotary blood pumps," Artif Organs, vol. 31, No. 5, Abstract (May 2007).

Isao Noda et al., "Effect of Flow Maldistribution on Hollow Fiber Dialysis—Experimental Studies," Journal of Membrane Science, vol. 5, pp. 209-225 (1979).

M.J. Costello et al., "The effect of shell side hydrodynamics on the performance of axial flow hollow fitbre modules," Journal of Membrane Science, vol. 80, pp. 1-11 (1993).

Norfamilabinti Che Mat et al., "Hollow fiber membrane modules," Current Opinion in Chemical Engineering, vol. 4, pp. 18-24 (2014).

P.W.T. Dierickx et al., "Blood flow around hollow fibers," The International Journal of Artificial Organs, vol. 23, No. 9, pp. 610-617 (2000).

ReNews® A publication on dialyzer reprocessing, vol. 13, Downloaded from http://www.medivators.com/renal/renews/, pp. 1-4 (2008).

Richard A. Ward et al., "Dialysate Flow Rate and Delivered Kt/Vurea for Dialyzers with Enhanced Dialysate Flow Distribution," Clinical Journal of the American Society of Nephrology, vol. 6, pp. 2235-2239 (2011).

Runolfur et al., "Regional citrate anticoagulation in continuous venovenous hemofiltration in critically ill patients with a high risk of bleeding," Kidney International, vol. 55, pp. 1991-1997 (1999).

(56) References Cited

OTHER PUBLICATIONS

Uchino et al., "Continuous is not continuous: the incidence and impact of circuit "down-time" on uraemic control during continuous veno-venous haemofiltration," Intensive Care Med, vol. 29, pp. 575-578 (2003).
William R. Clark et al., "Solute Removal by Hollow-Fiber Dialyzers," Contributions to Nephrology, vol. 158, pp. 20-33 (2007).
Yujun Wang et al., "Effect of random packing on shell-side flow and mass transfer in hollow fiber module described by normal distribution function," Journal of Membrane Science, vol. 216, pp. 81-93 (2003).
Zumoff, Rebecca, "Creating a Wearable Artificial Kidney: A Difficult But Necessary Goal," Nephrology News & Issues, https://www.nephrologynews.com/the-wearable-artificial-kidney-a-difficult-but-necessary-goal/, 7 pages (Apr. 21, 2017).
Exhibit B—Pending claims of U.S. Appl. No. 16/556,851.
Zhang et al., "Preparation of Polyvinylidene Fluoride (PVDF) Hollow Fiber Hemodialysis Membranes," Membranes 2014, 4, 81-95.
Kim, Fabrication of polyacrylonitrile hollow fiber membranes from ionic liquid solutions, Polymer Chemistry, Dec. 2015; https://www.researchgate.net/pubication/283244065.
European Office Action, European Application No. 15 767 687.5, dated Oct. 13, 2020.
Exhibit A—Pending claims of U.S. Appl. No. 16/460,643.
Exhibits B—Pending claims of U.S. Appl. No. 16/556,851.

* cited by examiner

FIG. 5
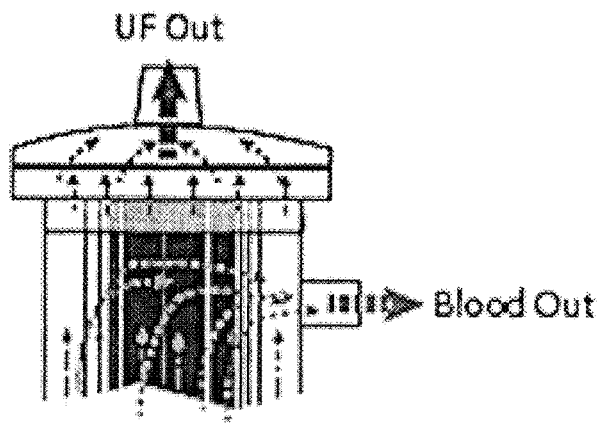
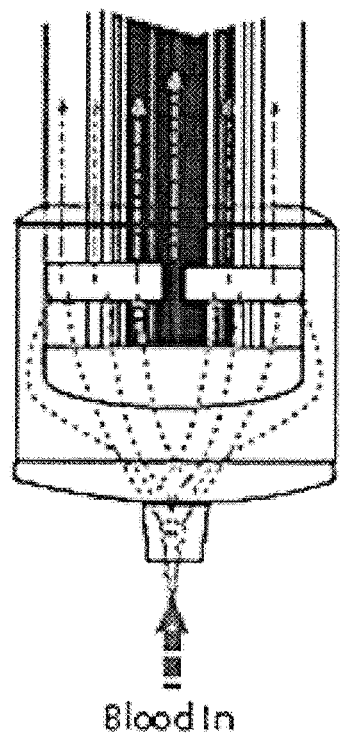

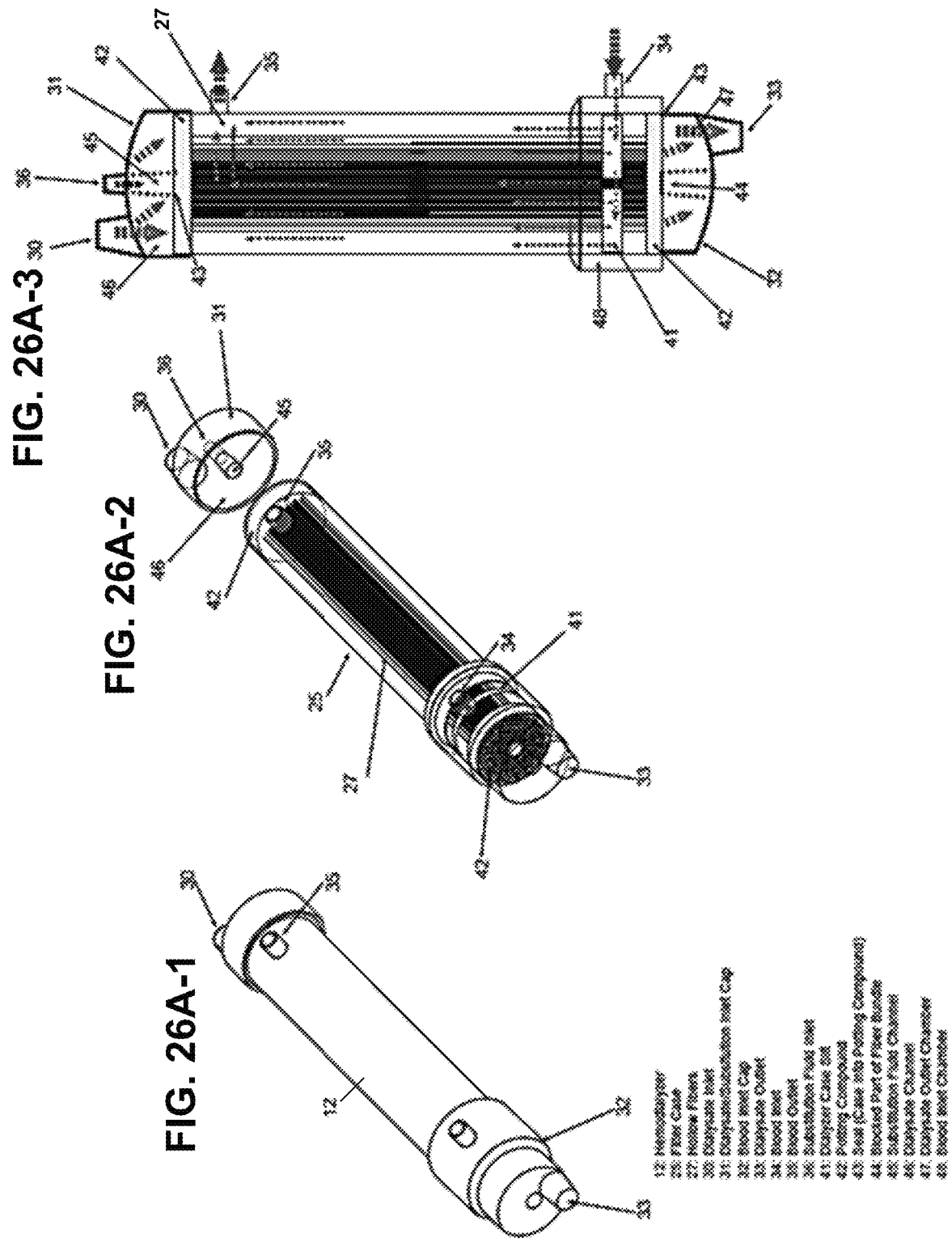

FIG. 34A
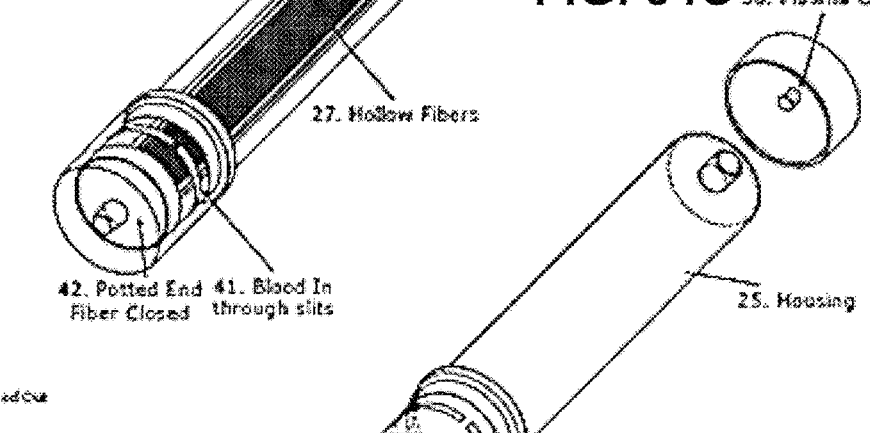
FIG. 34B
FIG. 34C
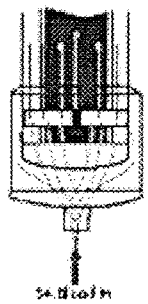
FIG. 34D

Circumferential-axial flow redirector

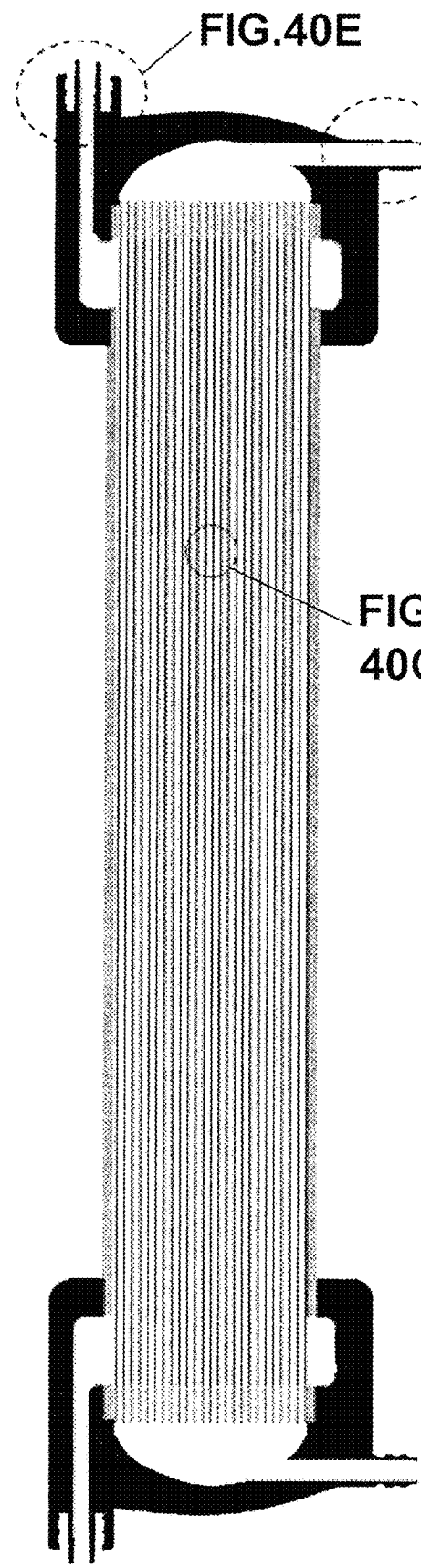
FIG. 40A
FIG. 40E
FIG. 40F
FIG. 40B, 40C, 40D
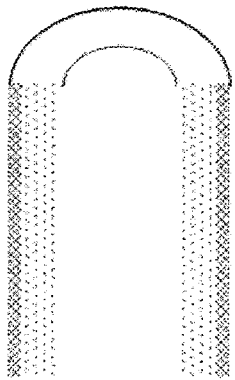
FIG. 40B
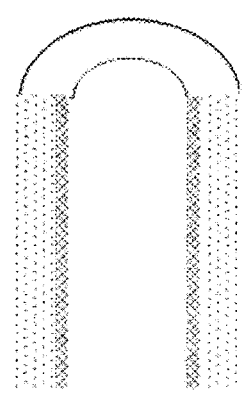
FIG. 40C
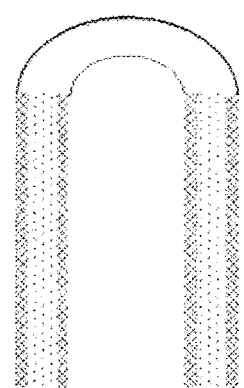
FIG. 40D Luer Lock fitting Hansen fitting

CARTRIDGES AND SYSTEMS FOR OUTSIDE-IN FLOW IN MEMBRANE-BASED THERAPIES

CROSS-REFERENCE TO RELATED APPLICATIONS

This application is a continuation of U.S. application Ser. No. 14/752,414 filed on Jun. 26, 2015. The entire disclosure of U.S. application Ser. No. 14/752,414 is incorporated herein by reference.

FIELD OF THE INVENTION

Embodiments of the invention pertain to blood processing cartridges, tube sets and systems, such as extracorporeal blood therapies, methods for treatment of diseases that can be managed by blood processing, use as implants and use in separation processes to prepare biopharmaceuticals and other useful compounds.

BACKGROUND OF THE INVENTION

Embodiments of the present invention relate to medical systems that can deliver therapies involving the use on an extracorporeal circuit or the use as an implant including but not limited to hemodialysis, hemodiafiltration, ultrafiltration, plasmapheresis, fluid exchange, gas exchange, drug delivery, and treatment of diseases or infections or combination of the above therapy modalities. These embodiments also pertain to the treatment of hypervolemia in patients with Congestive Heart Failure (CHF) and other organ failure, and to making portable and wearable devices that can treat a patient for long periods of times.

Traditionally in hollow fiber hemodialyzers, hemofilters, and hemodiafilters, the blood flows through the lumen of the fiber. These devices are susceptible to fiber clogging resulting from thrombus formation which results in unacceptable increase in circuit pressure and results in the termination of treatment.

A key requirement to enable a longer, more efficient and more cost-effective therapies is the ability to deliver long-term blood processing on a continuous basis without premature filter clogging. Thrombus formation and clogging necessitates frequent filter changes during treatment and is associated with negative consequences such as blood loss and life threatening infections. In the absence of long filter life, the use of ultrafiltration, dialysis or serum replacement devices is limited to treatment in the hospital setting. Numerous investigations by various groups have established that thrombosis causes fiber-clogging leading to an unacceptable growth in filter pressure drop and leading to short filter life not exceeding about 20 hours. The average filter life of intra-luminal conventional hemofiltration/ultrafiltration during Continuous Renal Replacement Therapy (CRRT) or ultrafiltration is typically less than 25 hours of operating time. With complex anticoagulation regimens using regional citrate anticoagulation (RCA) this time may be extended to 35 to 40 hours. Because of these filter life limitations and the complexity of the anticoagulant regimen, patients must be treated in a healthcare facility under supervision of trained medical professionals, which is costly to the healthcare system. The significant increase in cost and expenses is unacceptable in view of the already high cost incurred in treating the CHF, organ failure, sepsis and End Stage Renal Disease (ESRD) population in the United States.

In order to address these needs, it would be helpful to develop hemodialysis, hemodiafiltration, hemofiltration. CRRT and ultrafiltration methods and filters that can achieve long-term treatment without such frequent filter replacement. This would help to reduce the associated product and personnel costs. Thrombus formation during long duration ultrafiltration or other related treatment modalities needs to be minimized to allow safe hemofiltration or ultrafiltration for at least 72 hours without filter clogging. With the current state of technology, this is not possible. Achieving a reduction of thrombus formation or filter clogging would make it possible to develop new medical devices and treatment modalities for long-term therapy with minimal need for filter replacement. All therapies requiring the use of an extracorporeal circuit or an implant will equally benefit from such new methods and filters that can minimize filter clogging and that can provide better filter performance. Hence, there is a need for improvements in hemofiltration, hemodialysis, hemodiafiltration and other related blood processing therapies and methods that can minimize filter clogging.

SUMMARY OF THE INVENTION

The Outside-In Flow Filtration (OIFF) technology of embodiments of the present invention causes the blood to flow on the outside of the fibers. This eliminates much of the clogging and associated increase in filter pressure that arises due to thrombi formation in the interiors of the narrow (typically 180 to 220 micron inside diameter) fibers in conventional treatment. The change to the outside-in flow mode results in low hydrodynamic resistance and in only a small increase in filter pressure during long-term therapy. The inherent hydrodynamic advantage of the Outside-In Flow Filtration technology reduces or even eliminates the need for anticoagulant such as is traditionally required to maintain patency of the extracorporeal circuit.

An embodiment of the present invention pertains to the development of optimal Outside-In Flow Filtration filters that can be employed to perform many therapies performed with extracorporeal circuits. The resulting filter devices can be used for slow continuous ultrafiltration (SCUF) for diuretic resistant congestive heart failure and edematous patients and can also be configured in wearable devices for ultrafiltration or hemodialysis. In addition there are other embodiments where the filter in appropriate configurations can be used to perform hemofiltration (HF), CRRT, hemxlialysis (HD) and hemodiafiltration (HDF). The Outside-In Flow Filtration technology is particularly useful for extended therapies such as CRRT where long filter life is required. The described technology includes the use of the Outside-In Flow methodology as disclosed in related commonly assigned patent applications, which are incorporated by reference in their entirety.

In some embodiments the Outside-In Flow Filtration filter assembly can also provide a redundant in-situ method of ultrafiltration to remove bacteria and pyrogenic material, to prepare substitution fluids, and to perform online hemodiafiltration, CRRT, or other related therapy modalities. This makes the treatment modality safer as it provides a single use solution filter that does not add additional cost or the need for disposables, such as sterile fluid, to the system. Using a portion of the fiber bundle for making substitution solution or for priming the filter also helps to reduce the potential for clotting and platelet aggregation because the substitution solution is infused in a spatially distributed manner so that the infusion of substitution fluid extends over substantially the entire length of the filter.

The term Outside-In Flow Filtration or its subset applications as used herein, is herein intended to have its broadest interpretation as any method, circuit, tubing set, device, system, filter or item of manufacture that provides patient therapy or adjunct processes involving blood processing or substitution fluids with the aid of any extracorporeal circuit or with an implant where the outside-in flow mode is involved. In comparison with prior art, the inventive articles and systems and methods comprise Outside-In Flow Filtration filters, flow circuits, blood tubing configurations, methods for performing treatment and devices that control and handle fluids during therapy. Intended therapies include but not limited to hemodialysis, hemofiltration, hemodiafiltration, ultrafiltration, CRRT, plasmapheresis, and their combinations and adjunct processes such as preparation of infusion fluids and means to perform filter priming or returning blood back to patient at the end of treatment. Intended therapies comprise performing ultrafiltration, solute clearance by diffusion, adsorption, convection, infusion of drugs, removal of toxins and gases ($CO_2$), or their combinations. The invention further comprises methods for manufacturing Outside-In Flow Filtration filters and flow circuits and blood lines used to perform different treatment modalities as mentioned above.

In an embodiment of the invention, there may be provided a cartridge, comprising: a housing that is generally tubular, having a housing wall; a plurality of fibers contained inside the housing, at least some of the fibers being hollow and being made of semi-permeable membranes and having respective fiber lumens and fiber exteriors, wherein inter fiber space comprises space inside the housing between the fibers; housing connections to the housing that are in fluid communication with the inter fiber space; and a first header that is in fluid communication with the fiber lumens, the first header having a first header connection attached thereto, wherein the housing connections have fittings that are luer lock fittings and the first header connection has a first header fitting that is incompatible with the luer lock fittings.

In an embodiment of the invention, there may be provided a cartridge, comprising: a housing that is generally tubular, having a housing wall; a plurality of fibers contained inside the housing, at least some of the fibers being hollow and being made of semi-permeable membranes and having respective fiber lumens and fiber exteriors, wherein inter fiber space comprises space inside the housing between the fibers; housing connections to the housing that are in fluid communication with the inter fiber space; and a first header that is in fluid communication with the fiber lumens, the first header having a first header connection attached thereto, wherein the first header connection has a Hansen fitting and the housing connections have fittings that are incompatible with the Hansen fittings.

In an embodiment of the invention, there may be provided a cartridge, comprising: a housing that is generally tubular, having a housing wall; a plurality of fibers contained inside the housing, at least some of the fibers being hollow and being made of semi-permeable membranes and having respective fiber lumens and fiber exteriors, wherein inter fiber space comprises space inside the housing between the fibers; housing connections to the housing that are in fluid communication with the inter fiber space; and a first header that is in fluid communication with the fiber lumens, the first header having a first header connection attached thereto, wherein the housing connections have fittings having respective fitting axes that are generally parallel to the housing longitudinal axis and the first header connection has a first header fitting having a first header fitting axis that is generally perpendicular to the housing longitudinal axis.

In an embodiment of the invention, there may be provided a cartridge, comprising: a housing comprising a tubular component, the tubular component having a tubular wall and an interior and an exterior; a fiber bundle containing a plurality of fibers contained inside the housing, at least some of the fibers being hollow and being made of semi-permeable membranes and having respective fiber lumens and fiber exteriors, wherein inter fiber space comprises space inside the housing between the fibers; a compartment that is in fluid communication with the inter fiber space and with a housing port near an end of the housing and with an orbital distributor near the housing port, wherein the orbital distributor comprises a separator wall, the fiber bundle being located radially inward of the separator wall, and further comprises an orbital channel that is located radially outward of the separator wall, wherein the separator wall has a plurality of openings therethrough defined by remaining solid material of the separator wall.

In an embodiment of the invention, there may be provided a cartridge, comprising: a housing; a fiber bundle comprising a plurality of fibers contained inside the housing, at least some of the fibers being hollow and being made of semi-permeable membranes having respective fiber lumens and fiber exteriors, wherein inter fiber space comprises space inside the housing between the fibers; a first fluid flow compartment comprising the lumens of the hollow fibers; and a second fluid flow compartment comprising the inter fiber space, wherein the housing comprises a first housing port near a first end of the housing, and a second housing port near a second end of the housing, wherein the second fluid flow compartment comprises an orbital distributor comprising an orbital channel and an access region accessing the fiber bundle, further comprising, between the orbital channel and the access to the fiber bundle, a non-uniform-conductance flow element whose conductance varies as a function of position with respect to a circumferential angle.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors; a first fluid flow compartment comprising the lumens of the hollow fibers; and a second fluid flow compartment comprising an inter fiber space bordering the fiber exteriors, wherein the housing comprises a first housing port near a first end of the housing, and a second housing port near a second end of the housing, wherein the second fluid flow compartment comprises a forward-facing orbital distributor in communication with the inter fiber space, and wherein in a cross-section taken in a sectional plane that contains a longitudinal axis of the cartridge, the housing interior surface is composed entirely of surfaces that are either curved or vertical.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors, wherein inter fiber space comprises space inside the housing between the fibers, a port connected to a side of the housing; an orbital distributor inside the housing and connected to the port, wherein the orbital distributor comprises a separator wall that is generally circumferential, wherein the separator wall is at one of its ends joined to the housing and at its opposed end creates an open direction of the orbital distributor facing away from a midplane of the cartridge, wherein the separator wall has a shape, in a cross-section taken in a plane that contains a lengthwise axis of the cartridge, that has smoothly rounded end.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors, wherein inter fiber space comprises space inside the housing between the fibers, a port connected to a side of the housing; and an orbital distributor inside the housing and connected to the port, wherein the orbital distributor comprises a circumferential internal wall, wherein a surface of an interior of the port aligns with or smoothly transitions with a surface of an interior of the orbital distributor.

In an embodiment of the invention, there may be provided a cartridge, comprising: a housing, the housing having a housing supply port and a housing discharge port; a plurality of fibers contained inside the housing, at least some of the fibers being hollow and being made of semi-permeable membranes having respective fiber lumens and fiber exteriors; a first fluid flow compartment comprising the lumens of the hollow fibers; and a second fluid flow compartment comprising an inter fiber space bordering the fiber exteriors, wherein the housing comprises a first housing port near a first end of the housing, and a second housing port near a second end of the housing, wherein the second fluid flow compartment comprises an orbital distributor in communication with the inter fiber space, wherein the orbital distributor comprises a lateral-circumferential flow redirector near one of the housing ports, wherein the lateral-circumferential flow redirector comprises a smoothly curved surface that blends smoothly with a circumferential direction of the orbital distributor and forms a sharp or pointed geometry that points in a direction of the one of the housing ports near the orbital distributor.

In an embodiment of the invention, there may be provided a cartridge, comprising: a housing, the housing having a housing supply port and a housing discharge port; a plurality of fibers contained inside the housing, at least some of the fibers being hollow and being made of semi-permeable membranes having respective fiber lumens and fiber exteriors; a first fluid flow compartment comprising the lumens of the hollow fibers; and a second fluid flow compartment comprising an inter fiber space bordering the fiber exteriors, wherein the housing comprises a first housing port near a first end of the housing, and a second housing port near a second end of the housing, wherein the second fluid flow compartment comprises an orbital distributor in communication with the inter fiber space, wherein the orbital distributor comprises a circumferential-axial flow redirector, wherein the circumferential-axial flow redirector blends smoothly with the orbital distributor in a circumferential direction, and the circumferential-axial flow redirector has a tangential surface that is directed approximately along a lengthwise direction of the cartridge.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors, wherein inter fiber space comprises space inside the housing between the fibers, a port connected to a side of the housing; an orbital distributor inside the housing and connected to the port, wherein the orbital distributor comprises a circumferential internal wall, wherein the circumferential wall is at one of its ends joined to the housing and at its opposed end forms a separator wall creating an open direction of the orbital distributor facing away from a midplane of the cartridge, wherein a fiber entrance height is a distance between the circumferential internal wall and a barrier in which the plurality of fibers are potted, wherein an orbital distributor height is a maximum height of the circumferential wall inside the orbital distributor, wherein the fiber entrance height is greater than the orbital distributor height.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors; a first fluid flow compartment comprising the lumens of the hollow fibers; and a second fluid flow compartment comprising an inter fiber space bordering the fiber exteriors, wherein the fibers sieve as a function of molecular size and molecular shape, for molecules to which an outer surface of the fibers is exposed.

In an embodiment of the invention, there may be provided a cartridge, comprising: a housing comprising a tubular component, the tubular component having a tubular wall and a tubular interior; a plurality of fibers contained inside the tubular component, at least some of the fibers being hollow and being made of semi-permeable membranes and having respective fiber lumens and fiber exteriors; a first impermeable barrier adjoining the tubular interior and adjoining the fiber exteriors near a first end of the tubular component; and a second impermeable barrier adjoining the tubular interior and adjoining the fiber exteriors near a second end of the tubular component, wherein the first impermeable barrier is polished so as to expose the lumens of the hollow fibers, wherein the second impermeable barrier dead-ends the second ends of the hollow fibers, and the second impermeable barrier has a surface, facing away from the fiber bundle, that is curved.

In an embodiment of the invention, there may be provided a hemodialysis blood processing system, comprising: a cartridge comprising: a housing having a housing supply port and a housing discharge port; and a plurality of fibers contained inside the housing, at least some of the fibers being hollow and being made of semi-permeable membranes having respective fiber lumens and fiber exteriors; wherein the cartridge has at least one feature selected from the group consisting of: the fibers having waviness of the fibers; the fibers having an external surface that is smooth and hemocompatible; the fibers having a packing fraction of the fibers in the housing being in the range of 40% to 70%; and the cartridge having an air bleed connected to the cartridge in communication with an inter fiber space, wherein the system supplies blood to the housing supply port and receives blood from the housing discharge port, wherein the system supplies dialysate to a first end of the plurality of fibers and receives dialysate from a second end of the plurality of fibers, wherein the blood flowing outside the fibers and the dialysate flowing inside the fibers flow in opposite directions.

In an embodiment of the invention, there may be provided a slow continuous ultrafiltration blood processing system, comprising: a cartridge comprising: a housing having a housing supply port and a housing discharge port; and a plurality of fibers contained inside the housing, at least some of the fibers being hollow and being made of semi-permeable membranes having respective fiber lumens and fiber exteriors; wherein the cartridge has at least one feature selected from the group consisting of: the fibers having waviness of the fibers; the fibers having an external surface that is smooth and hemocompatible; the fibers having a packing fraction of the fibers in the housing being in the range of 40% to 70%; and the cartridge having an air bleed connected to the cartridge in communication with an inter fiber space, wherein the system supplies blood to the housing supply port and receives blood from the housing discharge port, wherein the system extracts filtrate from an end of the plurality of fibers.

In an embodiment of the invention, there may be provided a hemofiltration blood processing system, comprising: a cartridge comprising: a housing having a housing supply port and a housing discharge port; and a plurality of fibers contained inside the housing, at least some of the fibers being hollow and being made of semi-permeable membranes having respective fiber lumens and fiber exteriors; wherein the cartridge has at least one feature selected from the group consisting of: the fibers having waviness of the fibers; the fibers having an external surface that is smooth and hemocompatible; the fibers having a packing fraction of the fibers in the housing being in the range of 40% to 70%; and the cartridge having an air bleed connected to the cartridge in communication with an inter fiber space, wherein the system supplies blood to the housing supply port and receives blood from the housing discharge port, wherein the system extracts filtrate from an end of the plurality of fibers, wherein the system supplies a substitution fluid to the blood.

In an embodiment of the invention, there may be provided a hemodiafiltration blood processing system, comprising: a cartridge comprising: a housing having a housing supply port and a housing discharge port; and a plurality of fibers contained inside the housing, at least some of the fibers being hollow and being made of semi-permeable membranes having respective fiber lumens and fiber exteriors; wherein the cartridge has at least one feature selected from the group consisting of: the fibers having waviness of the fibers; the fibers having an external surface that is smooth and hemocompatible; the fibers having a packing fraction of the fibers in the housing being in the range of 40% to 70%; and the cartridge having an air bleed connected to the cartridge in communication with an inter fiber space, wherein the system supplies blood to the housing supply port and receives blood from the housing discharge port, wherein the system supplies dialysate to a first end of the plurality of fibers and receives dialysate from a second end of the plurality of fibers, wherein the system supplies a substitution fluid to the blood.

In an embodiment of the invention, there may be provided a tube set comprising: a cartridge having a housing and having a plurality of fibers contained inside the housing, and having an inter fiber space between the fibers inside the housing, and having a first housing port that is in fluid communication with the inter fiber space and a second housing port that is in fluid communication with the inter fiber space; a blood supply tubing adapted to attach to a patient's body, and further connecting to the first housing port; and a blood return tubing adapted to attach to the patient's body, and further connecting to the second housing port, wherein at least one of the blood supply tubing and the blood return tubing is adapted to be compressed by a roller of a peristaltic pump.

In an embodiment of the invention, there may be provided a system comprising: a cartridge, comprising: a housing; a plurality of fibers contained inside the housing, at least some of the fibers being hollow and being made of semi-permeable membranes having respective fiber lumens and fiber exteriors; a first fluid flow compartment comprising the lumens of the hollow fibers; and a second fluid flow compartment comprising an inter fiber space bordering the fiber exteriors, wherein the housing comprises at least one housing port in communication with an inter fiber space, wherein the system further comprises a dialysate supply for supplying purified dialysate to the lumens of the fibers, and for maintaining a pressure inside the lumens higher than a pressure at the fiber exteriors, whereby the dialysate passes through the semi-permeable membranes of the fibers and occupies the inter fiber space to produce a primed cartridge filled with priming liquid, wherein the system further comprises an air bleed for releasing air from the second fluid flow compartment, wherein the system further comprises a blood supply system for delivering blood to the primed cartridge, wherein the system further comprises a multi-position valve for releasing the priming liquid from the system when blood is displacing the priming liquid from the cartridge, and for retaining blood within the system after blood has reached the multi-position valve.

In an embodiment of the invention, there may be provided a system, comprising: a housing, the housing having a housing supply port and a housing discharge port; a plurality of fibers contained inside the housing, at least some of the fibers being hollow and being made of semi-permeable membranes having respective fiber interiors and fiber exteriors, the fibers being grouped into a first fiber group and a second fiber group; a first end having a first-end header first chamber that is in fluid communication with the fiber lumens of the first fiber group and a first-end header second chamber that is in fluid communication with the fiber lumens of the second fiber group; a second-end header that is in fluid communication with at least some of the fiber lumens; a first fluid supply system that supplies a first fluid to the first-end header first chamber and to the first-end header second chamber, wherein flow in lumens of the first fiber group and flow in lumens of the second fiber group are in an identical direction; and a second fluid supply system that supplies a second fluid to the housing supply port.

In an embodiment of the invention, there may be provided a cartridge, comprising: a housing, the housing having a housing supply port and a housing discharge port; and a plurality of fibers contained inside the housing, at least some of the fibers being hollow and being made of semi-permeable membranes having respective fiber lumens and fiber exteriors, the fibers being grouped into a first fiber group and a second fiber group, wherein the fibers, at a first end, are potted in a first barrier, such that at the first end the first group of fibers is open to a first fluid connection and the second group of fibers is open to a second fluid connection that is isolated from the first fluid connection, wherein the fibers, at a second end opposed to the first end, are all dead-ended.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors, the fibers being potted into a first-end barrier at one end of the fibers and being potted into a second-end barrier at an opposed end of the fibers; a first-end header having a first-end header first chamber that is in fluid communication with the lumens of some of the fibers of so as to define a first fiber group, and a first-end header second chamber that is in fluid communication with the lumens of others of the fibers so as to define a second fiber group; and a second-end header having a second-end header first chamber that is in fluid communication with the lumens of at least some of the fibers of the first fiber group and a second-end header second chamber that is in fluid communication with the lumens of at least some of the fibers of the second fiber group, wherein the first-end header first chamber and the first-end header second chamber are separated from each other at least in part by a first-end separator that contacts the first-end barrier, wherein the second-end header first chamber and the second-end header second chamber are separated from each other at least in part by a second-end separator that contacts the second-end barrier.

In an embodiment of the invention, there may be provided a method of performing hemodialysis, the method comprising: providing a cartridge, wherein the cartridge comprises a first dialysate inlet and a second dialysate inlet and a dialysate outlet, and comprises a blood inlet and a blood outlet, and the cartridge comprises a semi-permeable membrane separating blood and dialysate; providing a first fluid supply that supplies a dialysate to the first dialysate inlet and providing a second fluid supply that supplies the dialysate to the second dialysate inlet; removing the dialysate from the dialysate outlet; and performing hemodialysis by causing blood to flow into the blood inlet and out from the blood outlet.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors; a first-end header having a first-end header first chamber that is in fluid communication with the lumens of some of the fibers of so as to define a first fiber group, and a first-end header second chamber that is in fluid communication with the lumens of others of the fibers so as to define a second fiber group; and a second-end header that is in fluid communication with at least some of the fibers of one of the fiber groups, wherein at least some of the fibers of the other of the fiber groups are dead-ended.

In an embodiment of the invention, there may be provided a cartridge, comprising: a housing; a plurality of fibers contained inside the housing, at least some of the fibers being hollow and being made of semi-permeable membranes having respective fiber lumens and fiber exteriors; a first fluid flow compartment comprising the lumens of the hollow fibers; and a second fluid flow compartment comprising an inter fiber space bordering the fiber exteriors, wherein the housing comprises a first housing port near a first end of the housing, and a second housing port near a second end of the housing, wherein the housing comprises a third housing port located, in lengthwise position, between the first housing port and the second housing port and in fluid communication with the inter fiber space.

In an embodiment of the invention, there may be provided a cartridge, comprising: a housing, the housing having a housing supply port and a housing discharge port; and a plurality of fibers contained inside the housing, at least some of the fibers being hollow and being made of semi-permeable membranes having respective fiber lumens and fiber exteriors, a first fluid flow compartment comprising the lumens of the hollow fibers; and a second fluid flow compartment comprising an inter fiber space that touches the fiber exteriors, wherein flow from the housing supply port to the housing discharge port is, at a midplane of the cartridge, generally perpendicular to a lengthwise direction of the plurality of fibers, wherein the cartridge further comprises a flow resistance element between the housing supply port and the inter fiber space, or between the inter fiber space and the housing discharge port, the flow resistance element causing the flow in the inter fiber space to be more uniform than would occur without the flow resistance.

In an embodiment of the invention, there may be provided a cartridge comprising: a housing having a housing supply port and a housing discharge port; and a plurality of fibers contained inside the housing, at least some of the fibers being hollow and being made of semi-permeable membranes having respective fiber lumens and fiber exteriors; wherein the fibers have an external surface that is smooth and hemocompatible, wherein the fibers are wavy and have a porosity fraction inside the housing that is between 40% and 70%, wherein there is a maximum shear rate that occurs at some location in the cartridge during a flow of a fluid through the housing from the housing supply port to the housing discharge port at a defined flowrate, wherein there is a minimum shear rate that occurs at some other location in the cartridge during said flow of the fluid through the housing from the housing supply port to the housing discharge port at the defined flowrate, wherein a ratio of the maximum shear rate to the minimum shear rate is less than 9.

BRIEF DESCRIPTION OF THE ILLUSTRATIONS

Embodiments of the invention are further described in the following illustrations.

FIG. 5 is a close-up view of portions of the cartridge of FIGS. 4A-4C, showing flow patterns.

Figures 2, 39A:
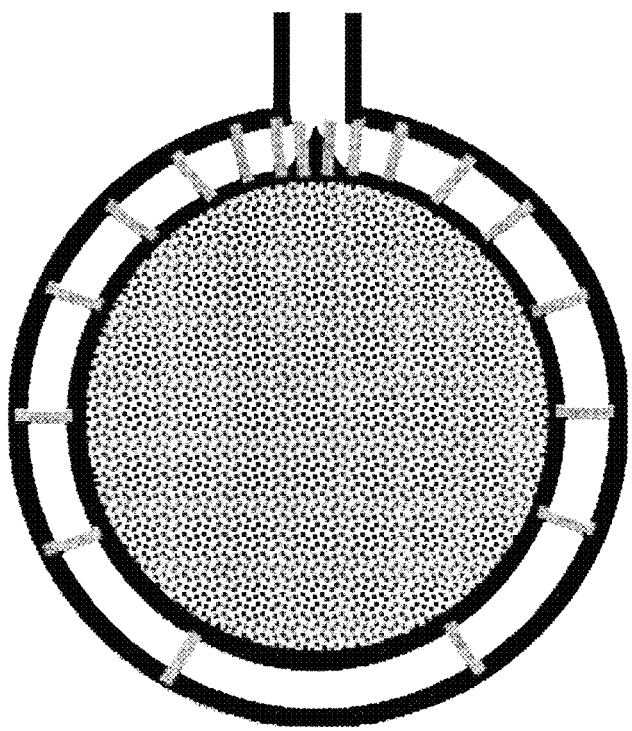
Figures 1, 39A:
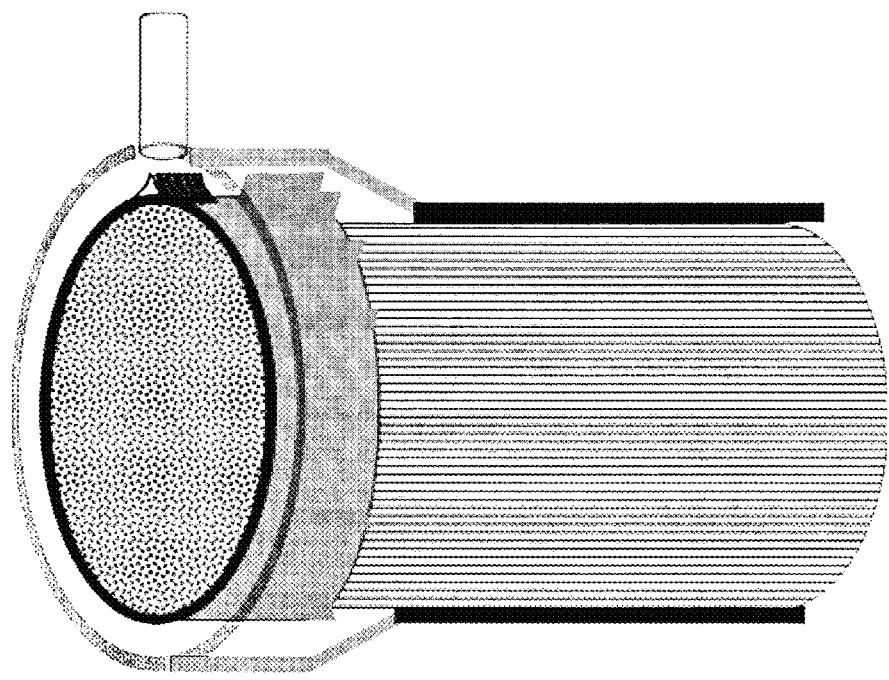

FIGS. 26A-1, A-2, and A-3 show a cartridge for hemodialysis or hemodiafiltration including internal substitution filtration.

Figure 26B:
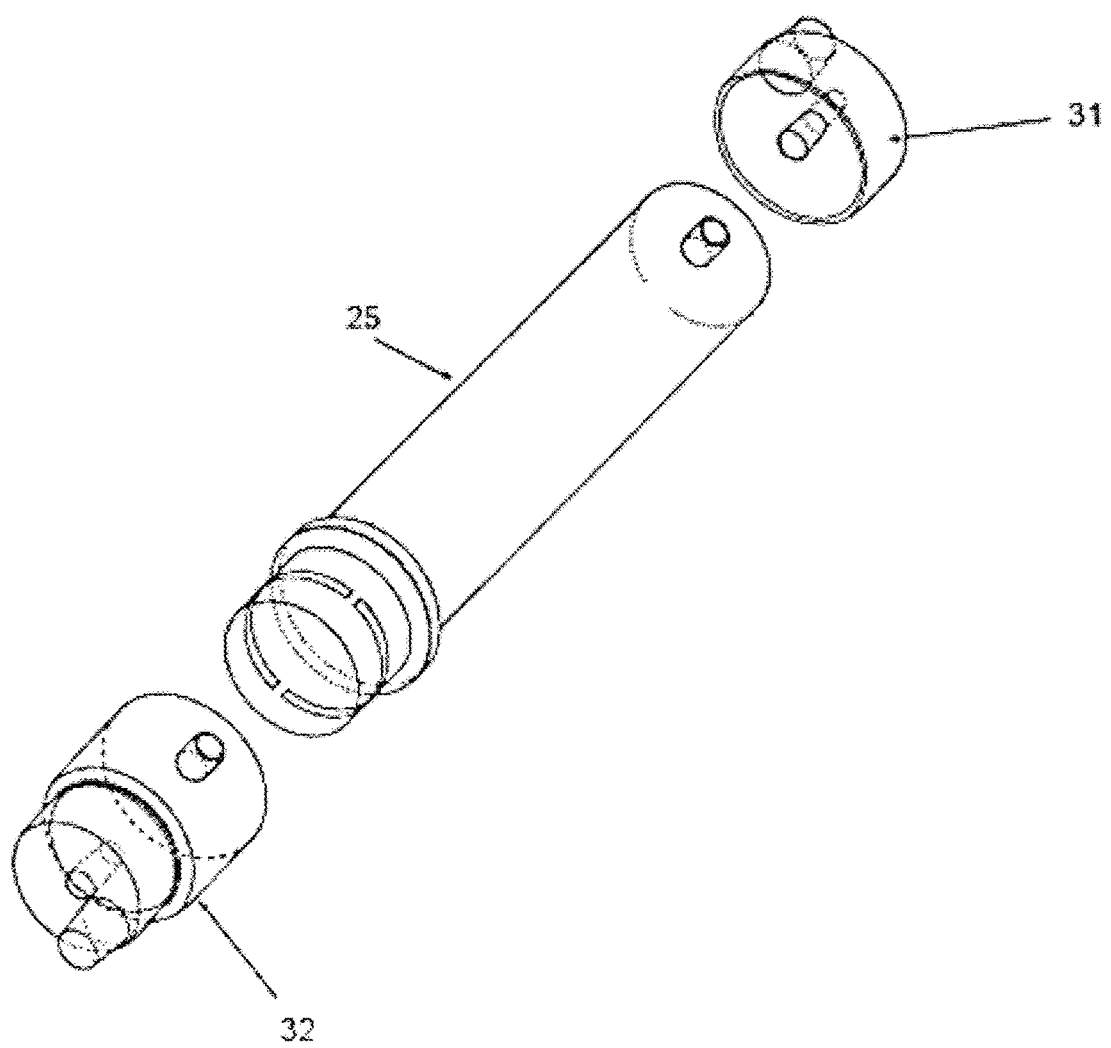

FIG. 26B is a more fully exploded view of the cartridge of FIG. 26A, with the fiber bundle omitted for clarity of illustration.

Figure 27:
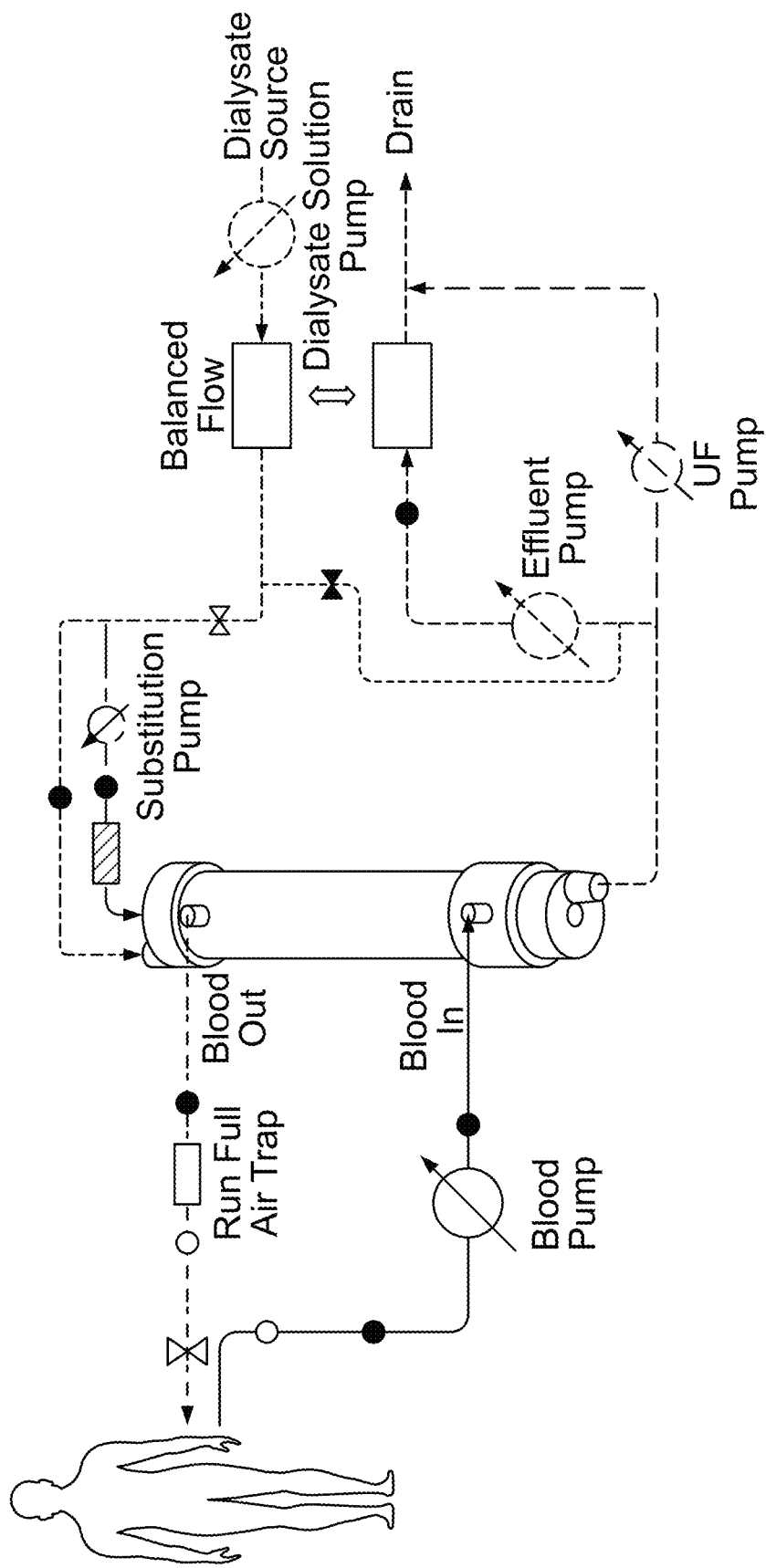

FIG. 27 shows a system for performing hemodialysis or hemodiafiltration with internal substitution, using a volumetric flow balancing system.

Figure 28:
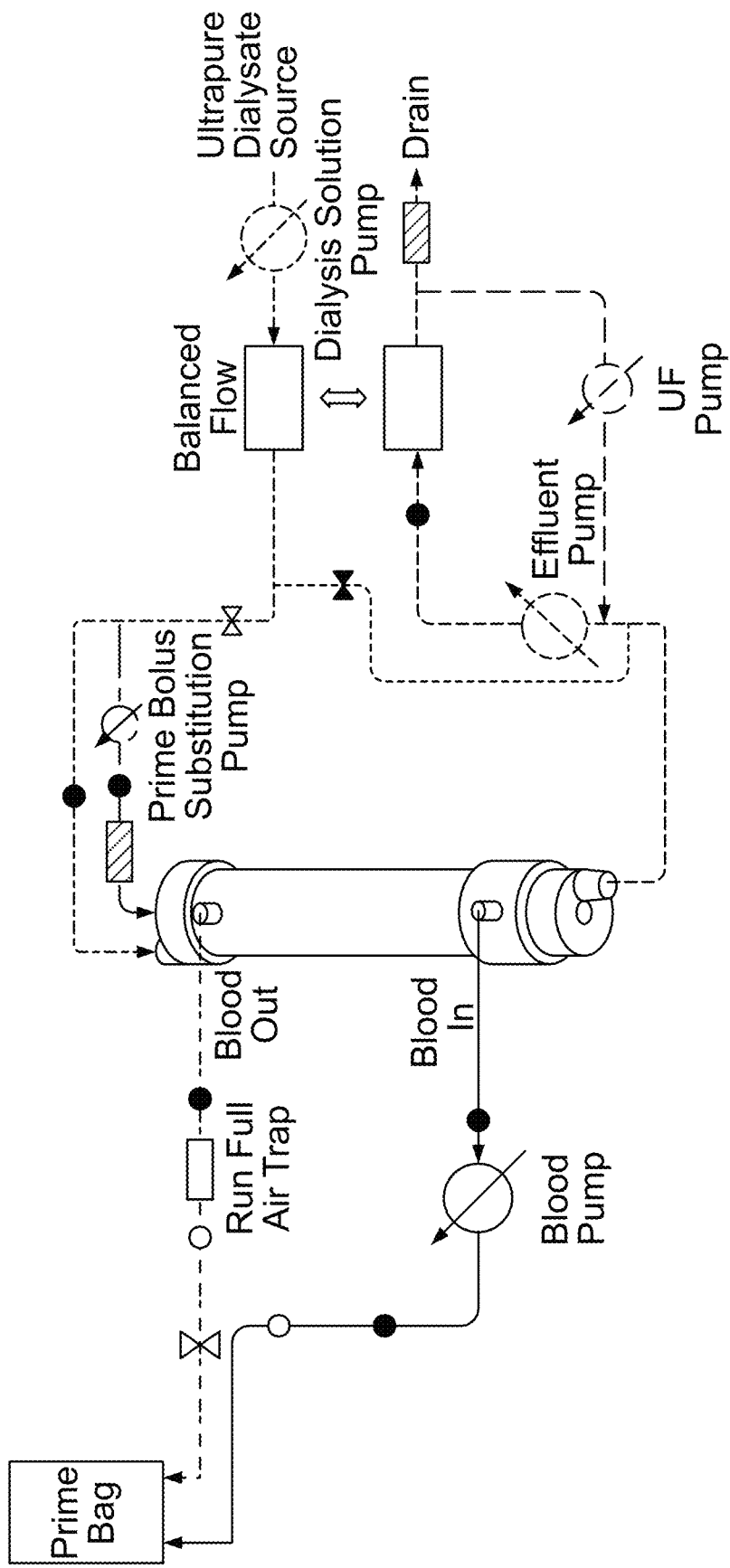

FIG. 28 shows a method of priming the system of FIG. 27.

Figure 29A:
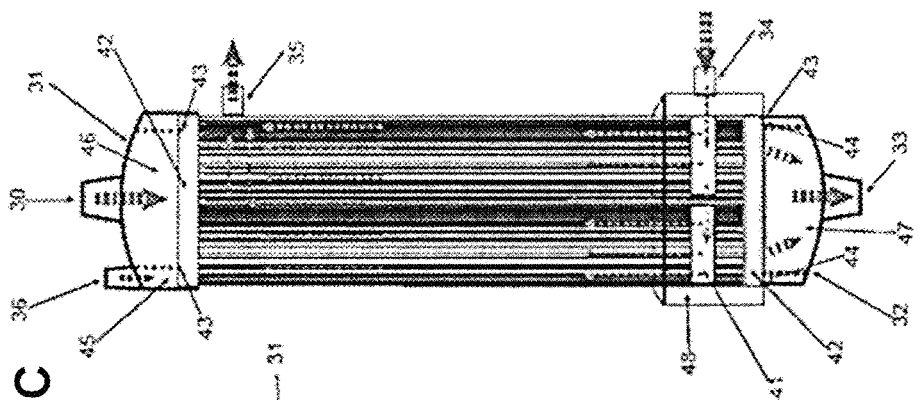
Figure 29B:
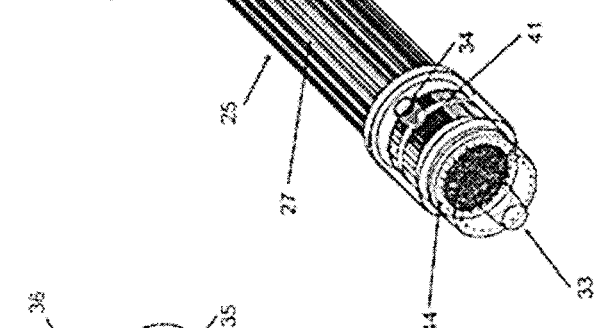
Figure 29C:
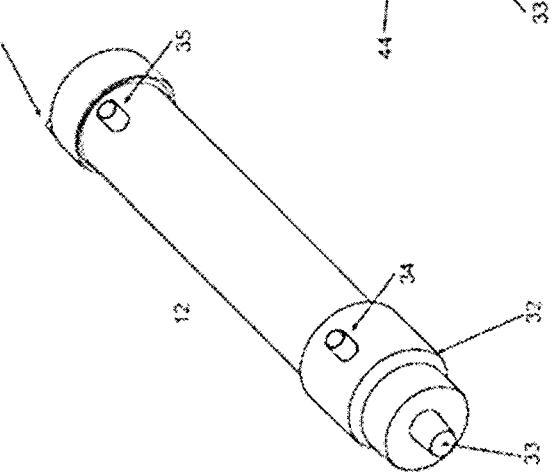

FIGS. 29A-29C show a cartridge similar to the cartridge of FIGS. 26A-1, 26A-2, and 26A-3 and 26B, which is able to provide internal substitution fluid down the entire length of the housing, and which uses a sealing ridge in the dialysate inlet cap.

Figure 30:
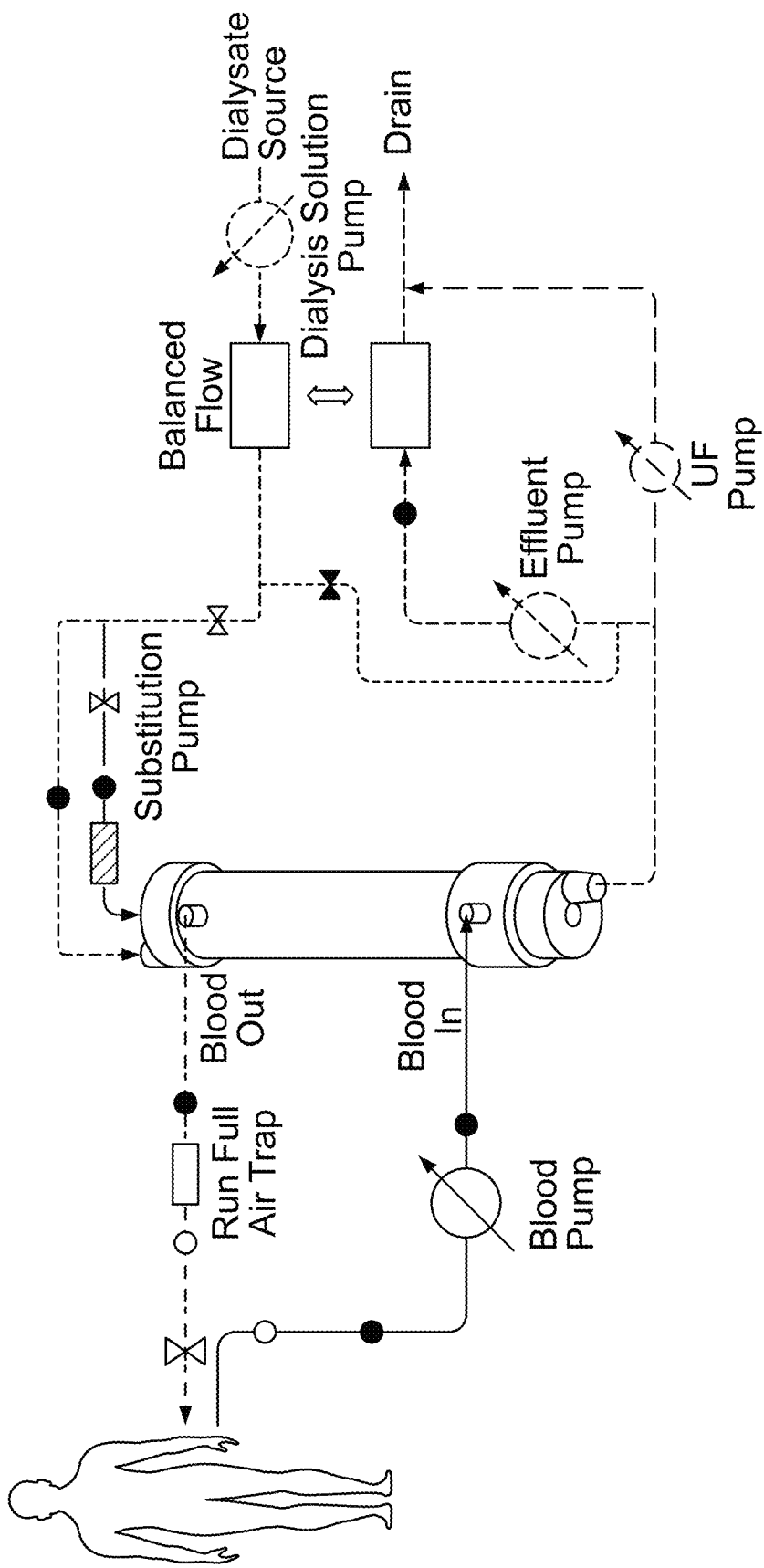

FIG. 30 shows a system for accomplishing hemodialysis or hemodiafiltration with internal substitution fluid.

Figure 31:
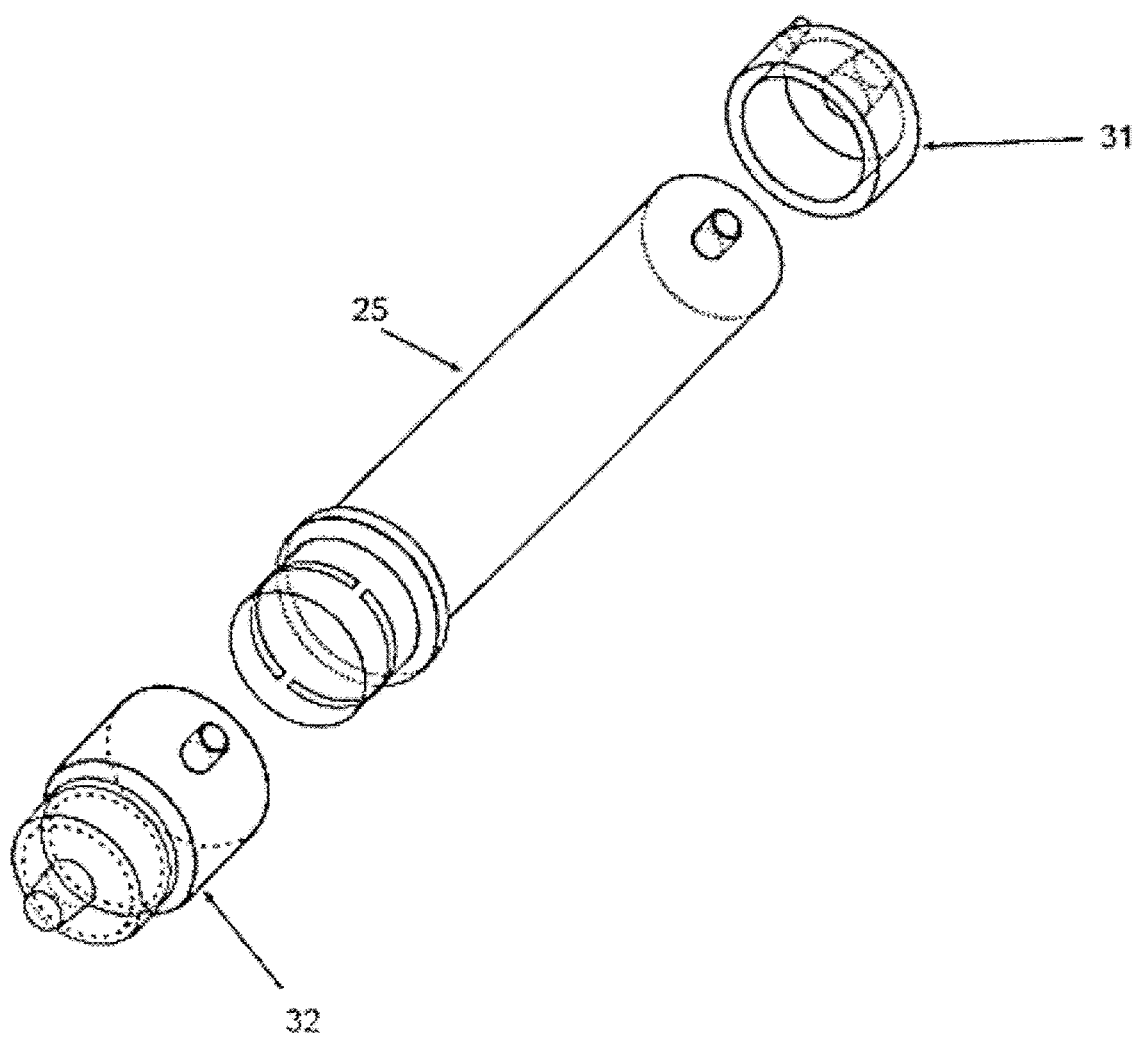

FIG. 31 is an exploded view showing component pieces that make up the cartridge of FIGS. 29A-29C.

Figure 32:
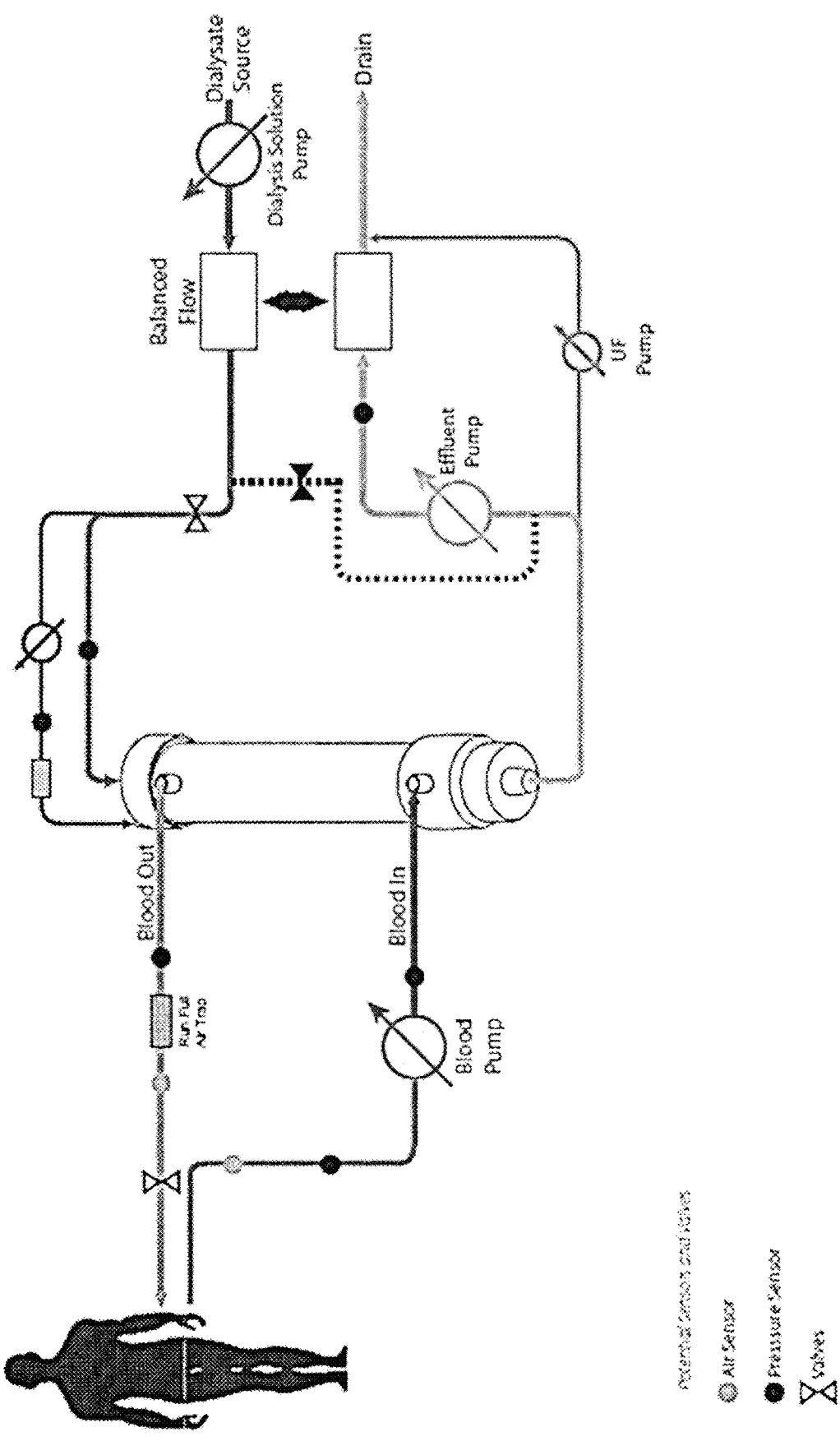

FIG. 32 shows a corresponding system, in which the substitution fluid goes into the fiber at the circumference of the filter housing rather than at the center of the fiber bundle.

Figure 33:
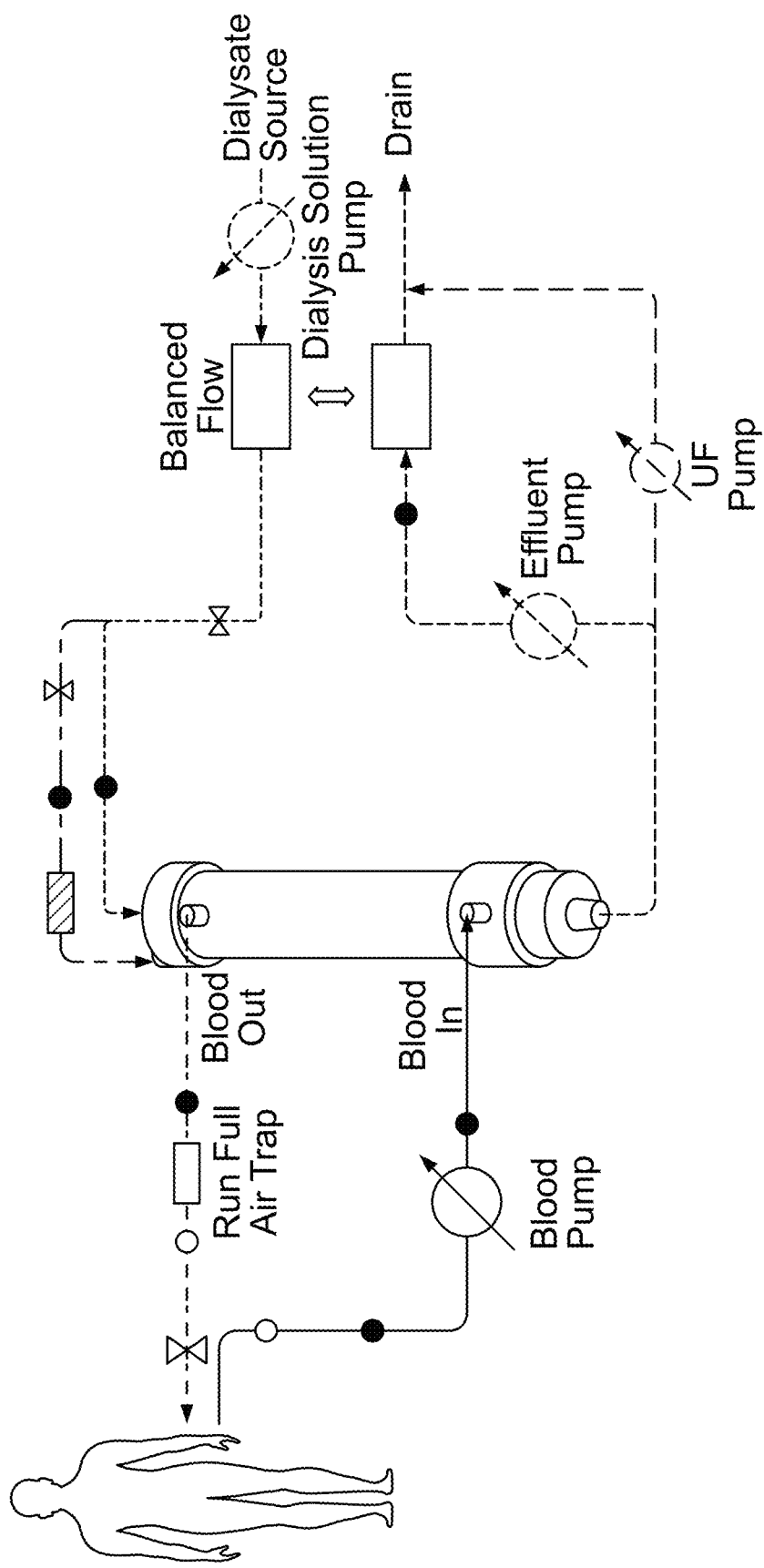

FIG. 33 shows another system that accomplishes hemodiafiltration similar to FIG. 30, with no substitution pump.

FIGS. 34A-34D show a cartridge for use in plasmapheresis.

Figure 35:
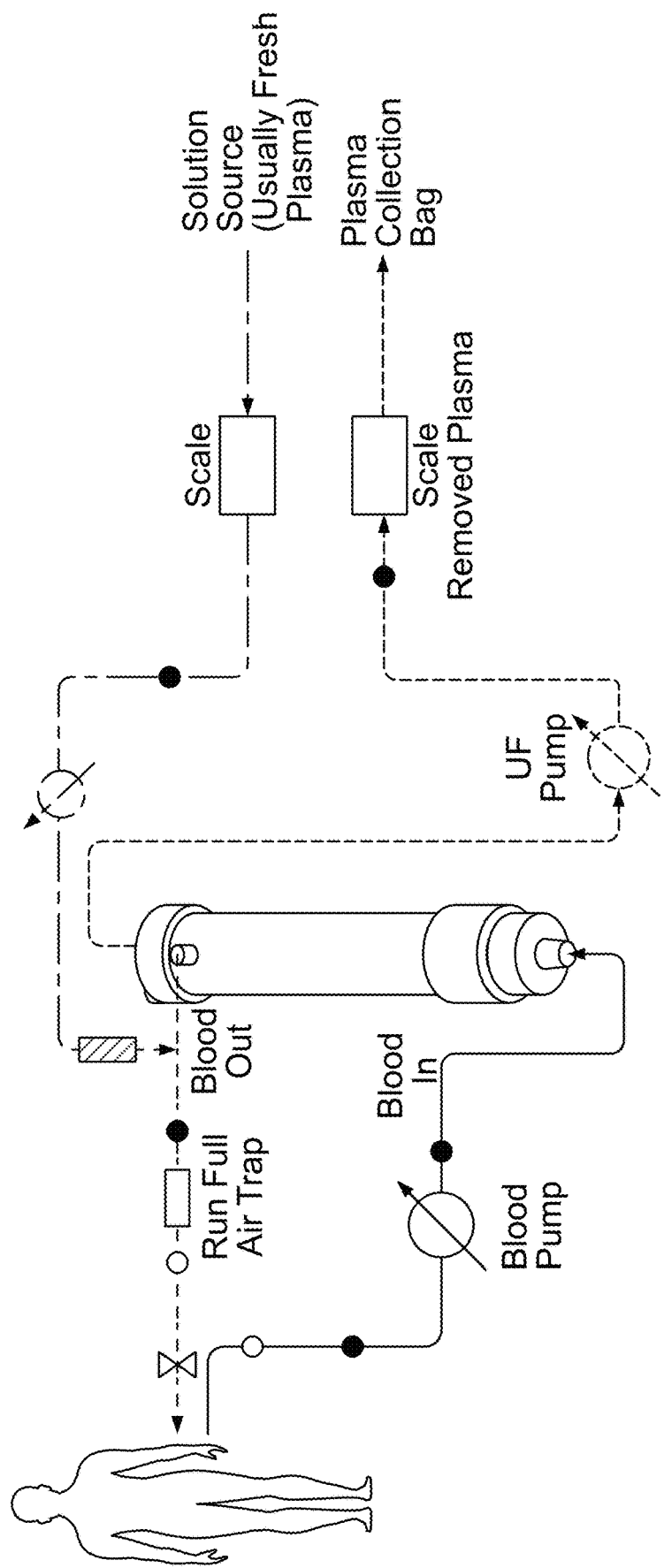

FIG. 35 shows a system for performing plasmapheresis.

Figure 36A:
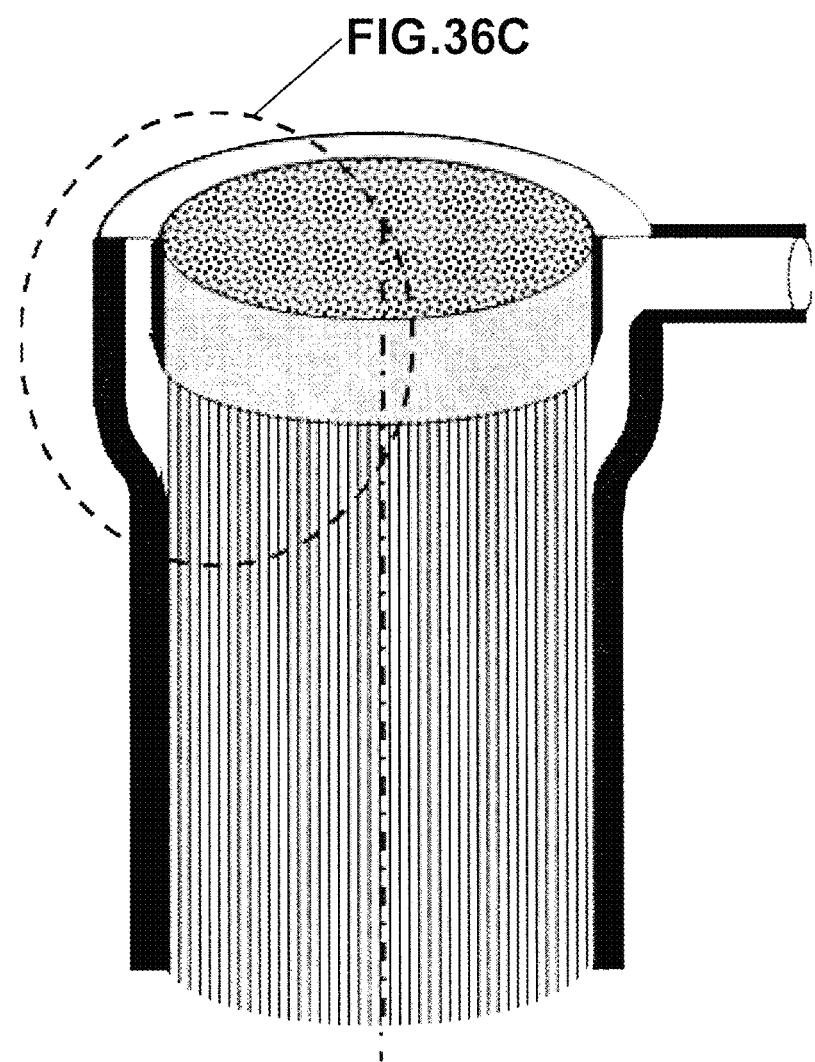
Figure 36B:
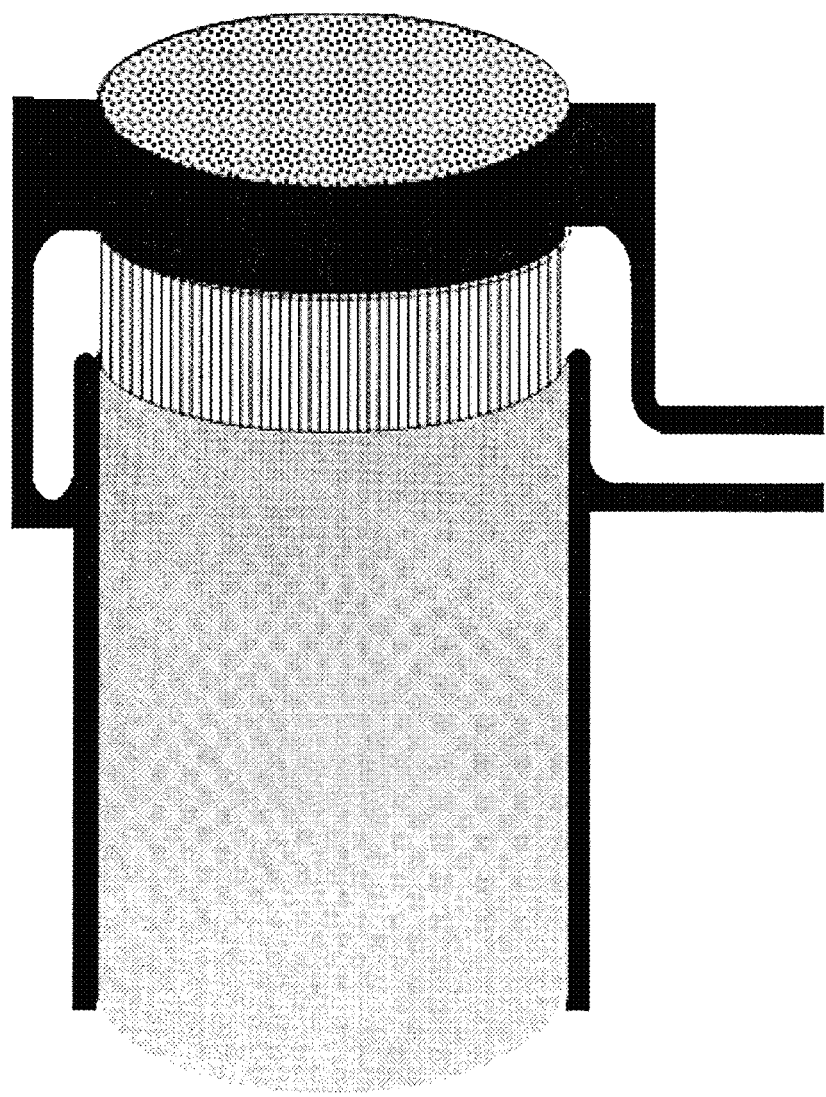
Figure 36C:
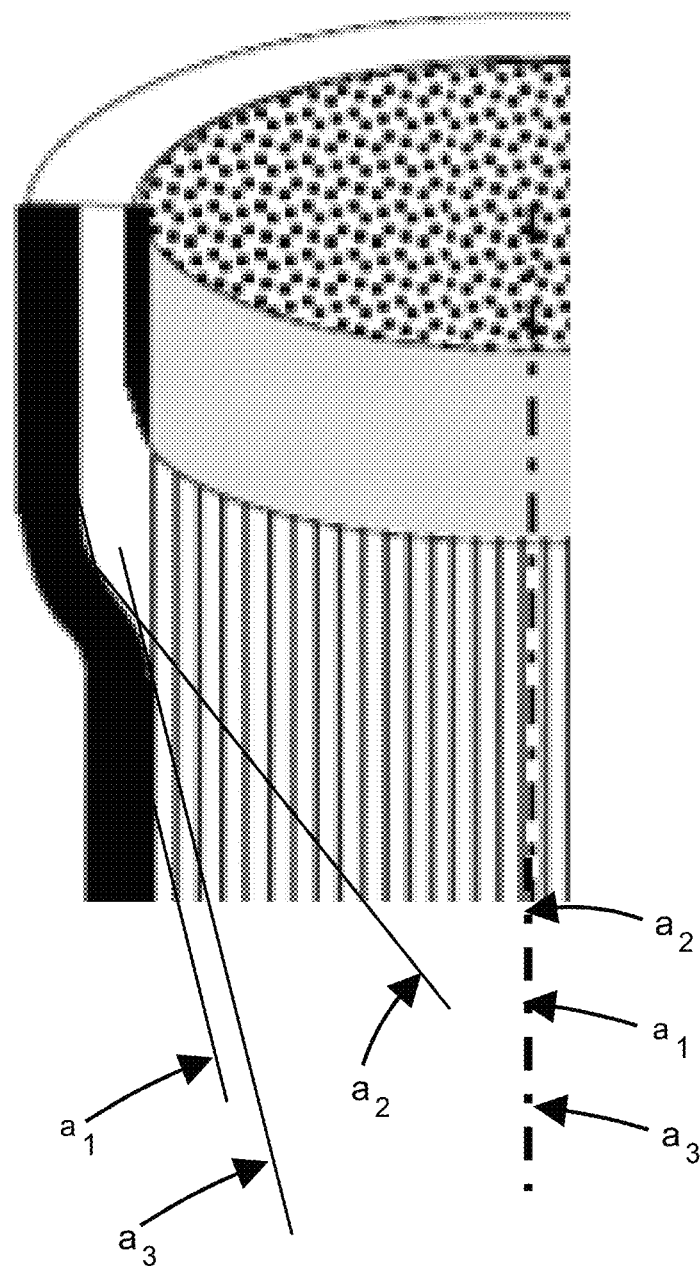

FIG. 36A shows a forward-facing orbital distributor having smoothly contoured internal features. FIG. 36B shows a rearward-facing orbital distributor having smoothly contoured internal features. FIG. 36C shows a portion of FIG. 36A.

Figure 37A:
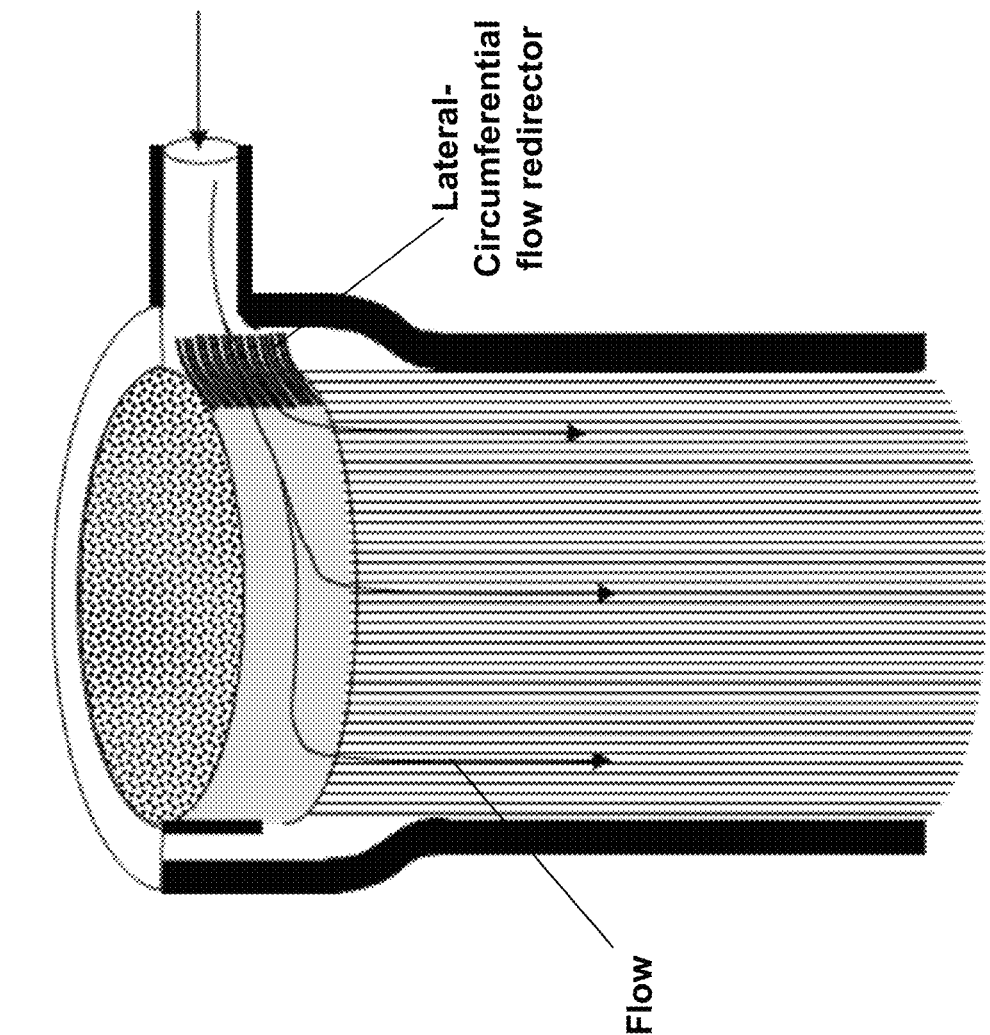
Figure 37B:
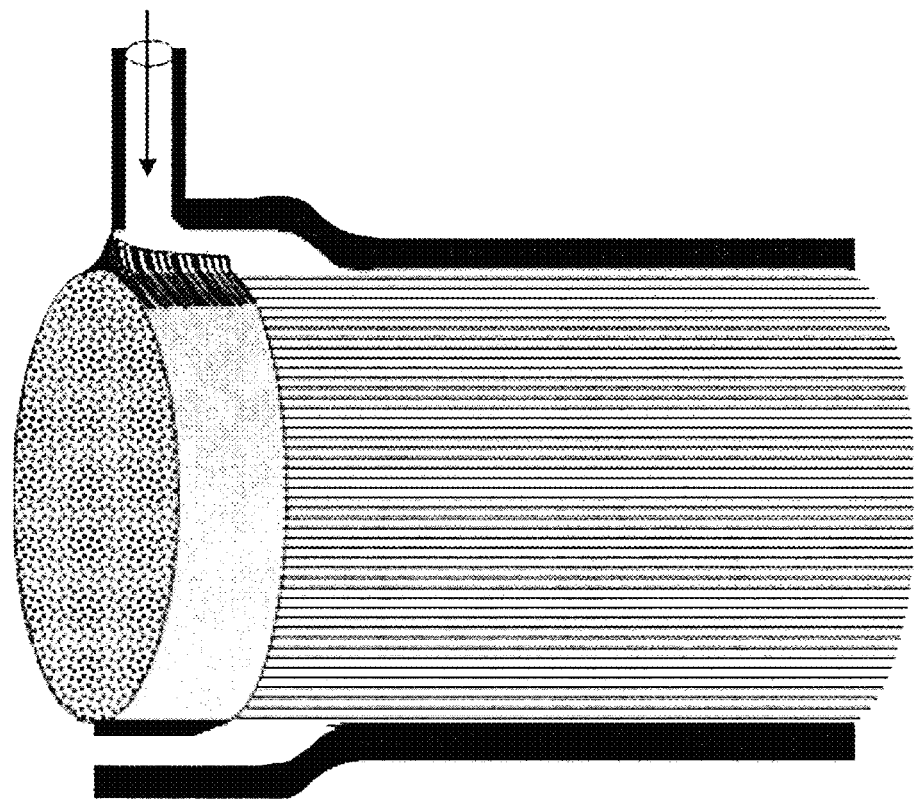
Figure 37C:
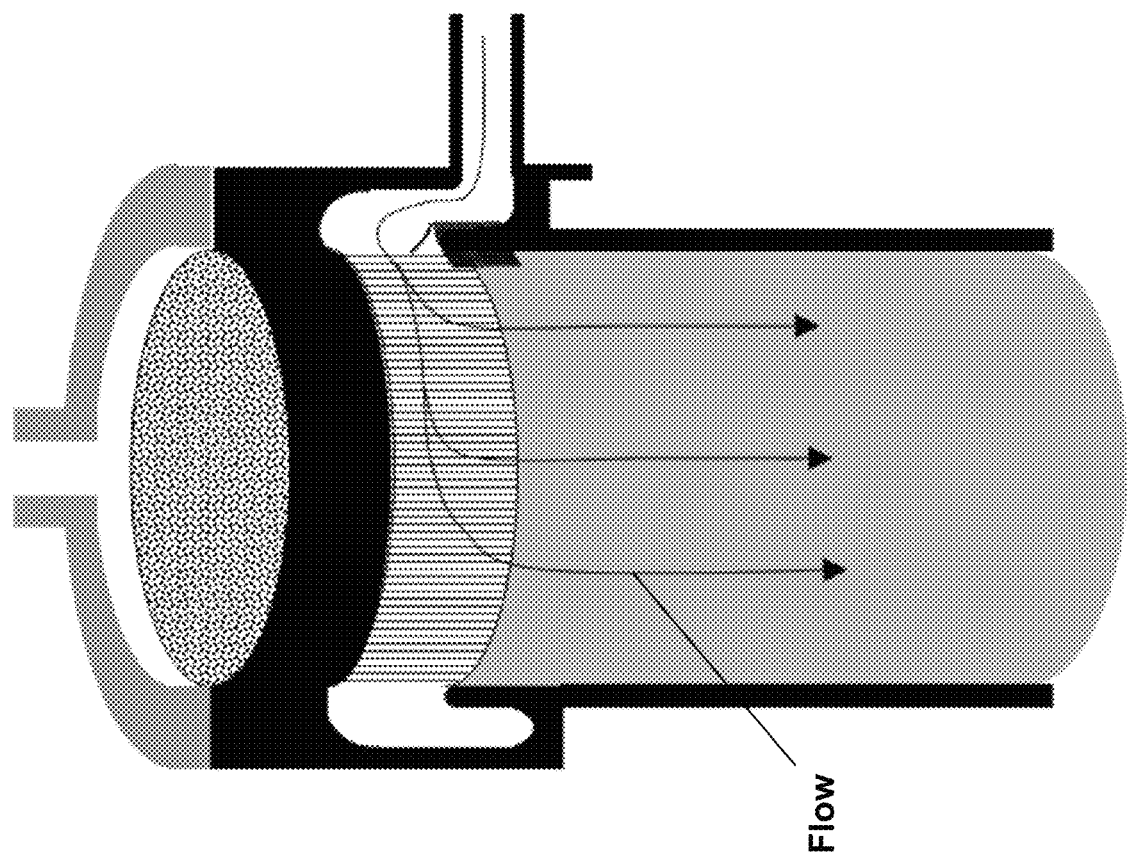

FIG. 37A shows a cartridge having a lateral-circumferential flow redirector, with a forward-facing orbital distributor, including representative flowpaths. FIG. 37B shows a similar situation in which the lateral-circumferential flow redirector has a more complicated shape that curves three-dimensionally. FIG. 37C shows a cartridge having a lateral-circumferential flow redirector, with a rearward-facing orbital distributor, showing representative flowpaths.

Figure 38B:
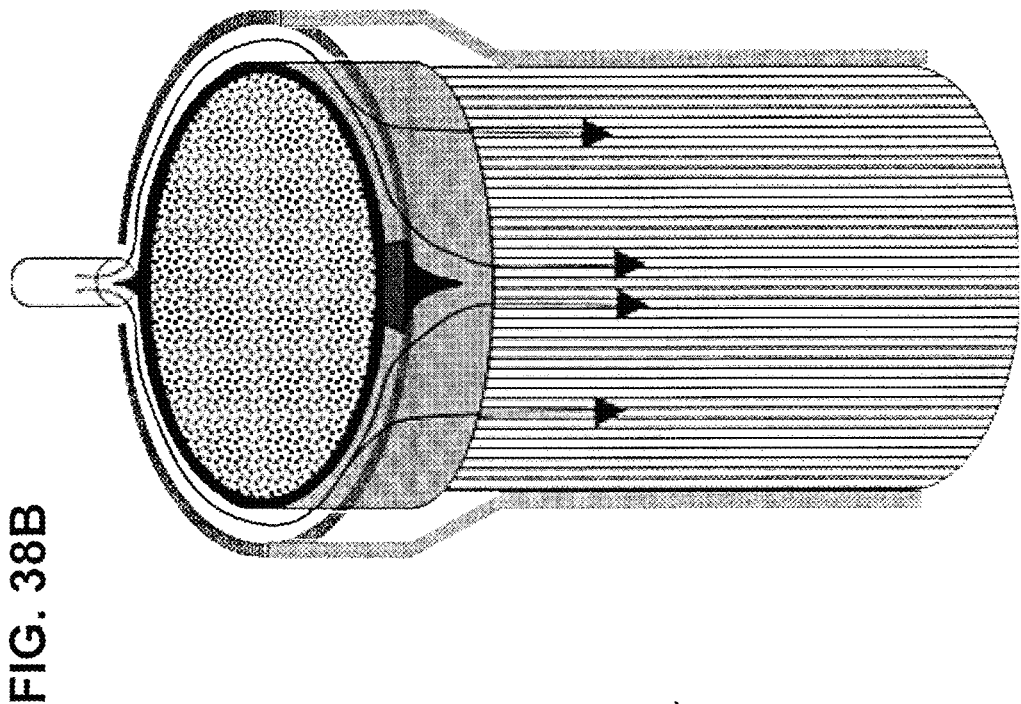
Figure 38A:
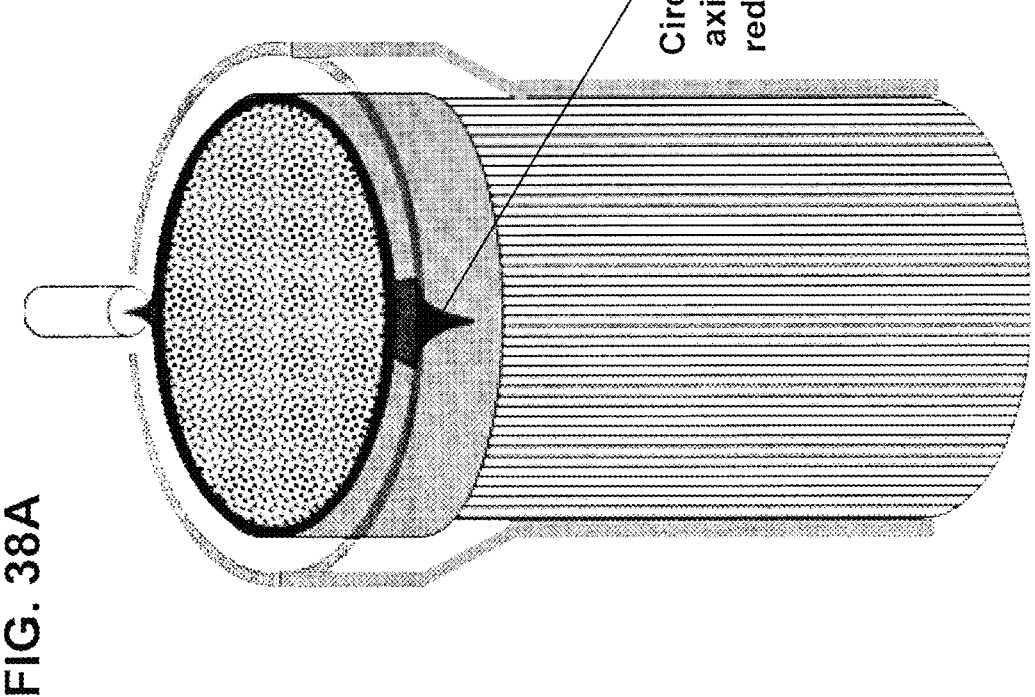
Figure 38D:
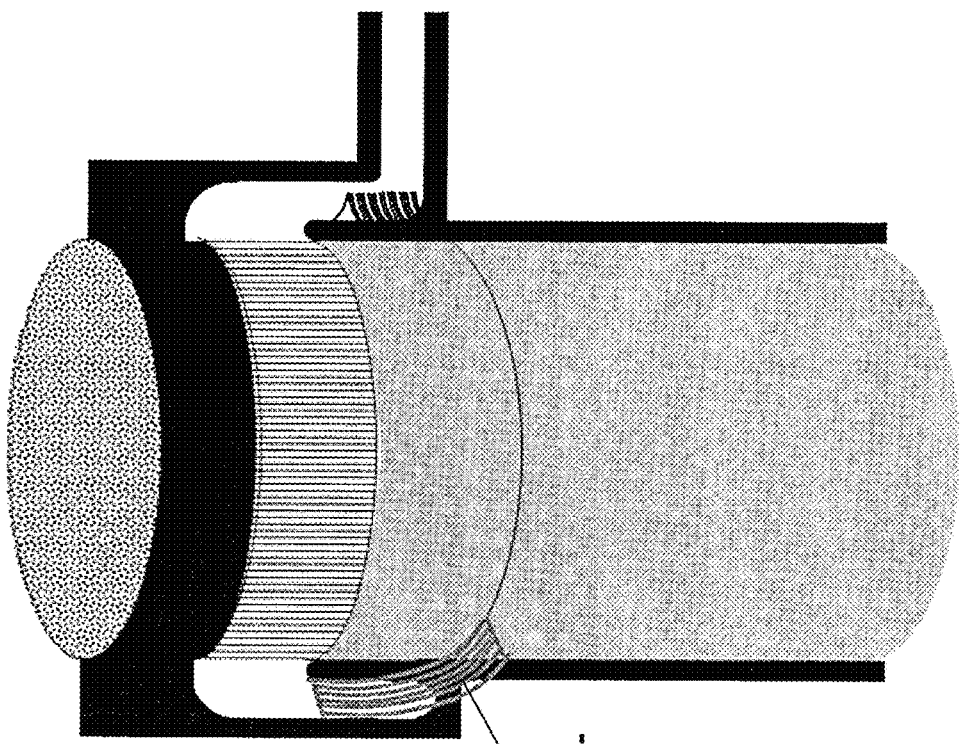
Figure 38C:
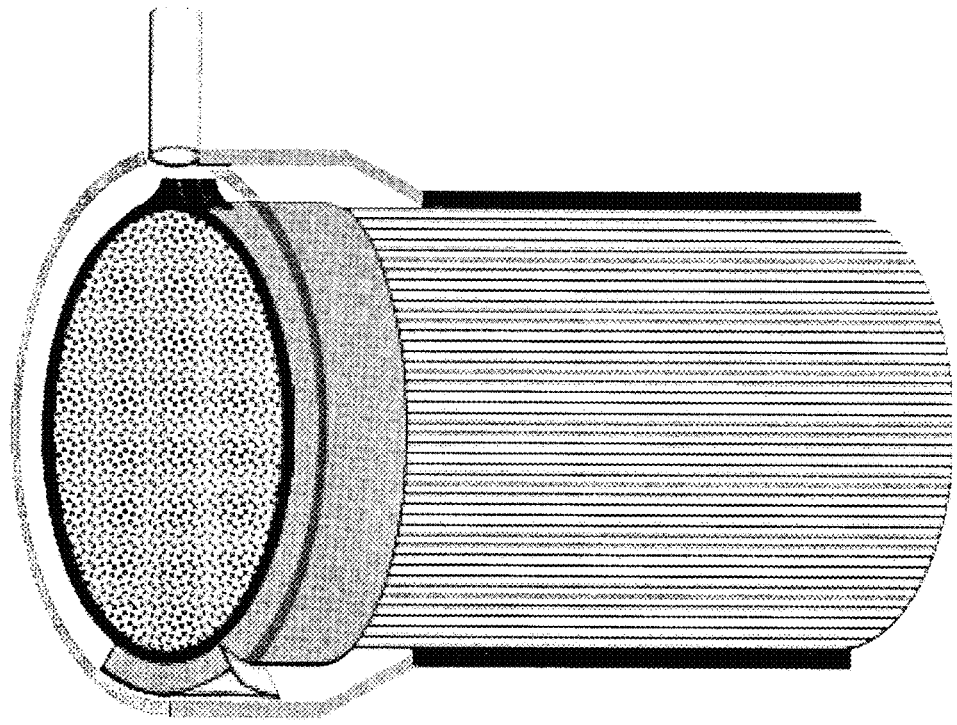

FIG. 38A is a three-dimensional view of a cartridge having a circumferential-axial flow redirector, in a forward-facing orbital director. FIG. 38B is the same view as FIG. 38A but additionally showing representative flowpaths. FIG. 38C is a view of the same structure as FIG. 38A, but from a vantage point 90 degrees different. FIG. 38D shows a cartridge having a circumferential-axial flow redirector, in a rearward-facing orbital distributor.

Figure 2:
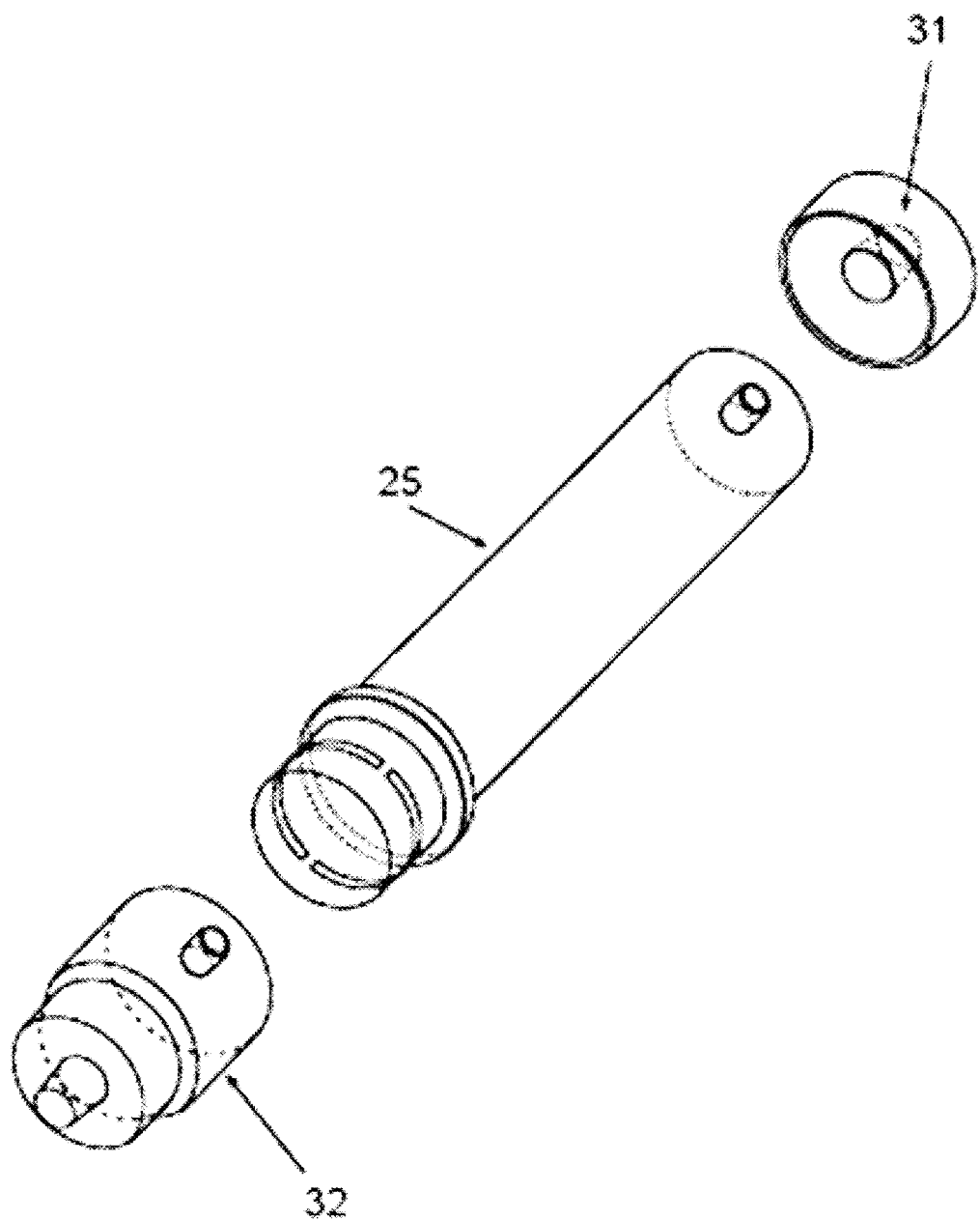
FIG. 2 illustrates the plastic pieces of the cartridge of FIG. 1A-1C in an exploded view.
Figure 39B:
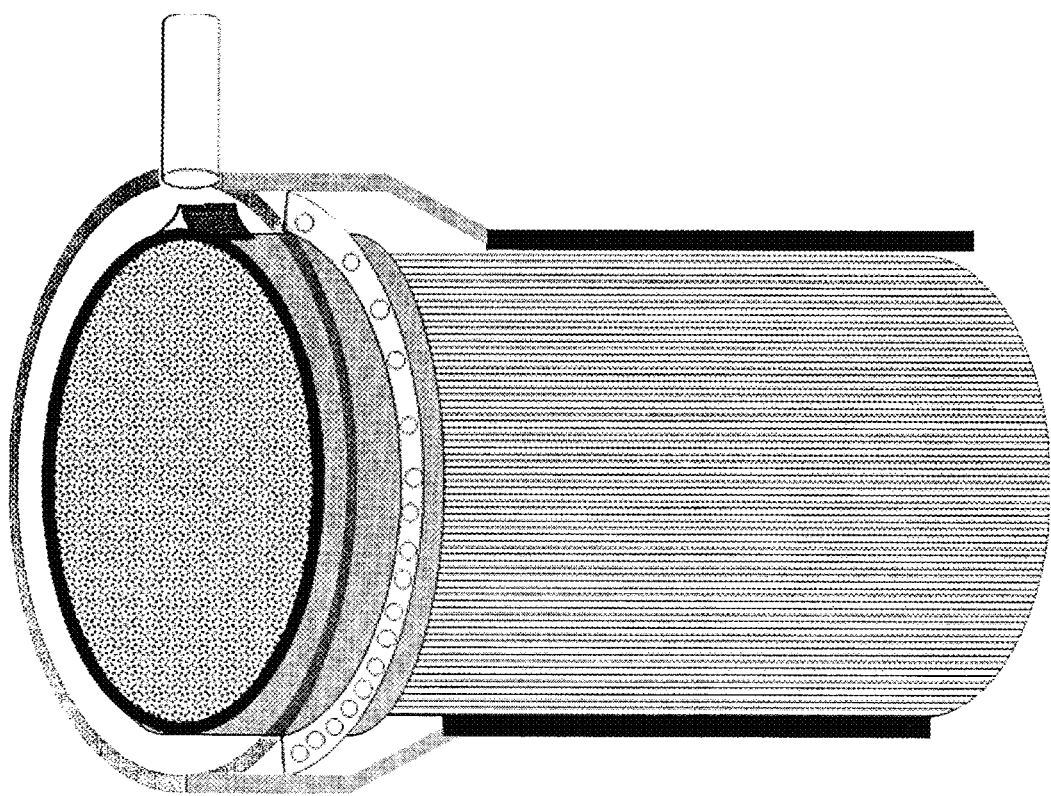
Figures 2, 39C:
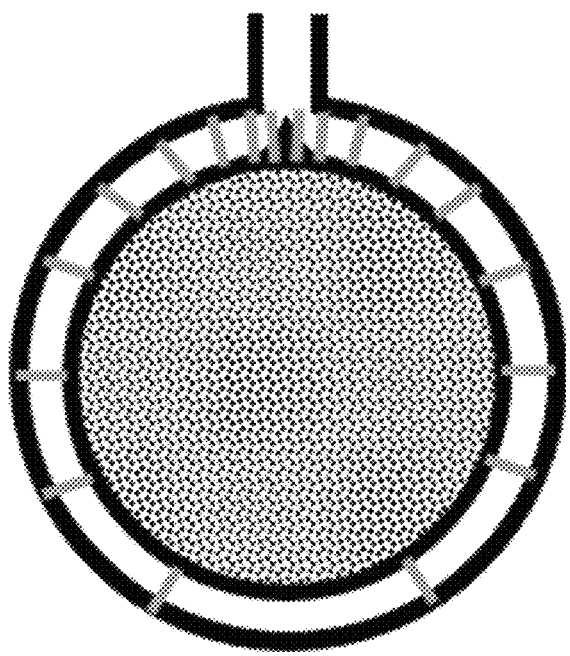
Figures 1, 39C:
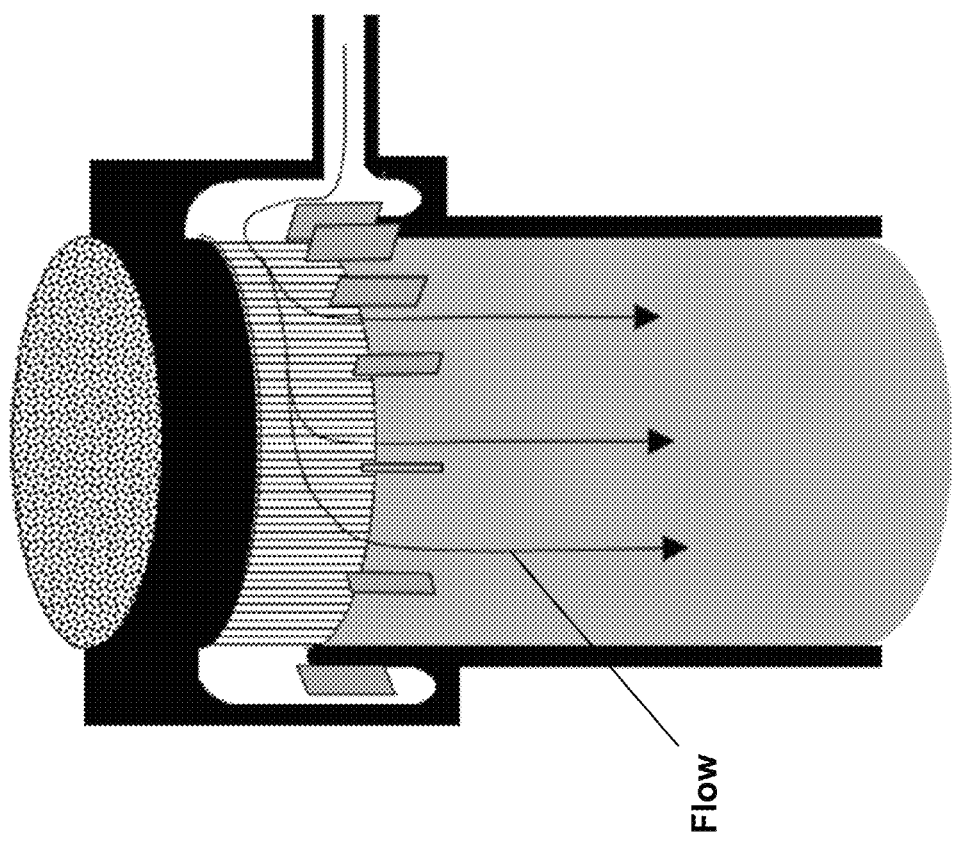
Figure 39D:
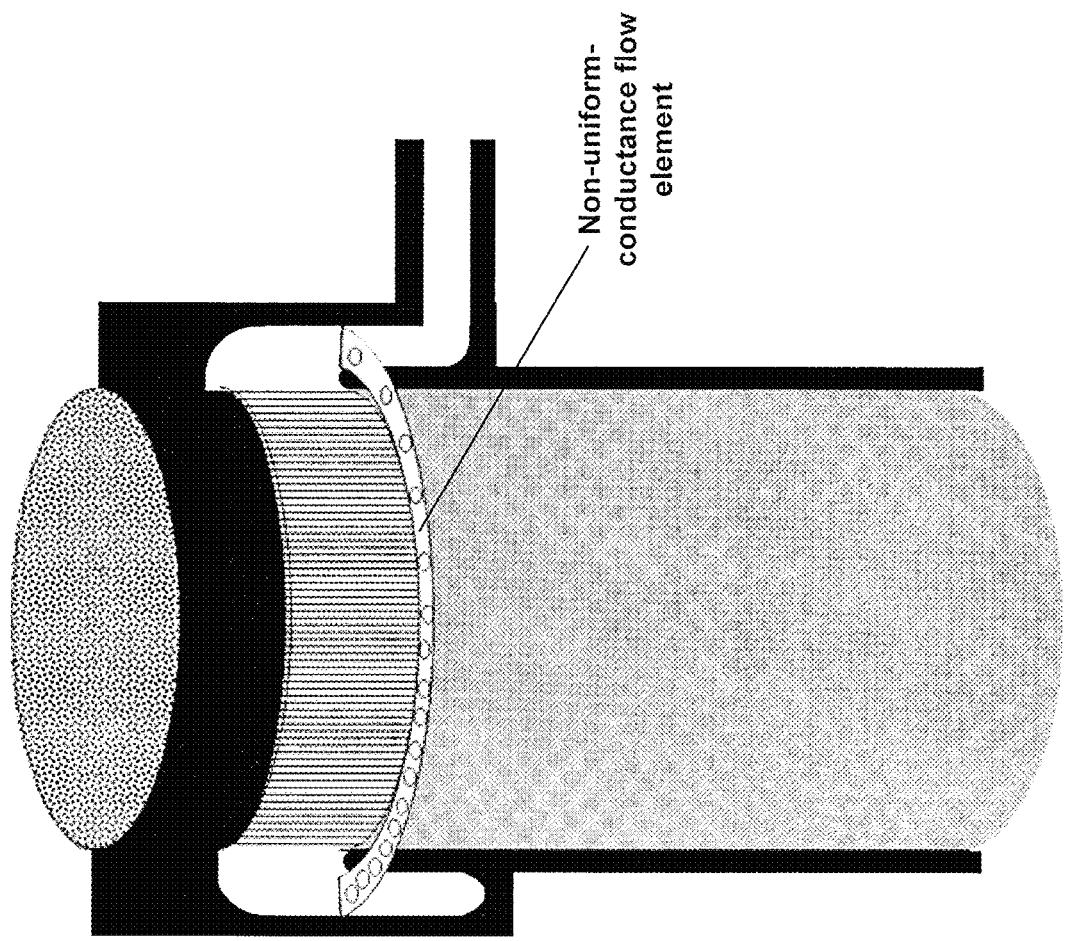
Figure 40E:
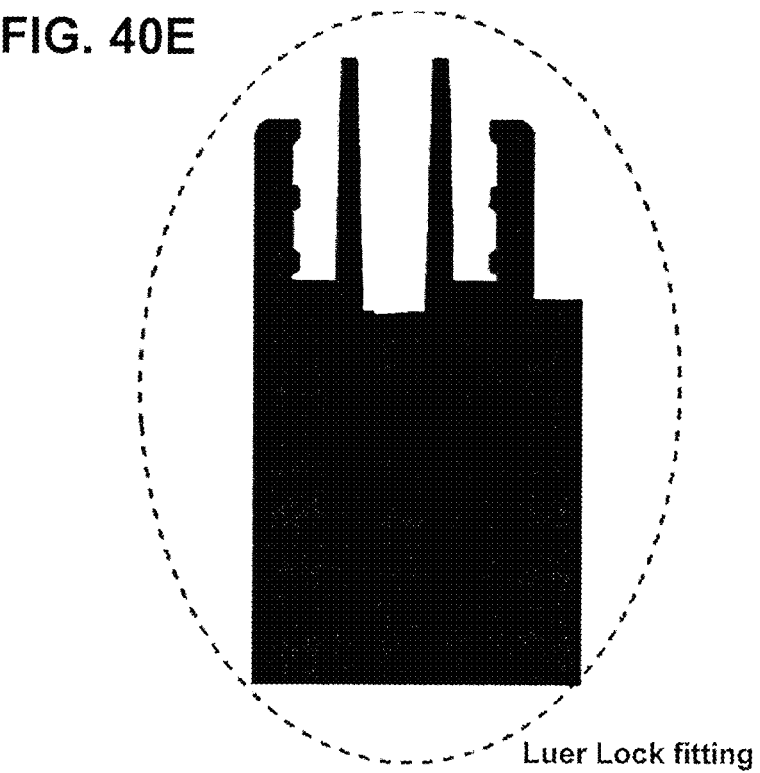
Figure 40F:
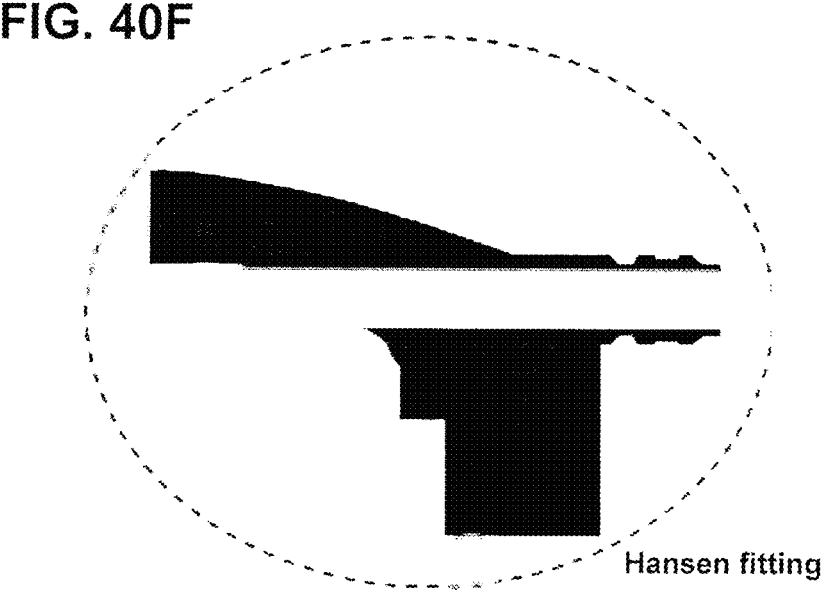

FIGS. 39A-1 and 39A-2 are three-dimensional views of a cartridge having a forward-facing orbital distributor having a non-uniform-conductance flow element, in the form of ribs, along with a top view of the same structure. FIG. 39B shows a forward-facing orbital distributor having a non-uniform-conductance flow element, in the form of a perforated plate. FIGS. 39C-1 and 39C-2 show a cartridge having a rearward-facing orbital distributor having a non-uniform-conductance flow element, in the form of ribs, along with a top view of the same structure. FIG. 39D a rearward-facing orbital distributor having a non-uniform-conductance flow element, in the form of a perforated plate.

FIGS. 40A-F show a cross-section of a cartridge that has luer lock fittings on the housing ports and Hansen fittings on the header ports. In this Figure, the luer lock fittings on the housing ports are vertically oriented, and the Hansen fittings on the header ports are horizontally oriented. Fiber cross-sections are also shown.

Figure 41A:
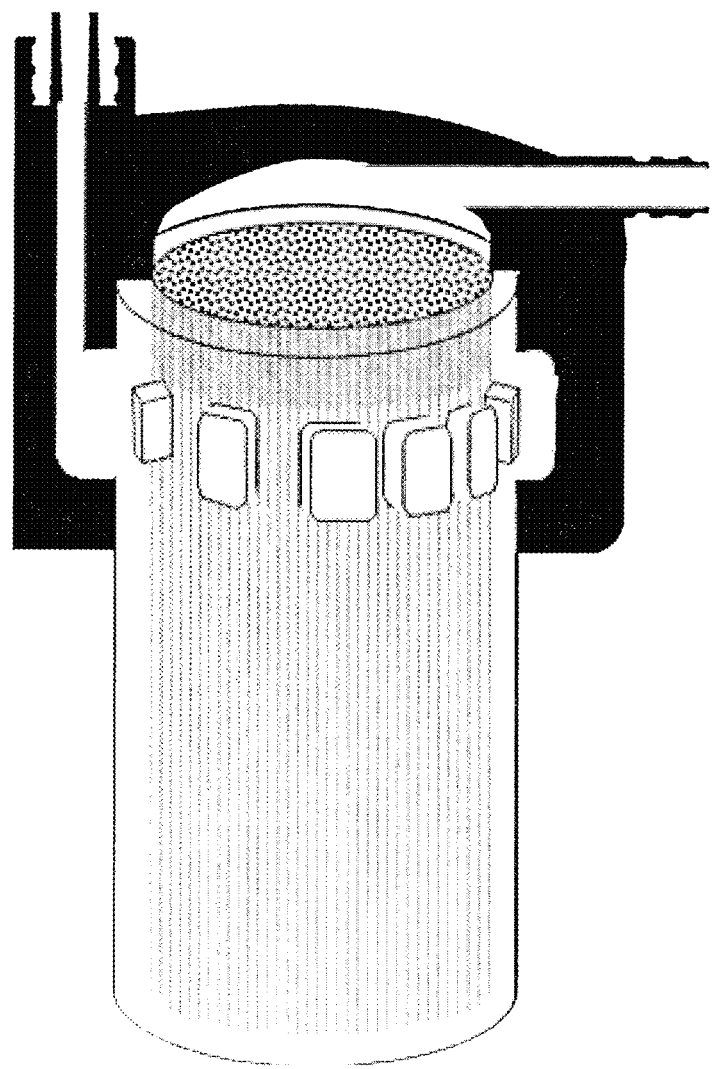
Figure 41B:
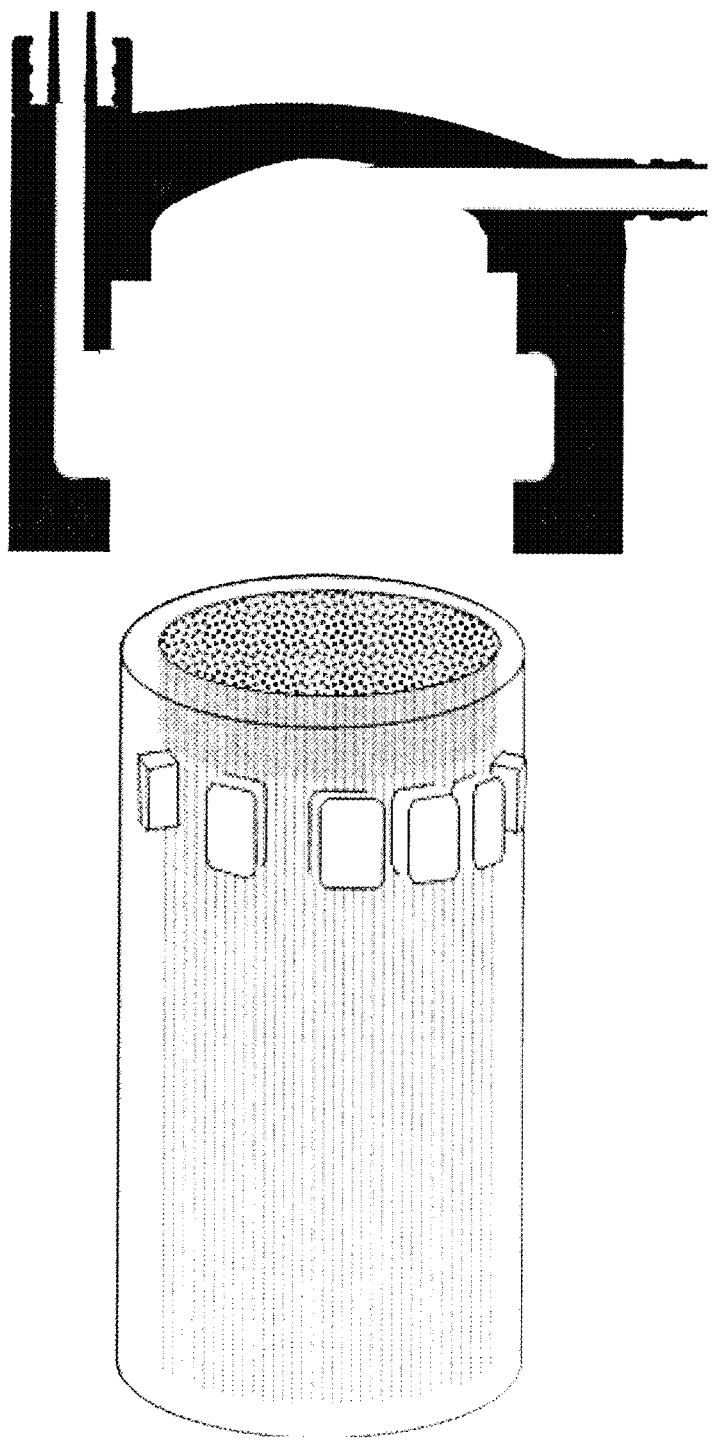
Figure 41C:
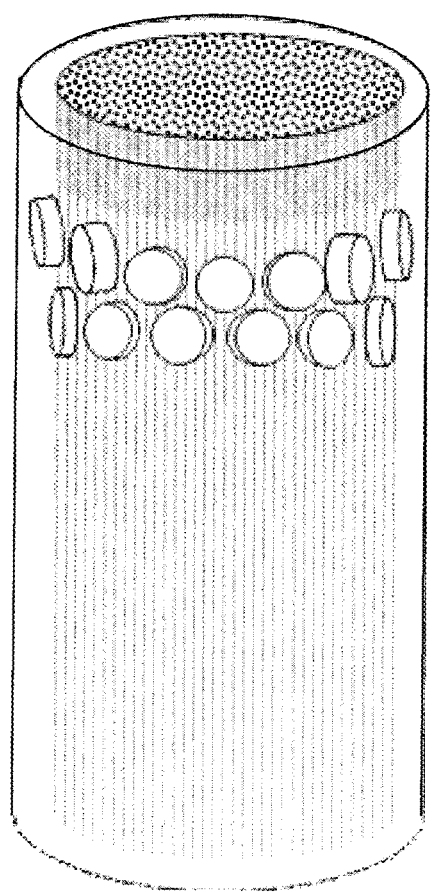
Figures 1, 41D:
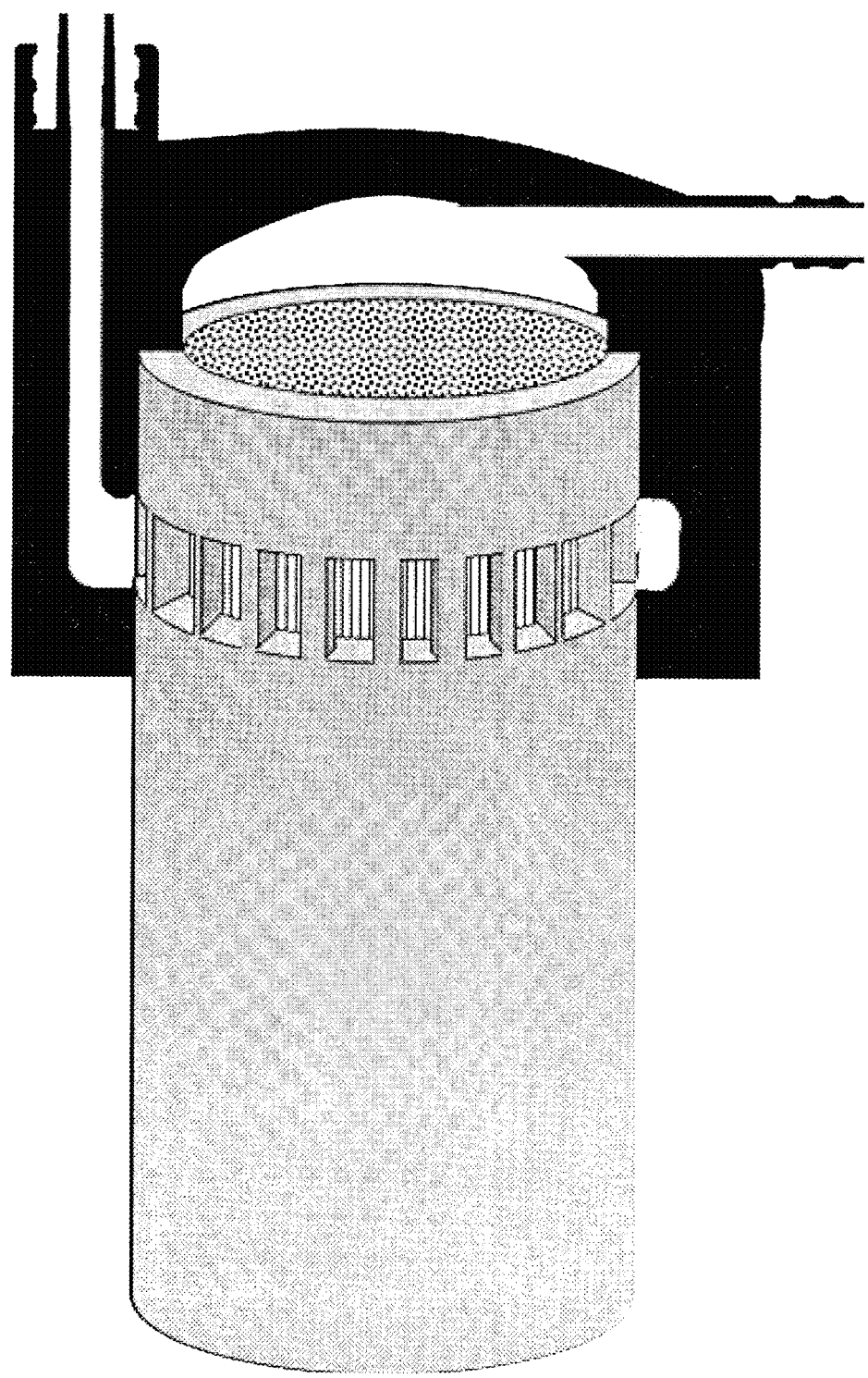
Figures 2, 41D:
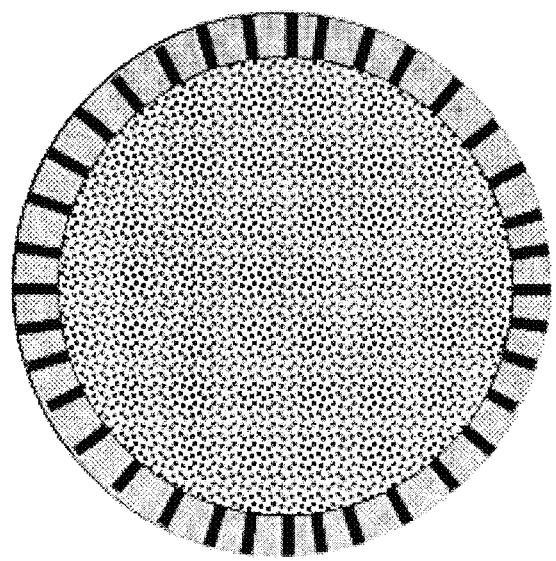
Figure 41E:
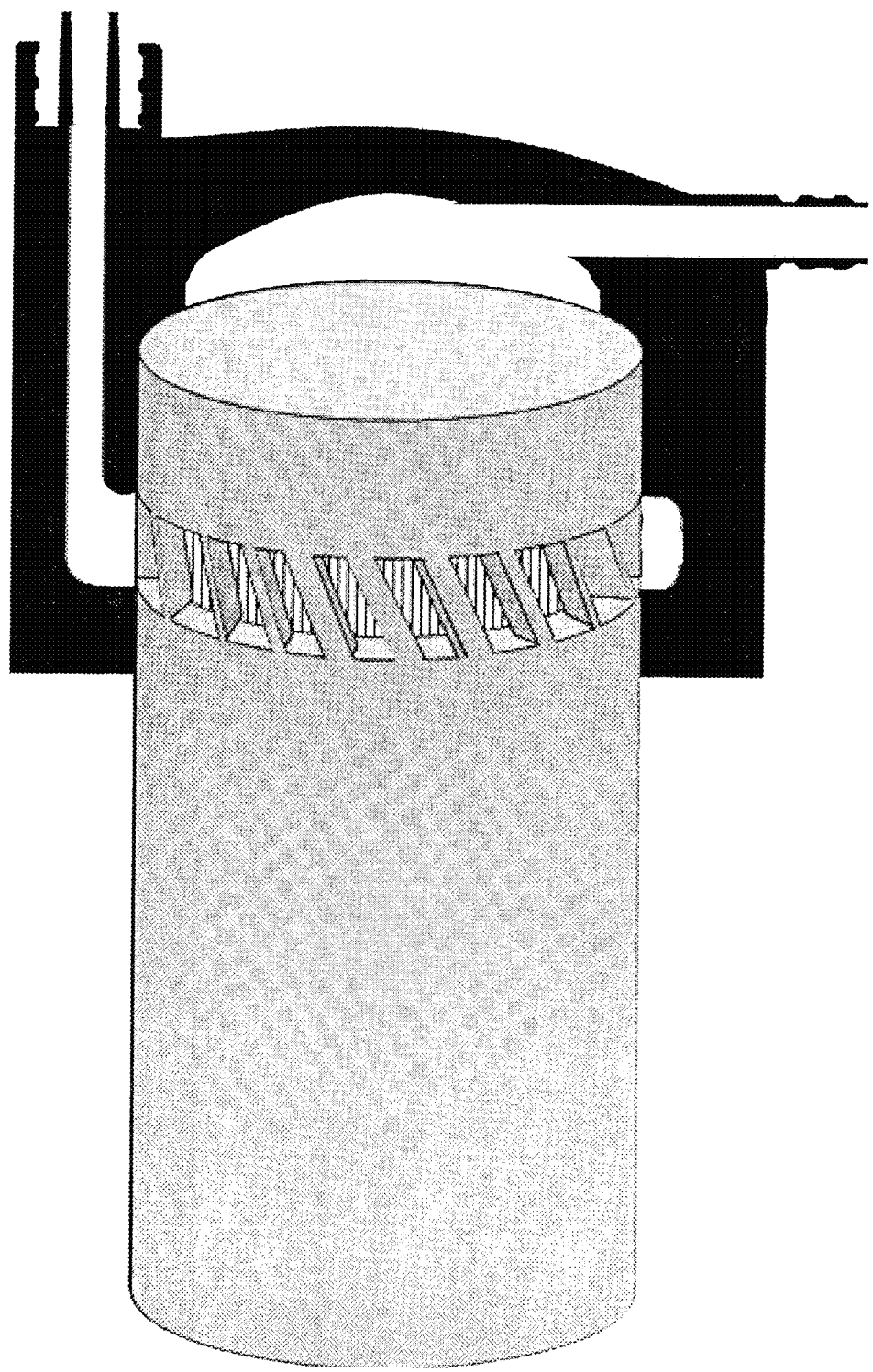

FIG. 41A shows an end of a cartridge having a through-wall orbital distributor, assembled. FIG. 41B shows the same device exploded, with the cap removed from the body. FIG. 41C shows a similar device having two rows of holes, staggered. FIGS. 41D-1 and 41D-2 show a similar view of another similar design of a cartridge having a through-wall orbital distributor. FIG. 41E shows yet another design of cartridge having a through-wall distributor, in which the bars of remaining solid material occupy a helical configuration.

Figure 42A:
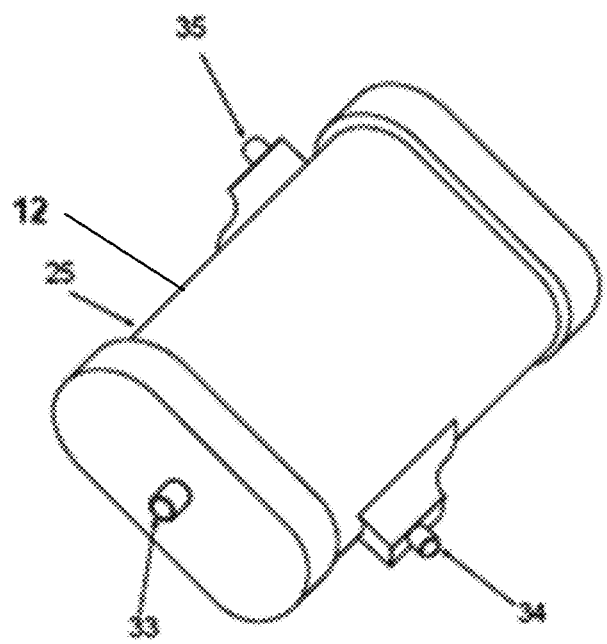
Figure 42B:
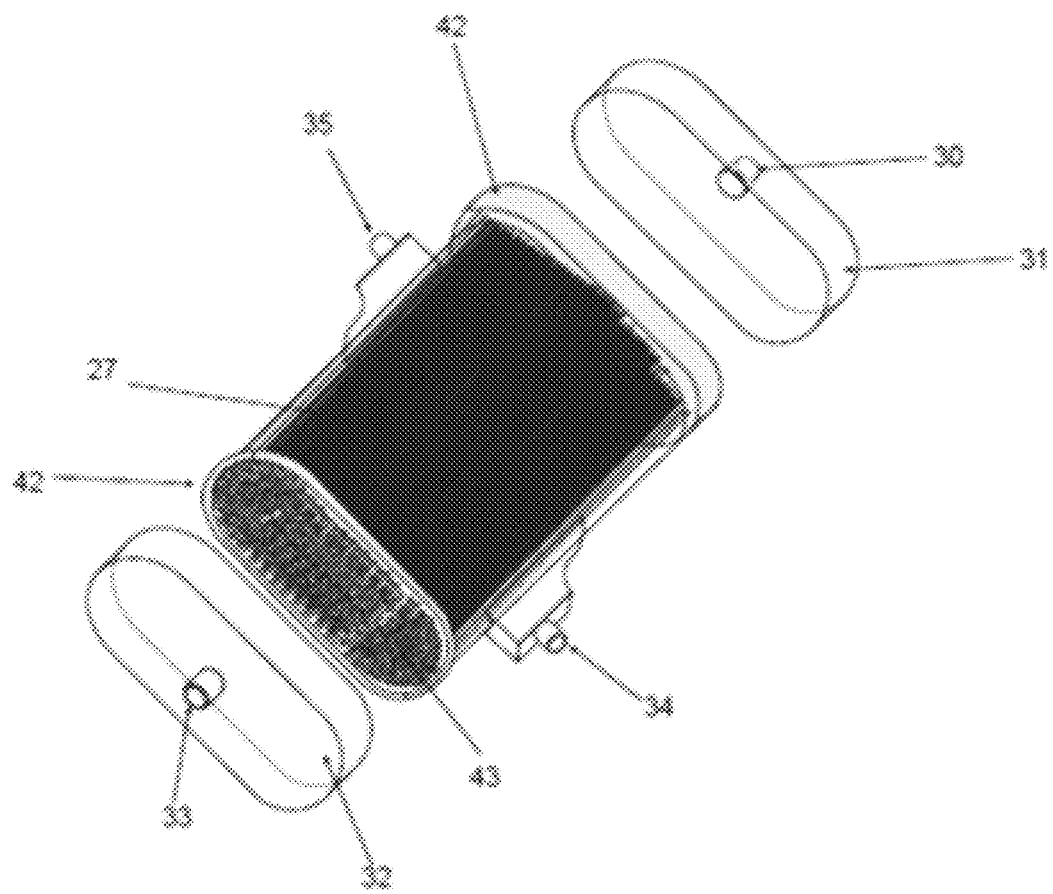
Figure 42C:
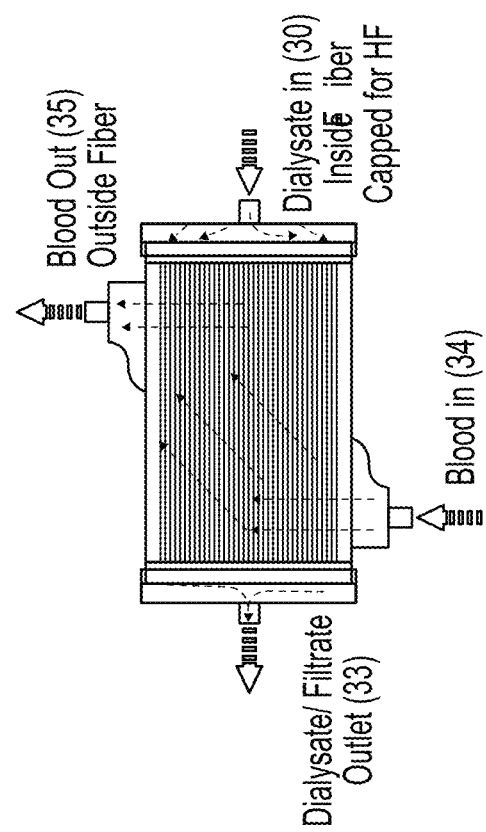

FIG. 42A is an external view showing a cartridge that has flow past the outsides of the fibers such that the flow is generally perpendicular to the long direction of the fibers. FIG. 42B is an exploded view of the same cartridge with the housing being transparent. FIG. 42C is a top view of the same cartridge with fluid flow patterns and directions indicated.

FIGS. 43A-43D show additional embodiments of cartridges that have flow past the outsides of the fibers such that the flow is generally perpendicular to the long direction of the fibers.

Figure 44A:
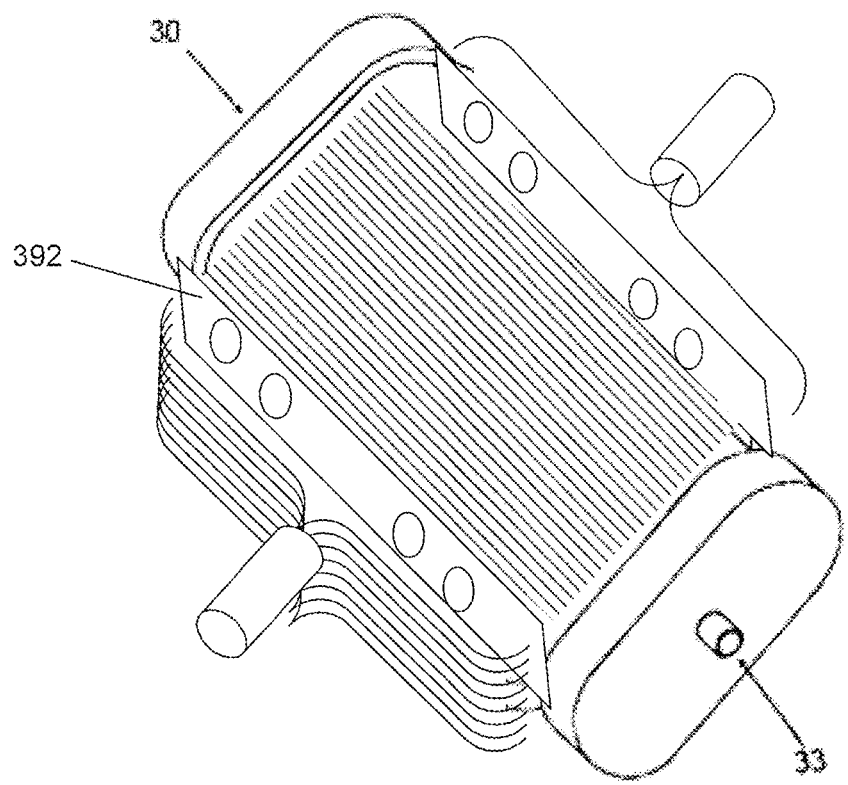
Figure 44B:
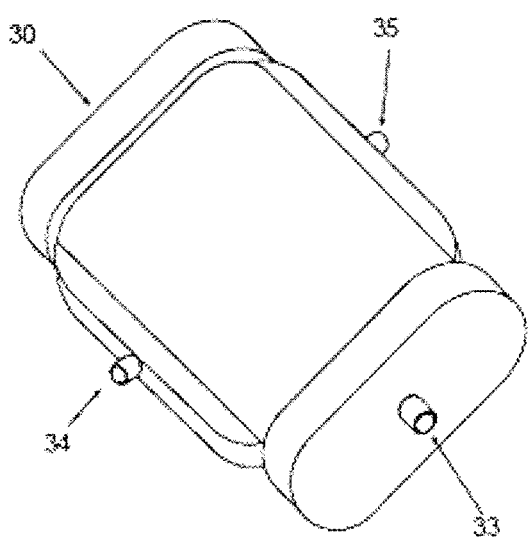

FIGS. 44A-B show the cartridge of FIG. 42D, with its cover removed, to illustrate possible internal features for creating a nearly-uniform flow distribution in the inter fiber space.

Figure 45:
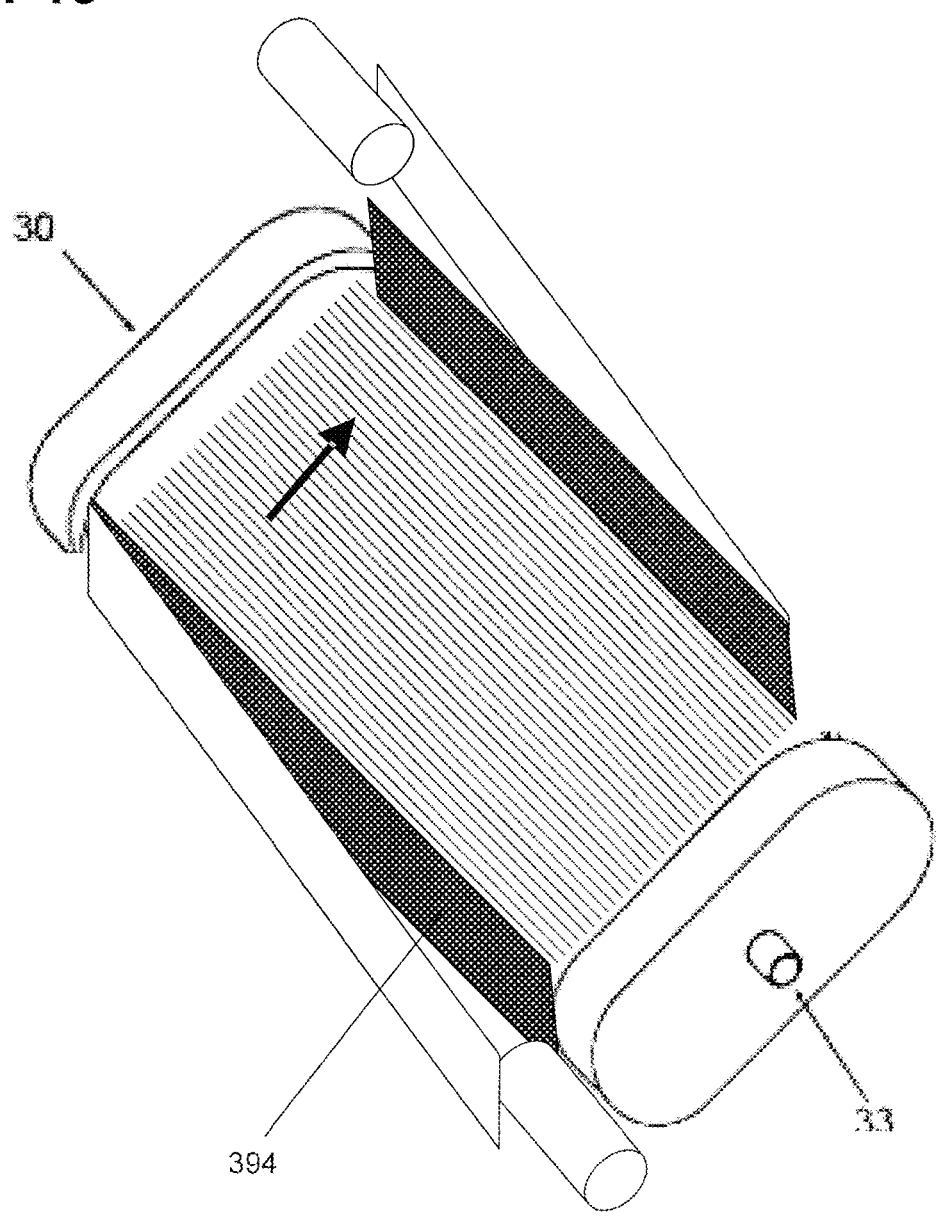

FIG. 45 shows a similar cartridge in which the supply to and the discharge from the inter fiber space are at least approximately aligned with the long direction of the cartridge.

Figure 46A:
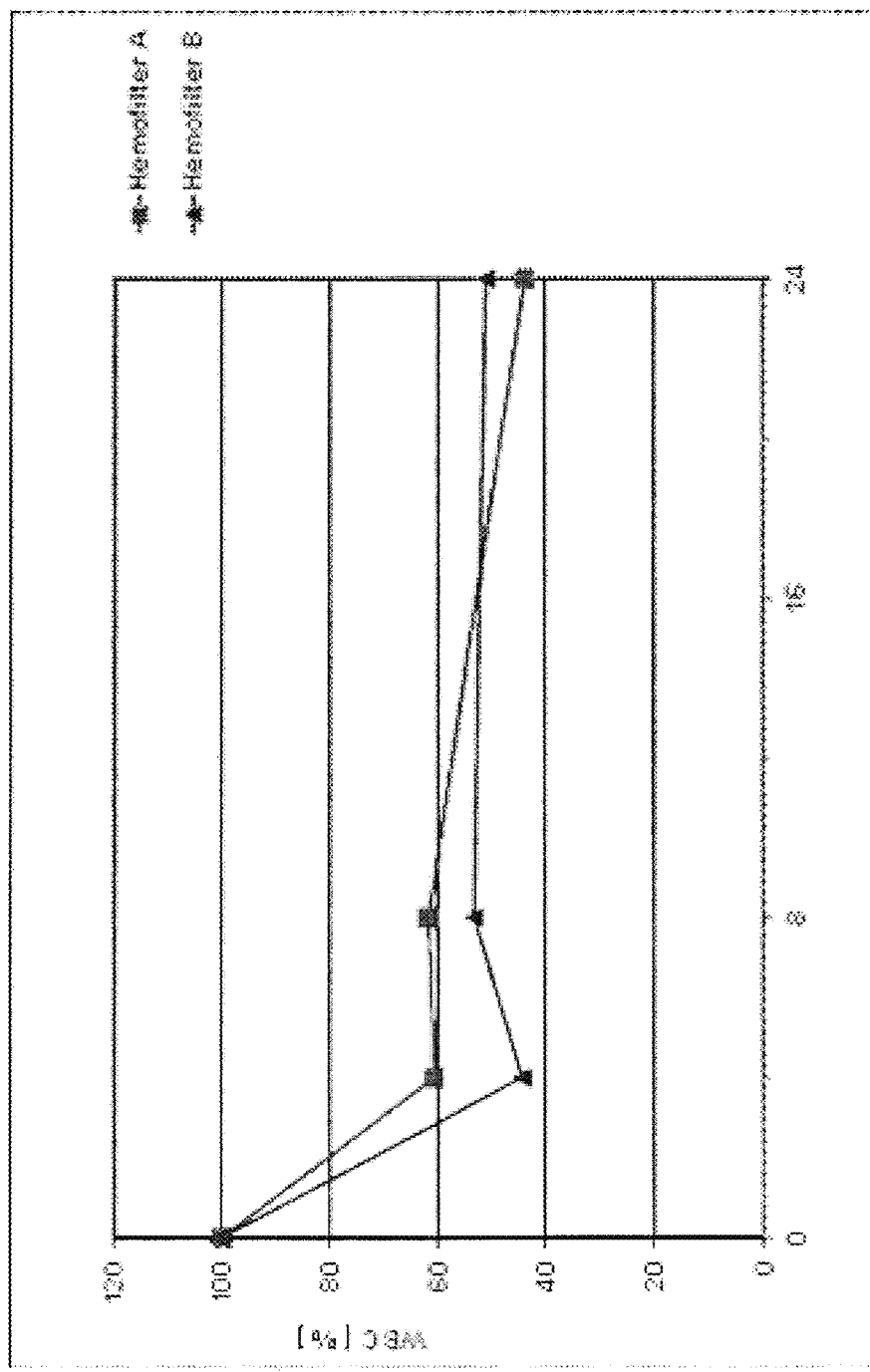
Figure 46B:
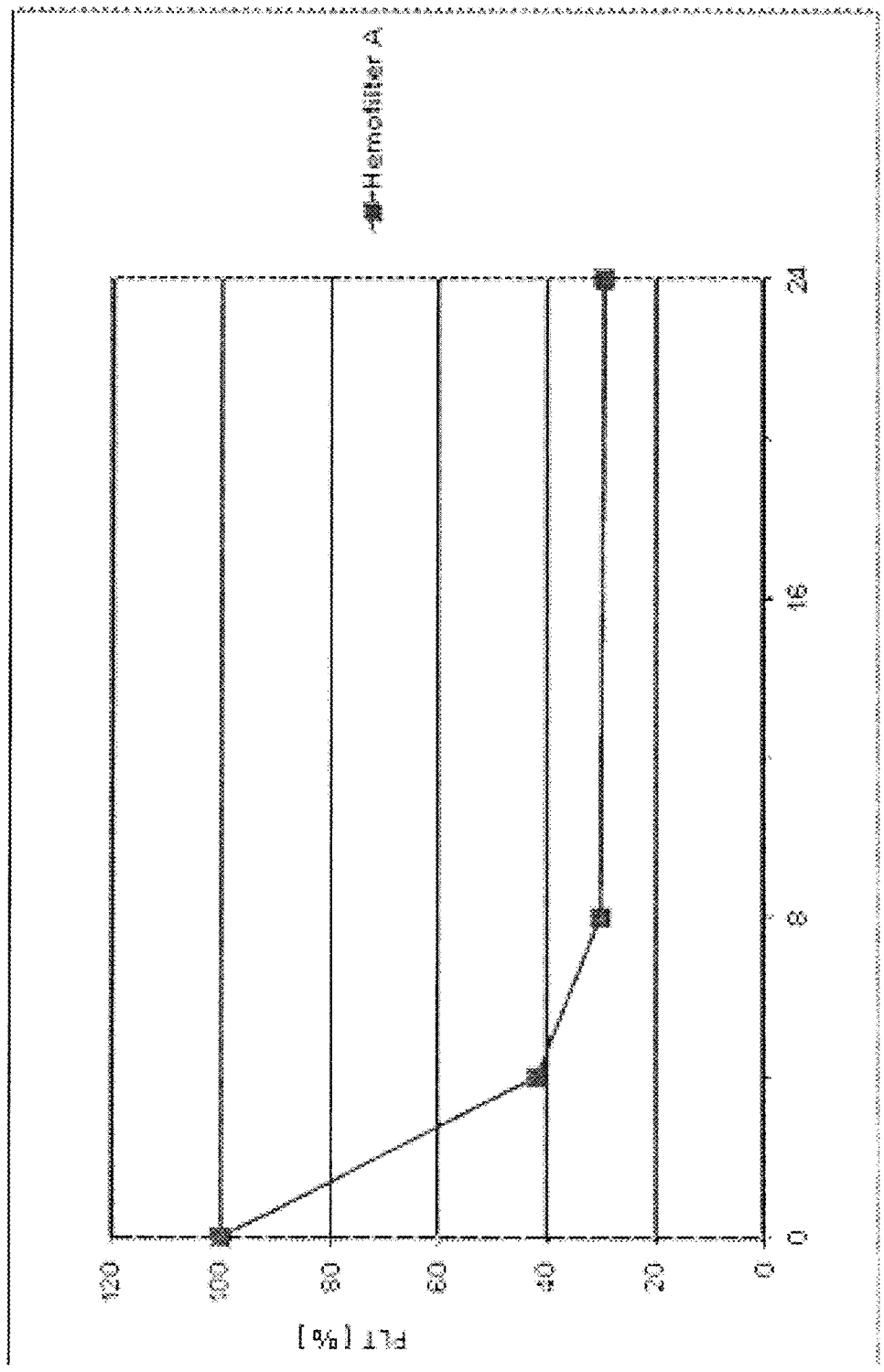

FIG. 46A shows, for a 24 hour continuous experiment, the white blood cell count normalized by the initial white blood cell count, as a function of time. FIG. 46B shows a platelet count for similar conditions.

Figure 47A:
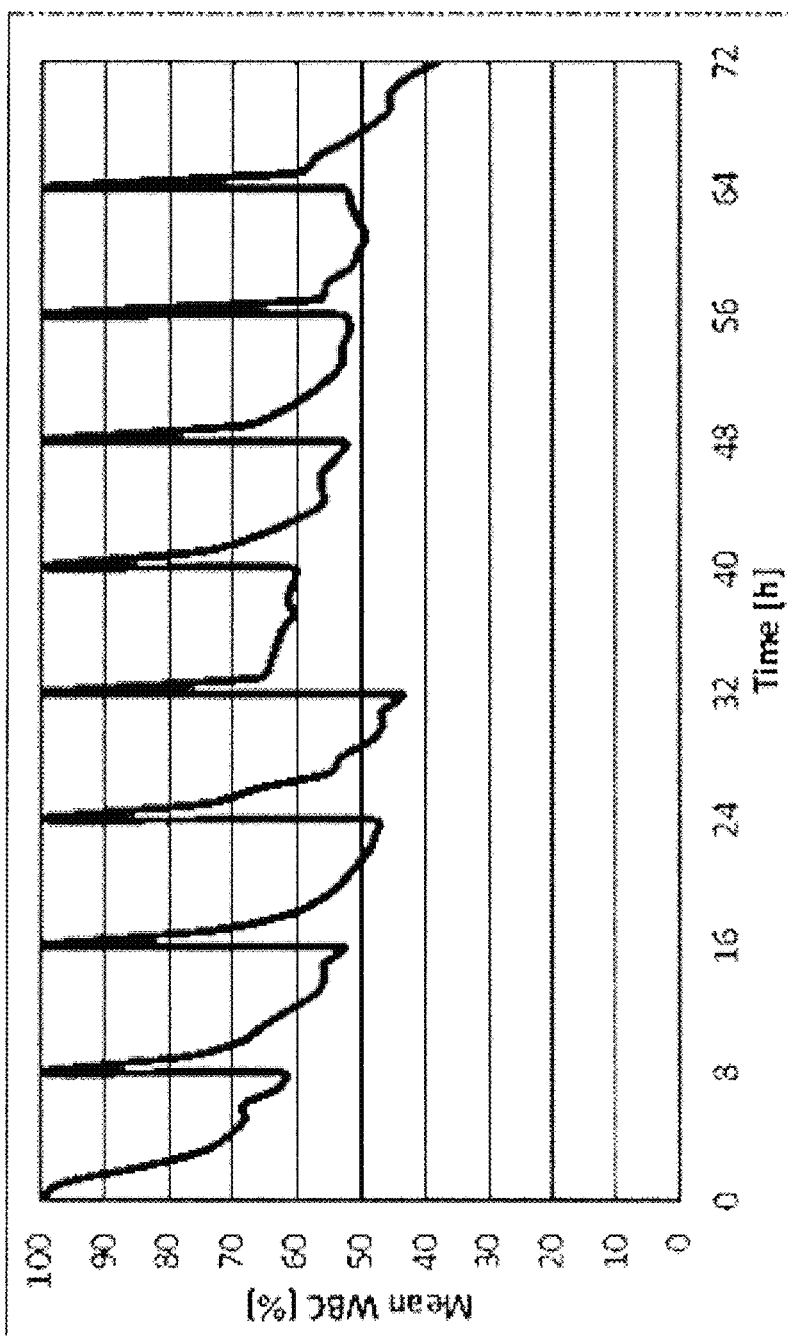

FIG. 47A shows, for an experiment of 72 hours total duration conducted intermittently, the white blood cell count normalized by the initial white blood cell count, as a function of time.

Figure 47B:
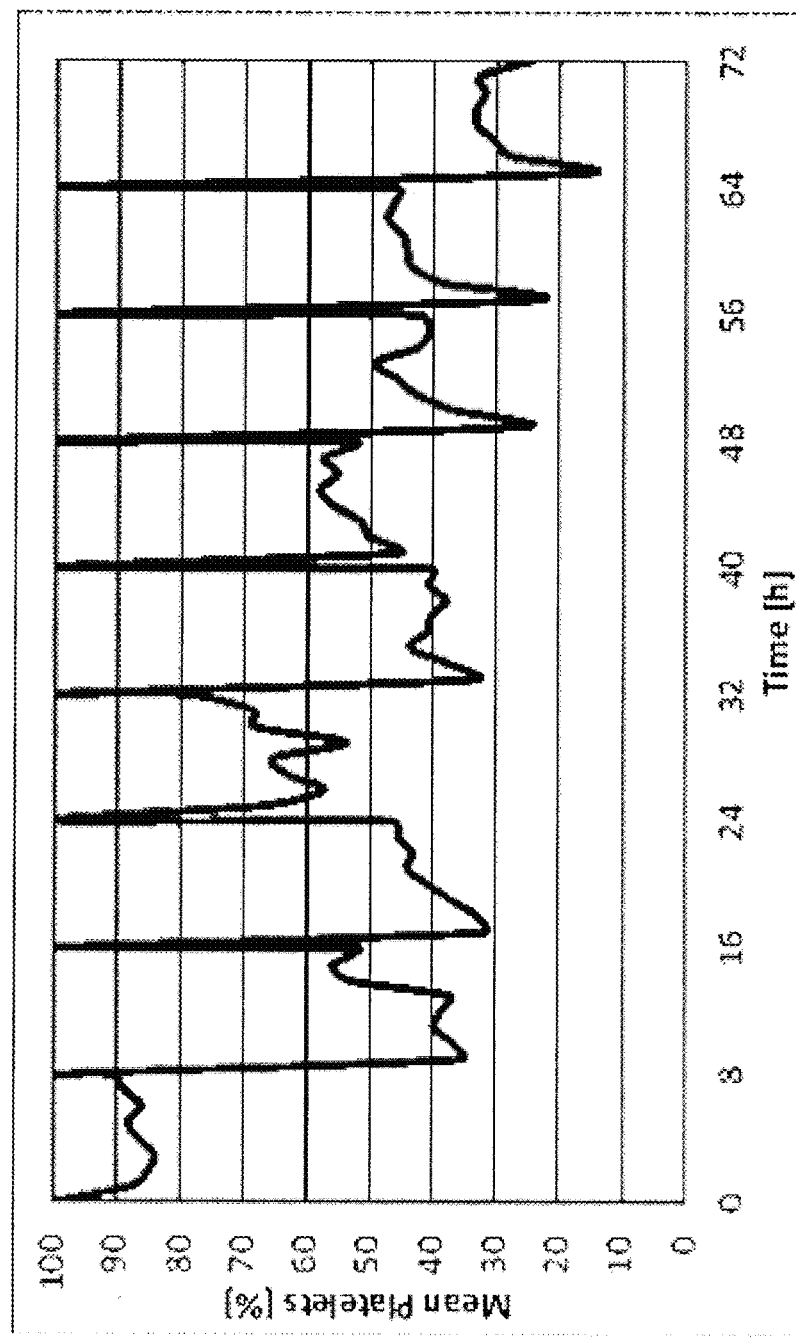

FIG. 47B shows a platelet count for similar conditions.

DETAILED DESCRIPTION OF THE INVENTION

The terms cartridge, filter, dialyzer, hemodialyzer, hemofilter and filter cartridge are synonymous. Dialyzer or hemodialyzer can refer to traditional hemodialysis but also can include any other filtration processing or solute clearance described herein.

Hemodialysis

Figure 1A:
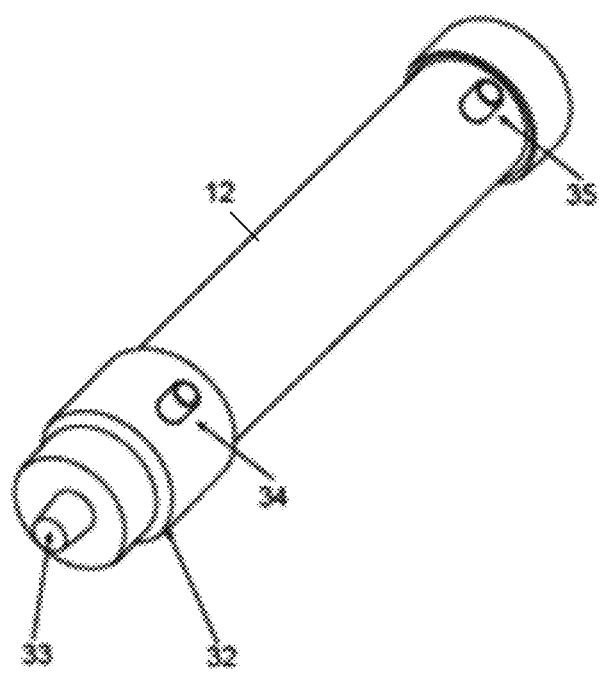
FIG. 1A-1C illustrate a cartridge of an embodiment of the invention, as would be used for hemodialysis.
Figure 1B:
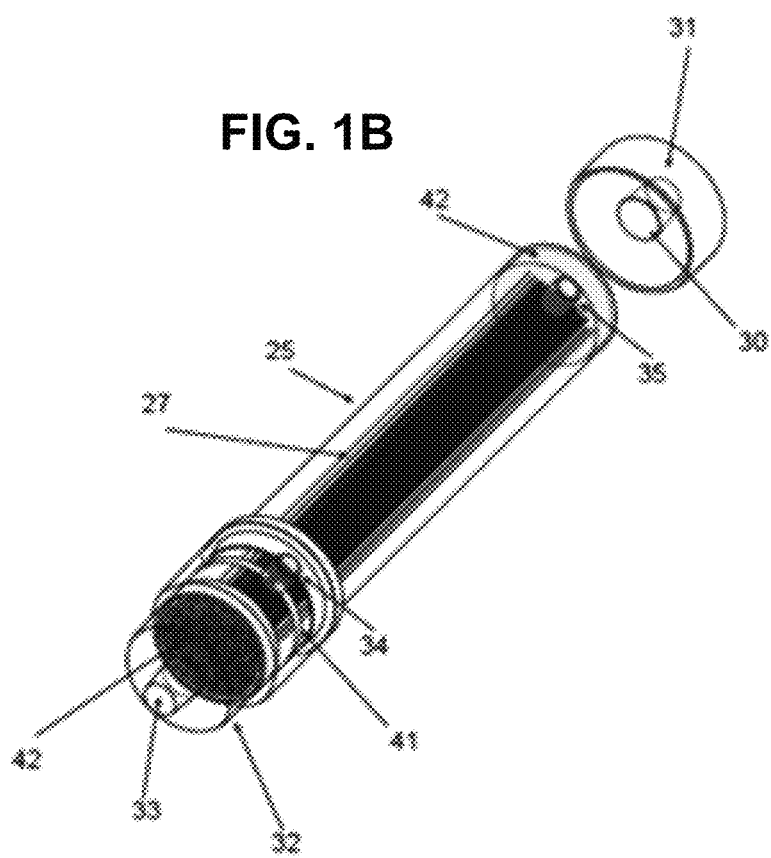
Figure 1C:
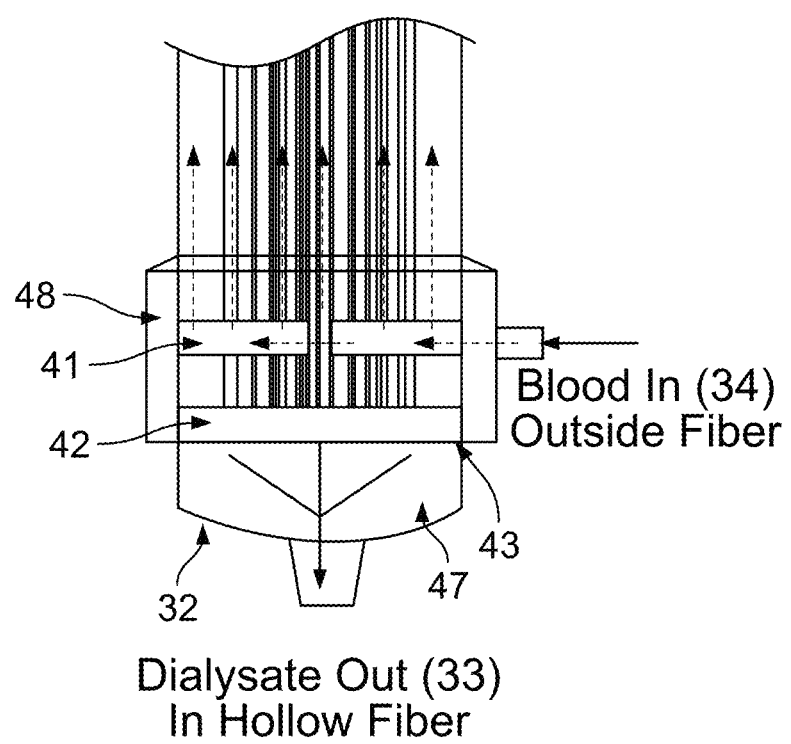
Figure 3:
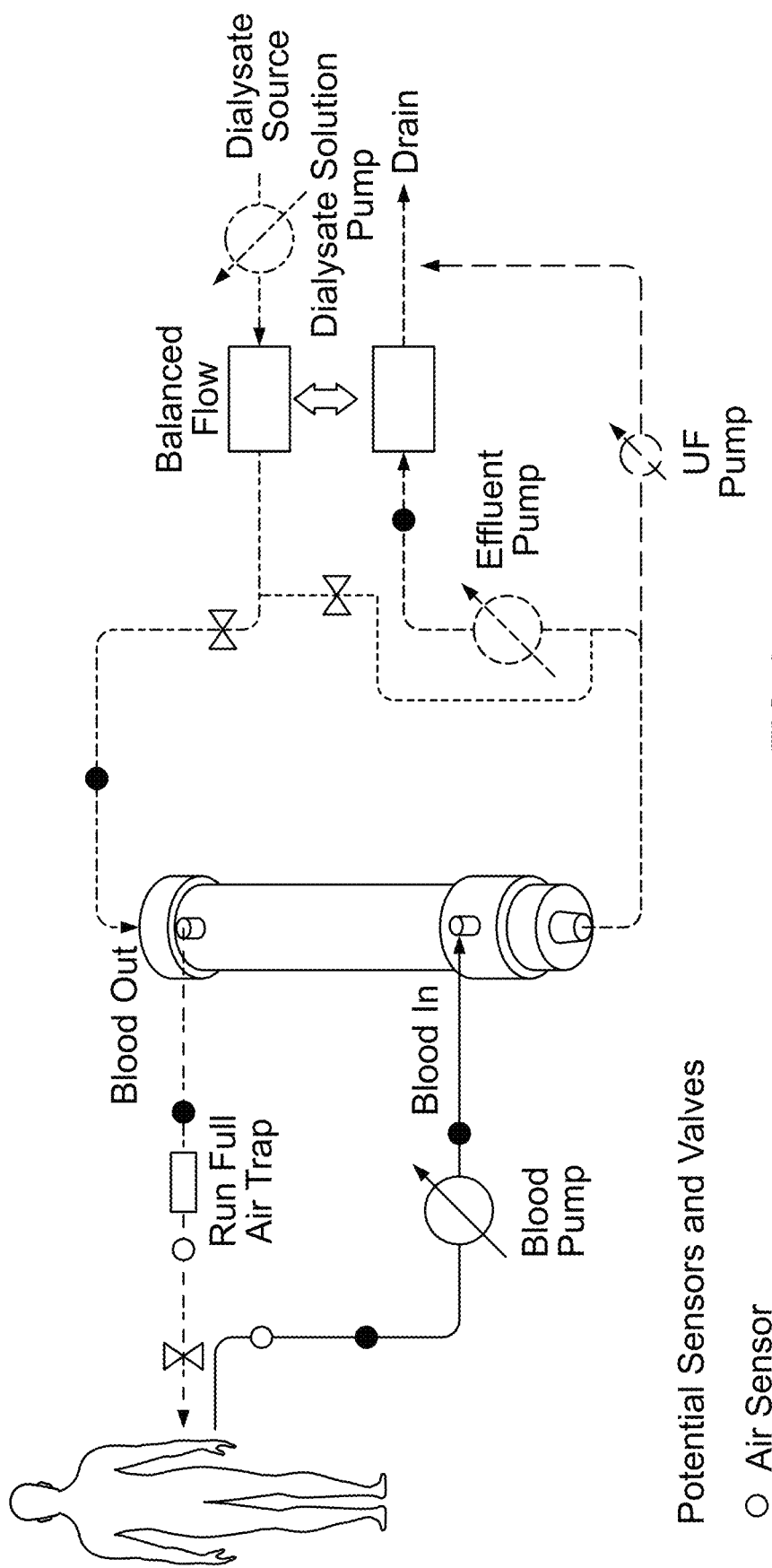
FIG. 3 illustrates a system as would be used for hemodialysis using the cartridge of FIGS. 1A-1C.

Referring now to FIGS. 1-3, in an embodiment of the invention, there is shown a cartridge 12 containing a filter configuration for use with the Outside-In Flow Filtration technology, such as for hemodialysis. FIG. 1A-1C show the assembled cartridge, while FIG. 2 shows the individual components in an exploded view. As illustrated in FIG. 3, the system associated with cartridge 12 may provide dialysate flowing in the lumens of the fibers 27 and may provide blood flowing in the inter fiber space.

The cartridge 12 may comprise a tubular housing 25 and may comprise caps 31, 32 that are adapted to slide onto an end of the tubular housing 25 during assembly of the cartridge 12. Caps 31, 32 may join tubular housing 25 either by being joined to tubular housing or by forming a seal in appropriate places, or a combination of both. In the absence of caps 31, 32, the ends of the tubular housing 25 may be, on their exteriors, truly cylindrical. Caps 31 and 32 can be of different design from each other.

The cartridge 12 may comprise a fiber bundle of hollow fibers 27 contained in Filter Housing 25. The number of hollow fibers may be several thousand, for example, depending on the surface area required for the treatment. Typical filter surface areas may range from 0.1 $m^2$ to 3 $m^2$ of fiber surface area. The outside diameter of the hollow fiber may range from 100 microns to 500 microns or more, and can even be as large as 1500 microns.

As described more fully in the related patent applications incorporated herein, the fibers and the cartridge construction may have certain features that are helpful in connection with the presence of blood on the outsides of the fibers and with the blood flow in the inter-fiber space. For example, the fibers 27 may occupy space inside said housing 25 at a porosity fraction of between 40% and 70%. At least a majority of the fibers 27 may have an outside surface that is smooth having a root-mean-square roughness of less than 100 nanometers and is hemocompatible. The exterior skin layer of the fiber may comprise selective membrane layers to perform the sieving function required to perform hemodialysis, or other related therapy. At least a majority of the fibers have a Molecular Weight Cutoff of less than about 50,000 Daltons, if the application is to hemodialysis or ultrafiltration or similar purposes. Other applications are discussed elsewhere herein. Sieving may be performed based on molecular size and/or by additional functions such as by adsorption or molecular shape.

At an end of cartridge 12 there may be Blood Inlet/Dialysate Outlet Cap 32. This cap 32 may form an isolated chamber 47 for the effluent dialysate 47 to collect from individual fiber lumens and then exit the filter. Dialysis solution may flow through the fiber lumens, and then through chamber 47, exiting at the dialysate outlet 33. The cap 32 may have a header separator 43. When the cap 32 is assembled onto the potted fiber and housing assembly, the header separator 43 may seal the dialysate outlet around the circumference to the edges of the polyurethane-potting compound. This may form two distinct chambers, one chamber 48 for the blood and the other chamber 47 for dialysate, and header separator 43 may maintain the dialysate and the blood separate and isolated from each other. As a result of this configuration, a blood inlet port 34 may connect with a blood inlet chamber that introduces the blood into the inter fiber space of cartridge 12 while keeping the blood separate from the dialysate. It can be noted that both dialysate and blood ports can comprise any type of appropriate fitting, but generally may conform to medical industry norms and standards such as "ANSI/AAMI/ISO 8637 ISO 8637:2010 Cardiovascular implants and extracorporeal systems: Hemodialysers, hemodiafilters, hemofilters and hemoconcentrators" or international equivalents to this standard. These standards call for Luer style connections for blood/substitution/dialysis solutions and/or Hansen fitting connections for dialysis solutions.

Cap 32 may comprise a fluid connection for fluid communication with the lumens of fibers 27, and may also comprise a different fluid connection for fluid communication with the inter fiber space. Fluid that communicates with the lumens of the fibers 27 may be isolated from fluid that communicates with the inter fiber space.

The blood inlet chamber 48 may extend around substantially the entire circumference of housing 25. The 360° blood entry chamber combined with the slots 41 through the wall of tubular housing 25 may allow the blood flow to be evenly distributed flow on the outside of the fibers in the fiber bundle and throughout the entire cross-section of the fiber bundle. The openings created by slots 41 may be distributed substantially uniformly around the circumference of the filter housing. This may also help to distribute the blood flow uniformly on the outside of the fibers 27. Such a design may function as a simplified form of an orbital distributor, which is a feature known on other designs of dialyzers. Alternatively, even if the blood inlet chamber does not occupy the entirety of the circumference of housing 25, it can occupy at least a majority of the circumference of housing 25. The dimension of slots 41 along the axial direction of cartridge 12 may be chosen to allow a smooth transition from radial to axial direction in the shortest possible axial distance as the blood flows in the inter fiber space of the bundle. Such dimension may be larger or smaller depending on the porosity of the fiber bundle and on whether the fibers are fanned our near the end of the bundle as disclosed in related application incorporated here by reference. This dimension may be adjusted to ensure that shear rate does not exceed 2500 sec$^{-1}$, and preferably remains less than 1500 sec$^{-1}$, so as to avoid hemolysis and platelet activation.

The flow of the blood on the outside of the fibers 27 may reduce the potential for blood clotting or filter clogging, as compared to conventional practice in which blood flows inside the lumens of the fibers. To a certain extent, such positioning of the blood may increase the membrane surface area of the blood relative to the surface area of the liquid on the fiber interior, such as dialysis solution.

Given that blood flows through the openings or slots 41, in order to reduce the likelihood of hemolysis, the openings or slots 41 may be designed and manufactured so that they do not have sharp corners or flash or other sharp features or debris from the manufacturing process.

As best illustrated in FIG. 2, if there are only two slots 41, the slots 41 themselves can serve as distribution channels creating a flow distribution pattern that is substantially symmetric with respect to the port 34. As can be seen in FIG. 2, between slots 41 are respective ligaments 411. The flow may enter through port 34, and may then partially or completely impact ligament 411, and may then split substantially equally flowing in two opposed directions proceeding circumferentially around housing 25 within the space defined by slots 41. In such instance, of course, the dimensions of ligament 411 and the dimensions and shape of the flow region within port 34 near ligament 411 may be chosen so as to provide sufficient cross-sectional space for flow everywhere along the flowpath. The slot 41, by virtue of the thickness of the wall of housing 25, may provide a flow channel for distribution of the incoming flow to flow in a generally circumferential direction while entering the fiber bundle. If there are only two slots 41, the slots 41 could conduct flow almost completely around the fiber bundle to the vicinity of the opposed ligament, thereby supplying incoming flow around almost the complete circumference of the fiber bundle. In this arrangement, one ligament 411 could serve as a flow impact feature and the opposed ligament 411 would be located where the flow had almost completely transitioned into the fiber bundle anyway, and so would essentially not constitute a significant flow disturbance. Alternatively, it is possible that more than two ligaments 411 could be provided, such as three or four or some other number. For example, the use of three uniformly-spaced ligaments 411 could distribute flow to almost 240 degrees of the circumference. It is possible that, although in such instance the slots might not supply fluid to as much of the circumference as happens with exactly two slots, the amount of circumference that is supplied might still provide sufficiently good supply of incoming liquid to achieve desired distribution of flow within the fiber bundle. Whatever is the number of ligaments 411, the ligaments 411 could be provided in either symmetrically distributed locations or non-symmetrically distributed locations. Although the ligaments 411 are illustrated as being of equal dimensions, it is possible that various ligaments 411 could have unequal dimensions.

A still further possibility is that the cap 31 could have an internal circumferential groove 415, as shown in FIGS. 1A-1C, around either all of the internal circumference or a large angular portion of the internal circumference. The groove 415 would be in fluid communication with the inlet port 34 and with openings 41. For example, the axial position of such a groove could be such that when the cap 31 is assembled to the housing 25, the internal circumferential groove lines up with the openings such as slots 41. Such a groove 415 could help to distribute the flow somewhat uniformly around the circumference of the housing. The circumferential groove 415 could be sized with an axial dimension as described in U.S. patent application Ser. No. 14/671,186, the entire disclosure of which is incorporated herein by reference. The axial dimension of the slots 41 could be sized with an axial dimension as described in U.S. patent application Ser. No. 14/671,186, the entire disclosure of which is incorporated herein by reference. The axial dimension of the groove 415 and the axial dimension of the slots 41 could be equal or approximately equal to each other, and the groove 415 and the slots 41 could align with each other in the assembled product.

At the other end of the cartridge opposite cap 32, there may be cap 31. In some designs as described further elsewhere herein, it is sufficient for cap 31 to have only one connection port. The dialysate inlet cap 31 may form the entry point for the dialysis solution into the lumens of fibers 27. Dialysis solution may flow into dialysate inlet cap 31 at the dialysate inlet 30. (In other configurations and embodiments, cap 31 may be an UltraFiltrate exit port.)

Blood may exit the filter housing via port 35. As illustrated in FIG. 1, the port 35 may simply be connected to a side of the tubular housing 25 near the appropriate end of tubular housing 25. In this situation, as illustrated in FIG. 1, cap 31 (opposite to cap 31) may be designed more simply than cap 32, so that cap 31 has only one port and that port communicates with the lumens of fibers 27. Alternatively, in this situation, if necessary or desired to prevent or reduce the risk of thrombus formation, the blood exit could be configured similarly to the blood inlet; e. g. to distribute the blood flow uniformly around the circumference of the housing at the blood exit (not shown). However, this is optional. There may be provided an air bleed, in fluid communication with the inter fiber space. This is further discussed in U.S. patent application Ser. No. 14/671,186, the entire disclosure of which is incorporated herein by reference.

The fibers 27 contained inside the cartridge 12 may ideally be made of synthetic masterial such as polysulfone or polyethersulfone, polyarylethersulfone/polyvinylpyrrolidone, or similar biocompatible synthetic fiber material. Alternatively, as would be known to one skilled in the art, a semi-synthetic membrane such as cellulose acetate or cellulose triacetate could also be used. The fiber bundle may have a relatively high ultrafiltration coefficient, but for some specific applications a low ultrafiltration coefficient may be desired and utilized. When used for renal applications the fibers should not have any appreciable albumin leakage, unless this is desired for a purpose such as to remove protein bound toxins such in sepsis patients. Ideally the fibers may have an outer surface that is smooth or hydrophilic or both, so as to reduce potential for the clotting cascade, platelet aggregation, etc.

By far the most common material for making the hollow fibers is a mixture of polyethersulfone (PES) and/or its polymer variants, combined with polyvinylpyrrolidone (PVP). This combination of materials is suitable to make a fiber that is smooth on one surface but not both surfaces, as a function of manufacturing process conditions. The combination of polyethersulfone and polyvinylpyrrolidone is not suitable for making so-called symmetric fibers where both internal and external surfaces of the fiber are smooth.

So-called symmetric fibers have also been made, having a smooth surface on both the inside surface and the outside surface, with both of those smooth surfaces containing the smallest pores. There may be larger pores between the two smooth surfaces. The smoothness on both surfaces generally has not been required for clinical or physiological applications or therapies. Instead, the smoothness on both surfaces has simply happened as a consequence of the manufacturing process in combination with the properties of certain particular polymeric materials. Only a few specific polymeric materials are suitable for manufacturing symmetric fibers. These materials include: polyacrilonitrile (referred to as AN69); cellulose triacetate and other cellulosics; PEPA (polyester polymer alloy, produced by Nikkiso); and polymethylmethacrylate (PMMA).

In embodiments of the invention, the fiber may have the sieving membrane skin layer on the outside (asymmetric). Alternatively, the fiber may be a so-called symmetric fiber, having a sieving membrane skin layer symmetric membrane on both sides. The sieving membrane skin layer may sieve both by size and also by the shape of the molecule if necessary.

The cartridge 12 may be designed either for single use or to be reusable. The cartridge 12 may be sterilized by a method known in the art such as gamma irradiation, electron beam irradiation, steam, citric heat, and ethylene oxide. If the cartridge 12 is to be reused, the cartridge may also be designed to be compatible with technologies that use peracetic acid/hydrogen peroxide combinations such as Renalin, and to be compatible with other known reuse chemicals. In particular, the cartridge 12 may be designed to be compatible with the ClearFlux™ reprocessing system of NovaFlux Technologies (Princeton, N.J.). Such a system uses a two-phase (gas and liquid) flow technology to reprocess cartridges without manual pre-cleaning and has been shown to maintain solute clearance for 40 treatments or more. The delivered product can also include temporary removable caps (not shown) to cover certain ports, and sterile packaging (not shown).

Embodiments of the invention are also provided in the circuit and system of FIG. 3. FIG. 3 shows a typical hemodialysis system and flow path configuration that can be used with the cartridge 12 of FIGS. 1-2. What is illustrated is a counterflow configuration, in which the flow direction of blood is the opposite to the flow direction of the dialysate. Alternatively, if desired, a co-current flow arrangement (not illustrated) could be utilized. The cartridge 12 integrates with this system and flow path. A balancing system of some type such as volumetric balance chambers, flow sensors or scales may control the flow of fresh dialysis solution to and the flow of used dialysate from the cartridge 12. What is illustrated in FIG. 3 is a volumetric balancing system. Pumps may be placed and operated appropriately to pressurize the balance chambers so they can fill and empty. As illustrated in FIG. 3, an ultrafiltration pump also may be used in this configuration to achieve a net removal of fluid equivalent to the desired patient fluid loss. The extracorporeal circuit illustrated in FIG. 3 is a modified special circuit to work with the equipment used to perform conventional hemodialysis. It is preferred that there be no air/blood interface, but if necessary there could be air bubble traps having a small air volume. Pressure sensors may be distributed throughout the flow path as appropriate. The exact location and number of these sensors may depend on the specific hemodialysis system and mode of operation and the desired pressure monitoring. For example the pre blood pump pressure sensor can be used to detect blockage in the proximal tubing or the access, while a post blood pump monitor can detect clotting in the filter or in distal end of the extracorporeal circuit. FIG. 3 shows a hemodialysis system with a balancing chamber or similar system to balance the fresh and used solutions. The fresh dialysis solution and effluent dialysate may be balanced. The Ultrafiltration pump may be used to remove the excess fluid from the patient.

Slow Continuous Ultrafiltration and Hemofiltration

Two other therapy processes that can use similar cartridges are Slow Continuous Ultrafiltration (SCUF) and Hemofiltration (HF). These processes differ from hemodialysis in that there is no supplying of dialysis solution to the cartridge, and the cartridge can be manufactured without the port that would in other circumstances be used to supply dialysate solution to the cartridge. In SCUF, fluid is removed from the patient to eliminate edema. In HF, large volumes of solution are ultrafiltered from the blood across the semipermeable membrane, which creates convective clearance of uremic wastes by causing the solute renal toxins to pass through the membrane wall of the fiber 27. Because of the relatively large amount of ultrafiltrate compared to the typical (5 to 6 liter) blood volume of a patient, a sterile replacement or substitution solution must be given to replace the ultrafiltrate liquid removed from the patient's bloodstream by ultrafiltration. It is also possible, if desired, that in HF there can be a net removal of fluid from the patient. In this situation, the volume of ultrafiltrate may be greater than the volume of substitution solution by the desired amount of patient fluid loss. The processes of HF and SCUF are physically the same, but in HF, due to the relatively large amount of ultrafiltration, it is necessary to provide the replacement or substitution fluid to make up for at least much of the loss that would otherwise occur in the patient's blood volume.

Figure 4:
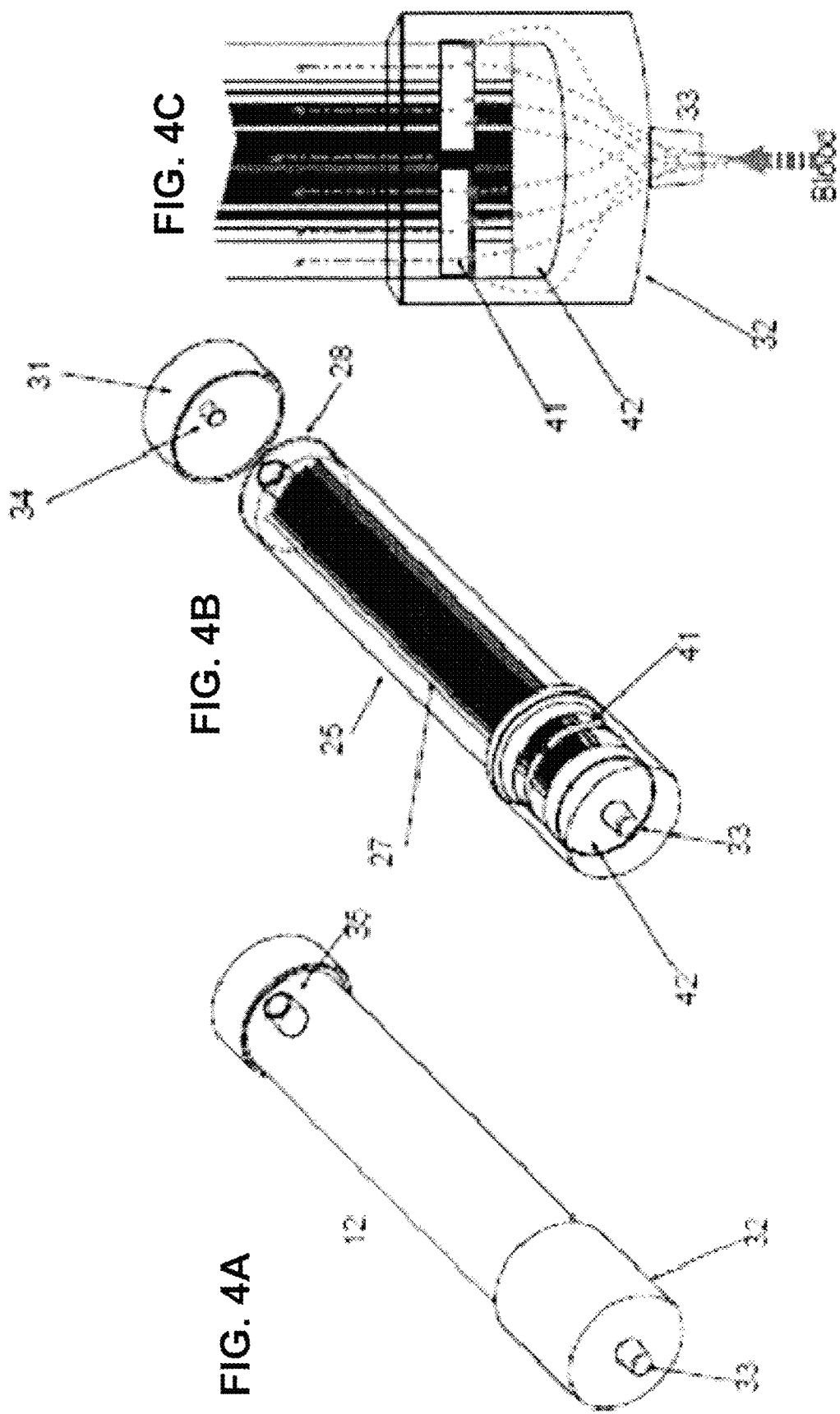
FIGS. 4A-4C illustrate a cartridge of an embodiment of the invention, as would be used for hemofiltration or slow continuous ultrafiltration.

FIGS. 4A-C and 5 illustrate Outside-In Flow Filtration embodiments for cartridges for SCUF or HF. In this cartridge 12, there are the following three connections to the cartridge 12: blood supply; blood removal; and ultrafiltrate removal. Referring now to FIGS. 4A-C, the blood may enter the cartridge 12 via port 33 of cap 32. In this embodiment, cap 32 only has one fluid connection, which is in fluid communication with the inter fiber space, and this fluid connection is illustrated as being placed at the center of cap 32 oriented in a generally axial direction. Because of this, there is no need within this cap 32 to keep two different fluid regions isolated from each other, as there was in cap 32 of FIGS. 11A-C in which the cartridge was used for hemodialysis. Also, as is illustrated in FIG. 5, the other end cap at the other end of the cartridge also only needs to have one connection, in this case for ultrafiltrate removal. The configuration illustrated in FIGS. 4A-C could be manufactured with the hollow fibers being dead-ended in the barrier 42 that is located near cap 32. Also illustrated is one connection 35 that is on the exterior of the cylindrical housing, which is used as the exit port for blood removal from the cartridge 12. It can be noted that although the illustrated blood connection 35 directly between a housing side port and the fiber bundle is a design possibility, it might not be ideal for fluid flow patterns in the inter fiber space, because the local pattern of blood flow in the inter fiber space might be conducive to clotting or clogging of blood. A possibly better design as illustrated in other embodiments herein might be to have an orbital distributor at both ends of the cartridge. A feature that is not illustrated is possible fanning of the fibers near the potting in the barrier. It is believed that for situations of embodiments of the invention, fanning is desirable at the inlet end of the cartridge. It is also believed that fanning is useful at the discharge end of the cartridge, although perhaps not as strongly desirable as at the inlet end of the cartridge. Fanning is used here to adjust the local porosity of the fiber bundle at the place where the blood enters (or leaves) the bundle, so as to avoid high shear rates that may cause hemolysis and/or platelet activation. FIG. 5 illustrates in somewhat greater detail the flowpath for blood flow through the SCUF/HF filter that is illustrated in FIGS. 4A-C. Blood may flow around the barrier 42, which may be polished potting compound, and may enter the inter fiber space through openings or slots 41 in the wall of the housing 25, and may further flow along the bundle of fibers 27 and may exit through blood exit port 35. Vacuum applied on ultrafiltrate port 34 may cause fluid to cross the membrane (i. e., the walls of the hollow fibers) from the blood and to exit the cartridge 12 via cap 31.

In this situation, the impermeable barrier 42 in which the fibers are dead-ended may have a surface, facing away from the fiber bundle, that is curved. The curved surface may be polished to provide a smooth surface, past which blood may flow. Such curved surface may be axisymmetric. In this situation, blood may flow tangentially over the curved surface of the barrier. The curved surface may still be polished, because a polished surface is favorable for avoiding damage to cells by mechanisms such as hemolysis of red blood cells, and a smooth surface can also help avoid activate leukocytes and platelets and the clotting cascade. Such a cartridge can be used in ultrafiltration such as SCUF.

Figure 6A:
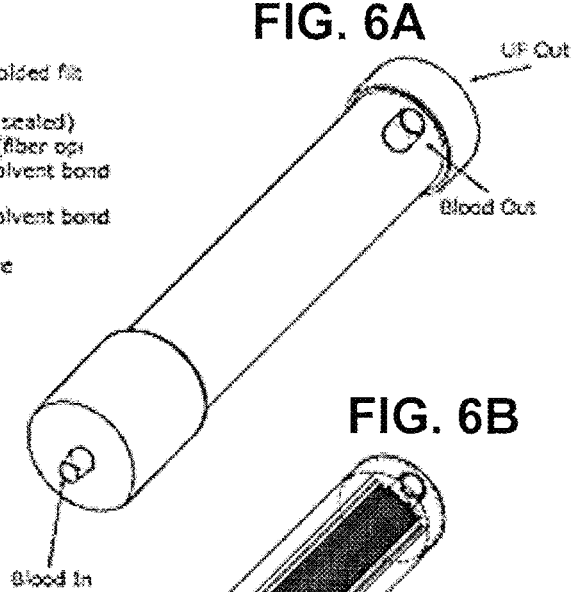
FIGS. 6A-6C show manufacturing steps for the cartridge of FIGS. 4A-4C with the style of blood supply connection illustrated in FIGS. 4A-4C and FIG. 5.
Figure 6B:
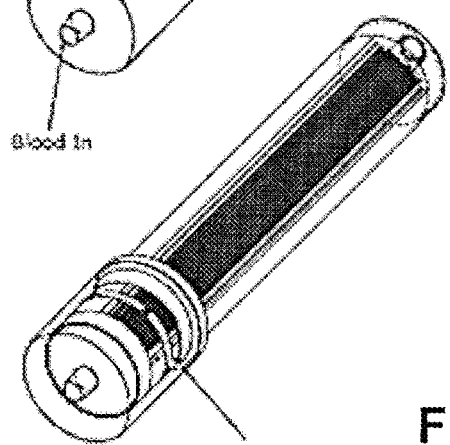
Figure 6C:
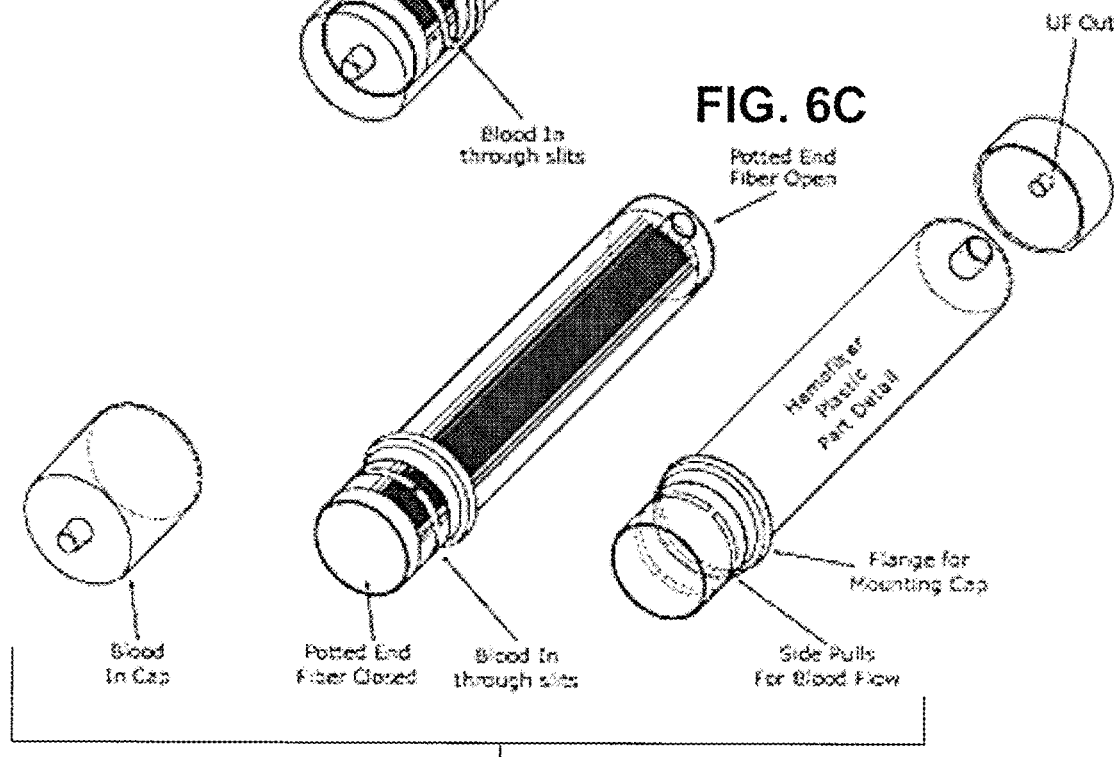
Figure 7A:
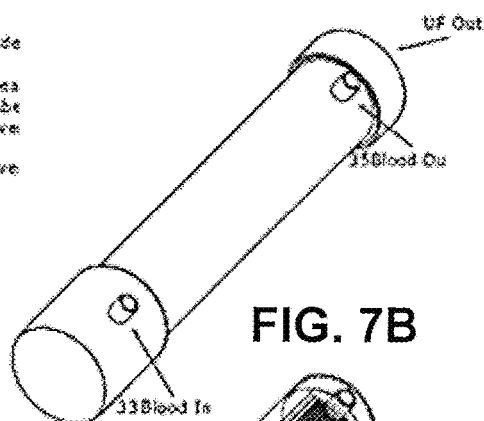
FIGS. 7A-7D show manufacturing steps for a cartridge similar to the cartridge of FIGS. 4A-4C, but having a slightly different style of blood supply connection.
Figure 7B:
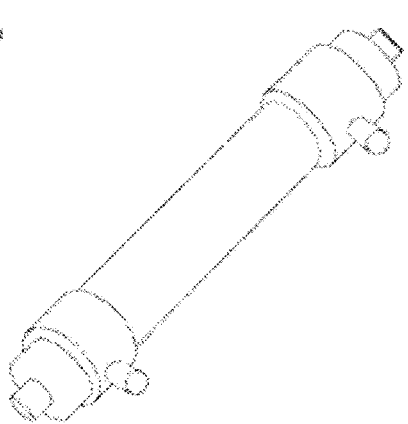
Figure 7C:
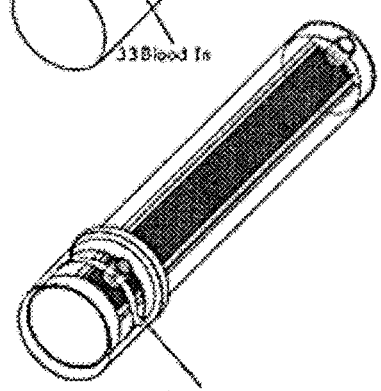
Figure 7D:
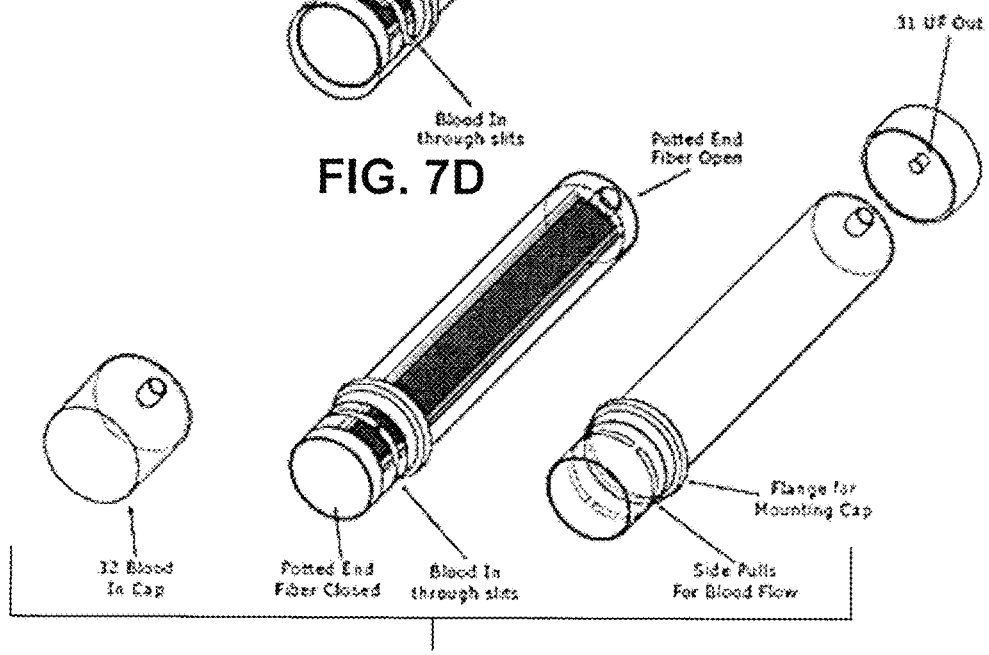

FIGS. 6A-C shows in more detail the components that may be used to make up the cartridge 12 of FIGS. 4A-C and FIG. 5. Because this cartridge is intended for ultrafiltration rather than dialysis, there is shown only one port connecting to the lumen space, rather than two ports as were shown in FIGS. 1A-C. The UltraFiltrate out port is shown as being from cap 31. Cap 32 is used for the blood inlet. The blood exit port is illustrated as coming from the side of the housing 25.

FIGS. 7A-D) show an alternative embodiment in which the blood inlet port is a side port 33 extending from the side of the cartridge 12, as may be desired for some applications, rather than being located at the end of the cartridge 12 as was shown in FIGS. 4A-C, 5, and 6A-C.

Figure 8:
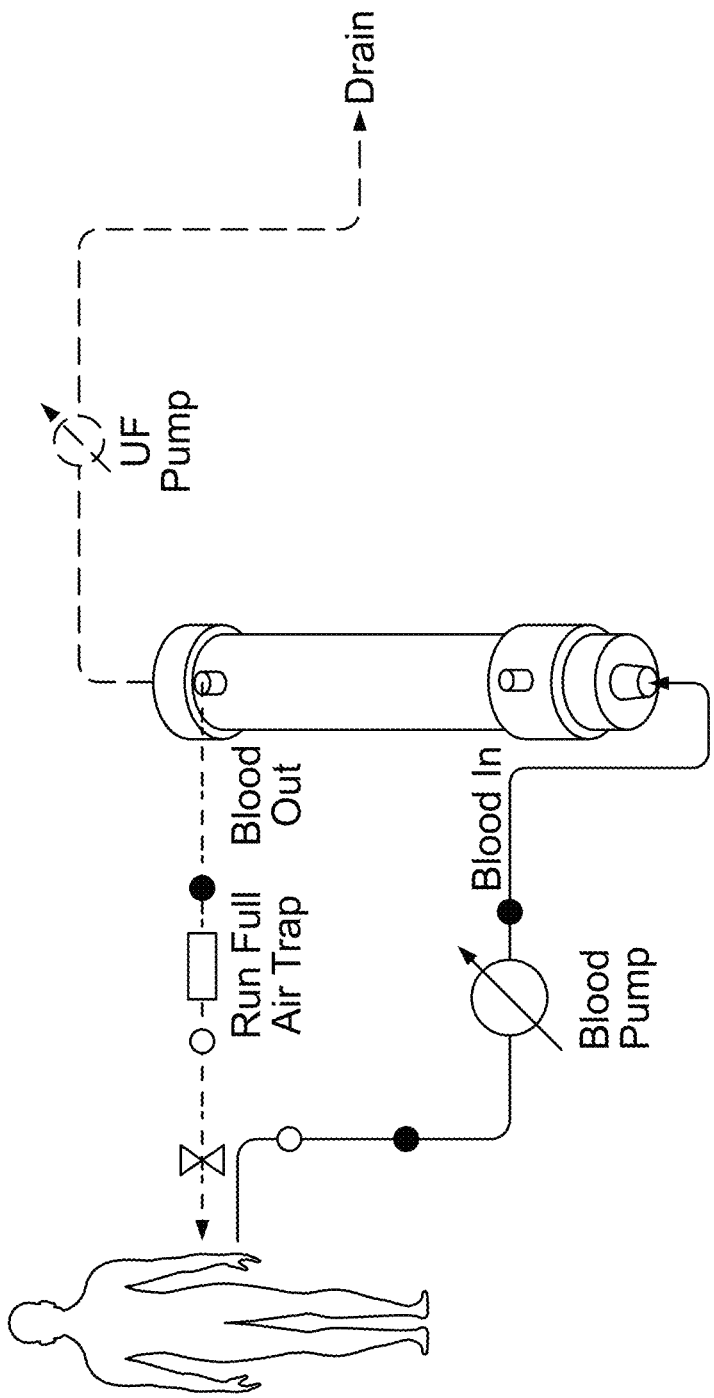
FIG. 8 illustrates a system for performing Slow Continuous Ultrafiltration.

FIG. 8 shows a corresponding system that would use a cartridge that was illustrated in FIGS. 4-7. As described elsewhere, there is a blood inlet port, a blood out port, and an ultrafiltrate out port. The illustrated system is configured as a SCUF system. The UltraFiltrate pump may be controlled by a scale that measures weight of fluid or it may be a volumetric metering device to control the rate and volume of ultrafiltration.

Systems for Hemofiltration and Hemodiafiltration

FIG. 9 through FIG. 20 show various systems that can be used with hemofiltration or hemodiafiltration.

FIG. 9 through FIG. 14 show forms of hemofiltration, including addition of substitution fluid. In all of these systems of FIG. 9 through FIG. 14, there are three active fluid connections to the cartridge 12 (a blood inlet, a blood outlet, and an ultrafiltrate outlet). Also there is substitution fluid provided to the blood flow externally of the cartridge. The provision of substitution fluid can be either upstream of the cartridge (pre dilution), downstream of the cartridge (post dilution) or both (pre/post dilution).

Figure 9:
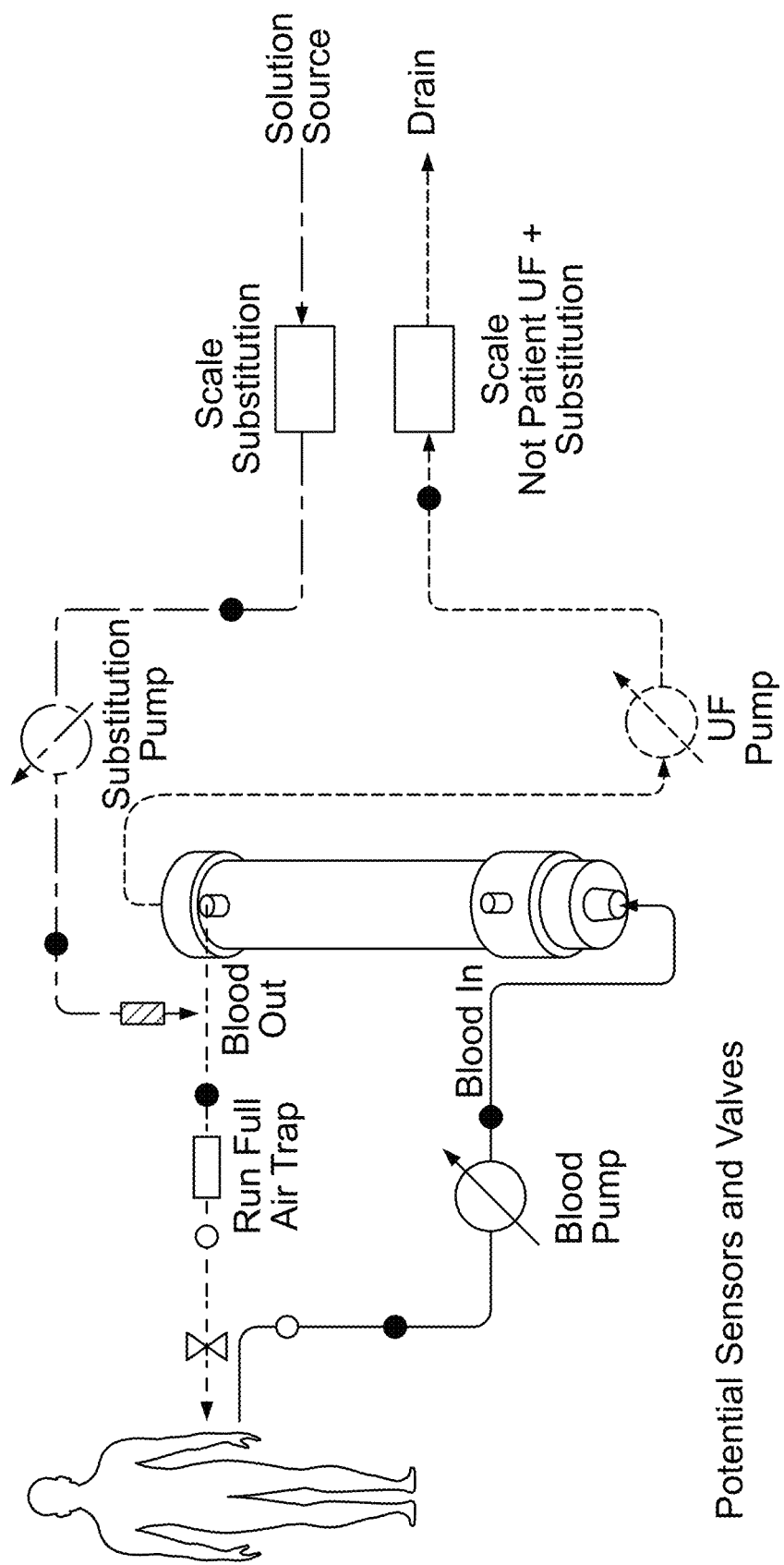
FIG. 9 shows a system for performing post dilution hemofiltration, in which scales are used to control the substitution pump and UF pump.
Figure 10:
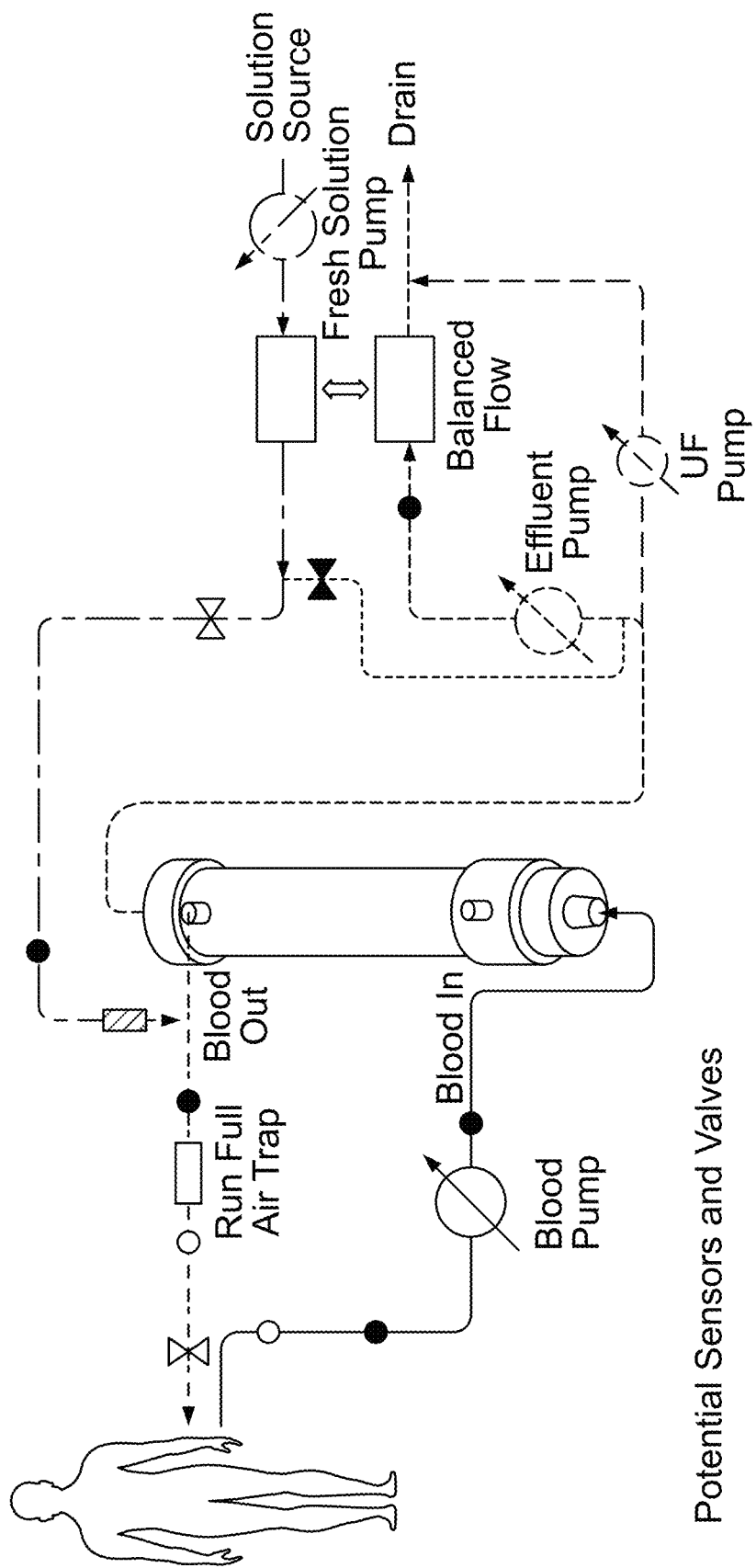
FIG. 10 shows a system for performing post dilution hemofiltration, using a volumetric flow balancing system.

FIGS. 9 and 10 show systems that perform post dilution hemofiltration. This system works similarly to previously described SCUF systems, but adds in substitution fluid. In this illustrated system, the substitution fluid is added post filter (that is, downstream from the filter). Post dilution HF clears the blood by convective clearance brought about by the removal of high volumes of solution from the blood. In this treatment modality, substitution or replacement solution is put back into the patient's blood, because the total volume of blood in a patient's body is only approximately 5 to 6 liters of blood. FIG. 9 shows that this could be used with the filter shown in FIG. 1 with one of the ports being unused (closed off). FIG. 10 (shown without the extra port) shows that this could be used with the filter configuration for Slow Continuous Ultrafiltration or Hemofiltration shown in FIGS. 4-7. FIG. 9 uses a system in which scales are used to control the substitution pump and UF pump respectively. By controlling the pumps the substitution flow and the ultrafiltration flow can be controlled to remove the desired amount of fluid from the patient and to clear the patient's blood from renal toxins and waste products. FIG. 10 shows the system configured with a balancing type system using balance chambers or other similar volumetric balancing scheme. The use of the balancing chambers or other balancing method controls the flow of substitution fluid and removes an equal amount of substitution fluid from the system. Either of these balancing systems controls the fluid used for convective clearance. If it is desired that there be net removal of fluid from the patient's blood during this process, an additional UF pump may remove a volumetric equivalent to the desired patient fluid loss.

Figure 11:
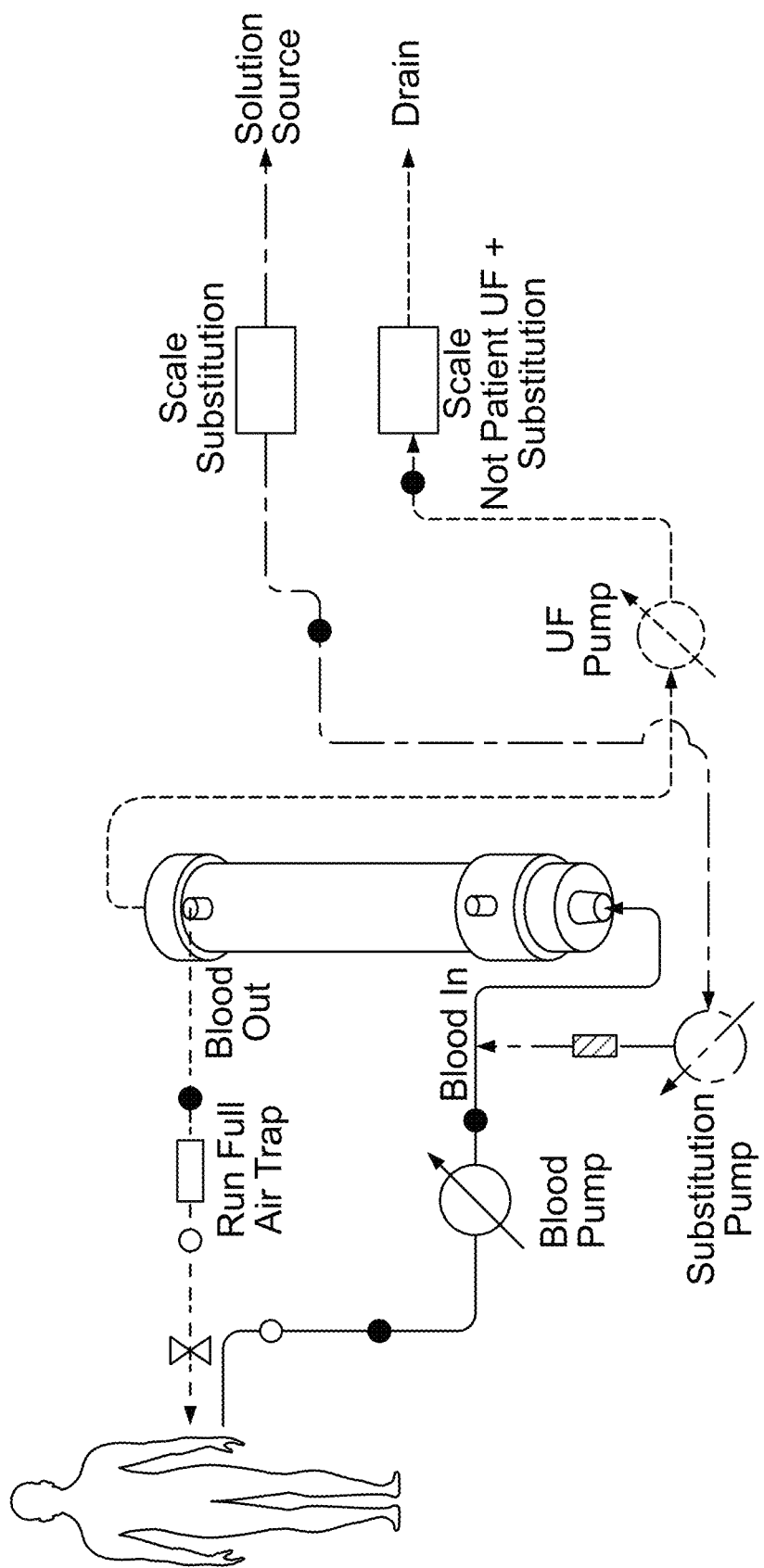
FIG. 11 shows a system for performing pre dilution hemofiltration, in which scales are used to control the substitution pump and UF pump.
Figure 12:
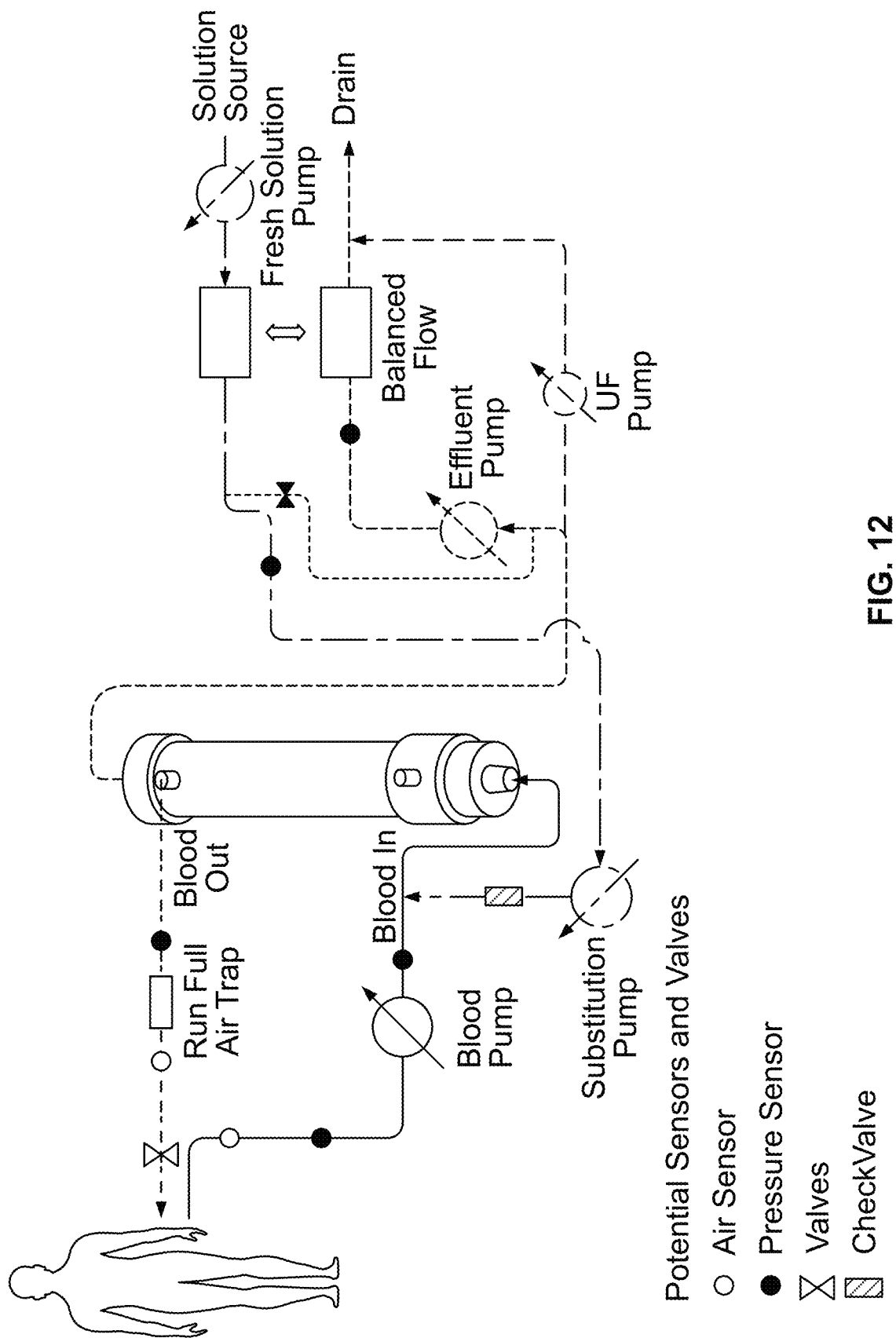
FIG. 12 shows a system for performing pre dilution hemofiltration, using a volumetric flow balancing system.

FIGS. 11 and 12 show systems that perform pre dilution hemofiltration. The system works similarly to the system of FIGS. 9 and 10, but the addition of substitution fluid to the extracorporeal circuit is performed pre-filter (upstream of the filter) rather than post filter. Both FIGS. 11 and 12 are shown with the type of cartridge illustrated in FIGS. 4-7.

Figure 13:
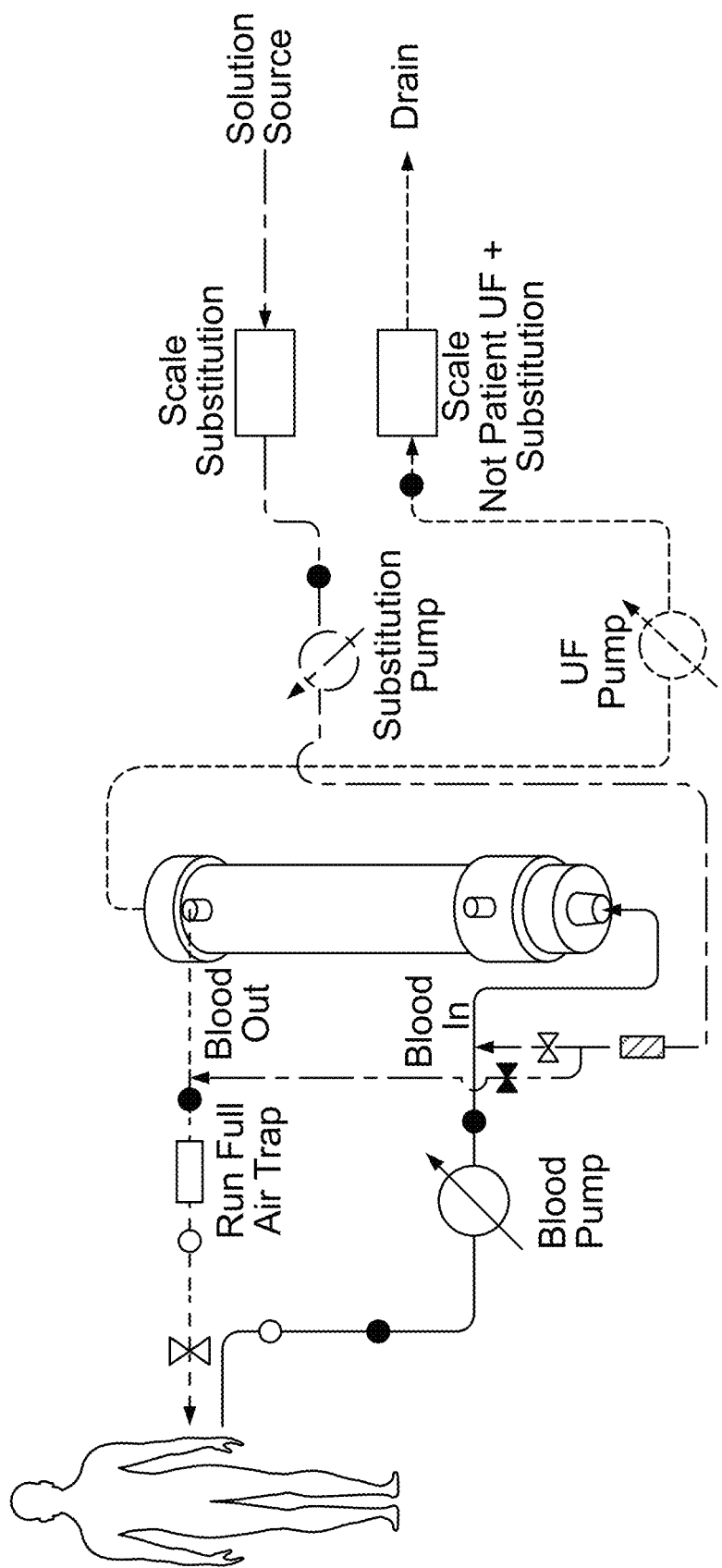
FIG. 13 shows a system for performing pre/post dilution hemofiltration, in which scales are used to control the substitution pump and UF pump.
Figure 14:
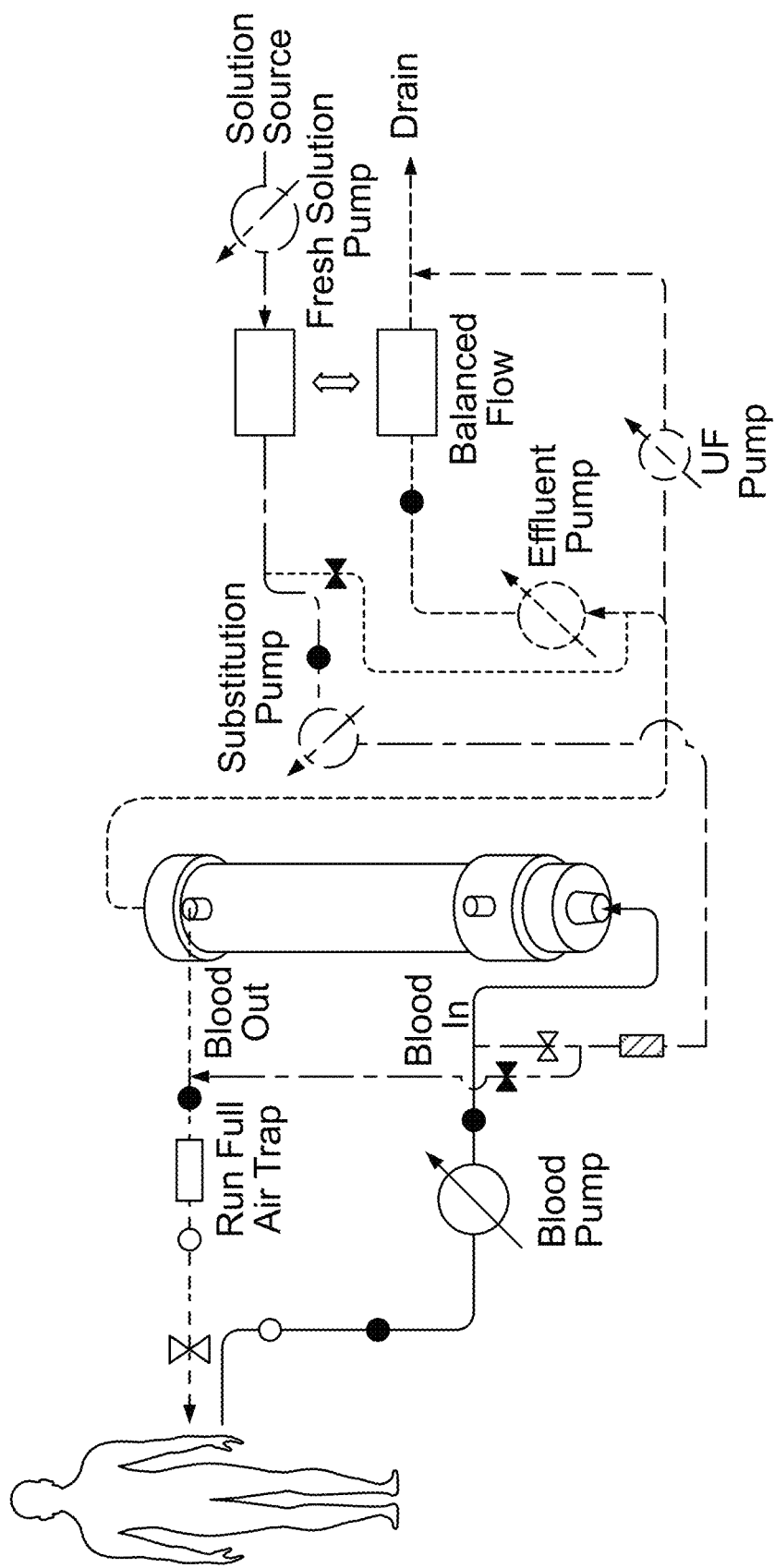
FIG. 14 shows a system for performing pre/post dilution hemofiltration, using a volumetric flow balancing system.

FIGS. 13 and 14 show yet another system configuration referred to as pre/post dilution configuration, in which substitution fluid is added both upstream of the cartridge and downstream of the cartridge. FIG. 13 and FIG. 14 are shown with the type of cartridge illustrated in FIGS. 4-7. However, this system configuration or any of the HemoFiltration systems could also be used with the filter shown in FIG. 1A-C if one of the ports of the cartridge was closed off. These systems work similarly to the pre or post dilution HF systems with the exception that the substitution solution is infused into the extracorporeal circuit in two locations, i. e., both prior to the cartridge and after the cartridge. Pre or post dilution flow can be controlled with valves that open to allow flow to the desired point: pre or post filter cartridge. In alternative configurations that are not illustrated, these valves could be replaced with pumps to meter the flow pre and/or post filter.

Hemodiafiltration (HDF) combines the features of hemodialysis and hemotiltration. It includes the use of a cartridge that has four fluid connection points (blood in, blood out, dialysate in, dialysate out) as is used for hemodialysis, and also there is the addition of substitution fluid to the blood flow externally of the cartridge. The provision of substitution fluid can be either upstream of the cartridge (pre dilution), downstream of the cartridge (post dilution) or both upstream and downstream (pre/post dilution).

Hemodiafiltration provides the diffusive clearance of hemodialysis while providing the convective clearance of hemofiltration. Diffusive clearance of uremic toxins is accomplished by the diffusion of wastes across the semipermeable membrane. Because the uremic toxins are not present in the dialysate solution that is supplied to the cartridge, urea, creatinine and other uremic wastes cross into the effluent dialysate. The convective clearance is accomplished by removing larger volumes of solution from the blood; this pulls additional renal toxins through semi-permeable membrane that is the wall of the fiber, due to a solute drag effect in the same manner as hemofiltration. To maintain the desired net patient fluid balance, substitution solution must be given to replace the excess ultrafiltrate volume used for convective clearance. A typical HDF treatment may have a twenty-liter fluid removal for clearance and a two-liter fluid removal to remove the excess fluid the patient has accumulated. In this example, 20 liters of substitution fluid would be given through the substitution source and 22 liters of ultrafiltrate would be removed. This compares to the typical overall volume of blood in a patient's body of 5 to 6 liters.

Figure 15:
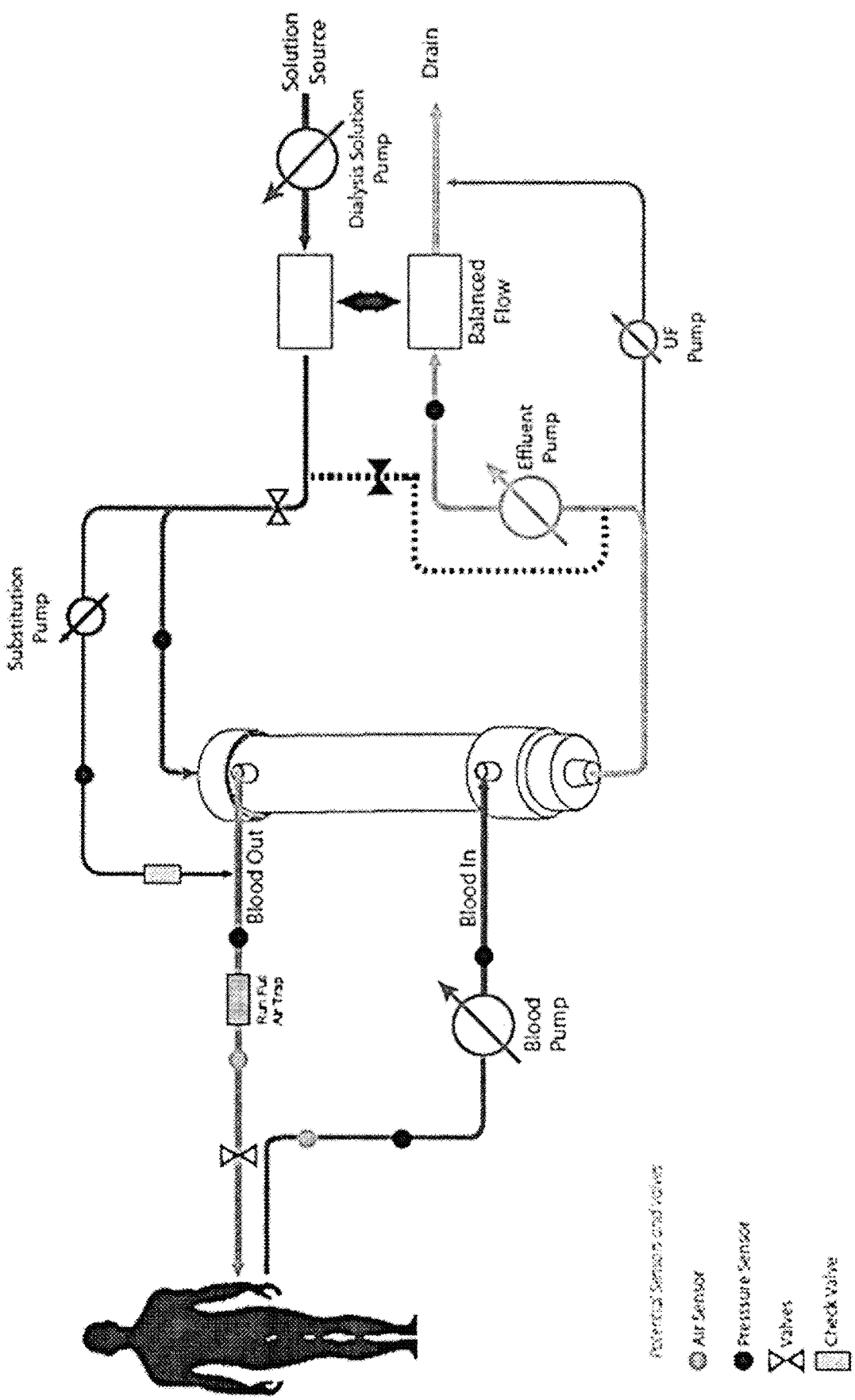
FIG. 15 shows a system for performing post dilution hemodiafiltration, using a volumetric flow balancing system.
Figure 16:
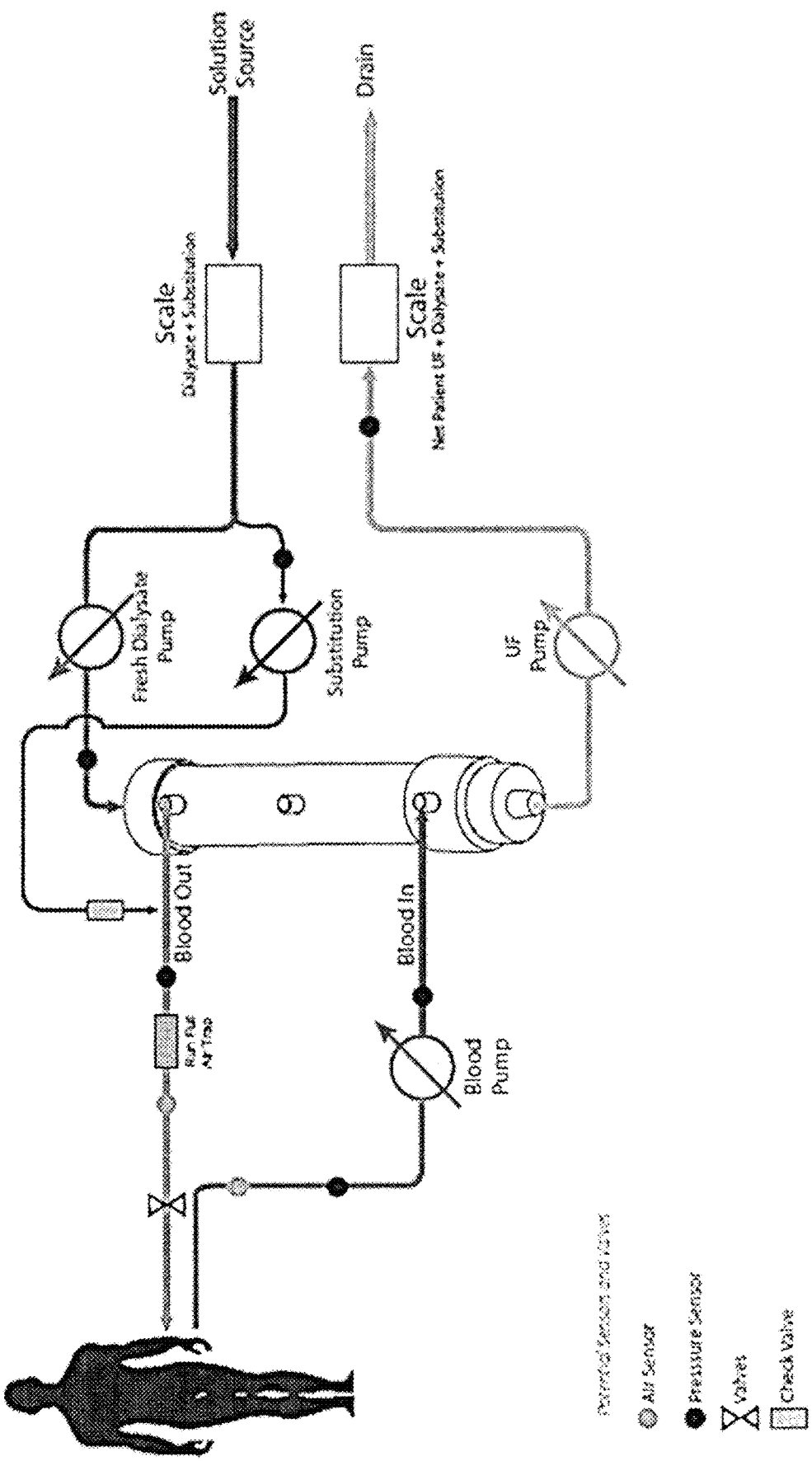
FIG. 16 shows a system for performing post dilution hemodiafiltration, using scales for flow balancing.

FIGS. 15 and 16 show hemodiafiltration systems having a post dilution feature. The substitution solution is infused into the extracorporeal circuit downstream of the filter. The filter configuration used is the filter shown in FIGS. 1A-C. Post dilution HDF provides higher clearance per liter of solution than pre-dilution HDF, and so for some patients it is a desirable modality. FIG. 15 shows a post dilution HDF system with a balancing chamber or similar system to balance the fresh and used solutions. The substitution solution is pumped into the extracorporeal circuit after the hemodiafilter. Because the fresh solution and the used solution are balanced, a volumetric equivalent to the substitution solution is automatically removed from the patient by the effluent balancing system. The UF pump is used to remove the excess fluid from the patient. FIG. 16 shows post dilution HDF with scales used to control the pumps. One skilled in the art would appreciate that there may be an additional scale so that the fresh dialysis solution and the substitution solution are controlled by separate scales.

Figure 17:
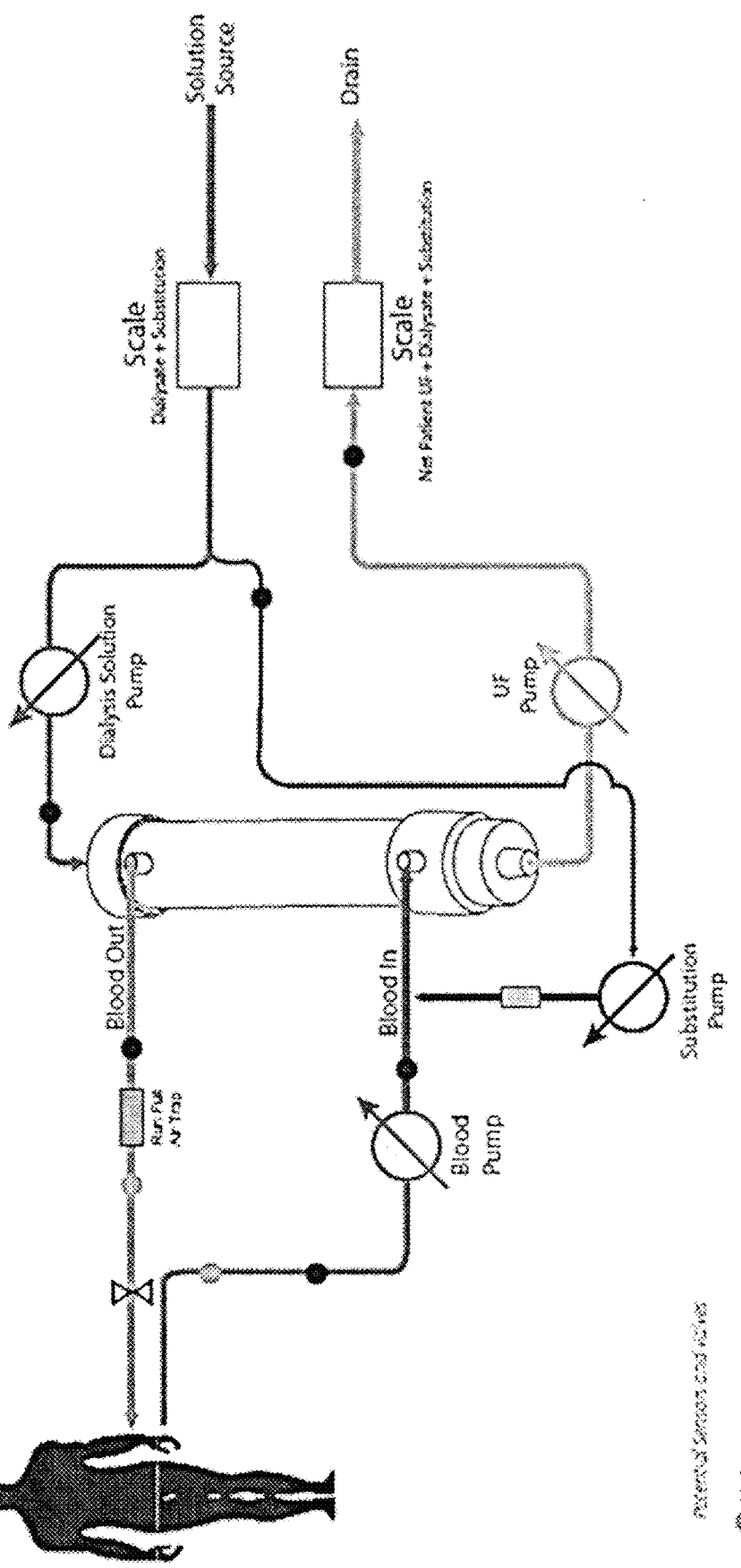
FIG. 17 shows a system for performing pre dilution hemodiafiltration, using scales for flow balancing.
Figure 18:
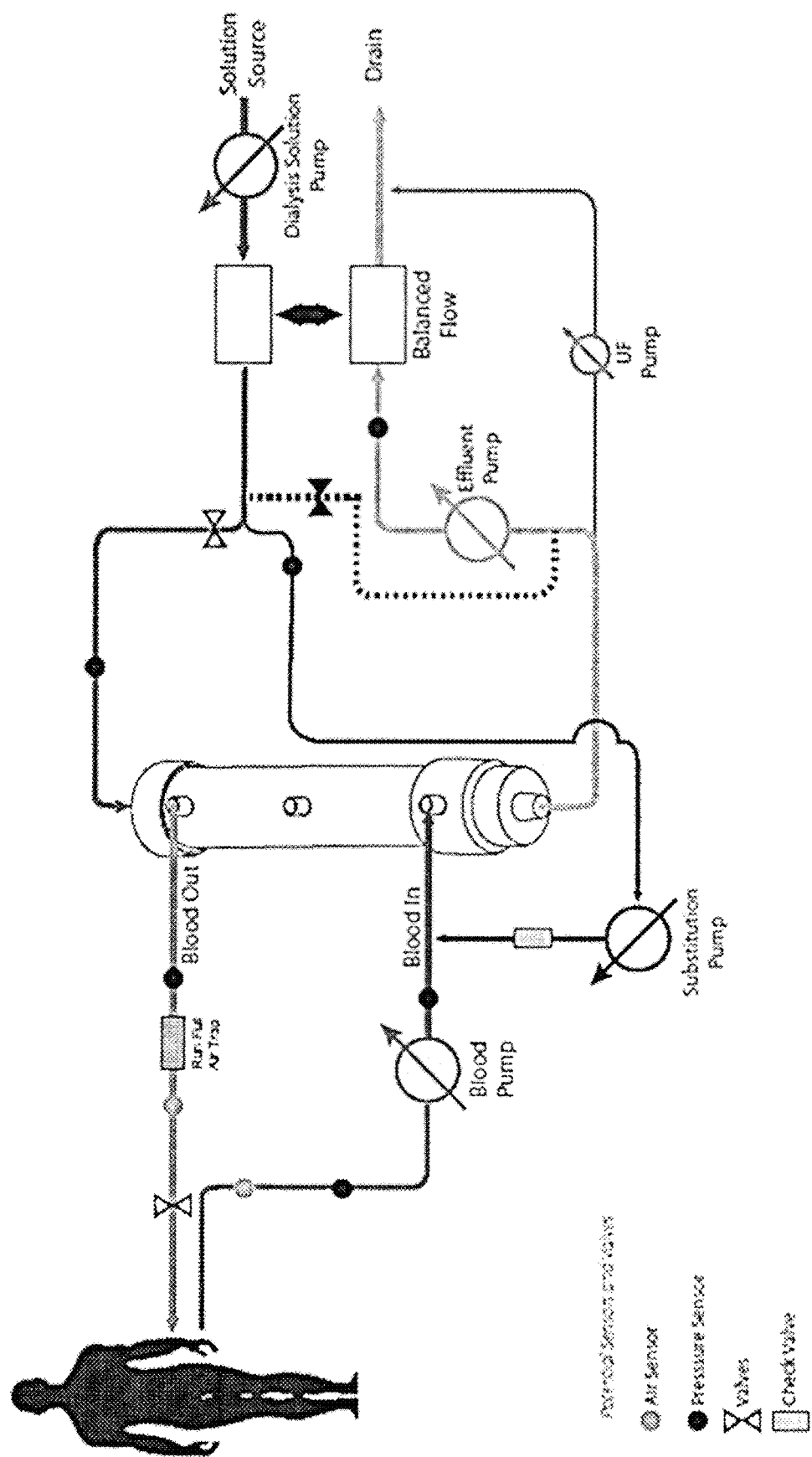
FIG. 18 shows a system for performing pre dilution hemodiafiltration, using a volumetric flow balancing system.

FIGS. 17 and 18 show hemodiafiltration systems having a pre-dilution configuration. Again, these systems could be used with the filter shown in FIGS. 1A-C. These systems operate similarly to the post dilution HDF systems with the exception that the substitution solution is infused into the extracorporeal circuit upstream of the filter.

Figure 19:
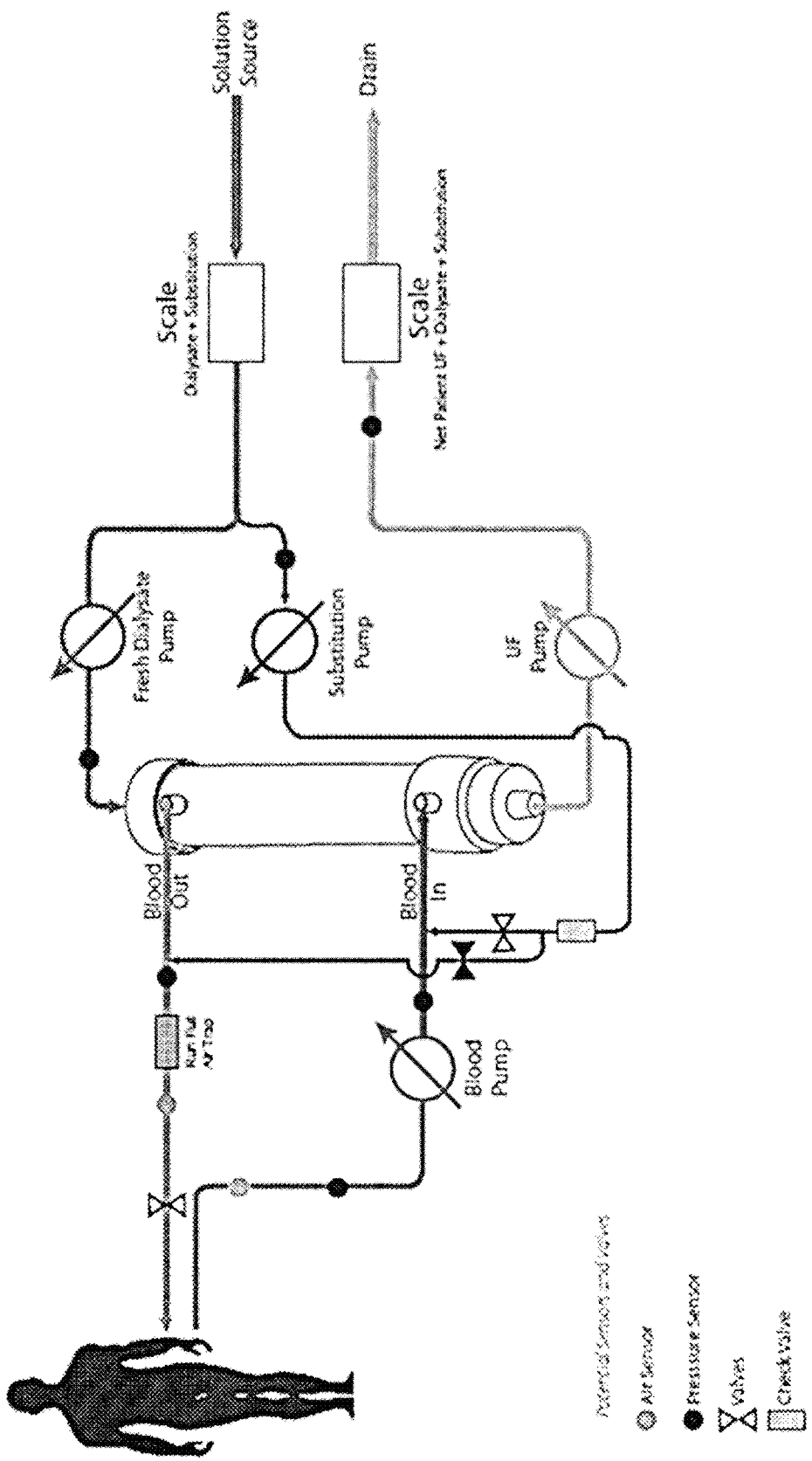
FIG. 19 shows a system for performing pre/post dilution hemodiafiltration, using scales for flow balancing.
Figure 20:
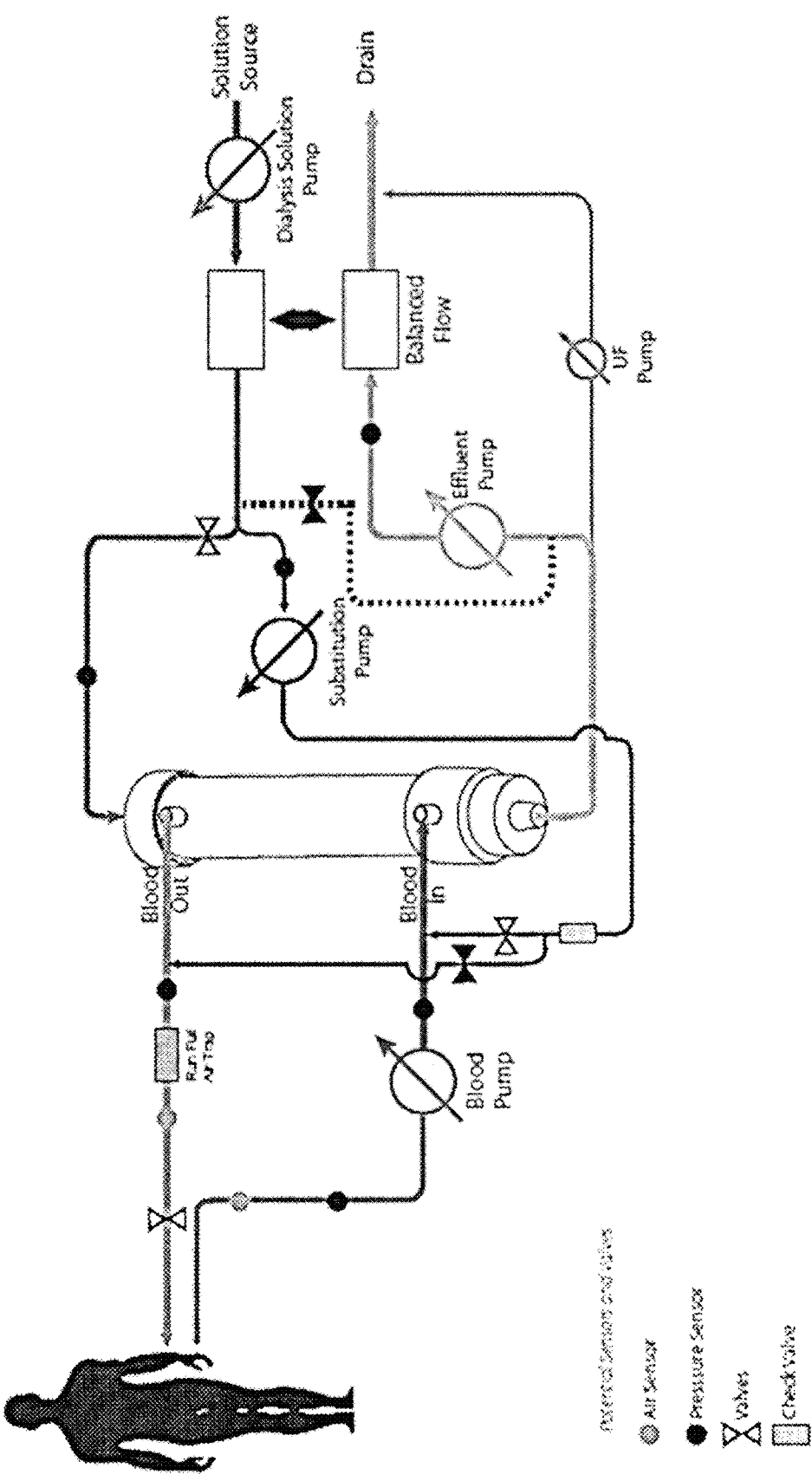
FIG. 20 shows a system for performing pre/post dilution hemodiafiltration, using a volumetric balancing system.

FIGS. 19 and 20 show hemodiafiltration systems having a pre/post dilution configuration of the system. Again, these systems could be used with the filter shown in FIGS. 1A-C. These systems operate similarly to the pre dilution HDF systems and the post dilution HDF systems, with the exception that the substitution solution is infused into the extracorporeal circuit in both the pre and post locations, i. e., both upstream of the filter and downstream of the filter. Pre or post dilution flow can be controlled with valves that open to allow flow to the desired fluid addition point, i. e., pre or post filter or both. These valves could alternatively be replaced with pumps to meter the flow pre and/or post filter. Such an alternative configuration involving pumps instead of valves is not illustrated.

Intermediate Port

Figure 21C:
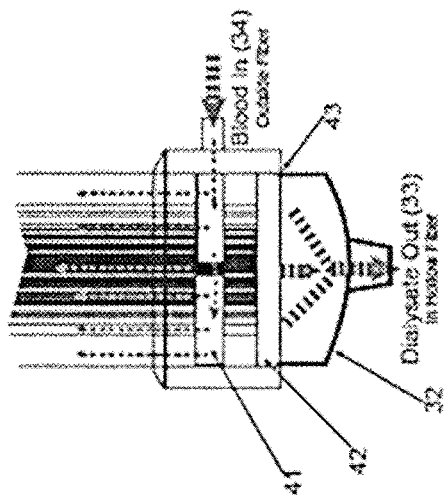
FIGS. 21A-21C show a hemodiafilter with a port for mid-dilution.
Figure 21B:
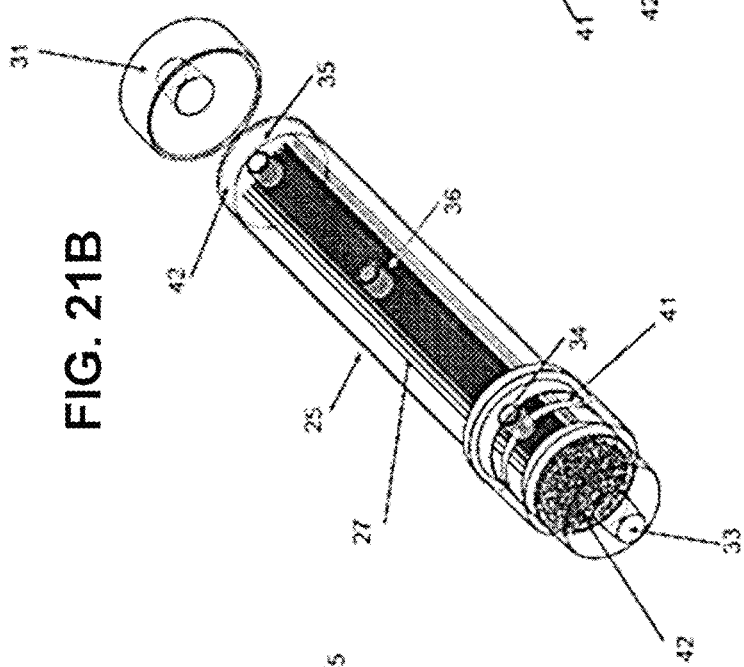
Figure 21A:
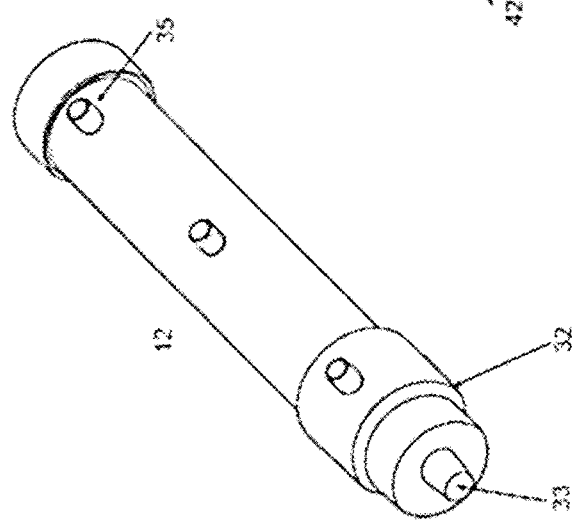
Figure 22:
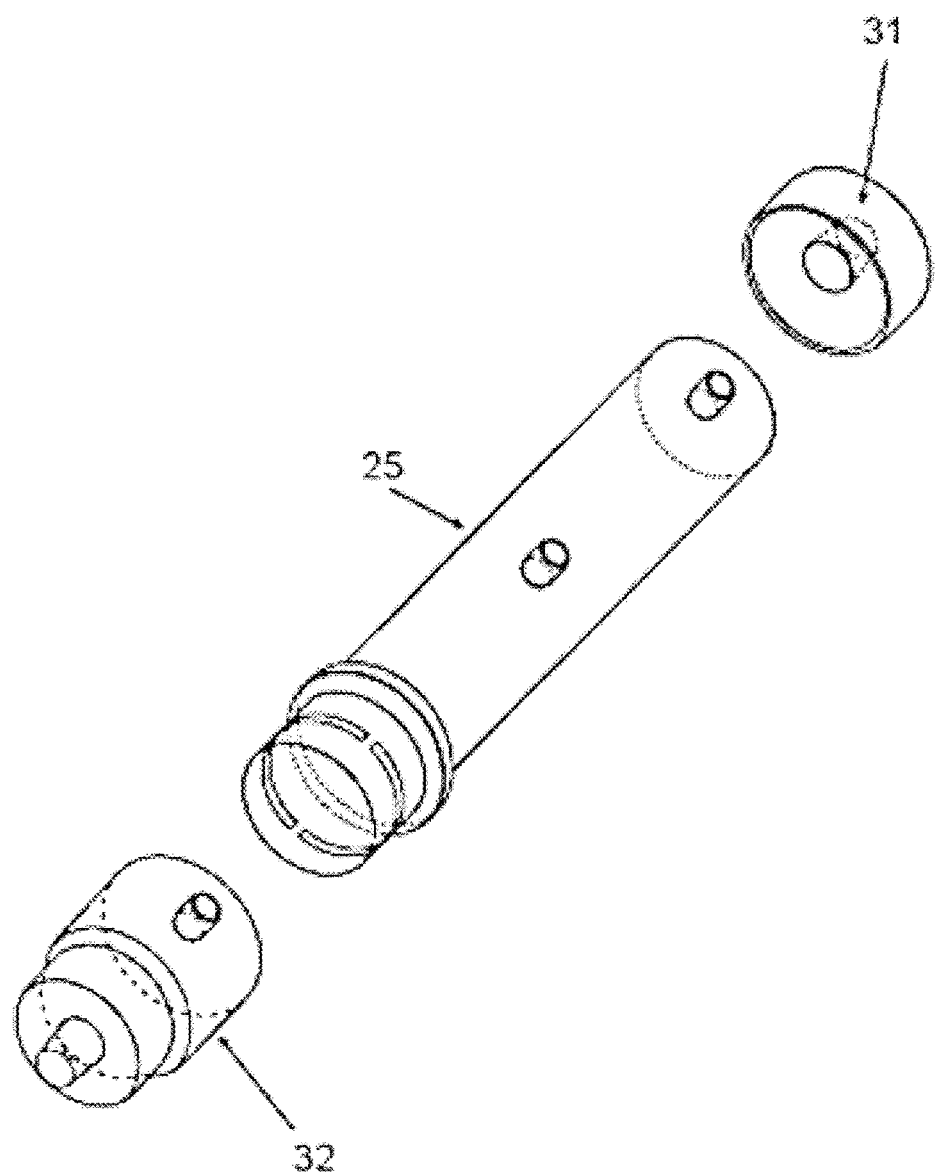
FIG. 22 is an exploded view of the cartridge of FIGS. 21A-21C.

Referring now to FIGS. 21-22, there is shown an embodiment of the invention in which the filter housing 25 contains port 34 and port 35 and also contains an intermediate port 36. Port 36 may be in fluid communication with the interior of housing 25, which contains the inter fiber space. Port 36 may be located midway between port 34 and port 35, as illustrated, or more generally could be located anywhere between port 34 and port 35 such as closer to one end port than to the other end port. For example, if intermediate port 36 is located closer to the inlet end, that might be helpful in promoting mixing in the inter fiber space of the fiber bundle. Intermediate port 36 is shown as having the same circumferential location as port 34 and port 35, but more generally any port 34, 35, 36 could have any circumferential angular location relative to any other port 34, 35, 36. It is further possible that near intermediate port 36, some sort of distributor could be provided to carry supplied liquid around the circumference of housing 25 in order to better distribute the supplied liquid into the inter fiber space. It can also be understood that if port 36 is closed off or capped during treatment, this filter cartridge can also be used as any conventional filter cartridge is used for hemodialysis or for other procedures.

Such a filter cartridge can be used for mid-dilution hemodiafiltration (HDF). Having an additional port 36 somewhere along the length of the housing 25 between ports 34 and 35 allows the filter to be used for HDF. The port 36 may be used as the supply port for supplying substitution solution at around the middle of the fiber bundle. Using the filter with the illustrated intermediate port 36, with appropriate system configurations, it would also be possible to perform still other hemofiltration and hemodiafiltration therapies.

Figure 23:
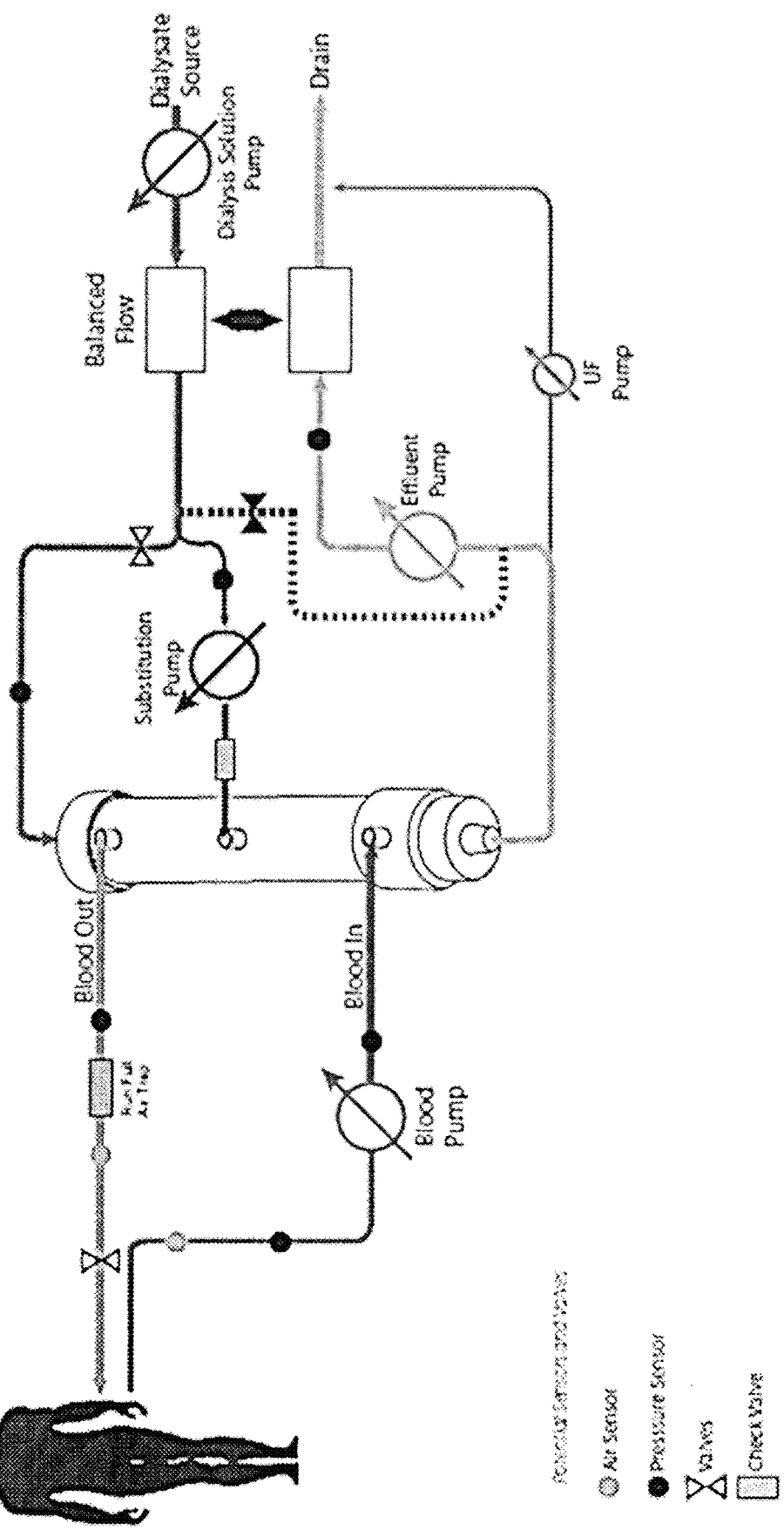
FIG. 23 shows a system for performing mid-dilution hemodiafiltration, using a volumetric flow balancing system.
Figure 24:
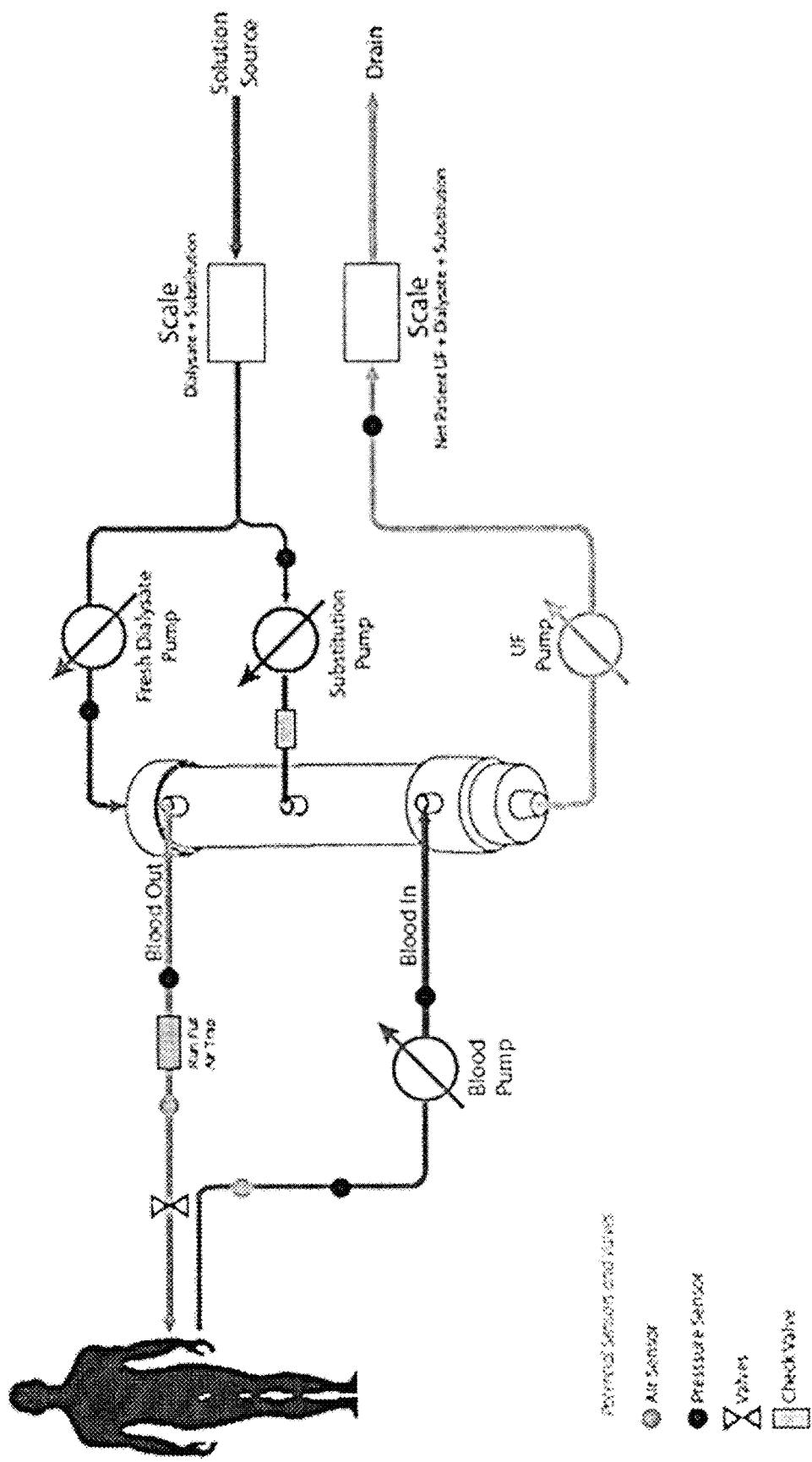
FIG. 24 shows a system for performing mid-dilution hemodiafiltration, using scales for flow balancing.

FIG. 23 and FIG. 24 show a system showing the apparatus of FIGS. 21-22 used with the mid dilution HDF configuration. It is to be understood that the dialysis solution and substitution fluid can be obtained from bagged solutions or can be solutions prepared by the dialysis equipment at the point of use. This includes substitution solution, which can be a bagged sterile solution or can be an on-line HDF (OLHDF) solution that is generated at the point of care by filtering the dialysis solution using some ultrafiltration steps. It can also be noted that FIGS. 23 and 24 show a check valve included on the incoming substitution pump line in the flow path of intermediate port 36 to prevent any egress of the blood into the substitution fluid supply line.

FIG. 23 and FIG. 24 show configurations of the filter as part of a system for mid dilution HDF. FIG. 23 shows a typical volumetric balancing system configuration such as would be used for On-Line Hemodiafiltration for chronic treatments (OLHDF). For such a purpose, this system should use injectable quality solution. The total volumes of substitution solution and dialysis solution may be controlled with balance chambers or other balancing means. The effluent dialysate may be balanced to ensure that a volume of fluid equal to the total of the introduced dialysis solution and the introduced substitution solution is removed from the filter. Because these volumes balance each other, whatever volume of fluid is removed by the UF pump (which is illustrated in FIG. 23 as a side path that goes around the balance chamber) is equivalent to the desired net volume of fluid removed from the patient.

It is believed that mid-dilution hemodiafiltration may approximate hemodiafiltration with pre/post dilution, although it is not wished to be limited to this explanation. A benefit of mid-dilution HDF is to provide clearances similar to post dilution HDF while lowering the clogging potential of the filter, because the blood does not become as concentrated as it would be at the point just before the fluid addition in post-dilution. However, it is not wished to be limited to this explanation.

FIG. 24 shows another configuration of mid dilution HDF, such as could be used for continuous renal replacement therapy (CRRT) for acute renal patients. FIG. 24 differs from FIG. 23 in that FIG. 24 uses scales instead of the volumetric balancing system of FIG. 23. It would be understood by one skilled in the art that there might be separate scales that control each of the pumps, even though for simplicity of illustration only one scale is shown for fresh solution and one scale for effluent solution. Drug registered solutions may be used for both the substitution and dialysis solution. Typically in CRRT, drug registered solutions in bags may be used to provide the solution source. If the system has separate scales for substitution solution and for dialysis solution, then device registered dialysis solution can be used for dialysate and drug registered substitution solution can be used for directly infusing into the blood. (This is not illustrated.) In addition, solution sources such as the small batch fluid systems such as the NxStage Pureflow could be used with this configuration.

Method of Manufacturing

With continued reference to FIGS. 1-7, a method for manufacturing cartridge 12 may be described. FIGS. 1-2 pertain to a cartridge for use in hemodialysis, and FIGS. 4-7 pertain to a cartridge for use in ultrafiltration or hemofiltration. A hemodialysis cartridge has a total of four ports, two of which are used for blood flow and two of which are used for dialysate flow. A cartridge that is used for ultrafiltration has three ports, i. e., two ports that are used for blood flow, and one port that is used for ultrafiltrate flow.

First, the semi-permeable hollow fibers may be manufactured. It may be desirable for the fibers to be manufactured so that they have smooth outside surfaces (because the outside surfaces face the blood) and have structure that performs sieving of solutes during therapy as normally accepted in hemodialysis. Fibers used can be either wavy or straight. The number of fibers and the dimensions of the fibers and the housing components may be chosen to provide a desired porosity fraction for the inter fiber space, as well as a desired mass transfer that is needed for effective clearance of solutes. All of these considerations are discussed elsewhere herein and in U.S. patent application Ser. No. 14/671,186, the entire disclosure of which is incorporated herein by reference.

A tubular component for housing 25 may be created by any appropriate manufacturing method such as extrusion or injection molding. Slots or openings 41 may be created in the tubular component housing 25, near an end of housing 25, via a side pull in the mold or by a secondary manufacturing operation, or by a combination of these, or by any other method. If necessary, flash or sharp features may be removed in a separate step or process. Cap 32 and cap 31 may be manufactured by a molding operation or by a combination of molding and machining. Cap 32 and cap 31 may be either identical to each other or different from each other.

The fiber bundle may then be inserted into the tubular component of housing 25. After insertion of the fibers 27, the fibers 27 may be potted on both ends with polyurethane or similar material to secure the fibers appropriately in the housing so as to form barrier 42. The potting may be done using centrifugal or similar potting techniques as would be familiar to one skilled in the art. Then, at whatever end or ends of the cartridge at which it is desired to establish fluid connection with the fiber lumens, the potting compound may be cut to expose the open fiber ends and may be polished to remove any debris left on the surface of the potting compound.

For a cartridge that is intended for ultrafiltration, on the distal end of the filter assembly, the fiber 27 may be cut and polished to open the fiber bundle for the ultrafiltrate to exit the filter assembly via UF out port 34 in cap 31. On the proximal end, the fibers 27 may end within the potting and may remain closed, because the illustrated application is ultrafiltration. For ultrafiltration, it is sufficient to have fluid communication with the fiber lumen at only one end of the fiber, and the other end may be anchored in the potting. As may be desired, even at the end where the fibers end in the potting, the potting may be polished so as to eliminate rough edges. A pressure decay test may be performed to ensure the integrity of the bundle during the appropriate step in the manufacturing process.

For a corresponding cartridge that is intended for use in hemodialysis, the potting at both ends may be cut to expose the open ends of fibers 27 at both ends of the fibers, and the potting may be polished to remove any debris left on the surface of the potting compound.

After either of these manufacturing operations, cap 32 may be solvent bonded or ultrasonically welded to tubular component or housing 25 to complete the assembly of that end of the filter cartridge. Alternatively, if appropriate for the design, cap 32 could be screwed on to the housing 25. This embodiment may also contain an elastomeric seal at an appropriate place. For ease of illustration, this embodiment, with its threads and seal, is not shown in the illustration.

Similarly, end cap 31 may be securely attached to the housing 25 by ultrasonic welding, solvent bonding, screwing on, or some other methodology known to one skilled in the art. The assembly may be tested, packaged and sterilized.

In general, it can be appreciated that any of the described cartridges may have certain features that are especially pertinent to the existence of blood flow on the outside of the fibers. Of course, blood flow on the outside of the hollow fibers is a feature opposite that of most conventional filters for the processing of blood in a variety of therapies. Such pertinent features have been described in U.S. patent application Ser. No. 14/671,186, the entire disclosure of which is incorporated herein by reference. Some of these features pertain to achieving uniformity of flow distribution in the inter fiber space. Some of these features pertain to compatibility of the fiber external surface with blood. Embodiments of the invention could comprise an air bleed in communication with the inter fiber space, at appropriate location(s), to prevent formation or entrapment of air bubbles, especially during the priming step. In embodiments of the invention, the hollow fibers could be either straight or wavy. The fiber bundle could be a mixture of some straight fibers and some wavy fibers. Spacer fibers, either solid or yarns, could also be included in the fiber bundle. In embodiments of the invention, a distributor such as an orbital distributor may be used at either end or at both ends of the cartridge, in order to improve the uniformity of flow in the inter fiber space. Similarly, any of the embodiments described or illustrated could be used together with fanning of the fibers at either end or at both ends of the cartridge, in order to increase the local porosity near the end(s) of the cartridge and thereby improve the uniformity of flow in the inter fiber space. Fanning of the fibers near the ends of the cartridge can be used in combination with any other feature described herein. Corners and edges that are exposed to blood may be rounded or smoothed as desired. Coatings, such as on the housing interior or the fibers, could be applied on either the entirety of such surface, or only on portions of such surface. The hollow fibers may have exteriors that are smooth, such as having an outside surface that has a root-mean square roughness of less than 100 nanometers. Fibers may possibly have rough interiors, although in embodiments of the invention it is also possible to use so-called symmetric membrane hollow fibers, which are smooth on both their interiors and their exteriors. Fibers may have exteriors that are hydrophilic and hemocompatible. The porosity of the fiber bundle may be in the range of 40% to 70%, or more specifically between 50% and 62%. The fiber bundle should fill the entire space of the selected housing, and should be uniformly spaced without propensity to channeling during processing or treatment.

Cartridges Having Fibers that are Grouped into Sub-Groups

Referring now to FIGS. 25A-26A, in embodiments of the invention, there is illustrated a cartridge 12 that comprises a housing, which may be tubular, and which contains therein a plurality of fibers. At least some of the fibers may be hollow and may be made of semi-permeable membranes and may have respective fiber lumens and fiber exteriors. The fibers may be potted into a first barrier 42 at one end of the fibers and may be potted into a second barrier 42 at an opposed end of the fibers. The fibers may be grouped into a first fiber group and a second fiber group, with the groups being defined at least partially by the fluid connections thereto.

At a first end of the cartridge, there may be a first-end header having a first-end header first chamber that is in fluid communication with the lumens of the fibers of the first fiber group and a first-end header second chamber that is in fluid communication with the lumens of the fibers in the second fiber group. At a second end of the cartridge, there may be a second-end header having a second-end header first chamber that is in fluid communication with the lumens of at least some of the fibers of the first fiber group and a second-end header second chamber that is in fluid communication with the lumens of at least some of the fibers of the second fiber group.

The first-end header first chamber and the first-end header second chamber may be separated from each other at least in part by a first-end separator that contacts the first-end barrier 42. The second-end header first chamber and the second-end header second chamber may be separated from each other at least in part by a second-end separator that contacts the second-end barrier 42.

Figure 25A:
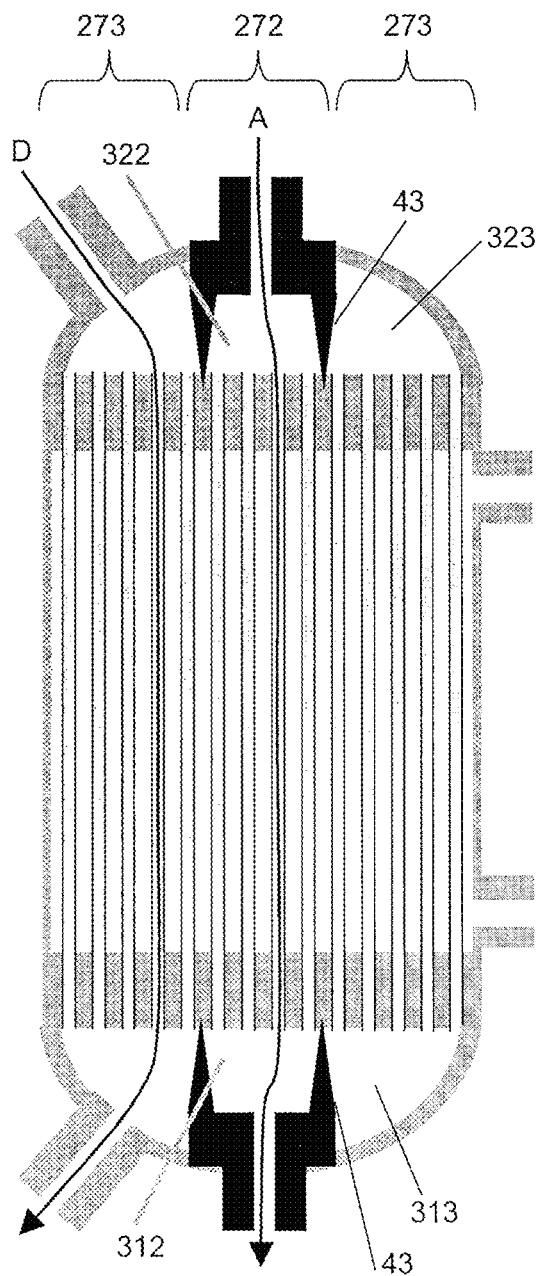
FIG. 25A shows a cross-section of a cartridge having two fiber groups and having flow through both fiber groups, in which the ends of the fiber groups are perfectly aligned with each other.
Figure 25B:
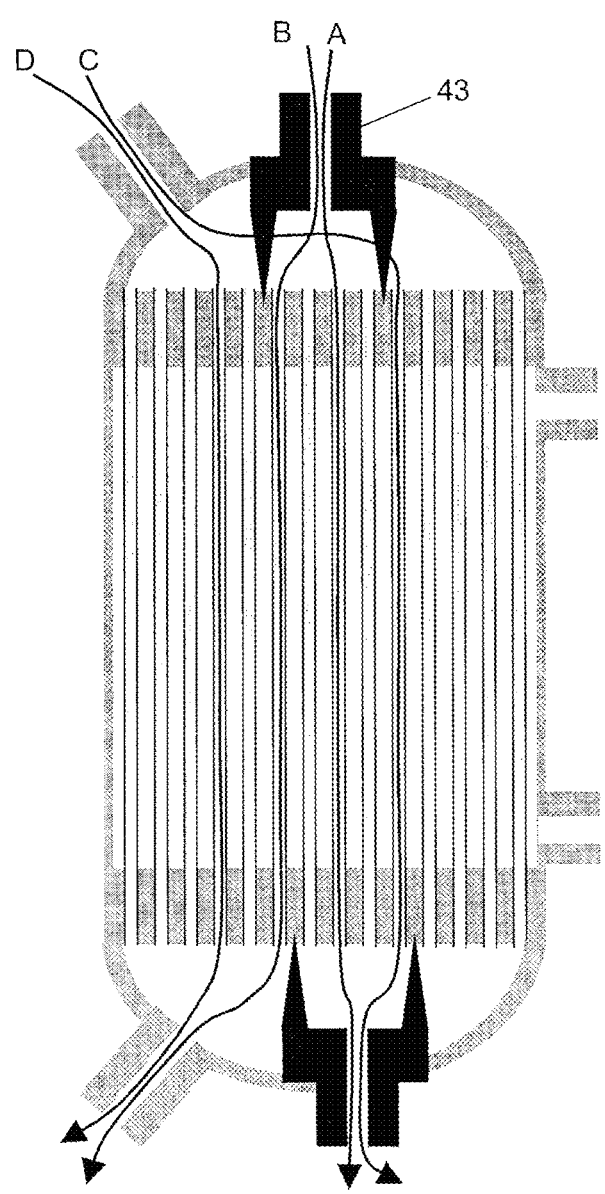
FIG. 25B shows a similar cross-section, but in which the ends of the fiber groups are not perfectly matched with each other.

Referring now to FIG. 25A, 25B and FIGS. 26A-1, 26A-2, and 26A-3, there is shown, in an embodiment of the invention, a filter that has two groups of fibers 27 and provides for the distribution of fluid to fibers according to individual group. With reference to FIGS. 25A and 25B, it is illustrated that both fiber bundles are flow-through, i. e., they have open connections at both ends. As illustrated, at one end of the cartridge, both fiber bundles have flow entrances, and at the other end of the cartridge, both fiber bundles have flow exits. However, it can be understood that other configurations are also possible if desired, and some other configurations are discussed elsewhere herein.

The use of multiple groups of fibers 27 provides the ability to have different groups of fibers perform differently, in terms of clearance, ultrafiltration, fluid addition or extraction etc., within the same cartridge. For example, there may be introduction of substitution solution somewhat continuously along the length of the filter. It is possible for ultrafiltration to occur somewhat continuously along the length of the filter. Pressure profiles with respect to the length of the fiber may be different for the two fiber groups. The existence of different pressure profiles in the different groups of fibers can affect such phenomena as dialysis and internal filtration.

As illustrated, it may be understood that the same solution such as dialysate may be supplied to both fiber groups, but it is possible that the supply pressure may be different, or the discharge pressure may be different, or the flowrate or mass flux may be different, among the fiber groups. In discussion of hemodialysis that involves internal filtration, in which one portion along the lengthwise direction of the cartridge exhibits forward filtration and another portion along the lengthwise direction of the cartridge exhibits backfiltration, the portions of the fibers that exhibit forward filtration and the portions of the fibers that exhibit backfiltration may be different for one fiber group as compared to another fiber group.

Referring now to FIG. 25A and FIGS. 26A-1, 26A-2, and 26A-3, there may be provided an inlet end cap 32. At the inlet header that adjoins the cut ends of the fibers at barrier 42, there may be provided a header separator 43 that separates the bundle of fibers 27 into a central fiber group 272 and an outer fiber group 273. As illustrated, the header separator 43 is axisymmetric and coaxial with the axis of the overall cartridge 12. Furthermore there may be provided a central fluid supply connection that is in communication with and supplies fluid to the central fiber group, and an outer fluid supply connection that is in communication with and supplies fluid to the outer fiber group. In order to accomplish this dividing or grouping of the fibers, the header separator 43 may comprise a sharp edge that may press against the barrier 42 (e. g., potting resin) to form a seal. The sharp edge, which may resemble a knife-edge, may form a circular perimeter that is concentric with other axisymmetric features of the end cap and the housing of the cartridge 12. If the inlet end cap screws onto the body of the housing with helical threads, the advancement of those threads may also urge the header separator 43 against the barrier 42 in order to form the seal against the barrier 42. As discussed here, the illustrated sub-groups of the fibers are a central group and an outer group, with the separator 43 being an axisymmetric shaped structure. However, it can be appreciated that other arrangements of sub-groups are possible, such as side-by-side groups. Furthermore, the separator 43 does not have to be an axisymmetric shaped structure as described; it could, alternatively, be a straight-line shape, or other shape, and the separator could be urged against the barrier by something other than the threads of end cap engagement.

In embodiments of the invention, the direction of flow in the lumens of the fibers in one sub-group may be the same as the direction of flow in the lumens of the fibers in the other sub-group.

In connection with the creation of sub-groups of fibers, it is appropriate to discuss details of the positioning of fibers 27 in the barriers 42. It may be expected that the fibers 27 are potted in the barrier 42 in locations that are distributed fairly uniformly over the cross-section of the barrier 42, but with some degree of randomness, especially at a size scale of the order of a fiber diameter. This randomness may be especially apparent with wavy fibers, although it is not wished to be limited to this explanation. Because of this small-scale randomness, and because a typical dialyzer contains thousands of fibers 27, it is not known exactly which fibers or how many fibers fall on which side of the separator 43 in the supply header 31 so as to be assigned to a particular fiber group such as the central fiber group 272. Similarly, it is not known exactly which fibers or how many fibers fall on the other side of the separator 43 so as to be assigned to another fiber group such as the outer fiber group 273. Related to this, again because of the unpredictability of exactly where individual fibers are located, it also is not known if this partitioning of the fibers 27 is perfectly reproducible down to an exact number of fibers, from one dialyzer to another dialyzer during manufacture. Furthermore, where the separator 43 presses against the barrier 42 to form a seal, even though the separator 43 may be sharp-tipped, it is possible that the separator 43 may effectively close off a small number of fibers by covering or pressing on their exposed ends, and so there might even be a small number of such fibers that do not belong to either group of fibers and substantially do not participate by carrying any fluid flow.

With continued reference to FIG. 25A, at the downstream end of the fibers 27, the fibers 27 may be potted in a second barrier 42. There may be an outlet header separator 43 that separates the outlet header into two regions 312, 313. As illustrated in FIG. 25A, a central region 312 may at least approximately establish fluid communication between the central fiber group 272 and the central fluid discharge connection. Another region 313, which may be annular in shape, may at least approximately establish fluid communication between the outer fiber group 273 and the outer fluid discharge connection. As part of establishing fluid communication with the central fiber group 272 and with the outer fiber group 273, there may be an outlet header separator 43 that may be sharp-edged and circular and may resemble the inlet header separator 43. It is possible that at the outlet header, the regions 272, 273 on the two sides of the outlet header separator 43 may be in fluid communication with respective exit flow connectors.

It is alternatively possible that one of the fiber groups may be blocked by having a cap applied to its port on the exterior of the cartridge. It is alternatively possible, as discussed elsewhere herein, that one of the fiber groups may be blocked at its downstream end inside the cartridge, such as by a stopper or other suitable device or mechanism.

With continued reference to FIG. 25A-25B, it is desirable that fibers of the central fiber group 272 connect to the central region 312 of the discharge header, and the fibers of the outer fiber group 273 connect to the outer region 313 of the discharge header, so as to maintain the distinct identities of the two fiber groups and the two fluid streams. It is likely that in any given dialyzer, most fibers do so. However, it is not guaranteed that every fiber will achieve such an appropriate connection, especially if the manufacturing processes are typical of those of conventional dialyzers. This is because of the possible local randomness or uncertainty of fiber location within the fiber bundle 27, as already discussed. Therefore, it is useful to consider the complete range of possibilities as far as the combinations of locations of ends of fibers at one end of the cartridge and at the other end of the cartridge.

With regard more specifically to details of physical construction, there are certain physical embodiments that can result in certain of these flowpaths. This will be explained here for the situation in which both fiber bundles have flow through them. For example, as illustrated in FIG. 25A, in an ideal situation the central fiber bundle completely connects to the central discharge region, and the outer fiber bundle completely connects to the outer discharge region. A non-ideal situation is illustrated in FIG. 25B. This is shown as the exit discharge separator being misplaced, although in reality it might be individual fibers that are misplaced.

Logically speaking, and as illustrated in FIGS. 25A-25B, there are the following four possible types of fibers and connections:

A. Fiber supplied by central supply, discharges at central discharge (Flowpath A)

B. Fiber supplied by central supply, discharges at outer discharge (Flowpath B)

C. Fiber supplied by outer supply, discharges at central discharge (Flowpath C)

D. Fiber supplied by outer supply, discharges at outer discharge (Flowpath D)

It can be appreciated that flowpaths A and D) preserve the separation of the fluids as created at the inlet header, but flowpaths B and C result in some redirection of fluid in some of the fibers.

In another embodiment of the invention, and referring now to FIG. 25C-25F, one fiber group may be closed off such as by pressing or urging a stopper against the second barrier 42 in the downstream header. The stopper may be made of a somewhat resilient material, or it may be made of a relatively hard material and may rely on the barrier 42 being somewhat resilient in order to form a seal. Although a seal by the stopper against the ends of certain fibers may be desirable for the illustrated configurations, it is not guaranteed that a perfect seal or stoppage will be formed, and it is probably not necessary that the seal or stoppage be perfect.

If one of the fiber sub-bundles is closed off at the downstream end, it is possible (as one example) that the fiber bundle that is closed off could be the central fiber bundle. If the central fiber bundle is closed off, that may be accomplished by a stopper that is at least approximately circularly shaped. As illustrated in FIGS. 25C, 25D, 25E, and 25F, the central fiber group is closed off. There are various possibilities as far as perfect or imperfect alignment of the stopper and the inlet separator.

Figure 25C:
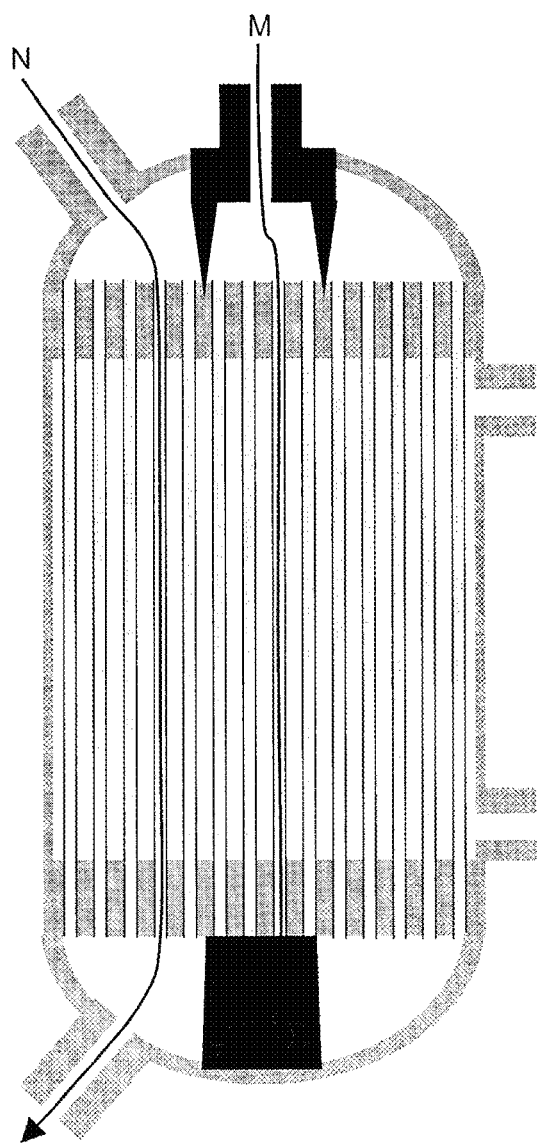
FIG. 25C shows a cross-section of a cartridge having two fiber groups and having flow through one of the fiber groups, with the other fiber group dead-ended, in which the ends of the fiber groups are perfectly aligned with each other, with the stopper blocking a central group of fibers.

Referring now to FIG. 25C, there is illustrated a situation in which the stopper and the inlet header separator 43 are aligned such that all of the fibers are perfectly aligned. All of the flow that goes into the central fiber bundle (labeled as flow M) will be blocked, as intended. All of the flow (labeled as flow N) that goes into the outer fiber bundle will flow through to the discharge header, as intended. Although what is illustrated is a stopper, it is possible that the fibers in the central fiber bundle could also be dead-ended by some other feature or manufacturing method.

Figure 25D:
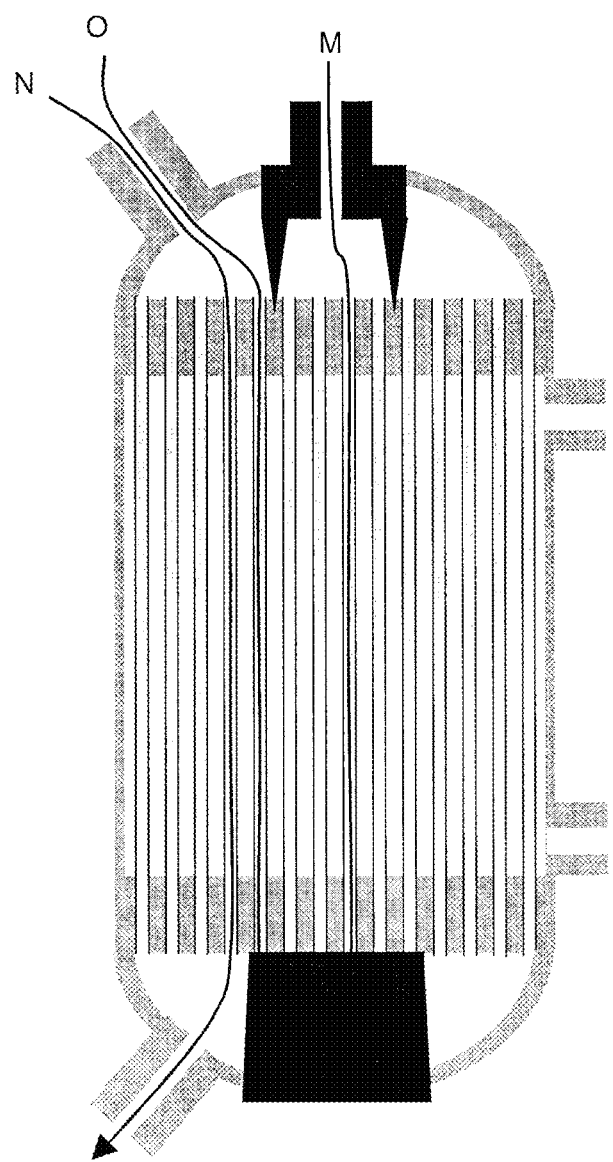
FIG. 25D shows a similar cross-section, but in which the fiber groups are slightly mismatched with each other in a first way.

Referring now to FIG. 25D, there is illustrated a form of imperfect alignment that can be thought of as the stopper 44 being too large but being concentric. In this illustrated situation, all of the central fiber bundle (labeled as flow M) is blocked as intended, and some of the outer fiber bundle (labeled as flow O) is blocked without that being the intent, and the remaining fibers in the outer fiber bundle (labeled as flow N) discharge to the discharge header as intended.

Figure 25E:
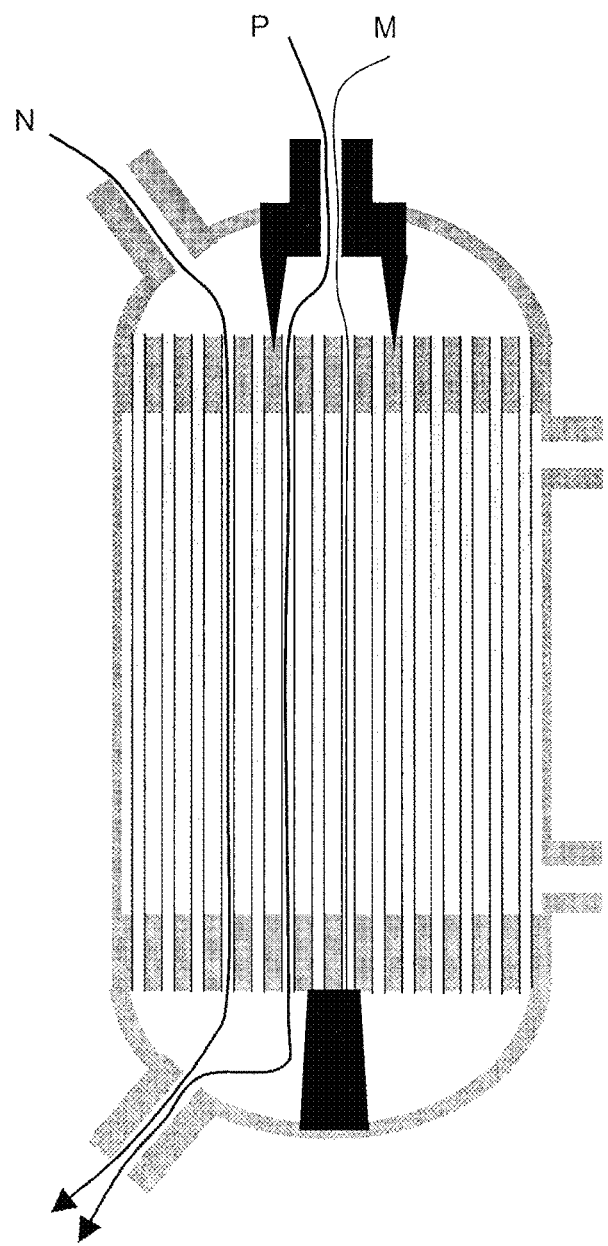
FIG. 25E shows a similar cross-section, but in which the fiber groups are slightly mismatched with each other in a second way.

Referring now to FIG. 25E, there is illustrated a form of imperfect alignment that can be thought of as the stopper 44 being too small but being appropriately located (concentric). In the illustrated situation, the fibers in the outer fiber bundle (labeled as flow N) all discharge to the discharge header as intended. Some of the fibers in the central fiber bundle may be blocked as intended (labeled as flow M), while other fibers in the central fiber bundle (labeled as flow P) discharge to the discharge header without that having been the intent.

Figure 25F:
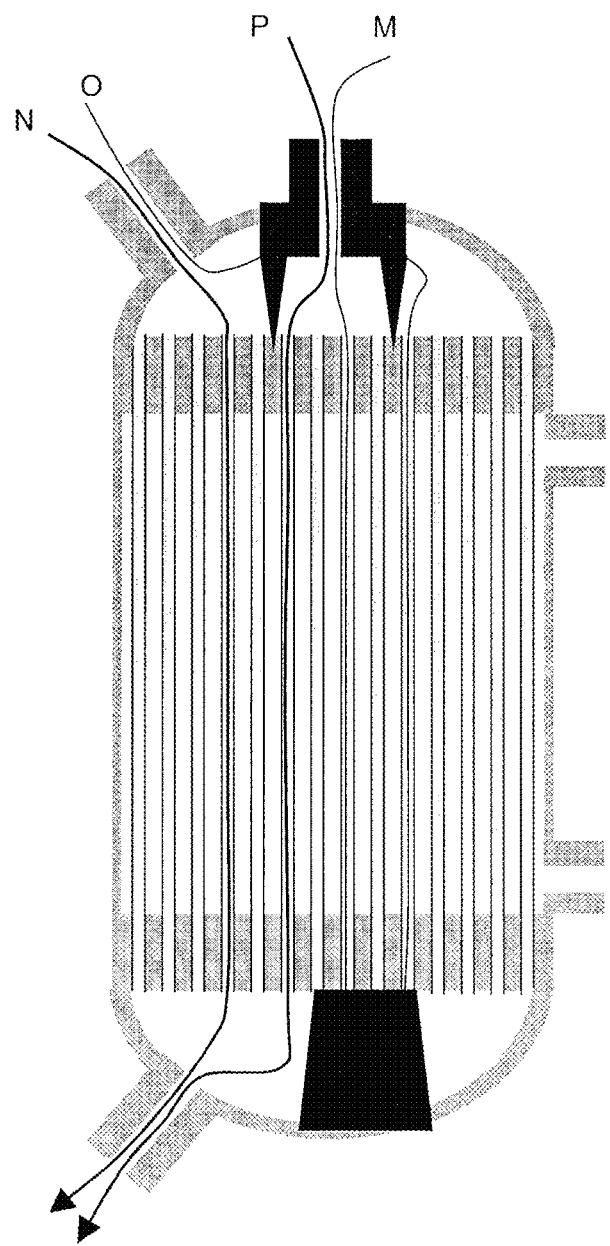
FIG. 25F shows a similar cross-section, but in which the fiber groups are slightly mismatched with each other in a third way.

Referring now to FIG. 25F, there is illustrated a form of imperfect alignment that can be thought of as the stopper 44 being offset. In this illustrated situation, some of the flow through fibers in the central fiber bundle (labeled as flow M) is blocked as intended, and some of the flow through fibers in the central fiber bundle flows (labeled as flow P) to the discharge header without that being intended. Also, some of the flow to the outer fiber bundle flows to the discharge header as intended (labeled as flow N), and some of the outer fiber bundle is blocked (labeled as flow O) without that being the intended.

Despite the apparent uncertainty in flow patterns that may be introduced by the possible interconnection of fibers among fiber groups, it also may be appreciated that in embodiments of the invention, the consequences of such mixing might not be unduly detrimental, especially if only a small number of fibers are interconnected as described. A consideration in this is that even if there are some "interconnected" or "redirected" fibers, it can be appreciated that the fluid supplied to the central fiber bundle and the fluid supplied to the outer fiber bundle may be substantially the same fluid in terms of the composition of the fluid. What is different between the respective fluids may be the pressure at which the respective fluids are supplied. Also, especially if one of the fluid paths is dead-ended, what is different can be the purpose of the respective fluids.

It is possible that the fibers in the central fiber bundle and the fibers in the outer fiber bundle may be physically identical to each other, such as being manufactured by the same processes. However, this is not required. It also is possible that the fibers in the central bundle could be physically different from the fibers in the outer bundle. For example, the ultrafiltration coefficients of the respective fiber types could be different, or there could be differences in the respective pore sizes or pore size distributions or the Molecular Weight Cutoffs. Even the materials of the respective fiber types could be different if desired.

If physical differences do exist among fibers in certain groups, the manufacturing processes may be such as to physically locate or segregate one type of fiber in the intended space of the central fiber bundle and to physically locate or segregate the other type of fiber in the intended space of the outer fiber bundle. This can include physical positioning of fibers when a loose bundle of fibers is assembled before insertion into the tube of the housing. Again, it may be appreciated that it is not possible to control placement of every fiber in the barriers to the extent of determining the exact number of fibers in each group and exactly which fibers are in each group when the seal bears against the barrier. However, it may be true, just as in the case of perfectly-routed fibers, that the cartridge may still work substantially as desired even if a small number of fibers are in the wrong group.

Figure 25G:
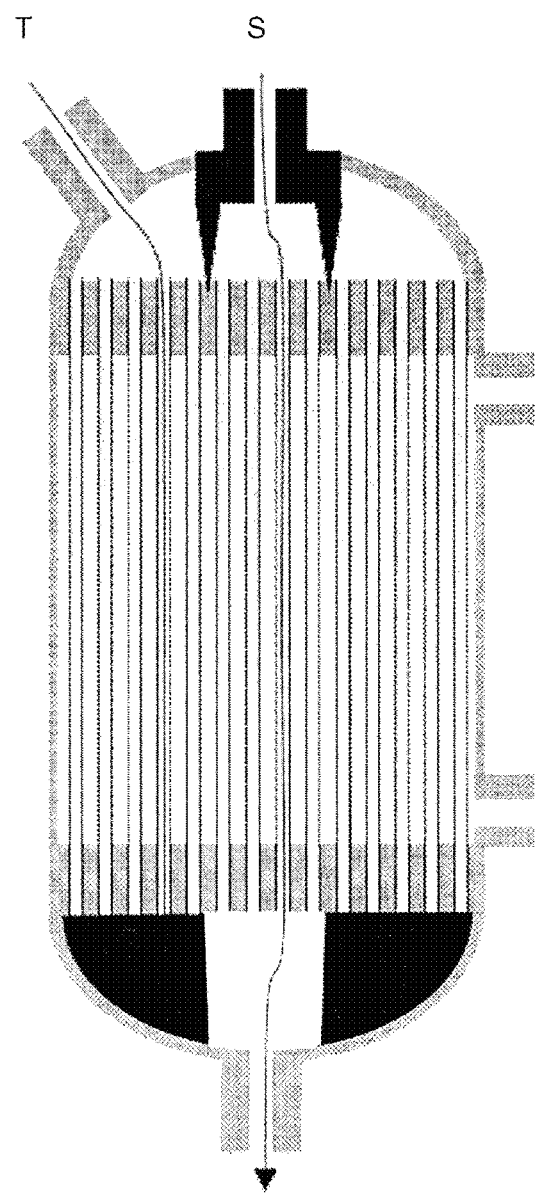
FIG. 25G shows a cross-section of a cartridge having two fiber groups and having flow through one of the fiber groups, with the other fiber group dead-ended, in which the ends of the fiber groups are perfectly aligned with each other, with the stopper having an annular shape and blocking an outer group of fibers.

It can also be appreciated that although an embodiment is illustrated in FIG. 25C such that the central fibers are stoppered and the outer fibers have through-flow, the opposite is also possible. Referring now to FIG. 25G, in such a situation, the stopper could be an annular-shaped stopper that closes off the group of outer fibers, while the central fibers have both ends open. The flow labeled as flow S flows through, while the flow labeled as T is dead-ended. This is also illustrated in FIG. 29.

Of course, there is complete design freedom as far as deciding the proportion of how many fibers and how much cross-sectional area of the fiber bundle is assigned to the central fiber region, and how many fibers and how much cross-sectional area of the fiber bundle is assigned to the outer fiber region.

Any of these embodiments that have a group of fibers that are dead-ended or stoppered, may be used to provide substitution fluid by dead-end ultrafiltration in a manner that is distributed along the length of the cartridge. This may have a somewhat similar effect as post-dilution, except that the addition of substitution fluid occurs further upstream and more gradually. This may have a somewhat similar effect as pre-dilution, except that the addition of substitution fluid occurs further downstream and more gradually. This may have a somewhat similar effect as mid-dilution, except that the addition of substitution fluid occurs more gradually.

Figure 25H:
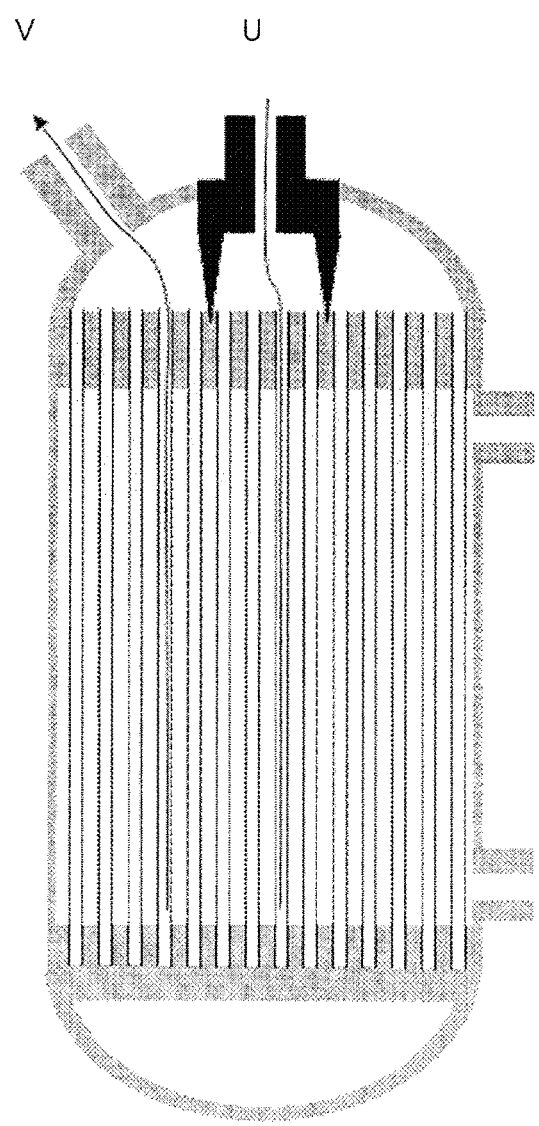
FIG. 25H shows a cross-section of a cartridge having two fiber groups defined by a separator in a supply header, and having all fibers dead-end in the second barrier.

Referring now to FIG. 25H, there is shown yet another embodiment of the invention. This embodiment is suitable for hemofiltration with internal substitution. In this embodiment the ends of the fibers at the lower end of the illustration may be potted in second barrier 42 such that all of the fibers are dead-ended in second barrier 42. At first barrier 42, the fibers may pass through first barrier 42. In this embodiment, similarly to what is shown in FIG. 25A and other Figures, there may be provided an inlet header separator 43 that separates the fiber bundle 27 into a central fiber group 272 and an outer fiber group 273. As illustrated, the inlet header separator 43 is axisymmetric and coaxial with the axis of the overall cartridge 12, although other configurations are also possible. As a result, a fluid connection to the central fiber group 272 can be connected to one part of the system to perform one function, and another fluid connection to the outer fiber group 273 can be connected to another part of the system to perform another function. As in other embodiments illustrated herein, blood may flow on the outsides of the fibers 27. For example, one of the fiber groups can be connected to a fluid supply that supplies substitution fluid (labeled Flowpath U in FIG. 25H), while the other of the fiber groups can be connected to a part of the system that provides removal of ultrafiltrate so that the fibers in that fiber group perform ultrafiltration or hemofiltration (or, more generally, filtration), which is labeled flowpath V in FIG. 25H. Such a cartridge can be used to perform ultrafiltration and addition of substitution fluid simultaneously, in a manner such that both the ultrafiltration and the addition of substitution fluid are distributed along the length of the cartridge. In such a situation, while blood is flowing along the length of the cartridge, and spaced out over the length of the cartridge, some of the fibers are gradually removing ultrafiltrate from the blood, which includes removing certain toxins, while at the same time and also spaced out over the length of the cartridge, others of the fibers are gradually adding substitution fluid to at least partially replace the removed ultrafiltrate. This may be done to achieve good mixing in the inter fiber space.

Figure 25I:
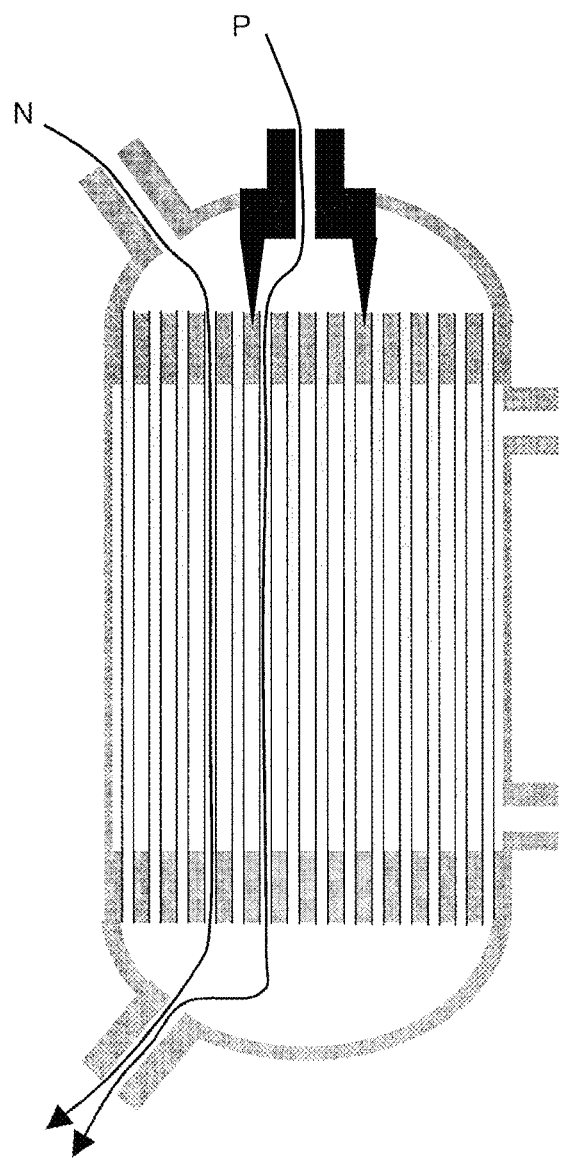
FIG. 25I shows a cross-section of a cartridge having two fiber groups defined by a separator in a supply header, with both fiber groups exiting into a common header.

Referring now to FIG. 25I, there is illustrated a situation in which a cartridge having two fiber groups defined by a separator in a supply header, with the fiber groups exiting into a common header. Such a situation could be used to perform hemodialysis, but with a greater degree of adjustability because of the presence of two different fiber groups that have separately controlled inlet pressures or flowrates. For example, in the situation of high flux hemodialysis, in which there is a internal filtration, somewhere between the two ends of the cartridge there is a crossover point at which there is a change in the direction of convective transfer across the membrane, i. e., convective mass flux changes from being outward across the membrane to inward across the membrane or vice versa. In the situation illustrated in FIG. 25I, there are two fiber groups each having its own respective crossover point that can be separately adjusted by adjusting the pressure profile of the dialysate inside the lumens of the fibers of the particular fiber group. This situation may provide possibilities for fine-tuning the performance of the dialyzer. It would even be possible, with appropriate plumbing, to provide dialysate flow that in one fiber group is counterflow and in the other fiber group is co-flow.

Figure 25J:
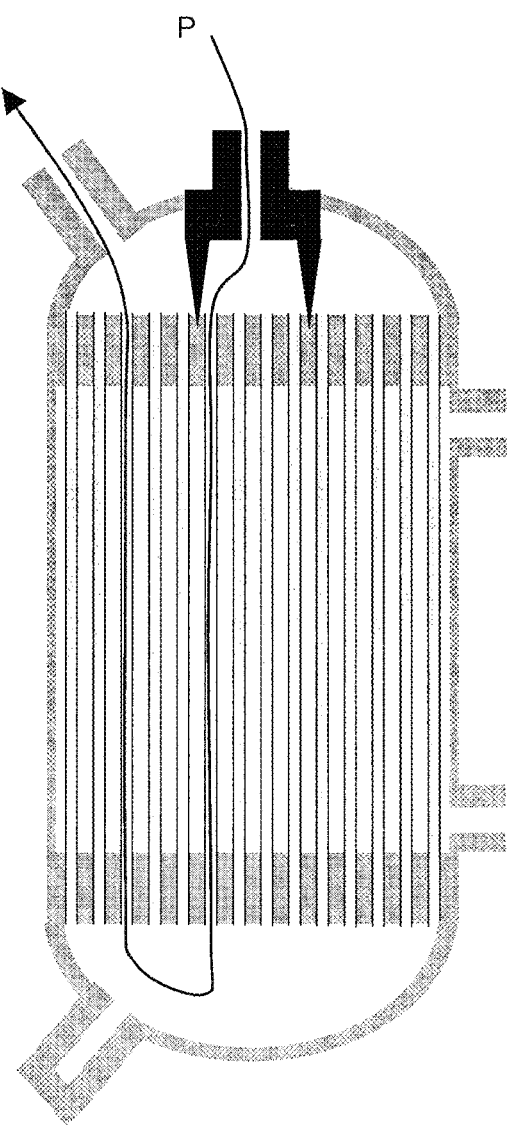
FIG. 25J shows a cross-section of a cartridge having two fiber groups defined by a separator in a supply header, in which dialysate enters at a header, flows inside the lumens of one fiber group, turns around at the other header, returns through the lumens of the other fiber group, and exits through the first header.

Referring now to FIG. 25J, in an embodiment of the invention there may be provided a cartridge having a fiber bundle having a first fiber group and a second fiber group, both of which carry dialysate. The fibers in one fiber group may carry dialysate in a first direction along the length of the cartridge and the fibers in the other group may carry the dialysate in a return path through the fibers in the second fiber group. In one header, there may be an appropriate compartmentalization to separate the two fiber groups. In the opposite header, the two fiber groups may be in fluid communication with each other allowing the dialysate flow to turn around. Thus, dialysate may enter a header and exit from another part of the same header. The blood may flow along the length of the housing from a blood inlet port to a blood outlet port. The blood that interacts with one fiber group may experience dialysis in a counterflow arrangement with that fiber group, in which the blood and the dialysate flow in opposite directions, while the blood that interacts with the other fiber group may experience a co-flow arrangement, in which the blood and the dialysate flow in the same direction. This situation also may provide possibilities for fine-tuning the performance of the dialyzer. It is illustrated in FIG. 25J that the dialysate entrance to the header is associated with the central fiber group and the dialysate exit is associated with the outer fiber group, but of course the opposite is possible also.

In general, referring to FIGS. 25C-25J, an advantage of a situation of internal substitution is that the substitution fluid is introduced into the blood distributed over space along the lengthwise direction of flow. Also, the substitution solution is introduced at the same time as other substance removal from the blood is taking place through ultrafiltration or dialysis. Another advantage is that although the cartridge is designed somewhat differently, there is no additional required component, such as a filter for producing substitution fluid, that requires separate handling and sterilization and purchase. Also it is not necessary to purchase pre-sterilized substitution fluid. Another advantage is that having some exiting flow from the downstream bundle that otherwise would be used for providing substitution solution allows those fibers and their associated surface area to be available for clearance such as diffusive mass transfer of small molecules.

An advantage of this configuration may be to provide an additional step for the removal of endotoxin and bacteria as a final polishing filter for on-line hemodiafiltration (OLHDF) without incurring additional cost. In such a system, some of the fibers of the fiber bundle serve as the second-stage filter to produce infusion fluid after a first-stage filter has already been used somewhere upstream in the preparation of the dialysate. During the manufacturing of the cartridge, the membrane is pressure checked for integrity. Nevertheless, because this final filtration step is part of the hemodiafilter, there is no additional cost for providing a substitution fluid filter in the form of some of the fibers in the cartridge. Another advantage may be that the substitution solution flows down the entire length of the filter, being added to the blood gradually over some distance. This addresses the pre dilution problem of less effective use of substitution solution, and addresses the post dilution problem of incurring increased risk of extracorporeal circuit clotting. It also may provide better distribution of the added fluid than the mid-dilution illustrated in FIGS. 21-24, in which fluid is added at a localized point.

Providing internal substitution fluid may be particularly effective if the fibers are wavy fibers. The presence of wavy fibers may promote mixing of the blood in the fiber space as the substitution fluid is added to the blood, so that the substitution fluid becomes mixed with blood beyond just the localized blood that is immediately adjacent to the fibers that deliver substitution fluid. A similar effect may occur with ultrafiltration. The presence of wavy fibers may promote mixing of blood that has been locally depleted of certain substances or components as a result of ultrafiltration, with blood that has not been so depleted.

On line hemodiafiltration (OLHDF) is a technique in which the solution is prepared in-situ at the point of care. The key to this technology is to have substitution solution that is sterile and non-pyrogenic. In contrast to the prepared commercial solutions, which are terminally sterilized with a representative sample tested prior to product release, OLHDF is done with an aseptic process and depends on process control. With the use of the therapy of OLHDF, it is preferred that a sterile single use filter is the last step in the process for the removal of endotoxin and bacteria. A single use filter provides an additional step to prevent patient exposure to bacteria and endotoxin. There is less chance of a filter failure because a single-use filter is not exposed to harsh chemicals and temperatures such as citric acid heat disinfection that is required to disinfect the system. However, a drawback to a single-use filter is a significant increase in cost per treatment, and additional complexity for the care provider to set up the machine, which is why many OLHDF devices do not use a single use filter. With the embodiment shown in FIGS. 25C, 25D, 25E, 25F and 26A, 26B, a portion of the fiber bundle may be used to introduce substitution solution and another portion of the fiber bundle may be used for dialysis solution. This may provide the benefits of a single-use substitution fluid filter at essentially the cost of a hemodiafilter.

With continued reference to FIGS. 26A-1, 26A-2, and 26A-3, cap 31 may have inlet port 36 for substitution solution 36 and inlet port 30 for dialysis solution respectively. Substitution inlet port 36 may form a separator 43 that may form a seal with the barrier 42 in which fibers 27 may be potted. This may provide a substitution fluid pathway 45 connecting to the central fiber group 272 in the central region of the fiber bundle. Substitution fluid may flow only through the fibers that are supplied by fluid pathway 45. The diameter of the substitution inlet port 36 can be varied depending on the amount of substitution solution desired for the therapy.

Normally an external substitution pump may control the volume of substitution solution provided. If large volumes of substitution fluid are required, increasing the diameter of port 36 and the size of internal channel 45 may increase membrane surface area of the fibers that are providing substitution fluid. In cap 32, stopper 44 blocks the ends of fibers that are in the central fiber group or are associated with channel 45. When substitution solution is pumped into port 36, the substitution fluid may push directly through the semi-permeable membrane into the blood on the outside of the fiber bundle 27 because this is the only open path for the substitution fluid to flow, at least for the perfect alignment of fibers that is assumed and illustrated in FIGS. 26A-1, 26A-2, and 26A-3.

Blood Inlet/Dialysate Outlet Cap 32 may form a fluid pathway 47 for the effluent dialysate to exit the cartridge 12. Dialysis solution may flow through the lumens of the fibers 27 in the fiber bundle, through fluid pathway 47 and may exit at the dialysate outlet 33. The plastic cap 32 may have a separator 43 comprising a seal. When the cap 32 is assembled onto the potted fiber assembly the separator ridge 43 may form a seal with the dialysate outlet around the circumference to the edges of the barrier 42 such as polyurethane potting compound. This separator seal 43 may form two distinct chambers, one for the blood 48 and one for the dialysate 47, and may prevent the dialysate and the blood from mixing. In this configuration a blood inlet port 34 may form a sealed blood inlet chamber 48 for the blood to flow into the cartridge. The dialysate port and the blood port can in general be any type of appropriate fitting, but generally may conform to medical industry norms and standards such as "ANSI/AAMI/ISO 8637 ISO 8637:2010 Cardiovascular implants and extracorporeal systems: Hemodialysers, hemodiafilters, hemofilters and hemoconcentrators" or international equivalents to this standard. These standards call for Luer style connections for blood/substitution/dialysis solutions and/or Hansen fitting connections for dialysis solutions.

In filter housing 25, slots 41 may be provided in a portion of the circumference. The blood from the blood inlet chamber 48 may flow around substantially the entire circumference of housing 25. The 360° blood entry chamber 48 combined with the slots 41 allows the blood flow to be uniformly distributed flow on the outside of the hollow fibers. The opening slots 41 may be distributed symmetrically or uniformly around the circumference of the filter housing. This may help to distribute the blood flow uniformly on the outside of the fibers. Because the blood flows on the outside of the fibers 27, this may reduce the potential for blood clotting and may increase the relative surface area of the blood to dialysis solution. To reduce the likelihood of hemolysis, the slots 41 may be designed and manufactured so that they do not have any flash or other sharp debris from the manufacturing process, so flash or debris can be removed in a separate process if necessary. Cap 32 may be solvent bonded or ultrasonically welded to complete that end of the filter assembly. Cap 32 could be alternatively screwed on to the filter housing 25; this embodiment would also contain an elastomeric seal. For simplicity of illustration, the threads or the seal for this embodiment are not shown.

Blood may exit the filter housing via port 35. If necessary to prevent thrombus formation, the blood exit 35 can be configured similarly to the blood inlet 34, e. g. to encourage uniform distribution of the blood flow around the circumference of the housing at the blood exit. However, initial testing does not suggest that this is necessary. Dialysate inlet cap 31 may be secured in a manner similar to that of the blood inlet cap 32 at the opposite end of the fiber bundle using solvent bond, ultrasonic welding, screwing on, or similar technology.

The dialysis solution may enter the filter at port 30 in cap 31. In cap 31, channel 46 may form a conduit for dialysis solution entry into the appropriate portion of the fiber bundle (the outer fiber group, as illustrated). The dialysis solution may exit cap 32 via port 33. The dialysis solution may flow through port 30 and chamber 46 through the other parts of the fiber bundle exiting at port 33.

FIG. 268 illustrates, in an exploded view, the major components that make up the cartridge 12 of FIGS. 26A-1, 26A-2, and 26A-C. The components may generally be made of polymeric materials. The fibers are not shown, for clarity of illustrations.

It may be appreciated that in arrangements such as these, in which substitution fluid is produced inside the cartridge by isolating and dedicating some of the fibers for that purpose, the substitution solution typically comes from the dialysate, which is more convenient than the option of providing pre-sterilized substitution fluid such as in pre-sterilized bags. In arrangements such as the present arrangements, the fibers serve as the second-stage filter for the preparation of substitution fluid. It is true that even in hemodialysis that includes internal filtration, depending on the relative pressure profiles, there is some dialysate that crosses into the blood at certain locations. However, in the arrangement illustrated here, the amount of substitution fluid is larger than the amount of fluid that crosses over during hemodialysis, and the substitution fluid comes from fibers that are used only for that purpose.

FIG. 27 shows a potential system configuration for using the cartridge of FIGS. 26A-1, 26A-2, and 26A-C and FIG. 25C, in a balancing system configuration. The dialysis solution and substitution flow into the circuit is balanced with an equal amount of effluent dialysate using a balance chamber or similar means to balance flow into and out of the circuit. The dialysis solution and effluent pumps may pressurize the balance chambers or there may be provided other means to balance the flow. A substitution pump may control the flow of substitution solution into the central fiber group of the fiber bundle via port 36 (FIGS. 26A-1, 26A-2, and 26A-C) and channel 45. The fresh dialysis solution flow through the fiber bundle may be the flow out of the balance chambers minus the substitution flow that has been pumped by the substitution pump. As described in connection with FIGS. 26A-1, 26A-2, and 26A-C, the substitution fluid may flow into a portion of the fiber bundle that is closed or blocked at its downstream end. This may force the substitution fluid through the semi-permeable fibers directly into the blood. Substitution fluid could come from the source of dialysate, as illustrated, or, if desired, could come from some other source.

In another embodiment of the invention, FIG. 30 shows another simpler means for the system to accomplish hemodiafiltration using the filter shown in FIG. 25C, FIGS. 26A-1, 26A-2, and 26A-3, and FIG. 26B. In this embodiment the system is similar to the system shown in FIG. 27 with the exception that there is no substitution pump. This methodology could be used on any volumetric balancing hemodialysis machine as long as it provides ultrapure dialysis solution. The only added features beyond what is in FIG. 27 are a check valve and a split in the dialysis solution line. In this embodiment the flow rate of the substitution solution to the hemodiafilter is controlled by the fraction of the fiber bundle that is used for substitution fluid. Based on the substitution fiber volume, flow rate and pressures within the system, a fraction of the dialysis solution may go through the substitution fluid inlet and through the semi-permeable membrane into the blood. The remainder of the dialysis solution may go through the fiber bundle as dialysis solution exiting at port 33 shown in FIGS. 26A-1, 26A-2, and 26A-3, and FIG. 26B. A valve may optionally be added on the substitution solution line to enable the substitution flow to be stopped if desired.

Referring now to FIGS. 29A-C, there is shown another approach for hemodiafiltration using a principle similar to that of FIGS. 26A-1, 26A-2, and 26A-3, and FIG. 26B. This configuration shown in FIGS. 29A-C also provides substitution fluid along the entire length of the housing 25. The basic difference is that in the cartridge of FIGS. 29A-C, the substitution fluid is generated by the outer fiber bundle, in contrast to the generation of substitution fluid by the central fiber bundle as in FIGS. 26A-1, 26A-2, and 26A-3, and 26. The dialysis solution inlet cap 31 is divided into two chambers 45 and 46. Dialysis solution flows in through port 30 into chamber 46; substitution solution comes into port 36 and into chamber 45. The separator 43 such as a ridge in the dialysate inlet cap may seal the two chambers 45 and 46 from each other and may demarcate an inlet for substitution fluid on the outside circumference of the fiber bundle and an inlet for dialysis solution on the middle of the fiber bundle. At the blood inlet cap, the flow of fluid is blocked by stopper 44 at the edge of the circumference of the fiber bundle. This may cause the substitution fluid to push into the blood.

Stopper 44 as illustrated in FIG. 29 may be annular or may be a wall, in contrast to the stopper 44 of FIG. 26A-26B, which was centrally located and cylindrical. It may be noted that in both situations, stopper 44 need not individually block every fiber within its region as long as it forms a seal that prevents fluid from particular fibers from escaping.

Blood may enter the filter 12 through the blood inlet cap 32. A chamber 48 may be formed for the inlet of blood by cap 32 sealing against the barrier 42 such as the polyurethane potting compound. Slots 41 in the case allow the blood to flow into the outside of the fiber bundle 27 around the circumference of the housing 25. This may reduce the clotting that might tend to occur with a single blood entry point and may evenly distribute the blood around the external circumference of the fiber bundle 27. After flowing the length of the cartridge, blood may exit via port 35. Dialysate may exit the center of the fiber bundle in cap 32 into chamber 47, and then may leave the filter housing via port 33.

The configuration shown in FIGS. 29A-C may provide the same advantages of the configuration shown in FIGS. 26A-1, 26A-2, and 26A-3, and FIG. 26B. The substitution fluid going through the filter may be given a final polishing step to remove bacteria and endotoxin before entering the blood. Since the substitution filter is part of the hemodiafilter cartridge, this arrangement may increase the safety of the treatment without increasing the cost of the treatment. In addition, the substitution fluid enters the blood all along the length of the fiber bundle, providing the benefits of lower clotting of pre dilution with the increased clearance of post dilution.

The fiber material, sterilization methods and construction techniques of all of these filters may be similar. FIG. 31 shows the individual pieces that can be used to assemble the embodiment of FIGS. 29A-C. During the manufacturing process, packaging and temporary covering caps for the various ports may be provided as required to keep the internal surfaces sterile and pyrogen-free after manufacture.

FIG. 32 shows a system and a flow path configuration that may be used with the filter configuration of FIGS. 29A-C, which also is illustrated in FIG. 25G. The system works identically to the description provided for FIGS. 27 and 28, with the exception that the substitution fluid goes into the fiber bundle at the perimeter of the filter housing rather than in the central region or group of the fiber bundle.

FIG. 33 shows a system, which might use a cartridge of FIG. 25G. The system illustrated in FIG. 33 is a relatively simple system to accomplish hemodiafiltration similar to FIG. 30. In this embodiment the system is identical to the system shown in FIG. 32 with the exception that there is no substitution pump, only a valve. This methodology could be used on any volumetric balancing hemodialysis machine as long as it provides ultrapure dialysis solution. It only requires the addition of a valve and a split in the dialysis solution line. In this embodiment, the flow rate of the substitution solution to the hemodiafilter may be controlled based on the fraction of the fiber bundle that is used to carry substitution fluid. Based on the substitution fiber volume, flow rate and pressures within the system, a fraction of the dialysis solution may flow through the substitution fluid inlet and through the semi-permeable membrane into the blood. The remainder of the dialysis solution may flow through the fiber bundle as dialysis solution exiting at port 33 shown in FIGS. 29A-C. Optionally, an additional valve may be added on the substitution solution line to enable the substitution flow to be stopped if desired. The system works identically to the description provided for FIGS. 27 and 28 with the exception that the substitution fluid flows through fibers that are located at the perimeter of the filter housing rather than through fibers that are located in the central fiber group of the fiber bundle.

Application to Plasmapheresis

The process of plasmapheresis, which is a process for removing deficient or diseased plasma components and replacing these components with fresh plasma, is a known therapy for a number of disease states, e. g. thrombotic thrombocytopenic purpura, anti-glomerular basement membrane disease, lupus nephritis, etc. In plasmapheresis, venous blood is removeded from the patient, plasma is separated from other blood cellular components, and the remaining blood cells, together with new plasma, autologous plasma or another replacement solution, is then re-infused back to the patient.

Membrane filtration is one method that can be used to perform plasmapheresis in a process similar to hemofiltration. Plasmafilter membranes usually have micropores of approximately 0.2 to 0.6 µm diameter, which is significantly larger than the pores of a hemodialysis filter, hemofiltration filter or ultrafilter discussed earlier herein.

Traditionally, in plasmafilters, the blood flows through the inner lumen of the fiber, which is similar to the traditional situation in hemodialysis. Outside-In Flow Filtration technology changes this approach by having the blood flowing on the outside of the fibers. Providing blood flow on the outside of the fibers may eliminate at least some of the clotting caused by over-filtration given that the cross sectional diameter of the hollow fiber is typically 180 to 220 microns. Providing blood flow on the outside of the fibers may also increase the surface area available for plasmafiltration. Assuming the use of appropriate materials and surfaces fir the fibers, the use of Outside-In Flow Filtration may result in lower thrombogenicity, reduced anticoagulation requirements, and lower shear stress to erythrocytes during the various therapies described elsewhere herein.

Referring now to FIGS. 34A-D, one can see the Outside-In Flow Filtration technology applied as a plasma filter. The configuration is similar to the use as a Slow Continuous UltraFilter (SCUF) or as a hemofiltration filter. As would be understood by one skilled in the art, the membrane used for plasmapheresis may be different from the membranes used in hemodialysis, hemofiltration and hemodiafiltration. HD, HF, and HDF membranes generally have a steep molecular cut off that prevents the loss of proteins during treatment. In contrast, plasmafilter membranes usually have micropores approximately 0.2 to 0.6 µm diameter, which is significantly larger than the pores of a hemofiltration filter. Such a pore size is sufficient to allow passage of plasma and proteins, through the membrane, while retaining cellular components of the blood. Blood may enter the filter through the Blood-in Port 34. The blood then may flow around the potted end of the fiber bundle, which has been polished to ensure smooth surfaces through 41 into the space formed between the outer edge of the fibers and the housing 25. When the pressure at Plasma Outlet Port 26 is sufficiently high, the plasma may cross the fiber wall membrane into the inner lumen of the fiber. The filtered plasma may be removed through Plasma-out Port 36.

FIG. 35 shows the application of plasmapheresis as a system. Blood is pumped from the patient into the plasmafilter, and an UltraFiltration pump controlled by a scale creates a pressure to urge the plasma through the fiber wall into the inner lumen of the fiber and eventually to a collection bag. The remaining blood cells plus autologous plasma or another replacement solution may then be infused back into the extracorporeal circuit by the substitution pump, which may be controlled by another scale. The scales may work with control and monitoring systems to balance the flow appropriately between the removed plasma and the replacement fluid given back to the patient. The blood may then be returned to the patient. As would be understood by one skilled the art, blood leak detectors, air detectors, pressure sensors, etc. necessary to control this type of circuit may be included in the device and in similar HD, HF, and HDF systems as necessary according to the appropriate risk analysis.

Flow Uniformity in the Inter Fiber Space

As a general design guide, in embodiments of the invention, the dialyzer may comprise features to encourage the distribution of flow in the inter fiber space to be as close as possible to uniform everywhere in the inter fiber space. One aspect of the goal can include achieving a velocity distribution that is as uniform as possible over the cross-section in the fully-developed region of the dialyzer, such as at the lengthwise midpoint of the dialyzer. Another aspect of the goal can pertain to the transition region where flow that may enter the cartridge in a lateral direction undergoes a transition to axial flow in the inter fiber space, and this aspect can include achieving this transition in as short a length of the dialyzer as possible, so that as much as possible of the dialyzer length can experience the type of uniform flow described in the first aspect. Although this description may be thought of in terms of flow entering the dialyzer, or may be described herein with reference to that situation, it can be appreciated that similar considerations may pertain at the exit of the dialyzer.

When the fluid that is flowing in the inter fiber space is blood, as in embodiments of the present invention, this flow uniformity may be especially important because blood is subject to clotting if flow conditions fall outside of an optimum range by being either too high or too low in certain parameters. Such considerations have been less important in traditional dialysis practice, because traditionally the fluid in the inter fiber space has been dialysate, which can tolerate a wide range of flow conditions and is not subject to clotting. In the past, uniformity of flow in the inter fiber space, i. e., flow of dialysate, has been investigated to a certain extent, but mainly just for its impact on the overall mass transfer efficiency and the delivered clearance of the dialyzer.

Experience shows that one factor that is useful for achieving uniform distribution of flow in the inter fiber space is having a distributor that goes 360 degrees around the perimeter of the dialyzer is, and another factor is to have fanning of the fibers near the barriers (potting).

U.S. patent application Ser. No. 14/671,186, the entire disclosure of which is incorporated herein by reference, contains discussion of fanning of fibers and other design features that are appropriate for promoting uniformity of flow or for appropriate conditions for blood to flow on the outsides of the fibers.

Orbital Distributor

In embodiments of the invention, there may be provided a cartridge comprising a conduit or housing port joining the housing from an approximately lateral direction, and there may be provided an associated flow transition region near that conduit and in communication with the inter fiber space. The flow transition region may comprise an orbital distributor, which may include an orbital channel, which may conduct flow around substantially 360 degrees of the perimeter of the fiber bundle.

Two possibilities for an orbital distributor are that it may be either forward-facing or rearward-facing. The term rearward-facing orbital distributor is used to refer to an orbital distributor in which the open edge of the distributor faces toward the nearby barrier 42. In such an orbital distributor, when there is a transition between flow along the lengthwise direction of the fiber bundle and flow in the orbital distributor, it is necessary for flow to make an approximately 180 degree turn upon passing the edge of the orbital distributor. The term forward-facing orbital distributor is used to refer to an orbital distributor in which the open aspect of the distributor faces away from the nearby barrier 42. In such an orbital distributor, when there is a transition between flow along the lengthwise direction of the fiber bundle and flow in the orbital distributor, there is no need for flow to make an approximately 180 degree turn upon passing the edge of the orbital distributor. These terms rearward-facing and forward-facing apply equally to flow entering the orbital distributor and the inter fiber space via an entrance conduit, and to flow leaving the orbital distributor and the inter fiber space via a discharge conduit.

In regard to the design of the orbital distributor itself, one possibility is that the cross-sectional dimensions or area of the orbital distributor can be constant, which is easy to manufacture. However, this does result in a gradual change of the fluid velocity in the orbital distributor in the circumferential direction, as fluid is added to or removed from the orbital distributor. Another possibility is that the cross-sectional area of the orbital distributor can be tapered, such as from a larger cross-section near where the conduit joins the housing, to a smaller cross-section away from that. The use of a taper may be appropriate for a situation where fluid is gradually being removed from or added to a flowpath along the length of the flowpath. For example, the use of a taper may tend to maintain a somewhat constant velocity in the flowpath, with the velocity in the orbital distributor being maintained closer to constant than would be the case with a constant-cross-section flowpath in the orbital distributor.

For an orbital distributor that has a separator wall, it is possible that the height of the separator wall can be uniform around the circumferential angle of the cartridge. Alternatively, it is possible that there be variation of height or other geometric parameter of the external edge of orbital distributor as a function of position around the circumference of the cartridge can be designed in to the cartridge. Such variation can influence the transition and distribution of flow in or into the inter fiber space.

Fanning of fibers can be used in conjunction with any of these design features. As described in U.S. patent application Ser. No. 14/671,186, the entire disclosure of which is incorporated herein by reference, fanning of fibers may improve the ability of the flow to quickly reach a fully-developed or nearly-fully-developed flow distribution in the inter fiber space, with a velocity distribution that is at least approximately uniform. The use of an orbital distributor can be used at either or both of the housing supply end of the cartridge and the housing discharge end of the cartridge. It is believed that the orbital distributor may be of more importance at the supply end, although it is not wished to be limited to this explanation. Orbital distributors at the two ends need not be identical to each other.

Smoothly Contoured Internal Features

FIGS. 36A and 36C show a forward-facing orbital distributor having smoothly contoured internal features in the vicinity of the orbital distributor. FIG. 36B shows a rearward-facing orbital distributor having smoothly contoured internal features.

With reference to FIG. 36A, it is illustrated that, with a forward-facing orbital distributor, when viewed in a cross-sectional plane that contains the longitudinal centerline of the cartridge 12, the interior surface of the housing 25 near the orbital distributor may be smoothly contoured, with no sharp corners. Such properties may be visualized in a cross-section taken in a plane that contains the lengthwise axis of the cartridge. More particularly, the cross-section shown in FIG. 36A also includes the housing port. In such a cross-section, assuming that the housing port is an inlet, the flow enters through the port on the side and eventually transitions to vertically downward flow, with the help of the orbital channel of the forward-facing orbital distributor. (The opposite is true for a discharge port.)

In FIG. 36A, with regard to the internal flow boundaries that are or are connect with the housing wall, it can be seen that those boundaries are either vertical or curved. Such situation can be discussed more quantitatively in terms of local tangent angles to the internal surfaces. First of all, as illustrated, the local tangent angle is such that there is no internal surface of the transition region that lies in a plane that is perpendicular to the lengthwise axis of the cartridge 12. Three local tangent angles are illustrated and their relations to the housing centerline are illustrated in FIG. 36A. There may be a concave (with respect to the internal region that comprises the orbital channel) portion of the surface, and an inflection point or a portion of the surface that has a straight-line segment in the illustrated cross-section, and a convex portion of the surface. All of these may have local tangent lines in the indicated cross-section, and the local tangent lines may make respective angles $\alpha_1$, $\alpha_2$ and $\alpha_3$ with respect to the to the housing centerline. In an embodiment of the invention, all of these angles may be less than a certain specified angle such as 30 degrees, 45 degrees (as illustrated) or 60 degrees. Such a criterion may help to create a smooth transition for flow into the fiber bundle (in the case of a housing supply port), or for flow out of the fiber bundle (in the case of a housing discharge port). Such a smooth transition may be appropriate when a liquid flowing through such transition is blood. Furthermore, in this situation, as illustrated, it is possible that the centerline of the housing port may have a position, in the direction of the lengthwise axis of the cartridge, that roughly corresponds with the position of the barrier in which the fibers are potted.

FIG. 36B shows the use of smoothly contoured internal features applied to a rearward-facing orbital distributor. As illustrated, in cross-section, the rearward-facing orbital distributor may have a U-shaped cross-sectional shape having a bottom, and also having a separator wall between the orbital channel and the fiber bundle. A feature that is illustrated is that the separator wall may have a top surface (in the illustrated orientation), and the top surface may be smoothly rounded. For example, the smoothly rounded end may have a radius of curvature that is at least one-quarter of the thickness of the separator wall. This may contrast with the sharp-cornered separator walls commonly found in dialyzers that are intended for directing dialysate through the inter fiber space.

Furthermore, in this situation, as illustrated, the housing port has a bottom (in the illustrated orientation), and the rearward-facing orbital distributor has a bottom, and the two bottoms may substantially align with each other, or at least may have a smooth transition with each other. This may avoid creating a dead space that might occur if the port were positioned differently with respect to the orbital distributor.

Flow Redirectors

Referring now to FIGS. 37A-37C, in an embodiment of the invention, the flow transition region near where the conduit joins the housing 25 further may comprise a lateral-circumferential flow redirector. FIG. 37A illustrates a cartridge having a forward-facing orbital distributor, and also illustrates representative flowpaths likely to exist with the illustrated geometry. In FIG. 37A, the lateral-circumferential flow redirector is illustrated as being substantially two-dimensional, i. e., having a shape that repeats in the axial direction. Other shapes are also possible, however. What is illustrated in FIG. 37B is a lateral-circumferential flow redirector that has shape variation all of three directions. As illustrated, in FIG. 37B, the shape of the lateral-circumferential flow redirector near the top (in the indicated orientation) of the housing port is different from the shape near the bottom of the housing port, thereby providing some three-dimensional "sweep" to the flow pattern and the redirection of the flow.

FIG. 37C illustrates a cartridge having a rearward-facing orbital distributor and having a lateral-circumferential flow redirector. In this situation again, the lateral-circumferential flow redirector smoothly sends incoming flow in the circumferential direction around the orbital channel, from which the flow enters the fiber bundle. The reverse happens at the discharge end of the cartridge. Although only a two-dimensional lateral-circumferential flow redirector is illustrated in FIG. 37C, a three-dimensional lateral-circumferential flow redirector could similarly be used.

The lateral-circumferential flow redirector may be smoothly contoured and may comprise smoothly curved surfaces. The lateral-circumferential flow redirector may have one or two curved surfaces. With respect to the overall principal directions of the cartridge 12, the curved surface may have a portion of its surface that is oriented approximately laterally and a portion of its surface that is oriented approximately circumferentially. The circumferentially oriented portion of the surface may blend smoothly with the portion of the orbital distributor that it abuts. The lateral-circumferential flow redirector may have two such curved surfaces, which may join each other resulting in a sharp edge, with the lateral-circumferential flow redirector pointing its sharp edge toward the conduit that connects to the housing. The sharp edge may be located at a plane of symmetry of the conduit that joins the housing near the lateral-circumferential flow redirector. The lateral-circumferential flow redirector may be symmetric about a plane of symmetry, and its plane of symmetry may coincide with a plane or line of symmetry of the conduit. The orbital distributor may have a gap width radial dimension, and the lateral-circumferential flow redirector may occupy all or just a portion of the gap width. The sharpness of the edge of the lateral-circumferential flow redirector, i. e., the angle at which the two curved surfaces meet, may be designed depending in part on available geometric space. For example, if the gap dimension is small, the lateral-circumferential flow redirector may have to be correspondingly short in certain directions.

Such a lateral-circumferential flow redirector may substantially eliminate a flow stagnation point that could otherwise occur in the vicinity of the conduit junction to the housing. In place of a stagnation point, the lateral-circumferential flow redirector may create a more smooth change of flow direction. Such an improved flow situation may be especially important when the fluid flowing through such geometry is blood. U.S. patent application Ser. No. 14/671, 186, the entire disclosure of which is incorporated herein by reference, contains discussion about there being a preferred range of shear rate for blood, and discussion indicating that smooth flow transitions are desirable and stagnation points are undesirable.

The described lateral-circumferential flow redirector may exist at either or both of a flow entrance conduit and a flow exit conduit at or near respective ends of the cartridge 12. At an inlet end of the cartridge 12, such a lateral-circumferential flow redirector may cause laterally inwardly directed flow to become circumferential flow, which may be split approximately equally between two opposed circumferential directions proceeding around the orbital distributor. At an outlet end of the cartridge 12, flow may come together from two opposed circumferential directions, and may form a laterally outwardly directed flow through the conduit. If the described lateral-circumferential flow redirector geometry exists at both ends of the cartridge 12, it may exist identically at both ends of the cartridge 12, or alternatively it may exist in ways that differ in some respect from one end of the cartridge 12 to the other end.

A lateral-circumferential redirector may be used in generally any situation, either with or without a separator wall or tubular wall.

Referring now to FIGS. 38A-38D, in an embodiment of the invention, there may be provided a circumferential-axial flow redirector. Such a flow redirector may address the possible existence of a flow stagnation point in an orbital distributor approximately 180 degrees away from a housing port that supplies or receives flow to or from the orbital distributor. In FIGS. 38A-38D, such a circumferential-axial flow redirector is illustrated in combination with a lateral-circumferential flow redirector as already described.

A circumferential-axial flow redirector may have a curved surface that is in some places circumferential or nearly circumferential with respect to the orbital distributor and the principal directions of the cartridge 12, and in another place is axial or nearly axial with respect to the principal directions of the cartridge 12. Such a circumferential-axial flow redirector may be located approximately 180 degrees away from where the conduit joins the housing for that orbital distributor. Such a circumferential-axial flow redirector may serve to receive flow that is traveling in a generally circumferential direction almost 180 degrees away from the place where the conduit joins the housing 25, and may redirect that flow into an axial direction. Such description would apply for an orbital distributor that is located near the inlet end of the cartridge 12. Near the outlet end of the cartridge 12, a similar circumferential-axial flow redirector, could serve to receive axially-directed flow and to redirect such flow in a circumferential direction to flow in the orbital distributor. If the circumferential-axial flow redirector has large enough dimensions, the circumferential-axial flow redirector may be curved in the sense that it may follow the curvature, around the circumference, of the orbital distributor in which it at least partially resides. Such a circumferential-axial flow redirector may substantially eliminate a flow stagnation point that could otherwise occur in the orbital distributor approximately 180 degrees away from the conduit junction to the housing, and may create a smooth change of flow direction in place of that stagnation point.

FIGS. 38A-38C show a forward-facing orbital distributor having a circumferential-axial flow redirector. (The lateral-circumferential flow redirector is also illustrated.) FIG. 38A is a three-dimensional view of such a cartridge and such a circumferential-axial flow redirector, and having a forward-facing orbital distributor. FIG. 38B illustrates representative flowpaths likely to exist with the geometry illustrated in FIG. 38A. FIG. 38C is a view of the structure of FIG. 38A, from a vantage point that is 90 degrees different. FIG. 38D shows a cartridge having a circumferential-axial flow redirector, in a rearward-facing orbital distributor.

In any cartridge 12 and at either end of such a cartridge 12, either or both of a lateral-circumferential flow redirector or a circumferential-axial flow redirector could be used. FIGS. 38A-D show the presence of both types of flow redirectors. The constructions at respective ends of cartridge 12 could be either identical to each other or different from each other.

All of these described features, such as smooth transition features, lateral-circumferential flow redirectors and circumferential-axial flow redirectors, may help, for example, to avoid causing hemolysis (the rupturing of red blood cells) due to unfavorable flow features such as large shear rate or shear rate gradient or stagnation. Such unfavorable flow features might occur at locations that lack the described smoothing or flow transition features. Such features assume special importance when the flow in the inter fiber space is blood, in contrast to the rather ordinary fluid such as dialysate that conventionally flows through the inter fiber space of a cartridge.

Non-Uniform-Conductance Flow Element

Referring now to FIGS. 39A-39D, in an embodiment of the invention, there may be provided a non-uniform-conductance flow element, which may be provided in combination with an orbital distributor. The orbital distributor could be either a forward-facing orbital distributor or a rearward-facing orbital distributor, and the non-uniform-conductance flow element may be used with either type of orbital distributor. A forward-facing orbital distributor is illustrated in FIGS. 39A-39B. If a non-uniform-conductance flow element is used with a forward-facing orbital distributor, the non-uniform-conductance flow element may be located between the orbital distributor and the inter fiber space. A rearward-facing orbital distributor is illustrated in FIGS. 39C-39D. If a non-uniform-conductance flow element is used with a rearward-facing orbital distributor, the non-uniform-conductance flow element may be located between the orbital distributor and the barrier 42.

A non-uniform-conductance flow element may operate by having different minimum flow cross-sectional areas at different places around its perimeter, thereby influencing the distribution of flow at different places around the perimeter. Alternatively, the non-uniform-conductance flow element may have flow passageways therethrough that have similar flow cross-sectional areas as each other but the effective hydraulic diameter of the passageways, and hence the flow resistance, may differ at different places around the perimeter. Of course, it is possible that both variation of local area and variation of hydraulic diameter may exist in combination. For example, a region where it is desired to have less axial flow than would occur in the absence of such a flow element, there may be provided reduced local flow area or increased flow resistance or both. In a region where it is desired to have more axial flow than would occur in the absence of such a flow element, the opposite may be provided.

As illustrated, the non-uniform-conductance flow element may have a relatively large conductance 180 degrees away from where the conduit joins the housing, and a relatively small conductance near where the conduit joins the housing. This is based on experimental experience which suggests that in the absence of suitable design features, due to the local pressure of fluid at various places in the flowpath and due to differences in flowpath lengths of various possible flowpaths, there will be a tendency for fluid flowing in the inter fiber space to take a "short-cut" or "path of least resistance" by preferentially transitioning into the inter fiber space closest to the conduit junction. The maximum conductance could occur 180 degrees away from where the conduit joins the housing, and the minimum conductance could occur at or near where the conduit joins the housing. The non-uniform-conductance flow element may have a conductance that varies with angular position around an orbital distributor circumference in a manner that is symmetric about a plane that passes through the associated conduit or housing port.

The non-uniform-conductance flow element may have any of several physical configurations. One possible configuration is as a plate with distributed apertures in it. Another configuration is as a plurality of ribs, which may have their largest surfaces oriented generally parallel to the long direction of the cartridge. In some embodiments of the invention, there may be provided an array comprising a plurality of ribs that are generally oriented along the lengthwise direction of the cartridge 12. Such ribs may be at least approximately planar and may lie in planes that may also contain the lengthwise centerline of the cartridge 12. Such a plurality of ribs may serve, for example, as a flow straightener and could also have a structural function.

In a rib-type flow element, the ribs may be non-uniformly distributed around the circumference of the cartridge 12 or may have respective thicknesses that are unequal. For example, the non-uniform-conductance flow element may have ribs that are closer to each other in some places and more widely spaced apart from each other in other places. This is illustrated in FIGS. 39A and 39C. In FIGS. 39A and 39C, the number of ribs illustrated is, for clarity of illustration, smaller than it might actually be in practice. It is possible that a larger number of ribs could be present, with a distribution of the ribs that is non-uniform similarly to what is illustrated. As illustrated in FIGS. 39A and 39C, the local density of number of ribs per unit of length of perimeter could vary by a factor of 2 or 3 when comparing the maximum-rib-density portion of the perimeter to the minimum-rib-density portion of the perimeter.

Referring now to FIGS. 39B, 39D, if the non-uniform-conductance flow element is conceptually like a plate with holes in it, the geometry of the holes therethrough may be such as to provide non-uniform-conductance. The holes may be located at locations that are non-uniformly distributed, in which case the holes might be of uniform diameter or dimension. It is also possible that the non-uniform-conductance flow element could have holes therethrough that are themselves non-uniform in their dimensions. Both possibilities could be used together.

The non-uniform-conductance flow element may extend fully around the perimeter of the cartridge, as illustrated, or, alternatively, the non-uniform-conductance flow element may extend only partway around the perimeter of the cartridge.

The non-uniform-conductance flow element may serve to achieve a distribution of flow in the inter fiber space that is more uniform with respect to angular position around the perimeter of the cartridge 12, than would otherwise be achieved. Alternatively, if some flow distribution other than perfectly uniform is desired, such distribution could also be achieved by appropriate design of the non-uniform-conductance flow element.

Referring now to FIGS. 40A-F, there are illustrated certain details of fluid handling fittings that may be used to connect to cartridges for hemodialysis and related therapies. In FIGS. 40A-F, for generality and for clarity of illustration, certain details about the orbital distributor are omitted.

In hemodialysis and related therapies, it is standard practice that the fittings used in the blood circuit are different from and are incompatible with fittings that are used in the other circuit, such as dialysate or ultrafiltrate.

A luer lock fitting is a standardized type of fitting that has a central fluid-sealing connection that is tapered, and also has an outer threaded engaging feature. In hemodialysis and related therapies, it is conventional that a luer lock fitting is used for tubing that carries blood in the blood flow circuit. In general, a luer connection can be characterized as a taper to taper connection, and the tapers can be characterized as shallow tapers. In general, a luer lock can be characterized as a taper to taper connection with a threaded connection to hold the tapers together.

In an embodiment of the invention, the connections on the housing, which are in fluid communication with the inter fiber space, may be luer lock fittings. This is determined by the intended presence of blood in the inter fiber space. More generally, if the fittings used in the circuit of the headers are Hansen fittings, then the fittings used in the blood circuit such as the connection to the housing, may be incompatible with Hansen fittings.

A luer connector is a type of connector that is conventionally known and used for connecting tubing, syringes and other devices in medical use. It has a pair fluid-sealing mating surfaces that are complementarily tapered, one of them being externally tapered and the other being internally tapered. Key features of luer connectors are defined in the following standards:

ISO 594:1986 "Conical fittings with a 6% (Luer) taper for syringes, needles and certain other medical equipment".

DIN and EN standard 1707:1996 "Conical fittings with a 6% (Luer) taper for syringes, needles and certain other medical equipment—Lock fittings".

DIN and EN 20594-1:1993 "Conical fittings with a 6% (Luer) taper for syringes, needles and certain other medical equipment described".

A related type of connector is a luer lock connector. A luer lock connector contains the described tapered fluid sealing feature, and additionally contains a helically threaded locking feature. The helically threaded locking feature is external to and surrounds the tapered-surface fluid seal.

A Hansen fitting is a standardized type of fitting that has axisymmetric ridges on an outer surface of one piece of the fitting. These ridges are used for forming the connection between mating parts, with the mating part being complementary to the ridges. In hemodialysis and related therapies, it is conventional that such a fitting is used for connections involving fluids other than blood, such as dialysate and ultrafiltrate. In an embodiment of the invention, the fittings on the headers may be Hansen fittings. This is determined by the intended presence of dialysate or ultrafiltrate in the header(s). More generally, if the fittings used in the circuit of the housing connections are luer lock fittings, then the fittings used in the header circuit such as the fittings for tubing that carries dialysate or ultrafiltrate, may be incompatible with luer lock fittings.

A Hansen fitting is a type of connector that is designed for quick and easy connection and disconnection of fluid lines. One member of the coupling is a male connector, which is often axisymmetric on its exterior including certain ridges that are axisymmetric. The other member of the coupling is a female connector. Such connectors are described further in standards such as: ANSI/AAMI/ISO 8637 ISO 8637:2010 Cardiovascular implants and extracorporeal systems: Hemodialysers, hemodiafilters, hemofilters and hemoconcentrators" or international equivalents to this standard, and in German standard DIN 58352.

With continued reference to FIGS. 40A-F, orientation of the various fittings can also be discussed. It can be pointed out that it is conventional in hemodialysis and related therapies that the blood connections are vertically oriented and the dialysate connections are horizontally oriented. In conventional practice, this is so for the blood connections because the blood flow through the fiber lumens conventionally uses headers that are at the extreme top and bottom ends of the cartridge (when the cartridge itself is vertically oriented, as it almost universally is). This is so for the housing connections because dialysate flow conventionally uses the housing connections, which are sideways because of the conventional geometry of accessing the inter fiber space while avoiding the header region.

In an embodiment of the invention, there may be provided a cartridge in which the fittings that are in fluid communication with the inter fiber space of the cartridge have fitting axes that are generally parallel to the lengthwise axis of the cartridge. These fittings would be used for connecting blood lines to the cartridge. In the usual mounting practice of the cartridge 12 during use, in which the cartridge itself is vertically oriented, this would result in such fittings being vertically oriented. Furthermore the cartridge may have a first header that has a first header fitting having a first header fitting axis that is generally perpendicular to the housing longitudinal axis. Such a fitting would be used for connecting a dialysate or an ultrafiltrate line to the cartridge. In the usual mounting practice of the cartridge 12 during use, this would result in such fittings being horizontally oriented. There could be either one such header fitting, such as might be used in an application such as ultrafiltration or hemofiltration, or there could be two such header fittings, such as might be used in an application such as hemodialysis or hemodiafiltration.

Taken together, these features would result in the orientation of all fluid fittings of the cartridge being substantially identical to the corresponding orientations that are familiar from conventional practice using conventional dialyzer cartridges that use intra-luminal blood flow.

With still further reference to FIGS. 40A-F, there is also shown, in magnified view, possible details of construction of the wall of an individual hollow fiber. Three possibilities are shown, and such features are also discussed in greater detail in U.S. patent application Ser. No. 14/671,186, the entire disclosure of which is incorporated herein by reference. The uppermost possible structure shows a hollow fiber that has an outer surface that is relatively smooth and performs a sieving function, and an inner surface that is relatively rough. This is a type of asymmetric fiber. For embodiments of the invention, it is believed this is the most desirable of the three possibilities. The outermost layer can perform the sieving based on molecule size and also on molecular shape, while the interior portions of the membrane, having greater pore size, can provide structural support while providing little resistance to flow through the membrane. The second illustrated possibility is a so-called symmetric fiber. Such a fiber has a smooth surface on both the outside surface and the inside surface. It is believed that for embodiments of the invention, the smooth outer later is the layer that performs the sieving function. It is further believed that the smooth inner layer is not necessary but it is not much of a problem either. The third illustrated possibility is an asymmetric fiber in which the outer surface is rough and the inner surface is smooth and performs the sieving function. It is believed that this is less desirable than the other possibilities, because the rough outer surface is not as appropriate for blood exposure as the smooth outer surface in the other possibilities, and also the pores leading up to the sieving layer can possibly become clogged during use. However, for some purposes this situation may still be acceptable.

Through-Wall Distributor

Typically in a rearward-facing orbital distributor, the wall that forms the tubular portion of the cartridge in the mid-region of the cartridge also extends into the orbital distributor region and forms the separator wall between the orbital distributor and the fiber bundle. Typically this separator wall has no passageways of any sort through it in the region of the orbital distributor. Instead, the fluid enters (or leaves) the fiber bundle in the place where the fiber bundle is exposed uninterruptedly to the orbital distributor. Typically the orbital distributor is substantially identical everywhere around the circumference of the housing, with several exceptions sometimes appearing in known dialyzers: in some dialyzers there is sometimes provided a localized impact plate close to the port; in some dialyzers there is sometimes provided a channel has a taper to reflect the fact that that the flowrate in the channel in the circumferential direction varies as fluid is withdrawn from or added to the channel as a function of angular position; and sometimes the height of the wall is not constant as a function of circumferential angle.

Reference is now made to FIGS. 41A-41E. In these illustrations, for clarity of illustration, the central portion of the cartridge including the fiber bundle is shown three-dimensionally, but the header is shown in cross-section. In these Figures there is illustrated an orbital distributor arrangement that is neither a rearward-facing orbital distributor as already discussed nor a forward-facing orbital distributor as already discussed. Rather, the illustrated distributor represents a type of orbital distributor that may be called a through-wall orbital distributor. FIG. 41A (as-sembled) and FIG. 41B (disassembled) illustrate an end of a cartridge that has a through-wall orbital distributor. The cap piece is similar to that illustrated in FIGS. 40A-E, and it comprises an orbital channel. The orbital channel may extend around the entire circumference of the cartridge. Such a channel may contain any of the flow redirectors described elsewhere herein, which may be located at possible stagnation points, but such are omitted for clarity of illustration. The tubular wall of the cartridge may extend into, through and beyond the region of the orbital channel, and indeed may extend all the way to the potting or barrier 42, which may be potted into that tubular wall. The interior of the tubular wall may have a local taper near the end so as to provide for fanning of the fibers, although such is not illustrated. In FIG. 41A-B there are shown a plurality of openings through the tubular wall. Such openings are illustrated as being rounded-rectangle openings, although of course other shapes are possible. Such openings put the inter fiber space of the fiber bundle in fluid communication with the orbital channel, although the fluid communication is less than perfect because there are some places where the remaining solid material of the tubing wall partially obstructs the fiber bundle. Because the ultimate direction of flow of fluid in the inter fiber space is axial, i. e., along the lengthwise direction of the cartridge, it may be of particular interest to consider whether there is an extended region along the lengthwise direction that is deprived of fluid communication with the orbital channel. In this view, another possible design may be considered in which there is more than one row of openings, and the openings partially overlap with each other with respect to the longitudinal direction of the cartridge. This is shown in FIG. 41C, with round openings, with two rows of openings although of course generally any number of rows of openings is possible. The openings are shown as being staggered with respect to each other, and being dimensioned and overlapped such that any angular position around the circumference is exposed and is in fluid communication with the orbital channel for at least a portion of the axial extent of the distributor (with respect to the lengthwise direction of the cartridge). In general, the tubular wall could have any pattern of small holes therethrough, and ligaments could simply be connecting material between holes, ligaments do not have to be straight ligaments.

Referring now to FIGS. 41D-1 and 41D-2, there is shown a similar design in which openings are defined by somewhat narrow ribs. The inter fiber bundle, shown as straight vertical lined region, is visible through the openings between the ribs. The ribs are shown as being identical and uniformly spaced around the circumference of the cartridge. However, it also is possible that the openings could be non-identically dimensioned or non-uniformly distributed, and could thereby form a non-uniform-conductance flow element as discussed elsewhere herein in connection with other configurations of orbital distributor. Also, omitted from the illustration for sake of clarity, any edges corners etc. associated with the openings could have fillets of other forms of smooth geometric contouring.

Referring now to FIG. 41E, there is shown a similar device in which the remaining solid material comprises bars that are distributed in a manner that is at least approximately helical. There may be an angular extent that is covered by any one bar from the place where it joins solid tubular wall material at one end of the bar to the place where it joins solid tubular wall material at the other end of the bar. There may be an angular dimension that is a bar-centerline-to-bar-centerline spacing at the same ends of the bars. The appropriate dimensions could be chosen to be such that the angular extent of a bar is greater than the angular dimension that is the bar-centerline-to-bar-centerline spacing. This criterion, which is at least approximately illustrated in FIG. 41E, would ensure that all angular locations of the fiber bundle have some fluid communication with the orbital channel, and that flow along the lengthwise direction of the cartridge might even out any local non-uniformities caused by local lack of fluid communication between the fiber bundle and the orbital channel. For example, at any angular position around the circumference of the cartridge, the fraction of the lengthwise dimension of the fiber bundle that is in actual fluid communication with the orbital channel could be substantially the same as at any other angular position. It is still further possible that the helicity of the remaining solid material as illustrated in FIG. 41E could contribute to smoothness of transition of flow from the radially inward direction (in the case of the supply port) of flow to the axial direction of flow.

In a through-wall distributor, the fluid delivery distributor such as the orbital channel may extend completely around the circumference of the cartridge, but there may be local paths through the described wall, as the orbital channel may deliver fluid to the fiber bundle through a series of openings in the cylindrical wall of the housing and there may be ligaments between the openings or paths. It is believed, although it is not wished to be limited to this explanation, that the fluid may be distributed to the fiber bundle effectively and uniformly if the individual ligaments are not especially large and if collectively the ligaments do not occupy an especially large portion of the circumference of the orbital distributor. There may be a plurality of such openings and there may be ligaments between the openings. The total portion of the circumferential area that is open as a result of such openings may for example exceed 50% of the circumferential area of the region in which the through-wall distributor is located.

Essentially this through-wall distributor may be a new type of orbital distributor, one that delivers fluid to (or receives fluid from) the fiber bundle from a channel that has access 360 degrees around the circumference of the fiber bundle, but one that delivers (or receives) fluid through a number of paths that go through the wall, i. e., paths between remaining solid material of the wall. The remaining solid material of the wall may, as illustrated in some illustrations, be ligaments which may be generally straight. Alternatively, the remaining solid material of the wall could be the material that remains that defines holes through the wall, and that remaining solid material could be curved or irregular. Still more generally, the ligaments could be any structural connection that maintains overall structural integrity of a wall despite the presence of openings through the wall. For example, the remaining solid material of the separator wall may form a structural connection between the central tubular component and a portion of the tubular element that contains the potting that holds the fibers in place.

Tube Set

Cartridges of embodiments of the invention may be provided in the form of a tube set. A tube set may comprise various components including a cartridge along with other components, all of which may be mounted on a sheet or similar unitary holder. The sheet may be suitable to be mounted on a machine, such as for ease of installation and use. For example, use of a tube set may reduce the number of fluid connections that have to be made by medical personnel at the time of a treatment session. A tube set may be designed for one-time use, followed by disposal. For example, a tube set may comprise a cartridge of an embodiment of the invention, along with tubes that connect to respective ports of the cartridge. The tube set may include fittings that may be chosen for interface with the rest of the system or machine. Additionally, if desired, a tube set may comprise tubing that is positioned and adapted to be operated by the roller of a peristaltic pump. The roller of the pump does not need to be part of the tube set, but rather can be part of the machine onto which the tube set is mounted. Additionally, if desired a tube set may comprise volume balancing chambers. Such chambers may be used to control or balance or compare the flow of fluid in and fluid out of a portion of the system. Additionally, if desired a tube set may contain valves as desired, either valves that are discrete components, or places in the tubing that can be pinched to close off flow. There may be provided pinch-clips as desired. Check-valves or one-way valves may be provided as desired. Filters may be provided as desired. A tube set may include features or provisions for air bleed or for priming of components with liquid. A drip chamber may be provided. A pressure-transmitting pod may be provided. A tube set may include one or more sensors if desired. Electrical connections may also be provided if the tube set contains electrical components. The tube set may be packaged and supplied in a sterile condition. For use, the tube set may be connected to a system that supplies and withdraws various fluids and that operates features of the tube set, such as through force or pressure or other means.

Cartridges Having Flow Perpendicular (Transverse) to Fibers

Referring now to FIGS. 42A-42C and FIG. 43A-43D, there are shown several embodiments of the invention in which flow through the inter fiber space occurs at least somewhat perpendicular or generally perpendicular, i. e., transverse, to the long direction of the fibers. Such flow orientation has been described in U.S. patent application Ser. No. 14/671,186, the entire disclosure of which is incorporated herein by reference.

In the cartridge of FIG. 42A-42C, there are shown dialysate inlet cap 30 and dialysate/filtrate outlet cap 33. These are shown as being such that the line connecting cap 30 and cap 33 is at least approximately parallel to the long direction of the fibers. Inlet 34 and outlet 35 are inlet and outlet, respectively, for flow of fluid, in this case blood through the inter fiber space. Ports 34 and 35 may have respective directions that are generally at least approximately perpendicular to the long direction of the fibers. Ports 34 and 35 may be offset from each other, with one port being closer to one end of the cartridge and the other port being closer to the other end of the cartridge. The directions of ports 34 and 35 may be at least approximately parallel to each other. Also as illustrated, smooth transitions may be provided near ports 34 and 35 to help distribute the flow. The shape of the housing is shown as being somewhat racetrack-shaped in cross-section, with the long direction of the racetrack shape at least approximately coinciding with the flow direction that is at least approximately perpendicular to the fiber direction. Further, the general proportions of the housing are shown such that the housing is somewhat longer in its lengthwise direction (the direction of the fibers) than the long direction of the racetrack or any other direction of the cartridge.

However, these relationships are optional.

In FIGS. 43A-43D) there are shown still other possible shapes and proportions of cartridges that have perpendicular (transverse) flow.

Figure 43A:
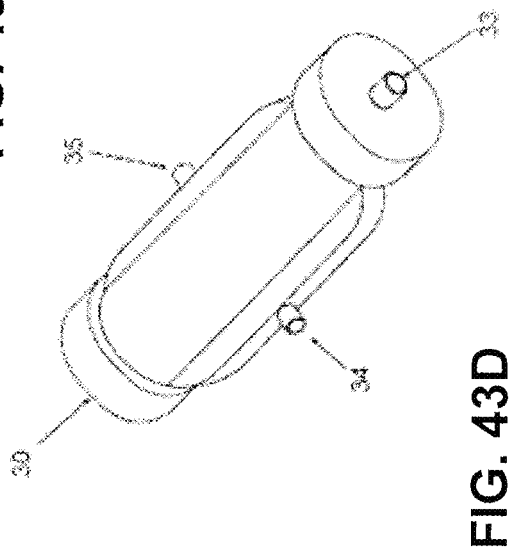
Figure 43B:
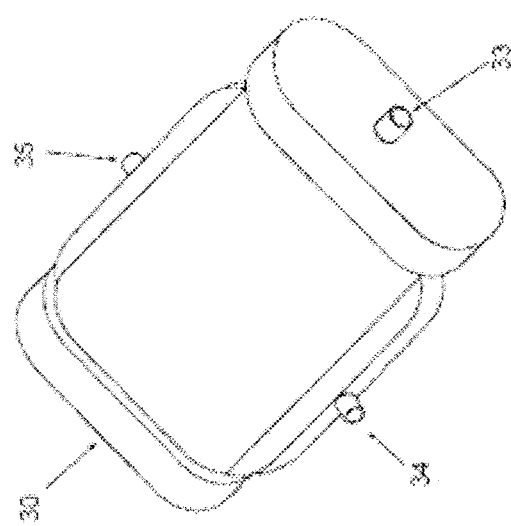
Figure 43C:
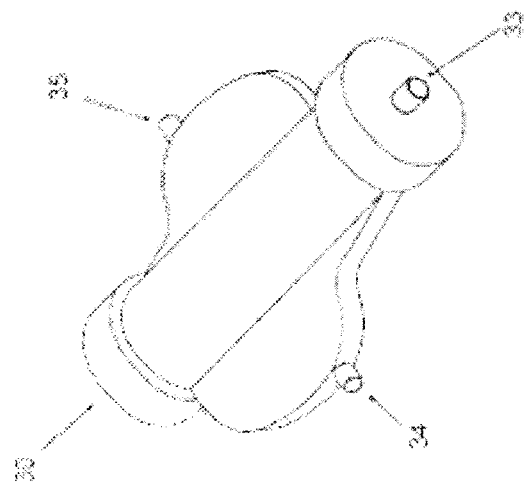
Figure 43D:
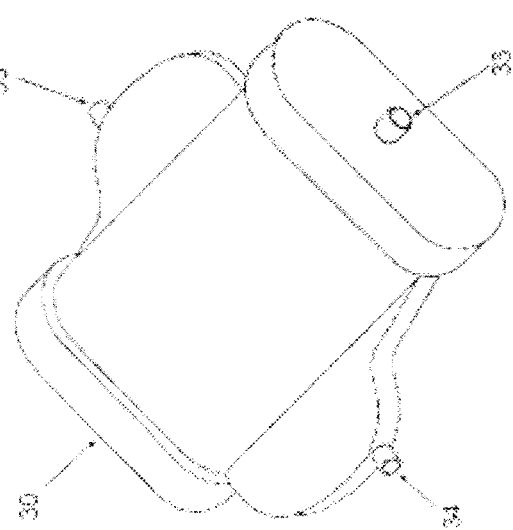

In FIGS. 44A-B there is shown an exploded view of the housing illustrated in FIG. 43D, illustrating a possible internal geometry of that cartridge. It can be seen that there is a baffle/distributor plate 392, which may also be described as a flow resistance element, which is impacted by incoming flow and which offers some flow resistance to flow passing through it. The flow resistance of the baffle/distributor plate may be chosen and designed so as to promote achievement of an approximately uniform distribution of flow perpendicular to the fibers at all places along the long directions of the fibers. The plate 392 is illustrated as showing a number of discrete holes that may be placed and sized to promote flow uniformity. For example, the distribution and sizes of holes in the baffle/distributor plate 392 could be uniform, or alternatively there could be a non-uniform distribution if that is found to better distribute the flow. For example, the resistance to flow through the flow resistance element 392 could be larger near the inlet port or outlet port, and the flow resistance could be smaller closer to the ends of the cartridge (closer to the ends of the fibers). There could be the same or a similar baffle/distributor plate at the inlet of the cartridge 12 and at the outlet of the cartridge 12. Details could be chosen based on experience with actual blood flow. It is further possible that the baffle/distributor plate 392 could instead be a porous fabric, rather than a plate with discrete holes. Such fabric could be chosen so that it has appropriately sized pores or holes so as to also serve as an emboli trap. For example, such pore or hole sizes could be no larger than hundreds of microns, or no larger than tens of microns. FIGS. 44A-B illustrates a version of the cartridge of FIG. 43D, which has a racetrack-shape in a cross-section taken perpendicular to the long direction of the fibers. However, it is to be understood that other cross-sectional shapes are also possible, such as are illustrated in FIGS. 43A and 43B. In particular, it is possible to use a cross-section that is circular or approximately circular.

In perpendicular-flow cartridges that have been illustrated so far, the direction of the ports that bring in and bring out the flow has been generally perpendicular to the long direction of the fibers. However, this is not essential. Referring now to FIG. 45, there is illustrated a cartridge, including appropriate internal structure, such that the direction of internal flow past the exteriors of the fibers is at least approximately perpendicular to the long direction of the fibers, but the entrance port and the exit port are not perpendicular to the long direction of the fibers. In this illustrated design, the inlet port conducts fluid in a direction that is generally parallel to the long direction of the fibers, and also, the exit port conducts fluid in a direction that is generally parallel to the long direction of the fibers. The inlet port and the exit port may be generally parallel to each other but offset from each other. Flow through the inlet port may continue after the inlet port into a manifold, which may run along the cartridge for at least a portion of the cartridge length in the long direction of the fibers. The inlet manifold may be tapered and may have a boundary 394 that allows fluid to flow therethrough. For example, the boundary 394 may have a porous, perforated or otherwise fluid-permeable nature so that flow from the manifold can pass therethrough. The inlet manifold may be tapered, for example being wider near the inlet port and narrower at the end away from the inlet port. The inlet manifold may be tapered and may have a boundary that allows fluid to flow therethrough. The discharge manifold may be generally similar to the inlet manifold but may be reversed in certain aspects. The discharge manifold may be tapered such that it is wider near the discharge port and narrower at the end away from the discharge port. Such tapering of either manifold or both manifolds may help to maintain the fluid velocity therein at a more constant value than would be the case in the absence of such tapering. Such tapering may, for example, be a linear tapering. The porous, perforated or otherwise fluid-permeable nature of the boundary in FIG. 45 may be similar to what is described in connection with FIGS. 44A-B. Any or all of these features may help to achieve flow past the fibers such that the flow is generally perpendicular to the long direction of the fibers and is approximately uniformly distributed. Such uniform distribution of flow may be especially helpful when the fluid flowing past the exterior of the fibers is blood.

Priming of Cartridge Using Dialysate

Priming of a cartridge may include filling empty spaces inside the cartridge with a liquid, typically an aqueous liquid, in order to displace the air normally contained in those spaces. In turn, the liquid may be displaced by blood for actual use of the cartridge in performing a desired function related to blood. In an embodiment of the invention, there may be provided a method of priming a cartridge.

In a method of priming of an embodiment of the invention, dialysate may be provided to the lumens of some or all of the fibers. The downstream end of the lumens may be closed off, or if there is more than one discharge port for the region that is in communication with the lumens, then at least one of the discharge ports of the space that is in communication with the lumens may be closed off. The dialysate in the lumens may be pressurized, or may be caused to flow into the cartridge 12, such that the dialysate permeates out through the walls of the fibers into the inter fiber space. At least one port of the housing may be kept open to allow air or liquid or both from the inter fiber space to exit the housing 25. Such port may be at a relatively high elevation in the cartridge 12, or the cartridge 12 may be appropriately tilted so that an air discharge point is at a local maximum elevation. In this way, the inter fiber space may be filled with liquid from a source that is readily available. The liquid may later be replaced by blood.

Method of Operating for Priming, Rinse Back, and Infusion

Referring now to FIGS. 27 and 28, FIG. 28 illustrates a system and a potential method in which the system shown in FIG. 27 can be used to automatically prime the extracorporeal circuit. This filter configuration can also be used for hemodialysis. When used for hemodiafiltration or hemodialysis the substitution fluid channel is used to prime the system with injectable quality dialysis solution. It can be noted that this is one embodiment to show how to prime the filter automatically during a prime cycle, but there also are other potential embodiments that can be used to prime the circuit when this filter is used. The embodiment illustrated is an embodiment that can easily be automated.

Prime the Extracorporeal Circuit
1. Install the bloodlines and the dialyzer on the machine. It does not matter if the ultrapure dialysate source is prepared by a proportioning system in situ or if bagged dialysis/substitution solution is used.
   a. If a proportioning system is the source of dialysis solution, the solution should be at the proper conductivity and temperature prior to priming the system. The system would determine this automatically based on conductivity and temperature sensors in the dialysate circuit of the system,
2. Make all connections to the filter, the extracorporeal circuit and the hydraulic system. (Connections would meet ISO 8637 and are color coded and/or keyed).
   a. Put the machine in bypass mode so that the dialysate flow stops.
   b. Connect the dialysis solution connection to the filter assembly.
   c. Connect the bloodlines to the filter assembly.
3. Take the machine out of bypass mode and run the Prime/Bolus/Substitution pump at the appropriate rate.
   a. The dialysate will begin to fill the inner lumen of the hollow fibers on the dialysis solution and will begin to fill the external blood chamber of the hemodialyzer/hemodiafilter via the substitution pump flow.
   b. This action continues until the entire dialysate flow path is filled with dialysis solution.
   c. As necessary to relieve pressures in the system, the IF pump can be run in the reverse direction to provide a replacement for the air in the system.
   d. As the substitution fluid channel is blocked at the distal end of the filter assembly, most of the outer blood chamber will be filled with purified dialysate solution.
4. When the dialysate circuit is full of dialysis solution.
   a. Alternative 1: The UF Pump is run in reverse at an appropriate rate to provide an appropriate volume to prime the venous bloodline, while running the Prime/Bolus/Substitution pump.
      i. Since this UF pump replaces some of the volume going into the effluent dialysate flow equalizer, the Prime/Bolus/Substitution pump fills the venous bloodline at an appropriate rate with fresh dialysis solution that has been filtered by the substitution fluid channel 45 in the FIG. 26B or FIG. 29 filter assembly drawing.
      ii. The venous line fills with injection quality dialysis solution.
      iii. When the line is full and an appropriate amount of priming solution has rinsed through the venous line, the venous clamp is closed. Note that the venous air detector can verify that there is no air in the venous line.
      iv. The arterial blood pump is then run in reverse to fill the arterial line in a manner similar to the filling of the venous line.
      v. When the appropriate amount of priming solution has filled the Prime Bag, the blood pump is stopped. Note that the arterial air detector can verify that there is no air in the arterial line.
   b. Alternative 2: The venous and arterial lines can be primed in a reverse order to alternative 1.
   c. Alternative 3: After priming the extracorporeal circuit by either Alternative 1 or 2, the priming solution can be recirculated through the priming bag to remove any air in the system.
5. When the user is ready to begin dialysis, the operator would begin dialysis per the normal method.
   a. Stop all pumps.
   b. Clamp the arterial and venous lines. As would be understood by one skilled in the art, this may be done with simple finger clamps integrated into the tubing set or with external clamps such as a hemostat or other clamping device.
   c. Discard the priming bag.
   d. Hook both connections to the patient access.
   e. Begin Dialysis
      i. Alternative 1: Ultrafiltrate an appropriate volume to remove the solution from the blood side.
      ii. Alternative 2: run the blood pump and give the patient the priming solution on the blood side of the filter.

Blood Rinse Back

Blood Rinse back is accomplished by a similar method to priming the circuit.
1. The Prime/Bolus/Substitution pump is run while the UF Pump is run in reverse.
   a. The UF pump satisfies the demand of the balancing system, because the UF pump replaces some of the volume going into the effluent dialysate flow equalizer the Prime/Bolus/Substitution pump fills the venous bloodline at an appropriate rate with fresh dialysis solution that has been filtered by the substitution fluid channel 45 in the filter assembly drawing.
2. After the venous line is rinsed back, the blood pump is run in reverse filling the arterial line with injectable quality dialysis solution.
3. Alternatively, this procedure can be reversed.

Bolus Infusion
1. The Prime/Bolus/Substitution pump is run while the UF Pump is run in reverse.
   a. The UF pump satisfies the demand of the balancing system, because the UF pump replaces some of the volume going into the effluent dialysate flow equalizer while the Prime/Bolus/Substitution pump pushes ultrapure dialysate through the substitution fluid channel 45 in the filter assembly FIG. 26B or FIG. 29 at an appropriate rate with fresh dialysis solution.
   b. The system is run this way to infuse the desired bolus infusion. Normally this fill volume may be the 50 to 300 ml needed to eliminate the patient's symptomatic hypotension or hypovolemia.

In an embodiment of the invention, a cartridge may be primed with aqueous liquid by causing dialysate liquid to flow into the lumens of the fibers and through the pores of the fibers and into the inter fiber space. In so doing, the air in the inter fiber space is displaced and is replaced by aqueous liquid. Appropriate air bleed features or components can be provided on either the cartridge or associated system components or both. Later, the aqueous liquid can be displaced by blood.

In particular, if a cartridge has its fiber bundle grouped into two fiber groups, one of the fiber groups can be used for inputting the aqueous liquid, and the other can be used to release air.

Shear Rate and Flowrate of Dialysate

In an embodiment of the invention, dimensional and other parameters of the cartridge may be chosen so as to meet a certain criterion about shear rate of the flowing fluids. In general, mass transfer near and through a semi-permeable membrane can be thought of as being controlled by a sum of several resistances. Some of those resistances can be in the nature of boundary layers such as either a fluid flow boundary layer or a mass transfer (concentration gradient) boundary layer region, while others of the resistances can pertain to the physical structure of the membrane itself. It is believed that some of the resistances are influenced by the shear rate of the fluid flowing past the membrane, which in an embodiment of the invention is flowing at least approximately tangential to the membrane surface. There is a flow of blood on one side of the membrane and a flow of dialysate on the other side of the membrane, and a respective resistance to mass transfer on each side of the membrane. For example, the shear rate of fluid flow adjacent to the membrane surface may influence the velocity gradient which in turn, through mixing or other mechanisms, may influence the concentration gradient of composition near the membrane surface. Shear rate in respective fluids is a function of overall velocity of the fluid, the viscosity of the fluid, and the transverse dimension of the passageway in which the fluid is flowing. In the case of a fluid flowing in the somewhat irregular inter fiber space, there also may be some mixing that is introduced by the irregularity of the fiber bundle, especially if the fibers are wavy. Blood has a viscosity that can be roughly described (given that blood is a non-Newtonian fluid) as being several times as large as the viscosity of the dialysate.

It is believed, although it is not wished to be limited to this explanation, that an optimum situation may be approached when the shear rate in the fluid on one side of the membrane approximately equals the shear rate of the fluid on the other side of the membrane. It is further believed that, in particular for the properties of blood, a desirable shear rate is in the range of 300 $sec^{-1}$ to 2700 $sec^{-1}$, and more preferably 1000 $sec^{-1}$ to 2000 $sec^{-1}$. For flow of any fluid in the inter fiber space, it is believed that one of the more important adjustable design parameters available to influence the shear rate is the porosity of the fiber bundle. For flow of any fluid in the lumens of the fibers, it is believed that one of the more important adjustable design parameters is the inside diameter of the hollow fibers. For example, in order to achieve approximately match the shear rate of dialysate inside the lumens with the shear rate of blood outside the lumens, it may be helpful to adjust the porosity or packing fraction of the fiber bundle slightly from what might otherwise be the case. For example, if a porosity of 60% (packing factor of 40%) does not produce a large enough shear rate of the blood flowing in the inter fiber space, then a re-designed porosity of 50% (packing factor of 50%) would increase the shear rate by a factor of approximately 2.7 and thereby help to bring the shear rates closer to matching each other.

It is further believed that achieving such a situation of matching shear rate may allow the flowrate of dialysate to be reduced so that the flowrate of dialysate is closer to being equal to the flowrate of blood. It is even possible that the dialysate flowrate could be made equal to the blood flowrate. In conventional practice, which places the blood inside the lumens of the fibers and places the dialysate in the inter fiber space, it is typical for the dialysate flowrate to be approximately twice the blood flowrate. Even though dialysate is a relatively simple fluid, the amount of dialysate used in any one dialysis treatment session represents a cost of several dollars for each one of the hundreds of millions of dialysis treatment sessions that are performed each year. Accordingly, if that cost were able to be reduced by half or by any significant fraction, the monetary savings could be significant.

Experimental Observations

Experiments were conducted with a stand-alone blood circulating loop system. The cartridges used were a variety of four kinds of commercially available conventional hemodialysis cartridges whose normal mode of use is with blood flowing in the conventional configuration, i. e., inside the lumens of the fibers. One of these cartridges had fibers that were asymmetric (smooth in the lumens, rough on the exterior) and three others had symmetric fibers (smooth on both inside and outside). For these experiments, these cartridges were used in the reverse manner, i. e., with blood flowing in the inter fiber space. The duration of the experiment was 24 hours.

The results of the experimentation suggest that among the phenomena that may be happening during blood flow through the inter fiber space are hemolysis due to shear, and adsorption and by adhesion of red blood cells to fiber surfaces or entrapment of red blood cells. Experimental evidence such as observed locations of clot formation further suggests that these phenomena especially occur in the region where blood enters the cartridge, i. e., enters the inter fiber space, including the orbital distributor and the inter fiber space very near the orbital distributor. In a limited amount of experimentation, it seemed that hemolysis appeared to be less severe with a forward-facing orbital distributor, as compared to a rearward-facing orbital distributor. Hemolysis is inferred from the presence of hemoglobin in the blood plasma, i. e., outside red blood cells themselves, and is observable by a decrease of the red blood cell count. However, hemolysis is not the only phenomenon that could cause a decrease in the red blood cell count, which is the concentration of red blood cells in the circulating blood. Such a decrease could also result from some other mechanism such as adhesion of red blood cells on the fiber surfaces, which was believed to be occurring also. Such adhesion would remove those red blood cells from circulation. This latter phenomenon might also be observable as an increase in the pressure drop for blood flow through the compartment that contains the inter fiber space.

Based on this it is believed, although it is not wished to be bound by this observation, that it is good for blood flow to be distributed to the inter fiber space by a distributor that is not a rearward-facing distributor. It has been estimated, in conjunction with the present work, that at a 180 degree turn-around of flow at the edge of the fiber bundle, the maximum local shear rate in a very localized region can be 7 times as large as the sear rate in the main section of fiber bundle.

Elimination of a rearward-facing distributor eliminates the relatively 180-degree turnaround that occurs in such a geometry, with resulting local shear rates in the blood that are relatively large and different from shear rates experienced by blood in other locations. For example, it might be more favorable to use a forward-facing orbital distributor or a through-wall orbital distributor as described elsewhere herein. Further, it is believed that it is helpful for there to be fanning of fibers in the region of the orbital distributor at the entrance of blood flow into the cartridge. In addition to the earlier development of a fully-developed flow pattern in the inter fiber space, perhaps the extra space in the fanned region provides the opportunity for entrance-related adsorption of blood components onto the fibers, and possible entrapment of red blood cells by the fibers, with less impact on the overall flow resistance of the cartridge.

Furthermore, the overall porosity of the fiber bundle, in the main part of the cartridge apart from the possible fanned regions, may be chosen to be in the range of approximately 60%. It is believed that lower porosities may encourage entrapment of red blood cells and associated increase in pressure drop for flow through the inter fiber space.

In a forward-facing orbital distributor, it is not required that the separator wall exist everywhere around the circumference of the cartridge, or that it exist uniformly around the circumference of the cartridge.

It is further believed that in the brief set of experiments, some cartridges exhibited channeling of flow due to clumping of fibers, and those same cartridges had time histories of pressure drop across the cartridge that exhibited unusual variations and hysteresis during a certain early portion of the experiments. Such variations could be associated with either physical shifting of fibers or the formation of clots. This suggests the importance of having and keeping the fibers uniformly distributed within the fiber space, and filling the entire fiber space, as discussed in U.S. patent application Ser. No. 14/671,186, the entire disclosure of which is incorporated herein by reference.

For applications such as embodiments of the invention, one concern is how much loss occurs of Leukocytes (white blood cells) and platelets during blood processing by Outside-In Flow Filtration, and related to that phenomenon, a design parameter of interest is the shear rate experienced by the flowing blood.

Humes et al., U.S. Pat. No. 8,430,832, employ a very low shear stress of blood flow in a device for the sole purpose of sequestering activated leukocytes and platelets in an attempt to treat patients with sepsis. It their device, Humes et al. use the space between hollow or solid fibers in a filter, as well as their exterior surfaces, as a trap for leukocytes in a low ionized calcium environment. During this form of treatment, Humes et al. do not provide any flow of any substance through the lumens of their hollow fibers. The use of the very low shear stress has the effect of sequestering leukocytes inside a filter bundle which they called Specific Cytophoretic Device (SCD). Typically Humes et al. use a blood flowrate of 100 to 150 ml/minute, fibers which have hemo-incompatible external surfaces, and very low shear rates (forces) to accomplish high level of cell sequestration between the fibers and to promote adhesion to the fiber exteriors. The shear forces or shear stresses employed by Humes et al. are about $10^6$ smaller compared to the parameters experienced during typical blood flow in fiber lumens in conventional hemodialysis. Humes et al. indicate that sequestration of white blood cells takes place mostly when such cells are primed or activated with endotoxin or lipopolysaccharide (LPS) or by direct inoculation or infection of blood with pathogens. The choice of the low-shear operating regime by Humes et al. promotes the effect that activated leukocytes and platelets are preferentially sequestered in the exterior space between the fibers compared to inactivated leukocytes.

In contrast, for embodiments of the present invention, the operating conditions may be chosen such that that the shear rate or shear stress of the blood flow used in embodiments of Outside-In Flow Filtration is in approximately the same range as that used in conventional intraluminal hemodialysis (in which the blood flows inside the lumens of the hollow fibers). In embodiments of the present invention, the fiber bundle porosity and the blood flowrate may be adjusted or chosen such that the shear rate of the blood flow has values approximately from 700 to 2600 $sec^{-1}$, and more preferably from 700 to 1500 $sec^{-1}$. More particularly, the design of the Outside-In Flow Filtration cartridge may be such that the shear rate has a value within the just-described shear rate range everywhere in all portions or zones of the cartridge. This includes both fully-developed flow regions and flow transition regions, and includes entrance, middle and exit regions of the cartridge, and includes regions near the ports of the cartridge where blood enters and exits the cartridge.

As part of the present work, two sets of experiments were conducted, using stand-alone blood circulating systems with selected conventional hemodialysis cartridges having blood flow through the inter fiber space. One set of experiments, previously referred to, was conducted with blood flowing continuously from the beginning to the end of the 24-hour experiment.

This experiment was conducted with filters having a surface area of 2.0 square meters, and at a blood flowrate $Q_b$=250 ml/min.

Another separate set of experiments also was conducted. In this other set of experiments, blood was caused to flow through the inter fiber space of dialyzer cartridges intermittently in segments of 8 hours each, for a total of 72 hours. The blood was replaced with fresh blood between each 8 hour segment of the experiment. The blood used was human blood, and all of the blood was of the same blood type. In between each segment of experimentation, the cartridge was rinsed out with saline solution until the cartridge was clear, which presumably included enough rinsing to remove deposited leukocytes and platelets from the surfaces inside the cartridge. The cartridge then was stored overnight, and then at the start of the next segment of the experiment, fresh blood was put into the cartridge. Presumably the fiber surfaces exposed to the new blood were fresh surfaces as a result of the rinse, and were again able to adsorb leukocytes and platelets.

Results from both of these experiments are presented in FIGS. 46A, 46B, 47A and 47B. FIG. 46A shows, for the 24 hour continuous experiment, the white blood cell count normalized by the initial white blood cell count, as a function of time. FIG. 46B shows a platelet count for similar conditions. FIG. 47A shows, for the 72 hour experiment conducted intermittently, the white blood cell count normalized by the initial white blood cell count, as a function of time. FIG. 47B shows a platelet count for similar conditions. It can be understood that in the data from the intermittent experiment, at the start of each segment of the experiment there is a spike in the reported cell concentration back up to a normalized value of 100%. This spike reflects the fact that at each of those times fresh blood was introduced, containing a full concentration of cells. The data in the later part of each segment of the experiment reports the dropoff of those types of cells during that particular segment of the experiment.

The 24 hour continuous experiment showed that some loss in white blood cells and platelets occurs early in the experiment, but the amount of such loss stabilizes after less than 4 hours of blood circulation through the cartridge. Furthermore, when the exterior fiber surfaces are smooth and hydrophilic, the amount of white blood cell or platelet loss becomes much smaller compared to fibers having rough and hemo-incompatible exterior surfaces.

In the intermittent experiment, it was observed that during each 8-hour segment, the concentration of white blood cells started at a nominal initial value and decreased by the end of the 8-hour segment to about half of that initial value. After each 8-hour segment, the cartridge was rinsed and then was stored overnight in anticipation of the next 8 hour run. It is believed that when the cartridge was rinsed out during every interruption of the experiment, the rinsing-out may have removed the leukocytes that became adhered to surfaces during the preceding segment of the experiment. It is believed that the fact that the decrease of white blood cells and platelets occurred anew with every new segment of the experimental sequence indicates that the decrease of these cells was a phenomenon of adhesion of the cells to fiber surfaces and other internal surfaces, and that it occurs anew during each experimental segment because the previously accumulated cells of that type were rinsed out during preparation for overnight storage of the cartridge. Furthermore, it is believed that such adhesion is a phenomenon that occurs at locations of low blood flow shear stress. Platelets showed similar behavior as white blood cells, although sometimes there is some recovery of the platelet count during portions of a segment of the experiment, which supports the suggestion that the platelets are not actually destroyed but rather just being removed and held in certain places. It can be noted that all of these results are for a blood volume in the experimental fluid flow circuit of 250 milliliters, which is about one-twentieth of the total volume of blood in a typical human body. Accordingly, it is believed that in an actual dialysis situation, the fractional loss of for a body blood volume of 5 liters would be significantly smaller, because the same amount of adsorption of cells that appears as roughly 50% in these experiments would only decrease the white blood cell count of an actual patient by 2.5%. Such a decrease is roughly similar to what is experienced by a patient in a session of conventional hemodialysis.

These results from both of these experiments, taken together, suggest that what is happening is some combination of adsorption and/or adhesion and/or entrapment of white blood cells on the surfaces of the fibers and on other surfaces. It is believed that this decrease of leukocytes and platelets, and the repetition of the decrease during successive intervals of the intermittently-conducted experiment, indicates that there were locations of low shear rate inside the cartridge at which adhesion of white blood cells and platelets occurred. A likely cause of this localized low shear rate is the formation of channels in the inter fiber space caused by clumping-together of fibers. The presence of channeling would be consistent with visual observations of particular cartridges. Another possible cause of localized low shear rate could be local flow geometries near fixed shapes and structures in the cartridge, such that certain local places might create a local shear rate that is significantly lower than the shear rate in most other places in the cartridge.

The experiments indicate that a blood flow rate of about 300 or 400 ml/minute may be used to minimize cell and platelet loss during OIFF processing or therapy. Lower blood flow rates may be used in outside-in flow filters if dimensions and parameters are adjusted to satisfy shear rate and other requirements in the embodiments of the invention. It is described elsewhere herein that the shear rate or shear stress of blood can be adjusted by selecting cartridge dimensions fiber dimensions and fiber bundle porosity. If for some form of therapy it is necessary to use smaller actual blood flow rates than these, then the dimensions of the cartridge and the porosity of the fiber bundle may be adjusted so as to satisfy the conditions needed to achieve the optimal ranges of shear rates and linear velocity described here for embodiments of the present invention. Accordingly, the concentrations of leukocyte and platelets that are maintained during extended operation may be employed as an indicator of successful design and operating parameters of the outside-in flow filters according to embodiments of the present invention.

In general, the experimental results from both sets of experiments suggest or confirm the desirability of keeping the shear rate of blood flow everywhere in the cartridge within a certain range, without going either above or below that range.

In particular, it may be desirable to avoid having localized regions of unusually large shear rates near the blood entrance and blood exit regions of the cartridge, which might cause the local shear rate in such a region to exceed the described preferred range of shear rate. For example, if the cartridge design uses a rearward-facing orbital distributor, which causes an approximately 180 degree turn-around of flow near the distributor, that could produce local shear rates significantly larger than the average shear rate in the distributor. An excessively large shear rate may rupture red blood cells by hemolysis.

Also, it may be desirable to avoid having localized regions of unusually small shear rates. Designing the cartridge such that the shear rate does not fall below the desired range anywhere in the cartridge, may help to avoid or minimize activation of white blood cells and platelets and would avoid the operating regime chosen by Humes. If such activation were to occur, it would make such cells strongly adhere to fiber exterior surfaces and other surfaces inside the cartridge, including the surface of the housing. Regions of low shear rates may be avoided by ensuring the absence of channeling in all sections of the fiber bundle used to make the outside-in flow filtration filter. If such channeling occurred, it would likely cause regions with low shear rates that might promote unwanted sequestration or adhesion of leukocytes and platelets. Another situation leading to unusually low localized shear rates is where stagnation regions occur such as at changes of flow direction. There are various places in connection with a flow distributor at which stagnation points and changes of flow direction could occur. Regions of low shear rates may be avoided by appropriate geometric design of such regions as described elsewhere herein.

In the design of a cartridge, for a given overall flowrate through the cartridge, it is possible to calculate a shear rate at any given location in the cartridge. For example, computational fluid dynamics (CFD) modeling is well suited to calculating the complete flow field for flow near fixed geometric boundaries in the cartridge such as inlets, outlets and distributors. Regarding flow in the inter fiber space, for certain idealized conditions such as flow between regularly spaced cylindrical fibers, the shear rate may be calculated from analytical solutions as discussed in U.S. patent application Ser. No. 14/671,186, the entire disclosure of which is incorporated herein by reference. If there is any non-uniformity of flow within the fiber bundle, such as due to transition effects prior to reaching a fully developed flow profile, or if flow is non-uniformly distributed across the cross-section of the fiber bundle, such effects may be quantified by Computational Fluid Dynamics modeling. Values of shear rate calculated by any such means are valid if channeling does not occur within the fiber bundle, i.e., if the fibers are uniformly distributed within the fiber bundle, which is desirable.

It is believed that, essentially everywhere inside the housing, shear rates associated with flow through the housing and its inter fiber space, increase with the overall flowrate of blood through the compartment that contains the inter fiber space. A cartridge design can be described in terms of a maximum shear rate anywhere within the cartridge for a given overall blood flowrate through the housing and inter fiber space, and a minimum shear rate anywhere within the cartridge for that same blood flowrate. Furthermore, once the maximum shear rate and the minimum shear rate are known, the cartridge can be described by the ratio of those two quantities, i.e., the maximum shear rate divided by the minimum shear rate. (It is believed that this ratio of maximum shear rate anywhere in the cartridge to minimum shear rate anywhere in the cartridge is approximately independent of the actual flowrate through the housing ports and the inter fiber space. However, if there is any need for the specificity of a particular magnitude of flowrate, this ratio of maximum shear rate to minimum shear rate may be calculated at a specified overall flowrate of blood through the housing and the inter fiber space, such as 300 milliliters per minute.)

It is possible to adopt certain choices in the design of the fiber bundle, as discussed in U.S. patent application Ser. No. 14/671,186, the entire disclosure of which is incorporated herein by reference, to eliminate or minimize clumping-together of fibers and channeling within the fiber bundle. If channeling does occur it is somewhat unpredictable and is undesirable, but cartridges can be designed such that channeling is unlikely, as discussed in the U.S. patent application Ser. No. 14/671,186. For example, waviness of the fibers is believed to be helpful in this regard. Also, a certain preferred range of porosity of the fiber bundle is believed to be helpful in this regard, such as a porosity in the range of 40% to 70%, or more specifically, 50% to 62%.

Furthermore, another design strategy can be to minimize or eliminate stagnation points inside the housing in and around the fiber bundle. This can be done by modifying certain local flow geometries near fixed shapes and structures in the cartridge, such as by providing contours and flow redirectors as discussed elsewhere herein. Also, places that have sharp changes of flow geometry not only have the potential to create regions of high local shear stress or shear rate, but also have the potential to create regions of low local shear stress or shear rate at other places nearby the same structure or geometry that creates a region of high local shear stress or shear rate. Therefore, situations having sharp changes of flow geometry may generally be avoided. For example, a rearward-facing orbital distributor inherently has a place in which the flow makes a turn-around of almost approximately 180 degrees and possibly also creates a related eddy or stagnation region. Therefore, it might be favorable to use a forward-facing distributor or a through-wall distributor (described herein), rather than a rearward-facing orbital distributor. A rearward-facing distributor might create especially high shear at certain places near the approximately 180 degree turn-around of flow where there are sharp velocity gradients, while also potentially creating an unusually low shear rate at other places that are somewhat shielded from the flow near that same geometric feature.

In general, sharp changes of direction can create both a high local shear rate because of the abrupt change of flow direction or velocity within a small region, and also can create local regions that are like eddies or stagnation regions having localized low shear stress or shear rate. Thus, sharp changes of direction can increase the ratio of maximum to minimum shear stress or shear rate in two ways; i. e., by causing the value of maximum shear stress or shear rate to become large, and by also creating a particularly small value of minimum shear stress or shear rate. It is believed that the ratio of these two shear rates can serve as an indicator of how suitable a particular geometry of inter fiber space and housing ports and distributors is for purposes of handling blood, given the propensity of blood as described herein to form clots and suffer losses of certain types of cells. Accordingly, a cartridge may be designed so that the ratio of maximum to minimum shear rate or shear stress experienced by fluid anywhere in the cartridge is less than 9, or more preferably less than 5, or even more preferably less than 3 or less than 2.

In embodiments of the invention we seek to employ treatment therapies that require preservation of blood properties as it is known in hemodialysis, hemofiltration, hemofiltration, CRRT and related extracorporeal-based treatment modalities. Additionally, the outside surface of fibers may preferably be smooth, hydrophilic and hemocompatible to prevent further leukocyte and platelet adhesion to fiber exterior surface.

In embodiments of the invention, it is also may be desirable that the cartridge be designed and operated such that the linear velocity of the blood inside the cartridge be everywhere greater than 0.25 cm/sec and preferably greater than 0.75 cm/sec, in order to minimize conditions that would promote adhesion and/or sequestration of all cell types and platelets at the exterior surfaces of the fibers or in between them.

Other Features and Observations

Herein, general features usable in blood processing cartridges and systems and methods for processing blood are described. They may be used independently of other features, or together with other features as deemed desirable for particular applications. In general accord with the present disclosure:

1. A cartridge, comprising:
a housing that is generally tubular, having a housing wall;
a plurality of fibers contained inside said housing, at least some of said fibers being hollow and being made of semi-permeable membranes and having respective fiber lumens and fiber exteriors, wherein inter fiber space comprises space inside said housing between said fibers;
housing connections to said housing that are in fluid communication with said inter fiber space; and
a first header that is in fluid communication with said fiber lumens, said first header having a first header connection attached thereto,
wherein said housing connections have fittings that are luer lock fittings and said first header connection has a first header fitting that is incompatible with said luer lock fittings.

2. The cartridge of characterization 1, wherein said fitting that is incompatible with said luer lock fittings is a Hansen fitting.

3. The cartridge of any of characterizations 1-2, further comprising a second header having a second header fitting that is that is incompatible with said luer lock fittings.

4. The cartridge of any of characterizations 1-3, further comprising a forward-facing orbital distributor near at least one end of said cartridge.

5. The cartridge of any of characterizations 1-4, further comprising a rearward-facing orbital distributor near at least one end of said cartridge.

6. The cartridge of any of characterizations 1-5, further comprising a through-wall orbital distributor near at least one end of said cartridge.

7. The cartridge of any of characterizations 1-6, further comprising fanning of said fibers near at least one end of said cartridge.

8. The cartridge of any of characterizations 1-7, further comprising an air bleed connected to said housing, suitable to release air from said inter fiber space.

9. A tube set comprising:
the cartridge of any of characterizations 1-8;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

10. A system, comprising:
the cartridge of any of characterizations 1-8;
a first fluid supply, supplying a first fluid to said fiber lumens; and
a second fluid supply, supplying a second fluid to an inter fiber space inside said housing.

11. The system of characterization 10, wherein said first fluid is dialysate and said second fluid is blood.

12. A cartridge, comprising:
a housing that is generally tubular, having a housing wall;
a plurality of fibers contained inside said housing, at least some of said fibers being hollow and being made of semi-permeable membranes and having respective fiber lumens and fiber exteriors, wherein inter fiber space comprises space inside said housing between said fibers;
housing connections to said housing that are in fluid communication with said inter fiber space; and
a first header that is in fluid communication with said fiber lumens, said first header having a first header connection attached thereto,
wherein said first header connection has a Hansen fitting and said housing connections have fittings that are incompatible with said Hansen fittings.

13. The cartridge of characterization 12, wherein said fittings that are incompatible with said Hansen fitting are luer lock fittings.

14. A cartridge, comprising:
a housing that is generally tubular, having a housing wall;
a plurality of fibers contained inside said housing, at least some of said fibers being hollow and being made of semi-permeable membranes and having respective fiber lumens and fiber exteriors, wherein inter fiber space comprises space inside said housing between said fibers;
housing connections to said housing that are in fluid communication with said inter fiber space; and
a first header that is in fluid communication with said fiber lumens, said first header having a first header connection attached thereto,
wherein said housing connections have fittings having respective fitting axes that are generally parallel to said housing longitudinal axis and said first header connection has a first header fitting having a first header fitting axis that is generally perpendicular to said housing longitudinal axis.

15. The cartridge of characterization 14, further comprising a second header having a second header fitting having a second header fitting axis that is generally perpendicular to said housing longitudinal axis.

16. The cartridge of any of characterizations 14-15, further comprising a forward-facing orbital distributor near at least one end of said cartridge.

17. The cartridge of any of characterizations 14-16, further comprising a rearward-facing orbital distributor near at least one end of said cartridge.

18. The cartridge of any of characterizations 14-17, further comprising a through-wall orbital distributor near at least one end of said cartridge.

19. The cartridge of any of characterizations 14-18, further comprising fanning of said fibers near at least one end of said cartridge.

20. The cartridge of any of characterizations 14-19, further comprising an air bleed connected to said housing, suitable to release air from said inter fiber space.

21. A tube set comprising:
the cartridge of any of characterizations 14-20;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

22. A system, comprising:
the cartridge of any of characterizations 14-20;
a first fluid supply, supplying a first fluid to said fiber lumens; and
a second fluid supply, supplying a second fluid to an inter fiber space inside said housing.

23. The system of characterization 22, wherein said first fluid is dialysate and said second fluid is blood.

24. A cartridge, comprising:
a housing comprising a tubular component, said tubular component having a tubular wall and an interior and an exterior;
a fiber bundle containing a plurality of fibers contained inside said housing, at least some of said fibers being hollow and being made of semi-permeable membranes and having respective fiber lumens and fiber exteriors, wherein inter fiber space comprises space inside said housing between said fibers;
a compartment that is in fluid communication with said inter fiber space and with a housing port near an end of said housing and with an orbital distributor near said housing port,
wherein said orbital distributor comprises a separator wall, said fiber bundle being located radially inward of said separator wall, and further comprises an orbital channel that is located radially outward of said separator wall, wherein said separator wall has a plurality of openings therethrough defined by remaining solid material of said separator wall.

25. The cartridge of characterization 24, wherein said remaining solid material of said separator wall comprises a plurality of ligaments that are straight.

26. The cartridge of any of characterizations 24-25, wherein said remaining solid material of said separator wall comprises a plurality of ligaments that are curved or irregular in shape.

27. The cartridge of any of characterizations 24-26, wherein said remaining solid material has rounded edges.

28. The cartridge of any of characterizations 24-27, wherein said openings through said separator wall are substantially identical to each other and are distributed uniformly around a circumference of said housing.

29. The cartridge of any of characterizations 24-28, wherein said openings through said separator wall vary around a circumference of said housing in at least one geometric parameter.

30. The cartridge of any of characterizations 24-29, wherein said openings through said separator wall vary around a circumference in a manner that is symmetric with respect to a plane that goes through a longitudinal axis of said housing and goes through a housing port.

31. The cartridge of any of characterizations 24-30, wherein said openings through said separator wall vary around a circumference in local fraction of open area, or in dimensions of said openings, or both.

32. The cartridge of any of characterizations 24-31, wherein said openings are holes of generally circular or ellipsoidal cross-section.

33. The cartridge of any of characterizations 24-32, wherein said openings are holes of rounded-polygon cross-section.

34. The cartridge of any of characterizations 24-33, wherein said openings are holes placed in a staggered configuration.

35. The cartridge of any of characterizations 24-34, wherein said openings through said separator wall extend in a helical configuration.

36. The cartridge of any of characterizations 24-35, wherein said openings through said separator wall are distributed in a way that creates a more uniform distribution of fluid flow in said fiber bundle than would occur with a uniform distribution of said openings.

37. The cartridge of any of characterizations 24-36, wherein said separator wall is an extension of said tubular component.

38. The cartridge of any of characterizations 24-37, wherein said separator wall is an extension of said tubular component having at least one surface that is substantially collinear with a corresponding surface of said tubular wall.

39. The cartridge of any of characterizations 24-38, further comprising an impermeable barrier in which said fibers are potted, said barrier forming a part of a boundary of said compartment.

40. The cartridge of any of characterizations 24-39, further comprising an end cap adapted to join to said tubular component, wherein said end cap contains said housing port such that said housing port is in communication with said orbital channel of said orbital distributor.

41. The cartridge of any of characterizations 24-40, further comprising an air bleed connected to said housing, suitable to release air from said inter fiber space.

42. A tube set comprising:
the cartridge of any of characterizations 24-41;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

43. A system, comprising:
the cartridge of any of characterizations 24-41;
a first fluid supply, supplying a first fluid to said first fiber group and supplying said first fluid to said second fiber group; and
a second fluid supply, supplying a second fluid to an inter fiber space inside said housing.

44. The system of characterization 43, wherein said first fluid is dialysate and said second fluid is blood.

45. A cartridge, comprising:
a housing;
a fiber bundle comprising a plurality of fibers contained inside said housing, at least some of said fibers being hollow and being made of semi-permeable membranes having respective fiber lumens and fiber exteriors, wherein inter fiber space comprises space inside said housing between said fibers;
a first fluid flow compartment comprising said lumens of said hollow fibers; and
a second fluid flow compartment comprising said inter fiber space,
wherein said housing comprises a first housing port near a first end of said housing, and a second housing port near a second end of said housing,
wherein said second fluid flow compartment comprises an orbital distributor comprising an orbital channel and an access region accessing said fiber bundle,
further comprising, between said orbital channel and said access to said fiber bundle, a non-uniform-conductance flow element whose conductance varies as a function of position with respect to a circumferential angle.

46. The cartridge of characterization 45, wherein said second fluid flow compartment comprises, in sequence in an axial direction starting closest to an adjacent end of said cartridge, said orbital channel, said non-uniform conductance flow element, and said access region.

47. The cartridge of any of characterizations 45-46, wherein said second fluid flow compartment comprises, in sequence in an axial direction starting closest to an adjacent end of said cartridge, said access region, said non-uniform conductance flow element, and said orbital channel.

48. The cartridge of any of characterizations 45-47, wherein said non-uniform-conductance flow element has a lesser conductance near said housing port and a greater conductance away from said housing port.

49. The cartridge of any of characterizations 45-48, wherein said non-uniform-conductance flow element has a conductance that varies with angular position around an orbital distributor circumference in a manner that is symmetric about a plane that passes through said housing port and passes through a longitudinal axis of said housing.

50. The cartridge of any of characterizations 45-49, wherein said non-uniform-conductance flow element has a maximum conductance at or near 180 degrees away from one of said housing ports.

51. The cartridge of any of characterizations 45-50, wherein said non-uniform-conductance flow element comprises ribs whose geometry provides non-uniform-conductance.

52. The cartridge of any of characterizations 45-51, wherein said non-uniform-conductance flow element comprises ribs that are distributed non-uniformly in their locations with respect to circumferential angle.

53. The cartridge of any of characterizations 45-52, wherein said non-uniform-conductance flow element has holes therethrough that provide non-uniform-conductance.

54. The cartridge of any of characterizations 45-53, wherein said non-uniform-conductance flow element has holes therethrough at locations that are non-uniformly distributed.

55. The cartridge of any of characterizations 45-54, wherein said non-uniform-conductance flow element has holes therethrough whose dimensions are non-uniform.

56. The cartridge of any of characterizations 45-55, wherein said non-uniform-conductance flow element has local conductance distributed in a way that creates a more uniform distribution of fluid flow in said fiber bundle than would occur with a uniform-conductance flow element or no flow element.

57. A tube set comprising:
the cartridge of any of characterizations 45-56;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

58. A filtration system, comprising:
the cartridge of any of characterizations 45-56, wherein said housing supply port is connected to a blood supply line and said housing discharge port is connected to a blood discharge line,
further comprising a dialysate connection from a dialysate system to lumens of at least some of said plurality of fibers, or an ultrafiltrate removal line connecting to lumens of at least some of said plurality of fibers.

59. A cartridge, comprising:
a housing;
a plurality of fibers contained inside said housing, at least some of said fibers being hollow and being made of semi-permeable membranes having respective fiber lumens and fiber exteriors;
a first fluid flow compartment comprising said lumens of said hollow fibers; and
a second fluid flow compartment comprising an inter fiber space bordering said fiber exteriors,
wherein said housing comprises a first housing port near a first end of said housing, and a second housing port near a second end of said housing,
wherein said second fluid flow compartment comprises a forward-facing orbital distributor in communication with said inter fiber space, and
wherein in a cross-section taken in a sectional plane that contains a longitudinal axis of said cartridge, said housing interior surface is composed entirely of surfaces that are either curved or vertical.

60. The cartridge of characterization 59, wherein in said cross-section, said housing interior surfaces have local tangent lines that are inclined by no more than 45 degrees with respect to a longitudinal axis of said housing.

61. A cartridge, comprising:
a housing;
a plurality of fibers contained inside said housing, at least some of said fibers being hollow and being made of semi-permeable membranes having respective fiber lumens and fiber exteriors, wherein inter fiber space comprises space inside said housing between said fibers,
a port connected to a side of said housing;
an orbital distributor inside said housing and connected to said port, wherein said orbital distributor comprises a separator wall that is generally circumferential,
wherein said separator wall is at one of its ends joined to said housing and at its opposed end creates an open direction of said orbital distributor facing away from a midplane of said cartridge,
wherein said separator wall has a shape, in a cross-section taken in a plane that contains a lengthwise axis of said cartridge, that has smoothly rounded end.

62. The cartridge of characterization 61, wherein said separator wall has a separator wall thickness, and said smoothly rounded end has a radius of curvature that is at least one-quarter of said separator wall thickness.

63. A cartridge, comprising:
a housing;
a plurality of fibers contained inside said housing, at least some of said fibers being hollow and being made of semi-permeable membranes having respective fiber lumens and fiber exteriors, wherein inter fiber space comprises space inside said housing between said fibers,
a port connected to a side of said housing; and
an orbital distributor inside said housing and connected to said port, wherein said orbital distributor comprises a circumferential internal wall,
wherein a surface of an interior of said port aligns with or smoothly transitions with a surface of an interior of said orbital distributor.

64. The cartridge of characterization 63, wherein, in cross-section, said orbital distributor has a bottom that is U-shaped or has a rounded corner.

65. A cartridge, comprising:
a housing, said housing having a housing supply port and a housing discharge port;
a plurality of fibers contained inside said housing, at least some of said fibers being hollow and being made of semi-permeable membranes having respective fiber lumens and fiber exteriors;
a first fluid flow compartment comprising said lumens of said hollow fibers; and
a second fluid flow compartment comprising an inter fiber space bordering said fiber exteriors,
wherein said housing comprises a first housing port near a first end of said housing, and a second housing port near a second end of said housing,
wherein said second fluid flow compartment comprises an orbital distributor in communication with said inter fiber space, wherein said orbital distributor comprises a lateral-circumferential flow redirector near one of said housing ports,
wherein said lateral-circumferential flow redirector comprises a smoothly curved surface that blends smoothly with a circumferential direction of said orbital distributor and forms a sharp or pointed geometry that points in a direction of said one of said housing ports near said orbital distributor.

66. The cartridge of characterization 65, wherein said lateral-circumferential flow redirector is in conjunction with a forward-facing orbital distributor.

67. The cartridge of any of characterizations 65-66, wherein said lateral-circumferential flow redirector is in conjunction with a rearward-facing orbital distributor.

68. The cartridge of any of characterizations 65-67, wherein said lateral-circumferential flow redirector has a three-dimensional shape.

69. The cartridge of any of characterizations 65-68, wherein said housing port is a housing supply port.

70. The cartridge of any of characterizations 65-69, wherein said housing port is a housing discharge port.

71. The cartridge of any of characterizations 65-70, wherein said lateral-circumferential flow redirector comprises two curved surfaces facing opposite each other, wherein said two curved surfaces join at a sharp edge that points toward said housing port.

72. The cartridge of characterization 71, wherein said two curved surfaces join at a sharp edge that substantially is on a centerline or plane of symmetry of said housing port.

73. A tube set comprising:
the cartridge of any of characterizations 65-71;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

74. A filtration system, comprising:
the cartridge of any of characterizations 65-71, wherein said housing supply port is connected to a blood supply line and said housing discharge port is connected to a blood discharge line,
further comprising a dialysate connection from a dialysate system to lumens of at least some of said plurality of fibers, or an ultrafiltrate removal line connecting to lumens of at least some of said plurality of fibers.

75. A cartridge, comprising:
a housing, said housing having a housing supply port and a housing discharge port; a plurality of fibers contained inside said housing, at least some of said fibers being hollow and being made of semi-permeable membranes having respective fiber lumens and fiber exteriors;
a first fluid flow compartment comprising said lumens of said hollow fibers; and
a second fluid flow compartment comprising an inter fiber space bordering said fiber exteriors,
wherein said housing comprises a first housing port near a first end of said housing, and a second housing port near a second end of said housing,
wherein said second fluid flow compartment comprises an orbital distributor in communication with said inter fiber space, wherein said orbital distributor comprises a circumferential-axial flow redirector,
wherein said circumferential-axial flow redirector blends smoothly with said orbital distributor in a circumferential direction, and said circumferential-axial flow redirector has a tangential surface that is directed approximately along a lengthwise direction of said cartridge.

76. The cartridge of characterization 75, wherein said circumferential-axial flow redirector is in conjunction with a forward-facing orbital distributor.

77. The cartridge of any of characterizations 75-76, wherein said circumferential-axial flow redirector is in conjunction with a rearward-facing orbital distributor.

78. The cartridge of any of characterizations 75-77, wherein said circumferential-axial flow redirector has a three-dimensional shape.

79. The cartridge of any of characterizations 75-78, wherein said circumferential-axial flow redirector has two curved surfaces and a sharp edge where said two curved surfaces meet each other.

80. The cartridge of any of characterizations 75-79, wherein said circumferential-axial flow redirector is located within said orbital distributor approximately 180 degrees around said circumference away from one of said housing ports.

81. The cartridge of any of characterizations 75-80, wherein a portion of said circumferential-axial flow redirector approximately follows a circumferential path of the orbital distributor.

82. The cartridge of any of characterizations 75-81, wherein said circumferential-axial flow redirector is located at said housing supply port.

83. The cartridge of any of characterizations 75-82, wherein said circumferential-axial flow redirector is located at said housing discharge port.

84. A tube set comprising:
the cartridge of any of characterizations 75-82;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

85. A filtration system, comprising:
the cartridge of any of characterizations 75-82, wherein said housing supply port is connected to a blood supply line and said housing discharge port is connected to a blood discharge line,
further comprising a dialysate connection from a dialysate system to lumens of at least some of said plurality of fibers, or an ultrafiltrate removal line connecting to lumens of at least some of said plurality of fibers.

86. A cartridge, comprising:
a housing;
a plurality of fibers contained inside said housing, at least some of said fibers being hollow and being made of semi-permeable membranes having respective fiber lumens and fiber exteriors, wherein inter fiber space comprises space inside said housing between said fibers,
a port connected to a side of said housing;
an orbital distributor inside said housing and connected to said port, wherein said orbital distributor comprises a circumferential internal wall,
wherein said circumferential wall is at one of its ends joined to said housing and at its opposed end forms a separator wall creating an open direction of said orbital distributor facing away from a midplane of said cartridge,
wherein a fiber entrance height is a distance between said circumferential internal wall and a barrier in which said plurality of fibers are potted,
wherein an orbital distributor height is a maximum height of said circumferential wall inside said orbital distributor, wherein said fiber entrance height is greater than said orbital distributor height.

87. The cartridge of characterization 86, wherein said fibers are fanned near said orbital distributor.

88. The cartridge of any of characterizations 86-87, wherein said orbital distributor has a radial dimension that is greater than 2 millimeters.

89. The cartridge of any of characterizations 86-88, wherein said orbital distributor has a height that varies as a function of circumferential position.

90. A cartridge, comprising:
a housing;
a plurality of fibers contained inside said housing, at least some of said fibers being hollow and being made of semi-permeable membranes having respective fiber lumens and fiber exteriors;
a first fluid flow compartment comprising said lumens of said hollow fibers; and
a second fluid flow compartment comprising an inter fiber space bordering said fiber exteriors,
wherein said fibers perform a sieving function according to molecular size and molecular shape, for molecules to which an outer surface of said fibers is exposed.

91. A cartridge, comprising:
a housing comprising a tubular component, said tubular component having a tubular wall and a tubular interior;
a plurality of fibers contained inside said tubular component, at least some of said fibers being hollow and being made of semi-permeable membranes and having respective fiber lumens and fiber exteriors;
a first impermeable barrier adjoining said tubular interior and adjoining said fiber exteriors near a first end of said tubular component; and
a second impermeable barrier adjoining said tubular interior and adjoining said fiber exteriors near a second end of said tubular component,
wherein said first impermeable barrier is polished so as to expose said lumens of said hollow fibers,
wherein said second impermeable barrier dead-ends said second ends of said hollow fibers, and said second impermeable barrier has a surface, facing away from said fiber bundle, that is curved.

92. The cartridge of characterization 91, wherein said curved surface of said second impermeable barrier is polished.

93. The cartridge of any of characterizations 91-92, wherein said curved surface of said second impermeable barrier is axisymmetric.

94. The cartridge of any of characterizations 91-93, wherein edges of said surface are also curved or rounded.

95. The cartridge of any of characterizations 91-94, wherein inter fiber space comprises space inside said housing between said fibers, and further comprising, at said second end of said cartridge, a port that is in fluid communication with said inter fiber space, wherein said port is located on an end cap of said cartridge.

96. The cartridge of characterization 95, wherein said port is located on an axis of said cartridge.

97. The cartridge of characterization 95, wherein said inter fiber space is in fluid communication with another port at or near said first end.

98. The cartridge of any of characterizations 91-97, wherein said cartridge has a port that is in fluid communication with said lumens of said fibers at or near said first end.

99. A hemodialysis blood processing system, comprising:
a cartridge comprising:
a housing having a housing supply port and a housing discharge port; and
a plurality of fibers contained inside said housing, at least some of said fibers being hollow and being made of semi-permeable membranes having respective fiber lumens and fiber exteriors;
wherein said cartridge has at least one feature selected from the group consisting of: said fibers having waviness of said fibers; said fibers having an external surface that is smooth and hemocompatible; said fibers having a packing fraction of said fibers in said housing being in the range of 40% to 70%; and said cartridge having an air bleed connected to said cartridge in communication with an inter fiber space,
wherein said system supplies blood to said housing supply port and receives blood from said housing discharge port,
wherein said system supplies dialysate to a first end of said plurality of fibers and receives dialysate from a second end of said plurality of fibers,
wherein said blood flowing outside said fibers and said dialysate flowing inside said fibers flow in opposite directions.

100. The system of characterization 99, wherein said cartridge has at least two features selected from said group.

101. A slow continuous ultrafiltration blood processing system, comprising:
a cartridge comprising:
a housing having a housing supply port and a housing discharge port; and
a plurality of fibers contained inside said housing, at least some of said fibers being hollow and being made of semi-permeable membranes having respective fiber lumens and fiber exteriors;
wherein said cartridge has at least one feature selected from the group consisting of: said fibers having waviness of said fibers; said fibers having an external surface that is smooth and hemocompatible; said fibers having a packing fraction of said fibers in said housing being in the range of 40% to 70%; and said cartridge having an air bleed connected to said cartridge in communication with an inter fiber space,
wherein said system supplies blood to said housing supply port and receives blood from said housing discharge port,
wherein said system extracts filtrate from an end of said plurality of fibers.

102. The system of characterization 101, wherein said cartridge has at least two features selected from said group.

103. A hemofiltration blood processing system, comprising:
a cartridge comprising:
a housing having a housing supply port and a housing discharge port; and
a plurality of fibers contained inside said housing, at least some of said fibers being hollow and being made of semi-permeable membranes having respective fiber lumens and fiber exteriors;
wherein said cartridge has at least one feature selected from the group consisting of: said fibers having waviness of said fibers; said fibers having an external surface that is smooth and hemocompatible; said fibers having a packing fraction of said fibers in said housing being in the range of 40% to 70%; and said cartridge having an air bleed connected to said cartridge in communication with an inter fiber space,
wherein said system supplies blood to said housing supply port and receives blood from said housing discharge port,
wherein said system extracts filtrate from an end of said plurality of fibers,
wherein said system supplies a substitution fluid to said blood.

104. The system of characterization 103, wherein said cartridge has at least two features selected from said group.

105. The system of any of characterizations 103-104, wherein said system supplies said substitution fluid to said blood upstream of said cartridge.

106. The system of any of characterizations 103-105, wherein said system supplies said substitution fluid to said blood downstream of said cartridge.

107. The system of any of characterizations 103-106, wherein said system supplies said substitution fluid to said blood both upstream of said cartridge and downstream of said cartridge.

108. The system of any of characterizations 103-107, wherein said system supplies said substitution fluid to said blood internally within said cartridge.

109. A hemodiafiltration blood processing system, comprising:
a cartridge comprising:
a housing having a housing supply port and a housing discharge port; and
a plurality of fibers contained inside said housing, at least some of said fibers being hollow and being made of semi-permeable membranes having respective fiber lumens and fiber exteriors;
wherein said cartridge has at least one feature selected from the group consisting of: said fibers having waviness of said fibers; said fibers having an external surface that is smooth and hemocompatible; said fibers having a packing fraction of said fibers in said housing being in the range of 40% to 70%; and said cartridge having an air bleed connected to said cartridge in communication with an inter fiber space,
wherein said system supplies blood to said housing supply port and receives blood from said housing discharge port,
wherein said system supplies dialysate to a first end of said plurality of fibers and receives dialysate from a second end of said plurality of fibers,
wherein said system supplies a substitution fluid to said blood.

110. The system of characterization 109, wherein said cartridge has at least two features selected from said group.

111. The system of any of characterizations 109-110, wherein said system supplies said substitution fluid to said blood upstream of said cartridge.

112. The system of any of characterizations 109-111, wherein said system supplies said substitution fluid to said blood downstream of said cartridge.

113. The system of any of characterizations 109-112, wherein said system supplies said substitution fluid to said blood both upstream of said cartridge and downstream of said cartridge.

114. The system of any of characterizations 109-113, wherein said system supplies said substitution fluid to said blood internally within said cartridge.

115. A tube set comprising:
a cartridge having a housing and having a plurality of fibers contained inside said housing, and having an inter fiber space between said fibers inside said housing, and having a first housing port that is in fluid communication with said inter fiber space and a second housing port that is in fluid communication with said inter fiber space;
a blood supply tubing adapted to attach to a patient's body, and further connecting to said first housing port; and
a blood return tubing adapted to attach to said patient's body, and further connecting to said second housing port,
wherein at least one of said blood supply tubing and said blood return tubing is adapted to be compressed by a roller of a peristaltic pump.

116. A system comprising:
a cartridge, comprising:
a housing;
a plurality of fibers contained inside said housing, at least some of said fibers being hollow and being made of semi-permeable membranes having respective fiber lumens and fiber exteriors;
a first fluid flow compartment comprising said lumens of said hollow fibers; and
a second fluid flow compartment comprising an inter fiber space bordering said fiber exteriors,
wherein said housing comprises at least one housing port in communication with an inter fiber space,
wherein said system further comprises a dialysate supply for supplying purified dialysate to said lumens of said fibers, and for maintaining a pressure inside said lumens higher than a pressure at said fiber exteriors, whereby said dialysate passes through said semi-permeable membranes of said fibers and occupies said inter fiber space to produce a primed cartridge filled with priming liquid,
wherein said system further comprises an air bleed for releasing air from said second fluid flow compartment,
wherein said system further comprises a blood supply system for delivering blood to said primed cartridge,
wherein said system further comprises a multi-position valve for releasing said priming liquid from said system when blood is displacing said priming liquid from said cartridge, and for retaining blood within said system after blood has reached said multi-position valve.

117. A system, comprising:
a housing, said housing having a housing supply port and a housing discharge port;
a plurality of fibers contained inside said housing, at least some of said fibers being hollow and being made of semi-permeable membranes having respective fiber interiors and fiber exteriors, said fibers being grouped into a first fiber group and a second fiber group;
a first end having a first-end header first chamber that is in fluid communication with said fiber lumens of said first fiber group and a first-end header second chamber that is in fluid communication with said fiber lumens of said second fiber group;
a second-end header that is in fluid communication with at least some of said fiber lumens;
a first fluid supply system that supplies a first fluid to said first-end header first chamber and to said first-end header second chamber, wherein flow in lumens of said first fiber group and flow in lumens of said second fiber group are in an identical direction; and
a second fluid supply system that supplies a second fluid to said housing supply port.

118. The system of characterization 117, wherein said second fluid supply system supplies blood to said housing supply port.

119. The system of any of characterizations 117-118, wherein said first fluid supply system supplies dialysate to both said first-end header first chamber and said first-end header second chamber.

120. The system of any of characterizations 117-119, wherein said first-end header first chamber has a supply pressure that is different from a supply pressure for said first-end header second chamber.

121. The system of any of characterizations 117-120, further comprising an impermeable barrier adjoining said housing interior and adjoining said fiber exteriors near an end of said tubular component, wherein said first-end header first chamber is separated from said first-end header second chamber by a separator that presses against said barrier.

122. The system of any of characterizations 117-121, wherein said second-end header has a second-end header first chamber that is in fluid communication with at least some of said fibers in said first fiber group and has a second-end header second chamber that is in fluid communication with at least some of said fibers in said second fiber group.

123. The system of any of characterizations 117-122, wherein at least some of said fibers in said first fiber group have at least one physical characteristic or dimension that is different from a corresponding physical characteristic or dimension of at least some of said fibers in said second fiber group.

124. The system of any of characterizations 117-123 wherein said second-end header has a second-end header first chamber and has a second-end header second chamber, and one of said second-end header chambers is in fluid communication with at least some of one group of said fibers and the other of said discharge header chambers is a blockage that blocks at least some of the other group of said fibers.

125. The system of characterization 124, wherein one of said fiber groups is a central group and the other of said fiber groups is an outer group.

126. The system of characterization 124, wherein said blockage is a centrally located plug.

127. The system of characterization 124, wherein said blockage is an annularly shaped plug.

128. A cartridge, comprising:
a housing, said housing having a housing supply port and a housing discharge port; and
a plurality of fibers contained inside said housing, at least some of said fibers being hollow and being made of semi-permeable membranes having respective fiber lumens and fiber exteriors,
said fibers being grouped into a first fiber group and a second fiber group,
wherein said fibers, at a first end, are potted in a first barrier, such that at said first end said first group of fibers is open to a first fluid connection and said second group of fibers is open to a second fluid connection that is isolated from said first fluid connection,
wherein said fibers, at a second end opposed to said first end, are all dead-ended.

129. The cartridge of characterization 128, wherein said fibers at said second end are dead-ended by being potted in a second barrier.

130. The cartridge of any of characterizations 128-129, wherein one of said groups of fibers is a fiber bundle of generally circular cross-section and the other of said groups of fibers is a fiber bundle of generally annular cross-section surrounding said fiber bundle of said generally circular cross-section.

131. A tube set comprising:
the cartridge of characterization 128;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

132. A system, comprising:
the cartridge of characterization 128, wherein said housing supply port is connected to a blood supply line and said housing discharge port is connected to a blood discharge line,
further comprising a dialysate connection from a dialysate system to said first group of fibers, and
further comprising an ultrafiltrate removal line connecting to said second group of fibers.

133. The system of characterization 132, wherein said housing supply port is located nearest an end of said cartridge in which said dialysate connection is located.

134. The system of characterization 132, wherein said housing discharge port is located nearest an end of said cartridge in which said dialysate connection is located.

135. A method of treating blood extracorporeally, comprising providing the system of characterization 132;
supplying blood through said housing supply port and removing blood through said housing discharge port;
supplying dialysate fluid to said lumens of said first group of fibers, whereby said dialysate passes through said semi-permeable membrane and into said blood; and
removing filtrate liquid from a connection that is in fluid communication with said lumens of said second group of fibers.

136. A cartridge, comprising:
a housing;
a plurality of fibers contained inside said housing, at least some of said fibers being hollow and being made of semi-permeable membranes having respective fiber lumens and fiber exteriors, said fibers being potted into a first-end barrier at one end of said fibers and being potted into a second-end barrier at an opposed end of said fibers;
a first-end header having a first-end header first chamber that is in fluid communication with said lumens of some of said fibers of so as to define a first fiber group, and a first-end header second chamber that is in fluid communication with said lumens of others of said fibers so as to define a second fiber group; and
a second-end header having a second-end header first chamber that is in fluid communication with said lumens of at least some of said fibers of said first fiber group and a second-end header second chamber that is in fluid communication with said lumens of at least some of said fibers of said second fiber group,
wherein said first-end header first chamber and said first-end header second chamber are separated from each other at least in part by a first-end separator that contacts said first-end barrier,
wherein said second-end header first chamber and said second-end header second chamber are separated from each other at least in part by a second-end separator that contacts said second-end barrier.

137. The cartridge of characterization 136, wherein one of said fiber groups is centrally located within said plurality of fibers and another of said fiber groups is located, within said plurality of fibers, in an annular region that surrounds said centrally located fiber group.

138. The cartridge of any of characterizations 136-137 wherein all of said fibers in said first fiber group are in fluid communication with said first-end header first chamber and are in fluid communication with said second-end header first chamber.

139. The cartridge of any of characterizations 136-138, wherein all of said fibers in said second fiber group are in fluid communication with said first-end header second chamber and are in fluid communication with said second-end header second chamber.

140. The cartridge of any of characterizations 136-139, wherein some of said fibers in said second fiber group are in fluid communication with said first-end header second chamber and are in fluid communication with said second-end header first chamber.

141. The cartridge of any of characterizations 136-140, wherein some of said fibers in said first fiber group are in fluid communication with said first-end header first chamber and are in fluid communication with said second-end header second chamber.

142. A tube set comprising:
the cartridge of characterization 136;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection,
wherein said tube set can be connected to a fluid supply system.

143. A system for processing blood, said system comprising:
the cartridge of characterization 136;
a dialysate supply system for supplying dialysate at a first pressure or a first flowrate to said first-end header first chamber and for supplying dialysate at a second pressure or a second flowrate to said first-end header second chamber;
a dialysate removal system for receiving dialysate from said second-end header first chamber and for receiving dialysate from said second-end header second chamber; and
a blood system, wherein said housing has a housing supply port and a housing discharge port, wherein said blood system supplies blood to said housing supply port and removes blood from said housing discharge port,
wherein said dialysate supply pressure at said first-end header first chamber and said dialysate supply pressure at said first-end header second chamber can be independently adjusted.

144. A system comprising the cartridge of characterization 136, wherein a direction of flow inside fibers in said first fiber group coincides with a direction of flow inside fibers in said second fiber group.

145. A system comprising the cartridge of characterization 136, wherein a direction of flow inside fibers in said first fiber group coincides with a direction of flow inside fibers in said second fiber group, and is opposite a direction of flow outside said plurality of fibers.

146. A system comprising the cartridge of characterization 136, wherein one of said chambers of one of said headers is capped, whereby no flow enters or exits through said capped chamber of said one of said headers.

147. A method of processing blood, said method comprising:
providing the cartridge of characterization 136;
supplying dialysate at a first pressure to said first-end header first chamber; supplying dialysate at a second pressure to said first-end header second chamber,
wherein said first pressure differs from said second pressure; and
removing dialysate from said second-end header first chamber and said second-end header second chamber.

148. A method of performing hemodialysis, said method comprising:
providing a cartridge, wherein said cartridge comprises a first dialysate inlet and a second dialysate inlet and a dialysate outlet, and comprises a blood inlet and a blood outlet, and said cartridge comprises a semipermeable membrane separating blood and dialysate;
providing a first fluid supply that supplies a dialysate to said first dialysate inlet and providing a second fluid supply that supplies said dialysate to said second dialysate inlet;
removing said dialysate from said dialysate outlet; and
performing hemodialysis by causing blood to flow into said blood inlet and out from said blood outlet.

149. The method of characterization 148, wherein said dialysate at said first dialysate inlet is at a same pressure as said dialysate at said second dialysate inlet.

150. The method of any of characterizations 148-149, wherein said dialysate at said first dialysate inlet is at a pressure different from a pressure of said dialysate at said second dialysate inlet.

151. The method of any of characterizations 148-150, wherein said dialysate at said first dialysate inlet is at a pressure greater than a pressure of said dialysate at said second dialysate inlet.

152. The method of any of characterizations 148-151, wherein at least a majority of said dialysate that enters at said first dialysate inlet passes through said semi-permeable membrane into said blood.

153. A cartridge, comprising:
a housing;
a plurality of fibers contained inside said housing, at least some of said fibers being hollow and being made of semi-permeable membranes having respective fiber lumens and fiber exteriors;
a first-end header having a first-end header first chamber that is in fluid communication with said lumens of some of said fibers of so as to define a first fiber group, and a first-end header second chamber that is in fluid communication with said lumens of others of said fibers so as to define a second fiber group; and
a second-end header that is in fluid communication with at least some of said fibers of one of said fiber groups,
wherein at least some of said fibers of the other of said fiber groups are dead-ended.

154. The cartridge of characterization 153, wherein said dead-ended fibers are dead-ended by a stopper that blocks at least some of said fibers of the other of said fiber groups.

155. The cartridge of any of characterizations 153-154, wherein one of said fiber groups is centrally located within said plurality of fibers and another of said fiber groups is located, within said plurality of fibers, in an annular region that surrounds said centrally located fiber group.

156. The cartridge of any of characterizations 153-155, wherein said first-end header comprises a separator that is circular, and wherein a boundary between said fibers and said housing comprises a barrier, and wherein said separator presses against said barrier.

157. The cartridge of any of characterizations 153-156, wherein said first-end header first chamber is in fluid communication with all of said fibers in said second fiber group and said first-end header second chamber is in fluid communication with all of said fibers in said second fiber group.

158. The cartridge of any of characterizations 153-157, wherein said first fiber group has a circular cross-sectional shape and said stopper, where said stopper contacts said second fiber group, has a cross-sectional shape that is at least approximately equal to said circular cross-sectional shape.

159. The cartridge of any of characterizations 153-158, wherein said second fiber group has an annular cross-sectional shape and said stopper, where said stopper contacts said second fiber group, has a cross-sectional shape that is at least approximately equal to said annular cross-sectional shape.

160. The cartridge of any of characterizations 153-159, wherein some of said fibers are in fluid communication with said first-end header first chamber and are blocked by said stopper.

161. The cartridge of any of characterizations 153-160, wherein some of said fibers are in fluid communication with said first-end header second chamber and are blocked by said stopper.

162. The cartridge of any of characterizations 153-161, wherein some of said fibers of said first fiber group are in fluid communication with said first-end header first chamber and are in fluid communication with said second header, and others of said fibers of said first fiber group are in fluid communication with said first-end header first chamber and are blocked by said stopper.

163. The cartridge of any of characterizations 153-162, wherein some of said fibers of said second fiber group are in fluid communication with said first-end header second chamber and are in fluid communication with said second header, and others of said fibers of said second fiber group are in fluid communication with said first-end header second chamber and are blocked by said stopper.

164. A tube set comprising:
the cartridge of characterization 153;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

165. A system, comprising:
the cartridge of characterization 153;
a first fluid supply, supplying a first fluid to said first fiber group and supplying said first fluid to said second fiber group; and
a second fluid supply, supplying a second fluid to an inter fiber space inside said housing.

166. The system of characterization 165, wherein said first fluid is dialysate.

167. The system of characterization 165, wherein said second fluid is blood.

168. The system of characterization 165, wherein delivery of said first fluid to said first fiber group by said first fluid supply, and said delivery of said first fluid to said second fiber group by said first fluid supply, and said second fluid supply, are all able to be controlled independently of each other.

169. A method of treating blood extracorporeally, comprising
providing the system of characterization 165;
supplying blood through a housing supply port and removing blood through a housing discharge port;
supplying dialysate fluid to said lumens of said first group of fibers, whereby said dialysate fluid passes into said blood through said semi-permeable membrane.

170. A cartridge, comprising:
a housing;
a plurality of fibers contained inside said housing, at least some of said fibers being hollow and being made of semi-permeable membranes having respective fiber lumens and fiber exteriors;
a first fluid flow compartment comprising said lumens of said hollow fibers; and
a second fluid flow compartment comprising an inter fiber space bordering said fiber exteriors,
wherein said housing comprises a first housing port near a first end of said housing, and a second housing port near a second end of said housing,
wherein said housing comprises a third housing port located, in lengthwise position, between said first housing port and said second housing port and in fluid communication with said inter fiber space.

171. The cartridge of characterization 170, wherein said third port is midway between said first housing port and said second housing port.

172. A tube set comprising:
the cartridge of characterization 170;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

173. A system comprising the cartridge of characterization 170 and further comprising a fluid management system that supplies blood to said first housing port and withdraws treated blood from said second housing port, and further supplies a liquid to said third port.

174. The system of characterization 173, wherein said liquid is dialysate.

175. A method of performing extracorporeal blood treatment, comprising:
providing the cartridge of characterization 170;
supplying blood to one of said first housing port and said second housing port and removing blood from the other of said first housing port and said second housing port; and
supplying substitution fluid to said third housing port.

176. A cartridge, comprising:
a housing, said housing having a housing supply port and a housing discharge port; and
a plurality of fibers contained inside said housing, at least some of said fibers being hollow and being made of semi-permeable membranes having respective fiber lumens and fiber exteriors, a first fluid flow compartment comprising said lumens of said hollow fibers; and
a second fluid flow compartment comprising an inter fiber space that touches said fiber exteriors, wherein flow from said housing supply port to said housing discharge port is, at a midplane of said cartridge, generally perpendicular to a lengthwise direction of said plurality of fibers, wherein said cartridge further comprises a flow resistance element between said housing supply port and said inter fiber space, or between said inter fiber space and said housing discharge port, said flow resistance element causing said flow in said inter fiber space to be more uniform than would occur without said flow resistance.

177. The cartridge of characterization 176, wherein said flow resistance element has a uniform flow resistance everywhere.

178. The cartridge of any of characterizations 176-177, wherein said flow resistance element has a flow resistance that differs among various places in said flow resistance element, said flow resistance element causing said flow in said inter fiber space to be more uniform than would occur if said flow resistance had a uniform flow resistance.

179. The cartridge of any of characterizations 176-178, wherein said fibers have a Molecular Weight cut-off of less than approximately 50,000 Daltons.

180. The cartridge of any of characterizations 176-179, wherein said housing supply port and said housing discharge port are directed generally perpendicularly to a long direction of said plurality of fibers, and are in-line with each other.

181. The cartridge of any of characterizations 176-180, wherein said housing supply port and said housing discharge port are directed generally perpendicularly to a long direction of said plurality of fibers, and are offset with respect to each other.

182. The cartridge of any of characterizations 176-181, wherein said housing supply port and said housing discharge port are directed generally parallel to each other and are offset with respect to each other.

183. A tube set comprising:
the cartridge of characterization 176;
tubing connected to said cartridge; and
at least one component selected from the group consisting of: a tube that is positioned and adapted to be operated by a roller of a peristaltic pump; a volume balancing chamber; a control valve; a check valve; a filter; a pinch-clip; an air bleed; a priming component; a drip chamber; a pressure-transmitting pod; a sensor; and an electrical connection.

184. A system, comprising:
the cartridge of characterization 176, wherein said housing supply port is connected to a blood supply line and said housing discharge port is connected to a blood discharge line,
further comprising a dialysate connection from a dialysate system to lumens of at least some of said plurality of fibers, or an ultrafiltrate removal line connecting to lumens of at least some of said plurality of fibers.

185. A method of performing extracorporeal blood treatment, comprising:
providing the cartridge of characterization 176;
supplying blood to one of said first housing port and said second housing port and removing blood from the other of said first housing port and said second housing port; and
supplying dialysate to or removing ultrafiltrate from lumens of at least some of said plurality of fibers.

186. A method of performing hemodialysis, said method comprising:
providing a cartridge, wherein said cartridge comprises a dialysate inlet and a dialysate outlet, said dialysate inlet and said dialysate outlet being located at a common end of said cartridge, and comprises a blood inlet and a blood outlet, and said cartridge comprises fibers comprising a semi-permeable membrane separating blood and dialysate from each other;
providing a first fluid supply that supplies a dialysate to said dialysate inlet, wherein said dialysate flows a first direction along a length of said cartridge through lumens of some of said fibers and returns flowing an opposite through lumens of others of said fibers;
removing said dialysate from said dialysate outlet; and
performing hemodialysis by causing blood to flow into said blood inlet and out from said blood outlet.

187. A cartridge comprising:
a housing having a housing supply port and a housing discharge port; and
a plurality of fibers contained inside said housing, at least some of said fibers being hollow and being made of semi-permeable membranes having respective fiber lumens and fiber exteriors;
wherein said fibers have an external surface that is smooth and hemocompatible,
wherein said fibers are wavy and have a porosity fraction inside said housing that is between 40% and 70%,
wherein there is a maximum shear rate that occurs at some location in said cartridge during a flow of a fluid through said housing from said housing supply port to said housing discharge port at a defined flowrate,
wherein there is a minimum shear rate that occurs at some other location in said cartridge during said flow of said fluid through said housing from said housing supply port to said housing discharge port at said defined flowrate,
wherein a ratio of said maximum shear rate to said minimum shear rate is less than 9.

188. The cartridge of characterization 187, wherein said porosity fraction of said fibers inside said housing is between 50% and 62%.

189. The cartridge of characterizations 187-188, wherein said maximum shear rate and said minimum shear rate are evaluated at a flowrate of blood through said cartridge of 300 milliliters per minute.

190. The cartridge of characterizations 187-189, wherein said fiber external surface performs sieving of molecules according to molecular size and molecular shape.

191. The cartridge of characterizations 187-190, wherein said minimum shear rate is greater than 300 sec-1 and said maximum shear rate is less than 2700 sec-1.

192. The cartridge of characterizations 187-191, wherein said ratio of said maximum shear rate to said minimum shear rate is less than 5.

193. The cartridge of characterizations 187-192, wherein said ratio of said maximum shear rate to said minimum shear rate is less than 3.

194. The cartridge of characterizations 187-193, wherein said ratio of said maximum shear rate to said minimum shear rate is less than 2.

Additional Comments

Applications of the cartridges, systems, apparatus and methods described herein could, first of all, be therapy applications. Such therapy applications could be long-term, such as up to 100 hours without needing to replace the cartridge, or up to 72 hours, or 24 to 40 hours, for example.

Examples of possible applications include Hemodialysis; HemoDiaFiltration; Slow Continuous UltraFiltration; Ultra-Filtration; Slow Continuous HemoDialysis; Continuous Renal Replacement Therapy; and other extended therapies. Continuous Renal Replacement Therapy may include any of: CVVH (Continuous Veno-Venous Hemofiltration); CVVHD (Continuous Veno-Venous hemodialysis); and CVVHDF (Continuous Veno-Venous Hemodiafiltration). Further, it is possible that new therapies could become possible because of embodiments of the invention.

Such cartridges could be used for treatment of blood in an extracorporeal blood circuit, or alternatively could be in the form of an implant for treatment of blood using an implant. This could, for example, make possible certain applications that involve long term use, implantable devices, portable devices, or wearable devices.

In addition, the applications do not all have to be therapy applications. Embodiments of the invention could also be used for blood processing such as for blood banks or fir separation of blood into components or for pharmaceutical manufacturing. Also, embodiments of the invention could use other fluids other than blood.

In general, any of the embodiments described or illustrated could be used together with any kind of distributor such as an orbital distributor at either end or at both ends of the cartridge, in order to improve the uniformity of flow in the inter fiber space. Similarly, any of the embodiments described or illustrated could be used together with fanning of the fibers at either end or at both ends of the cartridge, in order to improve the uniformity of flow in the inter fiber space.

Embodiments of the invention could comprise an air bleed at appropriate locations, to prevent formation or entrapment of air bubbles.

Where fibers are discussed, the fibers could be either straight or wavy. The fiber bundle could be a mixture of some straight fibers and some wavy fibers. Spacer fibers, either solid or yarns, could also be included in the fiber bundle.

Corners and edges that are exposed to blood may be rounded or smoothed as desired. Such corners and edges may have manufacturing burrs, flashing, and debris may be removed. Some illustrations shown herein are shown with ordinary sharp corners and edges on the remaining solid material, for ease of illustration, but it can be appreciated that the designs may be made with rounded corners and edges, for compatibility with the flow of blood past those corners and edges.

Coatings, such as on the housing interior or the fibers, could be applied on either the entirety of such surface, or only on portions of such surface. For example, sometimes surfaces such as the lumens of hollow fibers of conventional dialyzers are given a coating of heparin. In embodiments of the invention, the fiber exteriors may be given a coating of heparin. It is furthermore possible that with embodiments of the invention, it may be unnecessary to administer heparin systemically to the entire volume of blood in the patient's body. Instead, a modest and localized amount of heparin applied to and resident in certain surfaces of the dialyzer may discourage clotting, and together with the other features of outside-in flow that discourage thrombus formation or make the cartridge performance relatively unaffected by thrombus formation, may make it possible to routinely treat patients without any systemic administration of heparin to the patient at all. For example, there are some patients who have a reaction to or do not tolerate anticoagulants such as heparin or citrate. Also, for emergency situations or CRRT applications, there also may be advantages in being able to perform certain therapies while avoiding any systemic administration of heparin to the patient. Providing fibers that are externally smooth, hydrophilic and heparin-coated may enable such applications.

Although discussion has focused on fibers whose exteriors are smooth, with possibly rough interiors, in embodiments of the invention it is also possible to use so-called symmetric fibers, which are smooth on both their interiors and their exteriors. Fibers may have exteriors that are hydrophilic and hemocompatible.

Fanning of the fibers near the ends of the cartridge can be used in combination with any other feature described herein.

An air bleed can be provided wherever desired as an additional port built onto the cartridge or as a splitting-off from an existing port. Alternatively, an air bleed can be built in to the tubing or built into a tube sheet or tube set.

In general, with any of the described features, the flow of fluid such as blood in the inter fiber space could be any orientation including generally parallel to the overall fiber direction, and generally perpendicular or transverse to the overall fiber direction. Furthermore, it would even be possible to use radial flow. Radial flow is a configuration in which one fluid is supplied or received by a central distribution tube analogous to a header or distributor, which is generally parallel to the fibers. The general direction of the flow may be perpendicular (transverse) to the fibers. However, in such a situation it is possible for the velocity of such flow to vary as a function of radial location with respect to the overall axes and directions of the cartridge.

Although description has been given of embodiments in which blood flows outside the hollow fibers, it is also possible that features or embodiments disclosed herein could be used in situations in which dialysate flows outside the hollow fibers. Certain features disclosed herein that affect flow or flow distribution of liquid in the inter fiber space may have been designed for an application in which blood flows in the inter fiber space, but they can be of benefit generally for any fluid that flows in the inter fiber space. For example, features such as a lateral-circumferential flow redirector, or a circumferential-axial flow redirector, or a non-uniform-conductance flow element, or any combination thereof, could be used in a cartridge in which dialysate flows through those features and through the inter fiber space. Such flow improvement, even for dialysate or similar fluids, can be of benefit for certain therapies.

It can also be noted that, in regard to what has been referred herein to as dialysate, it is possible to use described embodiments with substantially any water-resembling fluid. Liquid that has been referred to as dialysate can refer to any aqueous fluid having simple chemistry, viscosity similar to that of water, and Newtonian fluid properties. Typical dialysate formulations include formulations based on bicarbonate, acetate and citrate. However, there may be other therapies for which embodiments of the invention may be useful, which involve other formulations of aqueous liquid being passed through the lumens of the hollow fibers. For example, extracorporeal blood processing can be used to treat liver failure, sepsis, and disturbance of the gas balance in the blood such as excess carbon dioxide in the blood. For therapies such as these or for still other therapies, what has been referred to herein as dialysate could be a formulation that is appropriate for the treatment of these or other conditions.

Any described cartridge could be part of a tube sheet or tube set as described, or part of any system as described. Any described cartridge could be part of any described method of treatment.

In the illustrations herein involving fiber groups within the fiber bundle, the fibers in the various fiber bundles are shown as identical fibers. However, it is also possible to have more than one fiber type within a dialyzer. Different fiber types can be grouped into respective fiber groups. Fiber types can differ in materials, overall dimensions, pore characteristics such as pore size and pore size distribution, surface treatment or properties, mass transfer properties, and generally any characteristic. Fibers may perform a sieving function according to molecular size and also molecular shape. Fibers also may have a molecular weight cutoff.

Embodiments of the invention can be used to oxygenate blood, to remove dissolved gases such as carbon dioxide from the blood, to perform clearance, to infuse drugs, and to perform any other function during extracorporeal therapy or in general during any therapy.

Embodiments of the invention may be used to treat organ failure. Organ failure can include any one or more of kidneys, liver, lung, blood function, lymph and other body systems.

Segmentation or subdivision of the fiber bundle into fiber groups has been illustrated in terms of a central fiber group and an annular fiber group. However, more generally, segmentation or subdivision of the fiber bundle can take any of various forms or geometries including circular, rectangular, straight-line boundaries between fiber groups, and can include whatever number of fiber groups may be desired. Groups may contain multiple fibers or single fibers. Fibers can be selected and placed so as to achieve uniformity and proper mixing of fluids in the cartridge before, during and after treatment.

Examples have been described herein in which a fiber group within the fiber bundle has been used for a specific purpose different from the purpose of other fibers. It is possible to use a small fiber group or a single fiber to sample dialysate during treatment, or to introduce a component to make or reconstitute dialysate or change its composition. Alternatively, such fibers can be used to administer an anticoagulant or other substance (such as calcium, drugs etc.) on either a continuous basis or an intermittent basis. Such fiber or fibers could be physically different from other fibers.

Selection of the parallel or perpendicular (transverse) orientation of flow past the fibers can depend on the type of therapy, on the level and type of anticoagulant (if used), and on the propensity to form clots. The dimensions of the cartridge also can be chosen or adjusted based on such factors.

The fluid in the lumen (which has been referred to as dialysate) can include a sorbent (for example, activated carbon) in either molecular or particulate form, to improve clearance or remove unwanted molecules from the blood, such as bilirubin, cytokines, urea, beta-2 microglobulin, protein-bound toxins, etc.

The described designs can be used, either with or without modifications, to make implantable devices. Those skilled in the art can use or modify embodiments of the invention to render them as implants. Therefore, the invention is not limited to extracorporeal-based therapies or to the designs disclosed herein.

The fluids may flow in the lumens in a steady state continuous manner or they may be supplied or removed in an intermittend controlled manner including the ability to perform a push-pull function or other functions.

Fibers used in embodiments of the invention may be coated with substances or molecules to prevent clotting or to promote adsorption of molecules such as cytokines, endotoxin, or other unwanted substances. Coatings may include heparin, perfluorocarbon or other molecules that prevent cell adhesion or cell adsorption.

Post-dilution can be used to effect high-volume serum replacement or other forms of convective clearance therapies while still not experiencing filter clogging, because filter clogging can be avoided through other advantages and features of the outside-in flow filtration mode. Post-dilution or mid-dilution (in situ) can be used to minimize clogging and clotting to allow achieving excellent mass transfer at the same time. High volume hemodiafiltration can be performed using only post-dilution, or using only in-situ mid-dilution, or using only pre-dilution, or using a combination of any of these.

With embodiments of the invention, it may be possible to achieve therapy that is completely free of externally or systemically administered anticoagulant, by using appropriate fibers and cartridge designs. Specially coated fibers and higher porosity of the fiber bundle, or a combination thereof, may be able to achieve desired cartridge performance and perform the desired therapy without the need for administration of heparin or citrate.

In general, any combination of disclosed features, components and methods is possible.

All cited references are incorporated by reference herein.

Although embodiments have been disclosed, it is not desired to be limited thereby. Rather, the scope should be determined only by the appended claims.

We claim:

1. A cartridge, comprising:
   a housing that extends along a housing longitudinal direction, said housing having a first housing end and an opposed second housing end, said housing having a housing wall;
   a plurality of fibers contained inside said housing and extending along said housing longitudinal direction, at least some of said fibers being hollow having respective fiber lumens and being made of a semi-permeable material;
   an inter fiber space that comprises space between said fibers inside said housing;
   a distributor region comprising a space between said housing wall and said plurality of fibers, said distributor region being located adjacent an end of said inter fiber space and extending around a circumference of said housing, wherein said inter fiber space and said distributor region are configured to receive blood flow therethrough; and
   a first housing connection to said housing, said first housing connection being located at said first housing end of said housing;
   wherein said first housing connection is in fluid communication with said distributor region and said distributor region is in fluid communication with said inter fiber space;
   wherein the distributor region has a cross-sectional area that tapers from a larger cross-sectional area proximate the first housing connection to a smaller cross-sectional area away from the first housing connection in a circumferential direction.

2. The cartridge of claim 1, wherein said housing comprises a generally cylindrical portion that is centrally located with respect to said housing longitudinal direction, and said housing further comprises a convex-concave transition between said generally cylindrical portion of said housing and said distributor region.

3. The cartridge of claim 1, wherein said cartridge does not comprise any barrier separating said distributor region from said plurality of fibers.

4. The cartridge of claim 1, wherein said cartridge comprises a perforated barrier between said distributor region and said plurality of fibers.

5. The cartridge of claim 1, wherein, in a portion of said cartridge that is centrally located with respect to said housing longitudinal direction, said plurality of fibers are generally parallel to each other, and wherein adjacent said distributor region, said fibers fan away from each other.

6. The cartridge of claim 1, wherein said first housing connection has a fitting that is a luer lock fitting.

7. The cartridge of claim 1, further comprising a first header that is in fluid communication with said fiber lumens, wherein said first header has a first header connection that has a first header fitting that is incompatible with a fitting on said first housing connection.

8. The cartridge of claim 1, further comprising a first header that is in fluid communication with said fiber lumens, wherein said first header has a first header connection connected to said first header, wherein said first header connection has an internal passageway direction that is generally perpendicular to said housing longitudinal direction.

9. The cartridge of claim 1, wherein said cartridge comprises a mass of potting material potting ends of said fibers, said potting material being located within a potting maximum radial dimension of said potting material, and wherein said first housing connection is located at a radial dimension with respect to said housing longitudinal direction that is greater than said potting maximum radial dimension.

10. The cartridge of claim 1, further comprising a circumferential-axial flow redirector located in the distributor region, the circumferential-axial flow redirector comprising a first curved surface extending in a first generally circumferential direction a second curved surface extending in a second generally circumferential direction opposite said first generally circumferential direction, and wherein said first curved surface and said second curved surface join so as to form a feature that points generally along said longitudinal direction.

11. The cartridge of claim 10, wherein said circumferential-axial flow redirector is located on an opposite side of said cartridge from said first housing connection.

12. A system, comprising:
the cartridge of claim 1;
a first fluid supply, supplying a first fluid to said fiber lumens; and
a second fluid supply, supplying a second fluid to said inter fiber space inside said housing,
wherein said first fluid is dialysate and said second fluid is blood.

13. A cartridge, comprising:
a housing that extends along a housing longitudinal direction, said housing having a first housing end and an opposed second housing end, said housing having a housing wall;
a plurality of fibers contained inside said housing and extending along said housing longitudinal direction, at least some of said fibers being hollow having respective fiber lumens and being made of a semi-permeable material;
an inter fiber space that comprises space between said fibers inside said housing;
a first housing connection to said housing, said first housing connection being located at said first housing end of said housing and being in fluid communication with said inter fiber space;
a second housing connection to said housing, said second housing connection being located at said second housing end of said housing and being in fluid communication with said inter fiber space;
further comprising a distributor region within said housing, said distributor region comprising a space between said housing wall and said plurality of fibers around a circumference of the plurality of fibers, wherein said inter fiber space and said distributor region are configured to receive blood flow therethough;
wherein said first housing connection has a first housing connection direction that is generally parallel to said housing longitudinal direction and said second housing connection has a second housing connection direction that is generally parallel to said housing longitudinal direction;
wherein the distributor region has a cross-sectional area in the space between said housing wall and said plurality of fibers that tapers from a larger cross-sectional area proximate the first housing connection to a smaller cross-sectional area away from the first housing connection in a circumferential direction.

14. The cartridge of claim 13, wherein said second housing connection is offset from said first housing connection.

15. The cartridge of claim 13, wherein said first housing connection and said second housing connection are generally aligned with each other.

16. A system, comprising:
the cartridge of claim 13;
a first fluid supply, supplying a first fluid to said fiber lumens; and
a second fluid supply, supplying a second fluid to said inter fiber space inside said housing,
wherein said first fluid is dialysate and said second fluid is blood.

17. The cartridge of claim 1, wherein said first housing connection has a first housing connection direction that is generally parallel to said housing longitudinal direction.

* * * * *